US012751825B2

(12) United States Patent
Schreck et al.

(10) Patent No.: US 12,751,825 B2
(45) **Date of Patent: *Oct. 6, 2026**

(54) HEART VALVE PROSTHESIS DELIVERY SYSTEM AND METHOD FOR DELIVERY OF HEART VALVE PROSTHESIS WITH INTRODUCER SHEATH

(71) Applicant: JenaValve Technology, Inc., Irvine, CA (US)

(72) Inventors: Stefan Schreck, San Clemente, CA (US); Teodoro S. Jimenez, Jr., Aliso Viejo, CA (US); Eileen Charlton, Garden Grove, CA (US); William Gould, Santa Fe, NM (US)

(73) Assignee: JenaValve Technology, Inc., Irvine, CA (US)

( * ) Notice: Subject to any disclaimer, the term of this patent is extended or adjusted under 35 U.S.C. 154(b) by 43 days.

This patent is subject to a terminal disclaimer.

(21) Appl. No.: 18/920,601

(22) Filed: Oct. 18, 2024

(65) Prior Publication Data

US 2025/0041089 A1 Feb. 6, 2025

Related U.S. Application Data

(63) Continuation of application No. 15/559,498, filed as application No. PCT/EP2016/055783 on Mar. 17, 2016, now Pat. No. 12,121,461.

(Continued)

(51) Int. Cl.

| | |
|---|---|
| *A61F 2/24* | (2006.01) |
| *A61F 2/966* | (2013.01) |

(Continued)

(52) U.S. Cl.

CPC .......... *A61F 2/2436* (2013.01); *A61F 2/2418* (2013.01); *A61F 2/2427* (2013.01);

(Continued)

(58) Field of Classification Search

CPC ...... A61F 2/2427; A61F 2/243; A61F 2/2436; A61F 2/2418; A61F 2/2433; A61F 2/966;

(Continued)

(56) References Cited

U.S. PATENT DOCUMENTS

| | | | |
|---|---|---|---|
| 15,192 | A | 6/1856 | Peale |
| 388,776 | A | 8/1888 | Hall |

(Continued)

FOREIGN PATENT DOCUMENTS

| | | | |
|---|---|---|---|
| AU | 757647 | B2 | 2/2003 |
| AU | 776895 | B2 | 9/2004 |

(Continued)

OTHER PUBLICATIONS

US 6,331,185 B1, 12/2001, Gambale et al. (withdrawn)

(Continued)

*Primary Examiner* — Sarah A Long

(74) *Attorney, Agent, or Firm* — Greenberg Traurig, LLP; Christopher C. Bolten; Robert D. Ward

(57) ABSTRACT

The present disclosure relates to a delivery system, a catheter system and a method for the minimally invasive application of prostheses to an individual in need thereof and a method for loading a prosthesis onto a catheter system and/or a delivery system.

21 Claims, 24 Drawing Sheets

Related U.S. Application Data

(60) Provisional application No. 62/136,092, filed on Mar. 20, 2015.

(51) Int. Cl.
*A61M 25/01* (2006.01)
*A61F 2/95* (2013.01)
*A61M 25/06* (2006.01)

(52) U.S. Cl.
CPC ............ *A61F 2/2433* (2013.01); *A61F 2/966* (2013.01); *A61M 25/0136* (2013.01); *A61F 2002/9505* (2013.01); *A61F 2/9517* (2020.05); *A61F 2/9522* (2020.05); *A61F 2250/0006* (2013.01); *A61M 2025/0681* (2013.01)

(58) Field of Classification Search
CPC .. A61F 2/9517; A61F 2/95; A61F 2/24; A61F 2002/9505; A61F 2250/0006; A61F 2025/0681; A61M 25/0136
See application file for complete search history.

(56) References Cited

U.S. PATENT DOCUMENTS 944,214 A 12/1909 Rydquist
2,121,182 A 6/1938 Benjamin
2,669,896 A 2/1954 Clough
2,682,057 A 6/1954 Lord
2,701,559 A 2/1955 Cooper
2,832,078 A 4/1958 Williams
3,029,819 A 4/1962 Edward et al.
3,099,016 A 7/1963 Lowell et al.
3,113,586 A 12/1963 Edmark, Jr. et al.
3,130,418 A 4/1964 Head et al.
3,143,742 A 8/1964 Cromie
3,210,836 A 10/1965 Johanson et al.
3,221,006 A 11/1965 Moore et al.
3,334,629 A 8/1967 Cohn
3,365,728 A 1/1968 Lowell et al.
3,367,364 A 2/1968 Cruz, Jr. et al.
3,409,013 A 11/1968 Henry et al.
3,445,916 A 5/1969 Schulte et al.
3,540,431 A 11/1970 Mobin-Uddin et al.
3,548,417 A 12/1970 Kischer et al.
3,570,014 A 3/1971 Hancock et al.
3,574,865 A 4/1971 Hamaker
3,587,115 A 6/1971 Shiley et al.
3,592,184 A 7/1971 Watkins et al.
3,628,535 A 12/1971 Ostrowsky et al.
3,642,004 A 2/1972 Osthagen et al.
3,657,744 A 4/1972 Ersek
3,671,979 A 6/1972 Moulopoulos
3,714,671 A 2/1973 Edwards et al.
3,725,961 A 4/1973 Magovern et al.
3,755,823 A 9/1973 Hancock
3,795,246 A 3/1974 Sturgeon
3,839,741 A 10/1974 Haller
3,868,956 A 3/1975 Alfidi et al.
3,874,388 A 4/1975 King et al.
3,983,581 A 10/1976 Angell et al.
3,997,923 A 12/1976 Possis
4,035,849 A 7/1977 Angell et al.
4,056,854 A 11/1977 Boretos et al.
4,078,268 A 3/1978 Possis
4,084,268 A 4/1978 Ionescu et al.
4,106,126 A 8/1978 Traenkle
4,106,129 A 8/1978 Carpentier et al.
4,118,806 A 10/1978 Porier et al.
4,164,046 A 8/1979 Cooley
4,182,446 A 1/1980 Penny
4,191,218 A 3/1980 Clark et al.
4,214,587 A 7/1980 Sakura, Jr.
4,215,871 A 8/1980 Hirsch et al.
4,222,126 A 9/1980 Boretos et al.
4,233,690 A 11/1980 Akins
4,261,342 A 4/1981 Aranguren Duo
4,263,680 A 4/1981 Reul et al.
4,265,694 A 5/1981 Boretos et al.
4,291,420 A 9/1981 Reul
4,297,749 A 11/1981 Davis et al.
4,319,831 A 3/1982 Matsui et al.
RE30,912 E 4/1982 Hancock
4,323,358 A 4/1982 Lentz et al.
4,326,306 A 4/1982 Poler
4,339,831 A 7/1982 Johnson
4,343,048 A 8/1982 Ross et al.
4,345,340 A 8/1982 Rosen
4,350,492 A 9/1982 Wright et al.
4,373,216 A 2/1983 Klawitter
4,388,735 A 6/1983 Ionescu et al.
4,406,022 A 9/1983 Roy
4,423,809 A 1/1984 Mazzocco
4,425,908 A 1/1984 Simon
4,441,215 A 4/1984 Kaster
4,441,216 A 4/1984 Ionescu et al.
4,470,157 A 9/1984 Love
4,484,579 A 11/1984 Meno et al.
4,485,816 A 12/1984 Krumme
4,491,986 A 1/1985 Gabbay
4,501,030 A 2/1985 Lane
4,502,488 A 3/1985 Degironimo et al.
4,531,943 A 7/1985 Van Tassel et al.
4,535,483 A 8/1985 Klawitter et al.
4,546,499 A 10/1985 Possis et al.
4,562,597 A 1/1986 Possis et al.
4,574,803 A 3/1986 Storz
4,580,568 A 4/1986 Gianturco
4,592,340 A 6/1986 Boyles
4,602,911 A 7/1986 Ahmadi et al.
4,605,407 A 8/1986 Black et al.
4,610,688 A 9/1986 Silvestrini et al.
4,612,011 A 9/1986 Kautzky
4,617,932 A 10/1986 Kornberg
4,619,246 A 10/1986 Molgaard-Nielsen et al.
4,643,732 A 2/1987 Pietsch et al.
4,647,283 A 3/1987 Carpentier et al.
4,648,881 A 3/1987 Carpentier et al.
4,655,218 A 4/1987 Kulik et al.
4,655,771 A 4/1987 Wallsten
4,662,885 A 5/1987 DiPisa, Jr.
4,665,906 A 5/1987 Jervis
4,665,918 A 5/1987 Garza et al.
4,680,031 A 7/1987 Alonso
4,681,908 A 7/1987 Broderick et al.
4,687,483 A 8/1987 Fisher et al.
4,692,164 A 9/1987 Dzemeshkevich et al.
4,705,516 A 11/1987 Barone et al.
4,710,192 A 12/1987 Liotta et al.
4,733,665 A 3/1988 Palmaz
4,755,181 A 7/1988 Igoe
4,759,758 A 7/1988 Gabbay
4,769,029 A 9/1988 Patel
4,777,951 A 10/1988 Cribier et al.
4,787,899 A 11/1988 Lazarus
4,787,901 A 11/1988 Baykut
4,796,629 A 1/1989 Grayzel
4,797,901 A 1/1989 Goerne et al.
4,806,595 A 2/1989 Noishiki et al.
4,819,751 A 4/1989 Shimada et al.
4,829,990 A 5/1989 Thuroff et al.
4,834,755 A 5/1989 Silvestrini et al.
4,846,830 A 7/1989 Knoch et al.
4,851,001 A 7/1989 Taheri
4,856,516 A 8/1989 Hillstead
4,865,600 A 9/1989 Carpentier et al.
4,872,874 A 10/1989 Taheri
4,873,978 A 10/1989 Ginsburg
4,878,495 A 11/1989 Grayzel
4,878,906 A 11/1989 Lindemann et al.
4,883,458 A 11/1989 Shiber
4,885,005 A 12/1989 Nashef et al.
4,909,252 A 3/1990 Goldberger
4,917,102 A 4/1990 Miller et al.

(56) References Cited

U.S. PATENT DOCUMENTS

| | | | |
|---|---|---|---|
| 4,922,905 | A | 5/1990 | Strecker |
| 4,927,426 | A | 5/1990 | Dretler |
| 4,950,227 | A | 8/1990 | Savin et al. |
| 4,953,553 | A | 9/1990 | Tremulis |
| 4,954,126 | A | 9/1990 | Wallsten |
| 4,966,604 | A | 10/1990 | Reiss |
| 4,969,890 | A | 11/1990 | Sugita et al. |
| 4,979,939 | A | 12/1990 | Shiber |
| 4,986,830 | A | 1/1991 | Owens et al. |
| 4,994,077 | A | 2/1991 | Dobben |
| 5,002,556 | A | 3/1991 | Ishida et al. |
| 5,002,559 | A | 3/1991 | Tower |
| 5,002,566 | A | 3/1991 | Carpentier et al. |
| 5,007,896 | A | 4/1991 | Shiber |
| 5,026,366 | A | 6/1991 | Leckrone |
| 5,026,377 | A | 6/1991 | Burton et al. |
| 5,032,128 | A | 7/1991 | Alonso |
| 5,035,706 | A | 7/1991 | Giantureo et al. |
| 5,037,434 | A | 8/1991 | Lane |
| 5,047,041 | A | 9/1991 | Samuels |
| 5,053,008 | A | 10/1991 | Bajaj |
| 5,059,177 | A | 10/1991 | Towne et al. |
| 5,061,273 | A | 10/1991 | Yock |
| 5,061,277 | A | 10/1991 | Carpentier et al. |
| 5,064,435 | A | 11/1991 | Porter |
| 5,078,720 | A | 1/1992 | Burton et al. |
| 5,080,668 | A | 1/1992 | Bolz et al. |
| 5,085,635 | A | 2/1992 | Cragg |
| 5,089,015 | A | 2/1992 | Ross |
| 5,094,661 | A | 3/1992 | Levy et al. |
| 5,104,399 | A | 4/1992 | Lazarus |
| 5,104,407 | A | 4/1992 | Lam et al. |
| 5,108,425 | A | 4/1992 | Hwang |
| 5,122,154 | A | 6/1992 | Rhodes |
| 5,132,473 | A | 7/1992 | Furutaka et al. |
| 5,141,494 | A | 8/1992 | Danforth et al. |
| 5,143,987 | A | 9/1992 | Hansel et al. |
| 5,147,388 | A | 9/1992 | Yamazaki |
| 5,152,771 | A | 10/1992 | Sabbaghian et al. |
| 5,159,937 | A | 11/1992 | Tremulis |
| 5,161,547 | A | 11/1992 | Tower |
| 5,163,953 | A | 11/1992 | Vince |
| 5,163,955 | A | 11/1992 | Love et al. |
| 5,167,628 | A | 12/1992 | Boyles |
| 5,178,632 | A | 1/1993 | Hanson |
| 5,192,301 | A | 3/1993 | Kamiya et al. |
| 5,193,546 | A | 3/1993 | Shaknovich |
| 5,197,979 | A | 3/1993 | Quintero et al. |
| 5,201,757 | A | 4/1993 | Heyn et al. |
| 5,207,695 | A | 5/1993 | Trout, III |
| 5,209,741 | A | 5/1993 | Spaeth |
| 5,211,183 | A | 5/1993 | Wilson |
| 5,215,541 | A | 6/1993 | Nashef et al. |
| 5,217,481 | A | 6/1993 | Barbara |
| 5,217,483 | A | 6/1993 | Tower |
| 5,232,445 | A | 8/1993 | Bonzel |
| 5,234,447 | A | 8/1993 | Kaster et al. |
| 5,234,456 | A | 8/1993 | Silvestrini |
| 5,238,004 | A | 8/1993 | Sahatjian et al. |
| 5,258,008 | A | 11/1993 | Wilk |
| 5,258,023 | A | 11/1993 | Reger |
| 5,258,042 | A | 11/1993 | Mehta |
| 5,272,909 | A | 12/1993 | Nguyen et al. |
| 5,275,580 | A | 1/1994 | Yamazaki |
| 5,279,612 | A | 1/1994 | Eberhardt |
| 5,282,847 | A | 2/1994 | Trescony et al. |
| 5,287,861 | A | 2/1994 | Wilk |
| 5,295,958 | A | 3/1994 | Shturman |
| 5,327,774 | A | 7/1994 | Nguyen et al. |
| 5,330,486 | A | 7/1994 | Wilk |
| 5,330,500 | A | 7/1994 | Song |
| 5,332,402 | A | 7/1994 | Teitelbaum |
| 5,336,258 | A | 8/1994 | Quintero et al. |
| 5,342,348 | A | 8/1994 | Kaplan |
| 5,344,426 | A | 9/1994 | Lau et al. |
| 5,344,427 | A | 9/1994 | Cottenceau et al. |
| 5,344,442 | A | 9/1994 | Deac |
| 5,350,398 | A | 9/1994 | Pavcnik et al. |
| 5,350,399 | A | 9/1994 | Erlebacher et al. |
| 5,352,240 | A | 10/1994 | Ross |
| 5,354,330 | A | 10/1994 | Hanson et al. |
| 5,360,444 | A | 11/1994 | Kusuhara |
| 5,368,608 | A | 11/1994 | Levy et al. |
| 5,370,685 | A | 12/1994 | Stevens |
| 5,380,054 | A | 1/1995 | Galvis |
| 5,387,235 | A | 2/1995 | Chuter |
| 5,389,096 | A | 2/1995 | Aita et al. |
| 5,389,106 | A | 2/1995 | Tower |
| 5,397,351 | A | 3/1995 | Pavcnik et al. |
| 5,397,355 | A | 3/1995 | Marin et al. |
| 5,409,019 | A | 4/1995 | Wilk |
| 5,411,552 | A | 5/1995 | Andersen et al. |
| 5,415,633 | A | 5/1995 | Lazarus et al. |
| 5,425,739 | A | 6/1995 | Jessen |
| 5,425,762 | A | 6/1995 | Muller |
| 5,429,144 | A | 7/1995 | Wilk |
| 5,431,676 | A | 7/1995 | Dubrul et al. |
| 5,433,723 | A | 7/1995 | Lindenberg et al. |
| 5,443,446 | A | 8/1995 | Shturman |
| 5,443,449 | A | 8/1995 | Buelna |
| 5,443,477 | A | 8/1995 | Marin et al. |
| 5,443,495 | A | 8/1995 | Buscemi et al. |
| 5,443,499 | A | 8/1995 | Schmitt |
| 5,449,384 | A | 9/1995 | Johnson |
| 5,456,712 | A | 10/1995 | Maginot |
| 5,456,713 | A | 10/1995 | Chuter |
| 5,464,449 | A | 11/1995 | Ryan et al. |
| 5,469,868 | A | 11/1995 | Reger |
| 5,470,320 | A | 11/1995 | Tiefenbrun et al. |
| 5,476,506 | A | 12/1995 | Lunn |
| 5,476,508 | A | 12/1995 | Amstrup |
| 5,476,510 | A | 12/1995 | Eberhardt et al. |
| 5,480,423 | A | 1/1996 | Ravenscroft et al. |
| 5,480,424 | A | 1/1996 | Cox |
| 5,486,193 | A | 1/1996 | Bourne et al. |
| 5,487,760 | A | 1/1996 | Villafana |
| 5,489,294 | A | 2/1996 | McVenes et al. |
| 5,489,297 | A | 2/1996 | Duran |
| 5,489,298 | A | 2/1996 | Love et al. |
| 5,496,346 | A | 3/1996 | Horzewski et al. |
| 5,499,995 | A | 3/1996 | Teirstein |
| 5,500,014 | A | 3/1996 | Quijano et al. |
| 5,500,015 | A | 3/1996 | Deac |
| 5,507,767 | A | 4/1996 | Maeda et al. |
| 5,509,930 | A | 4/1996 | Love |
| 5,522,881 | A | 6/1996 | Lentz |
| 5,527,337 | A | 6/1996 | Stack et al. |
| 5,530,949 | A | 6/1996 | Koda et al. |
| 5,534,007 | A | 7/1996 | St. Germain et al. |
| 5,540,712 | A | 7/1996 | Kleshinski et al. |
| 5,545,133 | A | 8/1996 | Burns et al. |
| 5,545,209 | A | 8/1996 | Roberts et al. |
| 5,545,211 | A | 8/1996 | An et al. |
| 5,545,214 | A | 8/1996 | Stevens |
| 5,549,665 | A | 8/1996 | Vesely et al. |
| 5,549,666 | A | 8/1996 | Hata et al. |
| 5,554,119 | A | 9/1996 | Harrison et al. |
| 5,554,185 | A | 9/1996 | Block et al. |
| 5,569,274 | A | 10/1996 | Rapacki et al. |
| 5,571,167 | A | 11/1996 | Maginot |
| 5,571,174 | A | 11/1996 | Love et al. |
| 5,571,175 | A | 11/1996 | Vanney et al. |
| 5,571,215 | A | 11/1996 | Sterman et al. |
| 5,573,520 | A | 11/1996 | Schwartz et al. |
| 5,575,818 | A | 11/1996 | Pinchuk |
| 5,580,922 | A | 12/1996 | Park et al. |
| 5,591,185 | A | 1/1997 | Kilmer et al. |
| 5,591,195 | A | 1/1997 | Taheri et al. |
| 5,593,434 | A | 1/1997 | Williams |
| 5,595,571 | A | 1/1997 | Jaffe et al. |
| 5,596,471 | A | 1/1997 | Hanlin |
| 5,607,464 | A | 3/1997 | Trescony et al. |
| 5,607,465 | A | 3/1997 | Camilli |
| 5,609,626 | A | 3/1997 | Quijano et al. |

(56) References Cited

U.S. PATENT DOCUMENTS 5,613,982 A 3/1997 Goldstein
5,618,299 A 4/1997 Khosravi et al.
5,626,553 A 5/1997 Frassica et al.
5,628,784 A 5/1997 Strecker
5,632,778 A 5/1997 Goldstein
5,634,942 A 6/1997 Chevillon et al.
5,643,278 A 7/1997 Wijay
5,645,559 A 7/1997 Hachtman et al.
5,653,684 A 8/1997 Laptewicz et al.
5,653,745 A 8/1997 Trescony et al.
5,653,749 A 8/1997 Love et al.
5,655,548 A 8/1997 Nelson et al.
5,662,124 A 9/1997 Wilk
5,662,671 A 9/1997 Barbut et al.
5,662,703 A 9/1997 Yurek et al.
5,665,115 A 9/1997 Cragg
5,667,523 A 9/1997 Bynon et al.
5,674,277 A 10/1997 Freitag
5,674,298 A 10/1997 Levy et al.
5,679,112 A 10/1997 Levy et al.
5,681,345 A 10/1997 Euteneuer
5,682,906 A 11/1997 Sterman et al.
5,683,451 A 11/1997 Lenker et al.
5,690,644 A 11/1997 Yurek et al.
5,693,083 A 12/1997 Baker et al.
5,693,088 A 12/1997 Lazarus
5,693,310 A 12/1997 Gries et al.
5,695,498 A 12/1997 Tower
5,697,972 A 12/1997 Kim et al.
5,700,269 A 12/1997 Pinchuk et al.
5,702,368 A 12/1997 Stevens et al.
5,709,713 A 1/1998 Evans et al.
5,713,917 A 2/1998 Leonhardt et al.
5,713,950 A 2/1998 Cox
5,713,951 A 2/1998 Garrison et al.
5,713,953 A 2/1998 Vallana et al.
5,716,370 A 2/1998 Williamson, IV et al.
5,716,417 A 2/1998 Girard et al.
5,718,725 A 2/1998 Sterman et al.
5,720,391 A 2/1998 Dohm et al.
5,720,776 A 2/1998 Chuter et al.
5,725,549 A 3/1998 Lam
5,725,550 A 3/1998 Nadal
5,728,068 A 3/1998 Leone et al.
5,728,151 A 3/1998 Garrison et al.
5,733,267 A 3/1998 Del Toro
5,733,325 A 3/1998 Robinson et al.
5,735,842 A 4/1998 Krueger et al.
5,746,476 A 5/1998 Novak et al.
5,746,709 A 5/1998 Rom et al.
5,746,765 A 5/1998 Kleshinski et al.
5,746,775 A 5/1998 Levy et al.
5,749,890 A 5/1998 Shaknovich
5,749,921 A 5/1998 Lenker et al.
5,755,682 A 5/1998 Knudson et al.
5,755,777 A 5/1998 Chuter
5,755,783 A 5/1998 Stobie et al.
5,756,476 A 5/1998 Epstein et al.
5,758,663 A 6/1998 Wilk et al.
5,766,151 A 6/1998 Valley et al.
5,769,780 A 6/1998 Hata et al.
5,769,812 A 6/1998 Stevens et al.
5,769,882 A 6/1998 Fogarty et al.
5,769,887 A 6/1998 Brown et al.
5,772,609 A 6/1998 Nguyen et al.
5,776,188 A 7/1998 Shepherd et al.
5,782,809 A 7/1998 Umeno et al.
5,782,904 A 7/1998 White et al.
5,795,331 A 8/1998 Cragg et al.
5,797,946 A 8/1998 Chin
5,797,960 A 8/1998 Stevens et al.
5,799,661 A 9/1998 Boyd et al.
5,800,456 A 9/1998 Maeda et al.
5,800,508 A 9/1998 Goicoechea et al.
5,800,531 A 9/1998 Cosgrove et al.
5,807,327 A 9/1998 Green et al.
5,807,384 A 9/1998 Mueller
5,807,405 A 9/1998 Vanney et al.
5,810,836 A 9/1998 Hussein et al.
5,814,016 A 9/1998 Valley et al.
5,817,113 A 10/1998 Gifford, III et al.
5,817,126 A 10/1998 Imran
5,823,956 A 10/1998 Roth et al.
5,824,037 A 10/1998 Fogarty et al.
5,824,038 A 10/1998 Wall
5,824,041 A 10/1998 Lenker et al.
5,824,043 A 10/1998 Cottone, Jr.
5,824,053 A 10/1998 Khosravi et al.
5,824,055 A 10/1998 Spiridigliozzi et al.
5,824,056 A 10/1998 Rosenberg
5,824,061 A 10/1998 Quijano et al.
5,824,063 A 10/1998 Cox
5,824,064 A 10/1998 Taheri
5,824,071 A 10/1998 Nelson et al.
5,824,080 A 10/1998 Lamuraglia
5,829,447 A 11/1998 Stevens et al.
5,830,222 A 11/1998 Makower
5,836,869 A 11/1998 Kudo et al.
5,840,081 A 11/1998 Andersen et al.
5,841,382 A 11/1998 Walden et al.
5,843,158 A 12/1998 Lenker et al.
5,843,161 A 12/1998 Solovay
5,843,181 A 12/1998 Jaffe et al.
5,851,232 A 12/1998 Lois
5,853,419 A 12/1998 Imran
5,853,420 A 12/1998 Chevillon et al.
5,855,210 A 1/1999 Sterman et al.
5,855,597 A 1/1999 Jayaraman
5,855,600 A 1/1999 Alt
5,855,601 A 1/1999 Bessler et al.
5,855,602 A 1/1999 Angell
5,860,966 A 1/1999 Tower
5,860,996 A 1/1999 Urban et al.
5,861,024 A 1/1999 Rashidi
5,861,028 A 1/1999 Angell
5,865,723 A 2/1999 Love
5,868,783 A 2/1999 Tower
5,873,812 A 2/1999 Ciana et al.
5,873,906 A 2/1999 Lau et al.
5,876,373 A 3/1999 Giba et al.
5,876,419 A 3/1999 Carpenter et al.
5,876,434 A 3/1999 Flomenblit et al.
5,876,448 A 3/1999 Thompson et al.
5,878,751 A 3/1999 Hussein et al.
5,880,242 A 3/1999 Hu et al.
5,885,228 A 3/1999 Rosenman et al.
5,885,238 A 3/1999 Stevens et al.
5,885,259 A 3/1999 Berg
5,888,201 A 3/1999 Stinson et al.
5,891,160 A 4/1999 Williamson, IV et al.
5,891,191 A 4/1999 Stinson
5,895,399 A 4/1999 Barbut et al.
5,895,420 A 4/1999 Mirsch, II et al.
5,899,936 A 5/1999 Goldstein
5,906,619 A 5/1999 Olson et al.
5,907,893 A 6/1999 Zadno-Azizi et al.
5,908,028 A 6/1999 Wilk
5,908,029 A 6/1999 Knudson et al.
5,908,451 A 6/1999 Yeo
5,908,452 A 6/1999 Bokros et al.
5,910,144 A 6/1999 Hayashi
5,910,154 A 6/1999 Tsugita et al.
5,911,734 A 6/1999 Tsugita et al.
5,911,752 A 6/1999 Dustrude et al.
5,913,842 A 6/1999 Boyd et al.
5,916,193 A 6/1999 Stevens et al.
5,922,022 A 7/1999 Nash et al.
5,924,424 A 7/1999 Stevens et al.
5,925,012 A 7/1999 Murphy-Chutorian et al.
5,925,063 A 7/1999 Khosravi
5,928,281 A 7/1999 Huynh et al.
5,931,848 A 8/1999 Saadat
5,935,119 A 8/1999 Guy et al.
5,935,161 A 8/1999 Robinson et al.

(56) References Cited

U.S. PATENT DOCUMENTS 5,935,163 A 8/1999 Gabbay
5,938,632 A 8/1999 Ellis
5,938,697 A 8/1999 Killion et al.
5,941,908 A 8/1999 Goldsteen et al.
5,944,019 A 8/1999 Knudson et al.
5,944,738 A 8/1999 Amplatz et al.
5,948,017 A 9/1999 Taheri
5,954,764 A 9/1999 Parodi
5,954,766 A 9/1999 Zadno-Azizi et al.
5,957,949 A 9/1999 Leonhardt et al.
5,961,549 A 10/1999 Nguyen et al.
5,964,405 A 10/1999 Benary et al.
5,964,798 A 10/1999 Imran
5,968,064 A 10/1999 Selmon et al.
5,968,068 A 10/1999 Dehdashtian et al.
5,968,070 A 10/1999 Bley et al.
5,971,993 A 10/1999 Hussein et al.
5,975,949 A 11/1999 Holliday et al.
5,976,153 A 11/1999 Fischell et al.
5,976,155 A 11/1999 Foreman et al.
5,976,174 A 11/1999 Ruiz
5,976,178 A 11/1999 Goldsteen et al.
5,976,192 A 11/1999 McIntyre et al.
5,976,650 A 11/1999 Campbell et al.
5,979,455 A 11/1999 Maginot
5,980,455 A 11/1999 Daniel et al.
5,980,533 A 11/1999 Holman
5,980,548 A 11/1999 Evans et al.
5,984,956 A 11/1999 Tweden et al.
5,984,957 A 11/1999 Laptewicz, Jr. et al.
5,984,959 A 11/1999 Robertson et al.
5,984,964 A 11/1999 Roberts et al.
5,987,344 A 11/1999 West
5,989,276 A 11/1999 Houser et al.
5,989,287 A 11/1999 Yang et al.
5,993,469 A 11/1999 McKenzie et al.
5,993,481 A 11/1999 Marcade et al.
5,997,525 A 12/1999 March et al.
5,997,557 A 12/1999 Barbut et al.
5,997,563 A 12/1999 Kretzers
5,997,573 A 12/1999 Quijano et al.
5,999,678 A 12/1999 Murphy-Chutorian et al.
6,001,123 A 12/1999 Lau
6,001,126 A 12/1999 Nguyen-Thien-Nhon
6,004,261 A 12/1999 Sinofsky et al.
6,004,347 A 12/1999 McNamara et al.
6,004,348 A 12/1999 Banas et al.
6,007,543 A 12/1999 Ellis et al.
6,010,449 A 1/2000 Selmon et al.
6,010,522 A 1/2000 Barbut et al.
6,010,530 A 1/2000 Goicoechea
6,010,531 A 1/2000 Donlon et al.
6,012,457 A 1/2000 Lesh
6,013,854 A 1/2000 Moriuchi
6,015,431 A 1/2000 Thornton et al.
6,019,777 A 2/2000 MacKenzie
6,019,778 A 2/2000 Wilson et al.
6,022,370 A 2/2000 Tower
6,026,814 A 2/2000 LaFontaine et al.
6,027,476 A 2/2000 Sterman et al.
6,027,520 A 2/2000 Tsugita et al.
6,027,525 A 2/2000 Suh et al.
6,029,671 A 2/2000 Stevens et al.
6,029,672 A 2/2000 Vanney et al.
6,033,582 A 3/2000 Lee et al.
6,035,856 A 3/2000 LaFontaine et al.
6,036,677 A 3/2000 Javier, Jr. et al.
6,036,697 A 3/2000 DiCaprio
6,042,554 A 3/2000 Rosenman et al.
6,042,581 A 3/2000 Ryan et al.
6,042,589 A 3/2000 Marianne
6,042,598 A 3/2000 Tsugita et al.
6,042,607 A 3/2000 Williamson, IV et al.
6,045,565 A 4/2000 Ellis et al.
6,051,014 A 4/2000 Jang
6,051,104 A 4/2000 Oriaran et al.
6,053,924 A 4/2000 Hussein
6,053,942 A 4/2000 Eno et al.
6,056,743 A 5/2000 Ellis et al.
6,059,809 A 5/2000 Amor et al.
6,059,827 A 5/2000 Fenton, Jr.
6,066,160 A 5/2000 Colvin et al.
6,067,988 A 5/2000 Mueller
6,068,638 A 5/2000 Makower
6,071,292 A 6/2000 Makower et al.
6,074,416 A 6/2000 Berg et al.
6,074,417 A 6/2000 Peredo
6,074,418 A 6/2000 Buchanan et al.
6,076,529 A 6/2000 Vanney et al.
6,076,742 A 6/2000 Benary
6,077,297 A 6/2000 Robinson et al.
6,079,414 A 6/2000 Roth
6,080,163 A 6/2000 Hussein et al.
6,080,170 A 6/2000 Nash et al.
6,083,257 A 7/2000 Taylor et al.
6,091,042 A 7/2000 Benary
6,092,526 A 7/2000 LaFontaine et al.
6,092,529 A 7/2000 Cox
6,093,166 A 7/2000 Knudson et al.
6,093,177 A 7/2000 Javier, Jr. et al.
6,093,185 A 7/2000 Ellis et al.
6,093,203 A 7/2000 Uflacker
6,093,530 A 7/2000 McIlroy et al.
6,096,074 A 8/2000 Pedros
6,102,941 A 8/2000 Tweden et al.
6,102,944 A 8/2000 Huynh et al.
6,106,550 A 8/2000 Magovern et al.
6,110,191 A 8/2000 Dehdashtian et al.
6,110,198 A 8/2000 Fogarty et al.
6,110,201 A 8/2000 Quijano et al.
6,113,612 A 9/2000 Swanson et al.
6,113,630 A 9/2000 Vanney et al.
6,113,823 A 9/2000 Eno
6,117,169 A 9/2000 Moe
6,120,520 A 9/2000 Saadat et al.
6,120,534 A 9/2000 Ruiz
6,123,682 A 9/2000 Knudson et al.
6,123,723 A 9/2000 Konya et al.
6,125,852 A 10/2000 Stevens et al.
6,126,649 A 10/2000 Vantassel et al.
6,126,654 A 10/2000 Giba et al.
6,126,685 A 10/2000 Lenker et al.
6,126,686 A 10/2000 Badylak et al.
6,132,451 A 10/2000 Payne et al.
6,132,473 A 10/2000 Williams et al.
6,132,986 A 10/2000 Pathak et al.
6,139,510 A 10/2000 Palermo
6,139,541 A 10/2000 Vanney et al.
6,142,987 A 11/2000 Tsugita
6,143,021 A 11/2000 Staehle
6,143,987 A 11/2000 Makita
6,146,366 A 11/2000 Schachar
6,146,415 A 11/2000 Fitz
6,146,417 A 11/2000 Ischinger
6,152,937 A 11/2000 Peterson et al.
6,152,956 A 11/2000 Pierce
6,155,264 A 12/2000 Ressemann et al.
6,156,031 A 12/2000 Aita et al.
6,156,055 A 12/2000 Ravenscroft
6,156,531 A 12/2000 Pathak et al.
6,157,852 A 12/2000 Selmon et al.
6,159,225 A 12/2000 Makower
6,159,239 A 12/2000 Greenhalgh
6,162,208 A 12/2000 Hipps
6,162,245 A 12/2000 Jayaraman
6,165,185 A 12/2000 Shennib et al.
6,165,188 A 12/2000 Saadat et al.
6,165,200 A 12/2000 Tsugita et al.
6,165,209 A 12/2000 Patterson et al.
6,167,605 B1 1/2001 Morales
6,168,579 B1 1/2001 Tsugita
6,168,614 B1 1/2001 Andersen et al.
6,168,616 B1 1/2001 Brown, III
6,171,251 B1 1/2001 Mueller et al.

(56) References Cited

U.S. PATENT DOCUMENTS 6,171,327 B1 1/2001 Daniel et al.
6,171,335 B1 1/2001 Wheatley et al.
6,177,514 B1 1/2001 Pathak et al.
6,179,859 B1 1/2001 Bates et al.
6,182,664 B1 2/2001 Cosgrove
6,182,668 B1 2/2001 Tweden et al.
6,183,481 B1 2/2001 Lee et al.
6,186,972 B1 2/2001 Nelson et al.
6,187,016 B1 2/2001 Hedges et al.
6,190,353 B1 2/2001 Makower et al.
6,190,393 B1 2/2001 Bevier et al.
6,190,405 B1 2/2001 Culombo et al.
6,193,726 B1 2/2001 Vanney
6,193,734 B1 2/2001 Bolduc et al.
6,196,230 B1 3/2001 Hall et al.
6,197,050 B1 3/2001 Eno et al.
6,197,053 B1 3/2001 Cosgrove et al.
6,197,296 B1 3/2001 Davies et al.
6,197,324 B1 3/2001 Crittenden
6,200,311 B1 3/2001 Danek et al.
6,200,336 B1 3/2001 Pavcnik et al.
6,203,550 B1 3/2001 Olson
6,203,556 B1 3/2001 Evans et al.
6,206,888 B1 3/2001 Bicek et al.
6,206,911 B1 3/2001 Milo
6,210,408 B1 4/2001 Chandrasekaran et al.
6,210,957 B1 4/2001 Carpentier et al.
6,213,126 B1 4/2001 LaFontaine et al.
6,214,036 B1 4/2001 Letendre et al.
6,214,041 B1 4/2001 Tweden et al.
6,214,054 B1 4/2001 Cunanan et al.
6,214,055 B1 4/2001 Simionescu et al.
6,217,527 B1 4/2001 Selmon et al.
6,217,549 B1 4/2001 Selmon et al.
6,217,575 B1 4/2001 DeVore et al.
6,217,609 B1 4/2001 Haverkost
6,218,662 B1 4/2001 Tchakarov et al.
6,221,006 B1 4/2001 Dubrul et al.
6,221,049 B1 4/2001 Selmon et al.
6,221,091 B1 4/2001 Khosravi
6,221,096 B1 4/2001 Aiba et al.
6,221,100 B1 4/2001 Strecker
6,223,752 B1 5/2001 Vanney et al.
6,224,584 B1 5/2001 March et al.
6,231,544 B1 5/2001 Tsugita et al.
6,231,546 B1 5/2001 Milo et al.
6,231,551 B1 5/2001 Barbut
6,231,587 B1 5/2001 Makower
6,231,602 B1 5/2001 Carpentier et al.
6,235,000 B1 5/2001 Milo et al.
6,237,607 B1 5/2001 Vanney et al.
6,238,406 B1 5/2001 Ellis et al.
6,241,667 B1 6/2001 Vetter et al.
6,241,738 B1 6/2001 Dereume
6,241,741 B1 6/2001 Duhaylongsod et al.
6,241,757 B1 6/2001 An et al.
6,245,102 B1 6/2001 Jayaraman
6,245,103 B1 6/2001 Stinson
6,245,105 B1 6/2001 Nguyen et al.
6,248,112 B1 6/2001 Gambale et al.
6,248,116 B1 6/2001 Chevillon et al.
6,250,305 B1 6/2001 Tweden
6,251,079 B1 6/2001 Gambale et al.
6,251,104 B1 6/2001 Kesten et al.
6,251,116 B1 6/2001 Shennib et al.
6,251,135 B1 6/2001 Stinson et al.
6,251,418 B1 6/2001 Ahern et al.
6,253,768 B1 7/2001 Wilk
6,253,769 B1 7/2001 LaFontaine et al.
6,254,564 B1 7/2001 Wilk et al.
6,254,635 B1 7/2001 Schroeder et al.
6,254,636 B1 7/2001 Peredo
6,257,634 B1 7/2001 Wei
6,258,052 B1 7/2001 Milo
6,258,087 B1 7/2001 Edwards et al.
6,258,114 B1 7/2001 Konya et al.
6,258,115 B1 7/2001 Dubrul
6,258,119 B1 7/2001 Hussein et al.
6,258,120 B1 7/2001 McKenzie et al.
6,258,129 B1 7/2001 Dybdal et al.
6,258,150 B1 7/2001 Mackellar
6,261,304 B1 7/2001 Hall et al.
6,267,783 B1 7/2001 Letendre et al.
6,269,819 B1 8/2001 Oz et al.
6,270,513 B1 8/2001 Tsugita et al.
6,270,521 B1 8/2001 Fischell et al.
6,270,526 B1 8/2001 Cox
6,273,876 B1 8/2001 Klima et al.
6,273,895 B1 8/2001 Pinchuk et al.
6,276,661 B1 8/2001 Laird
6,277,555 B1 8/2001 Duran et al.
6,283,127 B1 9/2001 Sterman et al.
6,283,951 B1 9/2001 Flaherty et al.
6,283,983 B1 9/2001 Makower et al.
6,283,995 B1 9/2001 Moe et al.
6,285,903 B1 9/2001 Rosenthal et al.
6,287,317 B1 9/2001 Makower et al.
6,287,334 B1 9/2001 Moll et al.
6,287,338 B1 9/2001 Sarnowski et al.
6,287,339 B1 9/2001 Vazquez et al.
6,290,709 B1 9/2001 Ellis et al.
6,290,728 B1 9/2001 Phelps et al.
6,296,662 B1 10/2001 Caffey
6,299,637 B1 10/2001 Shaolian et al.
6,302,875 B1 10/2001 Makower et al.
6,302,892 B1 10/2001 Wilk
6,302,906 B1 10/2001 Goicoechea et al.
6,306,164 B1 10/2001 Kujawski
6,309,382 B1 10/2001 Garrison et al.
6,309,417 B1 10/2001 Spence et al.
6,311,693 B1 11/2001 Sterman et al.
6,312,465 B1 11/2001 Griffin et al.
6,319,281 B1 11/2001 Patel
6,322,548 B1 11/2001 Payne et al.
6,322,593 B1 11/2001 Pathak et al.
6,325,067 B1 12/2001 Sterman et al.
6,327,772 B1 12/2001 Zadno-Azizi et al.
6,330,884 B1 12/2001 Kim
6,331,189 B1 12/2001 Wolinsky et al.
6,334,873 B1 1/2002 Lane et al.
6,336,934 B1 1/2002 Gilson et al.
6,336,937 B1 1/2002 Vonesh et al.
6,338,735 B1 1/2002 Stevens
6,338,740 B1 1/2002 Carpentier
6,342,070 B1 1/2002 Nguyen-Thien-Nhon
6,344,044 B1 2/2002 Fulkerson et al.
6,346,074 B1 2/2002 Roth
6,346,116 B1 2/2002 Brooks et al.
6,348,063 B1 2/2002 Yassour et al.
6,350,248 B1 2/2002 Knudson et al.
6,350,277 B1 2/2002 Kocur
6,350,278 B1 2/2002 Lenker et al.
6,352,547 B1 3/2002 Brown et al.
6,352,554 B2 3/2002 De Paulis
6,352,708 B1 3/2002 Duran et al.
6,357,104 B1 3/2002 Myers
6,358,277 B1 3/2002 Duran
6,361,519 B1 3/2002 Knudson et al.
6,361,545 B1 3/2002 Macoviak et al.
6,363,938 B2 4/2002 Saadat et al.
6,363,939 B1 4/2002 Wilk
6,364,895 B1 4/2002 Greenhalgh
6,368,338 B1 4/2002 Konya et al.
6,371,970 B1 4/2002 Khosravi et al.
6,371,983 B1 4/2002 Lane
6,375,615 B1 4/2002 Flaherty et al.
6,378,221 B1 4/2002 Ekholm, Jr. et al.
6,379,319 B1 4/2002 Garibotto et al.
6,379,365 B1 4/2002 Diaz
6,379,372 B1 4/2002 Dehdashtian et al.
6,379,383 B1 4/2002 Palmaz et al.
6,379,740 B1 4/2002 Rinaldi et al.
6,380,457 B1 4/2002 Yurek et al.
6,383,193 B1 5/2002 Cathcart et al.

(56) References Cited

U.S. PATENT DOCUMENTS 6,387,119 B2 5/2002 Wolf et al.
6,387,122 B1 5/2002 Cragg
6,390,098 B1 5/2002 LaFontaine et al.
6,391,051 B2 5/2002 Sullivan, III et al.
6,391,538 B1 5/2002 Vyavahare et al.
6,395,208 B1 5/2002 Herweck et al.
6,398,807 B1 6/2002 Chouinard et al.
6,401,720 B1 6/2002 Stevens et al.
6,402,736 B1 6/2002 Brown et al.
6,402,740 B1 6/2002 Ellis et al.
6,406,488 B1 6/2002 Tweden et al.
6,406,491 B1 6/2002 Vanney
6,406,493 B1 6/2002 Tu et al.
6,409,697 B2 6/2002 Eno et al.
6,409,750 B1 6/2002 Hyodoh et al.
6,409,751 B1 6/2002 Hall et al.
6,409,755 B1 6/2002 Vrba
6,409,759 B1 6/2002 Peredo
6,413,275 B1 7/2002 Nguyen et al.
6,416,490 B1 7/2002 Ellis et al.
6,416,510 B1 7/2002 Altman et al.
6,423,089 B1 7/2002 Gingras et al.
6,425,916 B1 7/2002 Garrison et al.
6,432,119 B1 8/2002 Saadat
6,432,126 B1 8/2002 Gambale et al.
6,432,127 B1 8/2002 Kim et al.
6,432,132 B1 8/2002 Cottone et al.
6,440,164 B1 8/2002 DiMatteo et al.
6,443,158 B1 9/2002 LaFontaine et al.
6,447,522 B2 9/2002 Gambale et al.
6,447,539 B1 9/2002 Nelson et al.
6,451,025 B1 9/2002 Jervis
6,451,054 B1 9/2002 Stevens
6,454,760 B2 9/2002 Vanney
6,454,794 B1 9/2002 Knudson et al.
6,454,799 B1 9/2002 Schreck
6,458,092 B1 10/2002 Gambale et al.
6,458,140 B2 10/2002 Akin et al.
6,458,153 B1 10/2002 Bailey et al.
6,458,323 B1 10/2002 Boekstegers
6,461,382 B1 10/2002 Cao
6,464,709 B2 10/2002 Shennib et al.
6,468,303 B1 10/2002 Amplatz et al.
6,468,660 B2 10/2002 Ogle et al.
6,471,723 B1 10/2002 Ashworth et al.
6,475,169 B2 11/2002 Ferrera
6,475,226 B1 11/2002 Belef et al.
6,475,239 B1 11/2002 Campbell et al.
6,475,244 B2 11/2002 Herweck et al.
6,478,819 B2 11/2002 Moe
6,479,079 B1 11/2002 Pathak et al.
6,482,220 B1 11/2002 Mueller
6,482,228 B1 11/2002 Norred
6,485,501 B1 11/2002 Green
6,485,502 B2 11/2002 Don Michael et al.
6,485,513 B1 11/2002 Fan
6,485,524 B2 11/2002 Strecker
6,487,581 B1 11/2002 Spence et al.
6,488,704 B1 12/2002 Connelly et al.
6,491,689 B1 12/2002 Ellis et al.
6,491,707 B2 12/2002 Makower et al.
6,494,211 B1 12/2002 Boyd et al.
6,494,897 B2 12/2002 Sterman et al.
6,494,909 B2 12/2002 Greenhalgh
6,503,272 B2 1/2003 Duerig et al.
6,508,496 B1 1/2003 Huang
6,508,803 B1 1/2003 Horikawa et al.
6,508,825 B1 1/2003 Selmon et al.
6,508,833 B2 1/2003 Pavcnik et al.
6,509,145 B1 1/2003 Torrianni
6,511,458 B2 1/2003 Milo et al.
6,511,491 B2 1/2003 Grudem et al.
6,514,217 B1 2/2003 Selmon et al.
6,514,271 B2 2/2003 Evans et al.
6,517,527 B2 2/2003 Gambale et al.
6,517,558 B2 2/2003 Gittings et al.
6,517,573 B1 2/2003 Pollock et al.
6,521,179 B1 2/2003 Girardot et al.
6,524,323 B1 2/2003 Nash et al.
6,524,335 B1 2/2003 Hartley et al.
6,527,800 B1 3/2003 McGuckin, Jr. et al.
6,530,949 B2 3/2003 Konya et al.
6,530,952 B2 3/2003 Vesely
6,533,807 B2 3/2003 Wolinsky et al.
6,537,297 B2 3/2003 Tsugita et al.
6,537,310 B1 3/2003 Palmaz et al.
6,540,768 B1 4/2003 Diaz et al.
6,540,782 B1 4/2003 Snyders
6,544,230 B1 4/2003 Flaherty et al.
6,547,827 B2 4/2003 Carpentier et al.
6,551,303 B1 4/2003 Van Tassel et al.
6,558,318 B1 5/2003 Daniel et al.
6,558,417 B2 5/2003 Peredo
6,558,418 B2 5/2003 Carpentier et al.
6,558,429 B2 5/2003 Taylor
6,559,132 B1 5/2003 Holmer
6,561,998 B1 5/2003 Roth et al.
6,562,031 B2 5/2003 Chandrasekaran et al.
6,562,058 B2 5/2003 Seguin et al.
6,562,063 B1 5/2003 Euteneuer et al.
6,562,069 B2 5/2003 Cai et al.
6,564,805 B2 5/2003 Garrison et al.
6,565,528 B1 5/2003 Mueller
6,565,594 B1 5/2003 Herweck et al.
6,569,145 B1 5/2003 Shmulewitz et al.
6,569,147 B1 5/2003 Evans et al.
6,569,196 B1 5/2003 Vesely
6,572,593 B1 * 6/2003 Daum ................ A61B 17/3417 604/164.13
6,572,642 B2 6/2003 Rinaldi et al.
6,572,643 B1 6/2003 Gharibadeh
6,572,652 B2 6/2003 Shaknovich
6,575,168 B2 6/2003 LaFontaine et al.
6,579,311 B1 6/2003 Makower
6,582,444 B2 6/2003 Wilk
6,582,460 B1 6/2003 Cryer
6,582,462 B1 6/2003 Andersen et al.
6,585,756 B1 7/2003 Strecker
6,585,758 B1 7/2003 Chouinard et al.
6,585,766 B1 7/2003 Huynh et al.
6,589,279 B1 7/2003 Anderson et al.
6,592,546 B1 7/2003 Barbut et al.
6,592,614 B2 7/2003 Lenker et al.
6,599,304 B1 7/2003 Selmon et al.
6,600,803 B2 7/2003 Bruder et al.
6,605,053 B1 8/2003 Kamm et al.
6,605,112 B1 8/2003 Moll et al.
6,605,113 B2 8/2003 Wilk
6,608,040 B1 8/2003 Lin et al.
6,610,077 B1 8/2003 Hancock et al.
6,610,085 B1 8/2003 Lazarus
6,610,100 B2 8/2003 Phelps et al.
6,613,069 B2 9/2003 Boyd et al.
6,613,077 B2 9/2003 Gilligan et al.
6,613,079 B1 9/2003 Wolinsky et al.
6,613,081 B2 9/2003 Kim et al.
6,613,086 B1 9/2003 Moe et al.
6,616,675 B1 9/2003 Evard et al.
6,616,682 B2 9/2003 Joergensen et al.
6,622,604 B1 9/2003 Chouinard et al.
6,623,491 B2 9/2003 Thompson
6,623,518 B2 9/2003 Thompson et al.
6,623,521 B2 9/2003 Steinke et al.
6,626,938 B1 9/2003 Butaric et al.
6,626,939 B1 9/2003 Burnside et al.
6,632,241 B1 10/2003 Hancock et al.
6,632,243 B1 10/2003 Zadno-Azizi et al.
6,632,470 B2 10/2003 Morra et al.
6,635,068 B1 10/2003 Dubrul et al.
6,635,079 B2 10/2003 Unsworth et al.
6,635,080 B1 10/2003 Lauterjung et al.
6,635,085 B1 10/2003 Caffey et al.
6,638,237 B1 10/2003 Guiles et al.
6,638,247 B1 10/2003 Selmon et al.

(56) References Cited

U.S. PATENT DOCUMENTS

| | | | |
|---|---|---|---|
| 6,638,293 | B1 | 10/2003 | Makower et al. |
| 6,641,610 | B2 | 11/2003 | Wolf et al. |
| 6,651,670 | B2 | 11/2003 | Rapacki et al. |
| 6,651,672 | B2 | 11/2003 | Roth |
| 6,652,540 | B1 | 11/2003 | Cole et al. |
| 6,652,546 | B1 | 11/2003 | Nash et al. |
| 6,652,555 | B1 | 11/2003 | Vantassel et al. |
| 6,652,571 | B1 | 11/2003 | White et al. |
| 6,652,578 | B2 | 11/2003 | Bailey et al. |
| 6,655,386 | B1 | 12/2003 | Makower et al. |
| 6,656,213 | B2 | 12/2003 | Solem |
| 6,660,003 | B1 | 12/2003 | DeVore et al. |
| 6,660,024 | B1 | 12/2003 | Flaherty et al. |
| 6,663,588 | B2 | 12/2003 | DuBois et al. |
| 6,663,663 | B2 | 12/2003 | Kim et al. |
| 6,663,667 | B2 | 12/2003 | Dehdashtian et al. |
| 6,666,863 | B2 | 12/2003 | Wentzel et al. |
| 6,669,709 | B1 | 12/2003 | Cohn et al. |
| 6,669,724 | B2 | 12/2003 | Park et al. |
| 6,673,089 | B1 | 1/2004 | Yassour et al. |
| 6,673,101 | B1 | 1/2004 | Fitzgerald et al. |
| 6,673,106 | B2 | 1/2004 | Mitelberg et al. |
| 6,673,109 | B2 | 1/2004 | Cox |
| 6,676,668 | B2 | 1/2004 | Mercereau et al. |
| 6,676,692 | B2 | 1/2004 | Rabkin et al. |
| 6,676,693 | B1 | 1/2004 | Belding et al. |
| 6,676,698 | B2 | 1/2004 | McGuckin, Jr. et al. |
| 6,679,268 | B2 | 1/2004 | Stevens et al. |
| 6,682,543 | B2 | 1/2004 | Barbut et al. |
| 6,682,558 | B2 | 1/2004 | Tu et al. |
| 6,682,559 | B2 | 1/2004 | Myers et al. |
| 6,685,648 | B2 | 2/2004 | Flaherty et al. |
| 6,685,739 | B2 | 2/2004 | DiMatteo et al. |
| 6,689,144 | B2 | 2/2004 | Gerberding |
| 6,689,164 | B1 | 2/2004 | Seguin |
| 6,692,512 | B2 | 2/2004 | Jang |
| 6,692,513 | B2 | 2/2004 | Streeter et al. |
| 6,694,983 | B2 | 2/2004 | Wolf et al. |
| 6,695,864 | B2 | 2/2004 | Macoviak et al. |
| 6,695,865 | B2 | 2/2004 | Boyle et al. |
| 6,695,875 | B2 | 2/2004 | Stelter et al. |
| 6,695,878 | B2 | 2/2004 | McGuckin, Jr. et al. |
| 6,699,274 | B2 | 3/2004 | Stinson |
| 6,701,932 | B2 | 3/2004 | Knudson et al. |
| 6,702,851 | B1 | 3/2004 | Chinn et al. |
| 6,709,425 | B2 | 3/2004 | Gambale et al. |
| 6,709,444 | B1 | 3/2004 | Makower |
| 6,712,842 | B1 | 3/2004 | Gifford, III et al. |
| 6,712,843 | B2 | 3/2004 | Elliott |
| 6,714,841 | B1 | 3/2004 | Wright et al. |
| 6,714,842 | B1 | 3/2004 | Ito |
| 6,719,770 | B2 | 4/2004 | Laufer et al. |
| 6,719,787 | B2 | 4/2004 | Cox |
| 6,719,788 | B2 | 4/2004 | Cox |
| 6,719,789 | B2 | 4/2004 | Cox |
| 6,723,116 | B2 | 4/2004 | Taheri |
| 6,723,122 | B2 | 4/2004 | Yang et al. |
| 6,726,677 | B1 | 4/2004 | Flaherty et al. |
| 6,729,356 | B1 | 5/2004 | Baker et al. |
| 6,730,118 | B2 | 5/2004 | Spenser et al. |
| 6,730,121 | B2 | 5/2004 | Ortiz et al. |
| 6,730,377 | B2 | 5/2004 | Wang |
| 6,733,513 | B2 | 5/2004 | Boyle et al. |
| 6,733,525 | B2 | 5/2004 | Yang et al. |
| 6,736,827 | B1 | 5/2004 | McAndrew et al. |
| 6,736,839 | B2 | 5/2004 | Cummings |
| 6,736,845 | B2 | 5/2004 | Marquez et al. |
| 6,736,846 | B2 | 5/2004 | Cox |
| 6,743,252 | B1 | 6/2004 | Bates et al. |
| 6,746,464 | B1 | 6/2004 | Makower |
| 6,752,828 | B2 | 6/2004 | Thornton |
| 6,755,854 | B2 | 6/2004 | Gillick et al. |
| 6,755,855 | B2 | 6/2004 | Yurek et al. |
| 6,758,855 | B2 | 7/2004 | Fulton, III et al. |
| 6,764,503 | B1 | 7/2004 | Ishimaru |
| 6,764,509 | B2 | 7/2004 | Chinn et al. |
| 6,767,345 | B2 | 7/2004 | St. Germain et al. |
| 6,767,362 | B2 | 7/2004 | Schreck |
| 6,769,434 | B2 | 8/2004 | Liddicoat et al. |
| 6,773,454 | B2 | 8/2004 | Wholey et al. |
| 6,773,455 | B2 | 8/2004 | Allen et al. |
| 6,773,456 | B1 | 8/2004 | Gordon et al. |
| 6,774,278 | B1 | 8/2004 | Ragheb et al. |
| 6,776,791 | B1 | 8/2004 | Stallings et al. |
| 6,786,925 | B1 | 9/2004 | Schoon et al. |
| 6,786,929 | B2 | 9/2004 | Gambale et al. |
| 6,790,229 | B1 | 9/2004 | Berreklouw |
| 6,790,230 | B2 | 9/2004 | Beyersdorf et al. |
| 6,790,237 | B2 | 9/2004 | Stinson |
| 6,792,979 | B2 | 9/2004 | Konya et al. |
| 6,797,000 | B2 | 9/2004 | Simpson et al. |
| 6,797,002 | B2 | 9/2004 | Spence et al. |
| 6,802,319 | B2 | 10/2004 | Stevens et al. |
| 6,802,858 | B2 | 10/2004 | Gambale et al. |
| 6,805,711 | B2 | 10/2004 | Quijano et al. |
| 6,808,498 | B2 | 10/2004 | Laroya et al. |
| 6,808,504 | B2 | 10/2004 | Schorgl et al. |
| 6,808,529 | B2 | 10/2004 | Fulkerson |
| 6,814,746 | B2 | 11/2004 | Thompson et al. |
| 6,814,754 | B2 | 11/2004 | Greenhalgh |
| 6,820,676 | B2 | 11/2004 | Palmaz et al. |
| 6,821,211 | B2 | 11/2004 | Otten et al. |
| 6,821,297 | B2 | 11/2004 | Snyders |
| 6,824,041 | B2 | 11/2004 | Grieder et al. |
| 6,824,970 | B2 | 11/2004 | Vyavahare et al. |
| 6,830,568 | B1 | 12/2004 | Kesten et al. |
| 6,830,575 | B2 | 12/2004 | Stenzel et al. |
| 6,830,584 | B1 | 12/2004 | Seguin |
| 6,830,585 | B1 | 12/2004 | Artof et al. |
| 6,830,586 | B2 | 12/2004 | Quijano et al. |
| 6,837,901 | B2 | 1/2005 | Rabkin et al. |
| 6,837,902 | B2 | 1/2005 | Nguyen et al. |
| 6,840,957 | B2 | 1/2005 | DiMatteo et al. |
| 6,843,802 | B1 | 1/2005 | Villalobos et al. |
| 6,846,325 | B2 | 1/2005 | Liddicoat |
| 6,849,084 | B2 | 2/2005 | Rabkin et al. |
| 6,849,085 | B2 | 2/2005 | Marton |
| 6,854,467 | B2 | 2/2005 | Boekstegers |
| 6,860,898 | B2 | 3/2005 | Stack et al. |
| 6,861,211 | B2 | 3/2005 | Levy et al. |
| 6,863,668 | B2 | 3/2005 | Gillespie et al. |
| 6,863,684 | B2 | 3/2005 | Kim et al. |
| 6,863,688 | B2 | 3/2005 | Ralph et al. |
| 6,866,650 | B2 | 3/2005 | Stevens et al. |
| 6,866,669 | B2 | 3/2005 | Buzzard et al. |
| 6,872,223 | B2 | 3/2005 | Roberts et al. |
| 6,872,226 | B2 | 3/2005 | Cali et al. |
| 6,875,231 | B2 | 4/2005 | Anduiza et al. |
| 6,881,199 | B2 | 4/2005 | Wilk et al. |
| 6,881,220 | B2 | 4/2005 | Edwin et al. |
| 6,883,522 | B2 | 4/2005 | Spence et al. |
| 6,887,266 | B2 | 5/2005 | Williams et al. |
| 6,890,330 | B2 | 5/2005 | Streeter et al. |
| 6,890,340 | B2 | 5/2005 | Duane |
| 6,893,459 | B1 | 5/2005 | Macoviak |
| 6,893,460 | B2 | 5/2005 | Spenser et al. |
| 6,896,690 | B1 | 5/2005 | Lambrecht et al. |
| 6,899,704 | B2 | 5/2005 | Sterman et al. |
| 6,905,743 | B1 | 6/2005 | Chen et al. |
| 6,908,481 | B2 | 6/2005 | Cribier |
| 6,911,036 | B2 | 6/2005 | Douk et al. |
| 6,911,040 | B2 | 6/2005 | Johnson et al. |
| 6,911,043 | B2 | 6/2005 | Myers et al. |
| 6,913,021 | B2 | 7/2005 | Knudson et al. |
| 6,913,600 | B2 | 7/2005 | Valley et al. |
| 6,916,304 | B2 | 7/2005 | Eno et al. |
| 6,920,674 | B2 | 7/2005 | Thornton |
| 6,920,732 | B2 | 7/2005 | Mårtensson |
| 6,926,690 | B2 | 8/2005 | Renati |
| 6,926,732 | B2 | 8/2005 | Derus et al. |
| 6,929,009 | B2 | 8/2005 | Makower et al. |
| 6,929,011 | B2 | 8/2005 | Knudson et al. |
| 6,929,653 | B2 | 8/2005 | Strecter |
| 6,936,058 | B2 | 8/2005 | Forde et al. |

(56) References Cited

U.S. PATENT DOCUMENTS

| | | | |
|---|---|---|---|
| 6,936,066 | B2 | 8/2005 | Palmaz et al. |
| 6,936,067 | B2 | 8/2005 | Buchanan |
| 6,939,352 | B2 | 9/2005 | Buzzard et al. |
| 6,939,359 | B2 | 9/2005 | Tu et al. |
| 6,939,365 | B1 | 9/2005 | Fogarty et al. |
| 6,939,370 | B2 | 9/2005 | Hartley et al. |
| 6,942,682 | B2 | 9/2005 | Vrba et al. |
| 6,945,949 | B2 | 9/2005 | Wilk |
| 6,945,997 | B2 | 9/2005 | Huynh et al. |
| 6,949,080 | B2 | 9/2005 | Wolf et al. |
| 6,949,118 | B2 | 9/2005 | Kohler et al. |
| 6,951,571 | B1 | 10/2005 | Srivastava |
| 6,953,332 | B1 | 10/2005 | Kurk et al. |
| 6,953,481 | B2 | 10/2005 | Phelps et al. |
| 6,955,175 | B2 | 10/2005 | Stevens et al. |
| 6,955,681 | B2 | 10/2005 | Evans et al. |
| 6,964,652 | B2 | 11/2005 | Guiles et al. |
| 6,964,673 | B2 | 11/2005 | Tsugita et al. |
| 6,964,676 | B1 | 11/2005 | Gerberding et al. |
| 6,969,395 | B2 | 11/2005 | Eskuri |
| 6,972,025 | B2 | 12/2005 | Wasdyke |
| 6,972,029 | B2 | 12/2005 | Mayrhofer et al. |
| 6,974,464 | B2 | 12/2005 | Quijano et al. |
| 6,974,474 | B2 | 12/2005 | Pavcnik et al. |
| 6,974,476 | B2 | 12/2005 | McGuckin, Jr. et al. |
| 6,976,990 | B2 | 12/2005 | Mowry |
| 6,979,350 | B2 | 12/2005 | Moll et al. |
| 6,984,242 | B2 | 1/2006 | Campbell et al. |
| 6,984,244 | B2 | 1/2006 | Perez et al. |
| 6,986,742 | B2 | 1/2006 | Hart et al. |
| 6,986,784 | B1 | 1/2006 | Weiser et al. |
| 6,988,949 | B2 | 1/2006 | Wang |
| 6,989,027 | B2 | 1/2006 | Allen et al. |
| 6,989,028 | B2 | 1/2006 | Lashinski et al. |
| 6,991,649 | B2 | 1/2006 | Sievers |
| 7,001,425 | B2 | 2/2006 | McCullagh et al. |
| 7,004,176 | B2 | 2/2006 | Lau |
| 7,008,397 | B2 | 3/2006 | Tweden et al. |
| 7,011,095 | B2 | 3/2006 | Wolf et al. |
| 7,011,681 | B2 | 3/2006 | Vesely |
| 7,014,655 | B2 | 3/2006 | Barbarash et al. |
| 7,018,401 | B1 | 3/2006 | Hyodoh et al. |
| 7,018,406 | B2 | 3/2006 | Seguin et al. |
| 7,018,408 | B2 | 3/2006 | Bailey et al. |
| 7,022,134 | B1 | 4/2006 | Quijano et al. |
| 7,025,773 | B2 | 4/2006 | Gittings et al. |
| 7,025,780 | B2 | 4/2006 | Gabbay |
| 7,025,791 | B2 | 4/2006 | Levine et al. |
| 7,028,692 | B2 | 4/2006 | Sterman et al. |
| 7,037,331 | B2 | 5/2006 | Mitelberg et al. |
| 7,037,333 | B2 | 5/2006 | Myers et al. |
| 7,041,128 | B2 | 5/2006 | McGuckin, Jr. et al. |
| 7,041,132 | B2 | 5/2006 | Quijano et al. |
| 7,044,966 | B2 | 5/2006 | Svanidze et al. |
| 7,048,014 | B2 | 5/2006 | Hyodoh et al. |
| 7,048,757 | B2 | 5/2006 | Shaknovich |
| 7,050,276 | B2 | 5/2006 | Nishiyama |
| 7,074,236 | B2 | 7/2006 | Rabkin et al. |
| 7,078,163 | B2 | 7/2006 | Torrianni |
| 7,081,132 | B2 | 7/2006 | Cook et al. |
| 7,097,658 | B2 | 8/2006 | Oktay |
| 7,097,659 | B2 | 8/2006 | Woolfson et al. |
| 7,101,396 | B2 | 9/2006 | Artof et al. |
| 7,105,016 | B2 | 9/2006 | Shiu et al. |
| 7,108,715 | B2 | 9/2006 | Lawrence-Brown et al. |
| 7,115,141 | B2 | 10/2006 | Menz et al. |
| 7,118,585 | B2 | 10/2006 | Addis |
| 7,122,020 | B2 | 10/2006 | Mogul |
| 7,125,418 | B2 | 10/2006 | Duran et al. |
| 7,128,759 | B2 | 10/2006 | Osborne et al. |
| 7,137,184 | B2 | 11/2006 | Schreck |
| 7,141,063 | B2 | 11/2006 | White et al. |
| 7,141,064 | B2 | 11/2006 | Scott et al. |
| 7,143,312 | B1 | 11/2006 | Wang et al. |
| 7,147,662 | B1 | 12/2006 | Pollock et al. |
| 7,147,663 | B1 | 12/2006 | Berg et al. |
| 7,153,324 | B2 | 12/2006 | Case et al. |
| 7,160,319 | B2 | 1/2007 | Chouinard et al. |
| 7,163,556 | B2 | 1/2007 | Xie et al. |
| 7,166,097 | B2 | 1/2007 | Barbut |
| 7,175,652 | B2 | 2/2007 | Cook et al. |
| 7,175,653 | B2 | 2/2007 | Gaber |
| 7,175,654 | B2 | 2/2007 | Bonsignore et al. |
| 7,175,656 | B2 | 2/2007 | Khairkhahan |
| 7,179,290 | B2 | 2/2007 | Cao |
| 7,186,265 | B2 | 3/2007 | Sharkawy et al. |
| 7,189,258 | B2 | 3/2007 | Johnson et al. |
| 7,189,259 | B2 | 3/2007 | Simionescu et al. |
| 7,191,018 | B2 | 3/2007 | Gielen et al. |
| 7,191,406 | B1 | 3/2007 | Barber et al. |
| 7,195,641 | B2 | 3/2007 | Palmaz et al. |
| 7,198,646 | B2 | 4/2007 | Figulla et al. |
| 7,201,761 | B2 | 4/2007 | Woolfson et al. |
| 7,201,772 | B2 | 4/2007 | Schwammenthal et al. |
| 7,214,344 | B2 | 5/2007 | Carpentier et al. |
| 7,217,287 | B2 | 5/2007 | Wilson et al. |
| 7,235,092 | B2 | 6/2007 | Banas et al. |
| 7,235,093 | B2 | 6/2007 | Gregorich |
| 7,238,200 | B2 | 7/2007 | Lee et al. |
| 7,241,257 | B1 | 7/2007 | Ainsworth et al. |
| 7,252,682 | B2 | 8/2007 | Seguin |
| 7,258,696 | B2 | 8/2007 | Rabkin et al. |
| 7,258,891 | B2 | 8/2007 | Pacetti et al. |
| 7,261,732 | B2 | 8/2007 | Justino |
| 7,264,632 | B2 | 9/2007 | Wright et al. |
| 7,267,686 | B2 | 9/2007 | DiMatteo et al. |
| 7,276,078 | B2 | 10/2007 | Spenser et al. |
| 7,276,084 | B2 | 10/2007 | Yang et al. |
| 7,285,130 | B2 | 10/2007 | Austin |
| 7,297,150 | B2 | 11/2007 | Cartledge et al. |
| 7,300,457 | B2 | 11/2007 | Palmaz |
| 7,300,463 | B2 | 11/2007 | Liddicoat |
| 7,311,730 | B2 | 12/2007 | Gabbay |
| 7,314,449 | B2 | 1/2008 | Pfeiffer et al. |
| 7,314,485 | B2 | 1/2008 | Mathis |
| 7,314,880 | B2 | 1/2008 | Chang et al. |
| 7,316,706 | B2 | 1/2008 | Bloom et al. |
| 7,316,712 | B2 | 1/2008 | Peredo |
| 7,317,005 | B2 | 1/2008 | Hoekstra et al. |
| 7,317,942 | B2 | 1/2008 | Brown |
| 7,317,950 | B2 | 1/2008 | Lee |
| 7,318,278 | B2 | 1/2008 | Zhang et al. |
| 7,318,998 | B2 | 1/2008 | Goldstein et al. |
| 7,319,096 | B2 | 1/2008 | Malm et al. |
| 7,320,692 | B1 | 1/2008 | Bender et al. |
| 7,320,704 | B2 | 1/2008 | Lashinski et al. |
| 7,320,705 | B2 | 1/2008 | Quintessenza |
| 7,320,706 | B2 | 1/2008 | Al-Najjar |
| 7,322,932 | B2 | 1/2008 | Xie et al. |
| 7,323,006 | B2 | 1/2008 | Andreas et al. |
| 7,323,066 | B1 | 1/2008 | Budron |
| 7,326,174 | B2 | 2/2008 | Cox et al. |
| 7,326,219 | B2 | 2/2008 | Mowry et al. |
| 7,326,236 | B2 | 2/2008 | Andreas et al. |
| 7,327,862 | B2 | 2/2008 | Murphy et al. |
| 7,329,278 | B2 | 2/2008 | Seguin et al. |
| 7,329,279 | B2 | 2/2008 | Haug et al. |
| 7,329,280 | B2 | 2/2008 | Bolling et al. |
| 7,329,777 | B2 | 2/2008 | Harter et al. |
| 7,331,991 | B2 | 2/2008 | Kheradvar et al. |
| 7,331,993 | B2 | 2/2008 | White |
| 7,333,643 | B2 | 2/2008 | Murphy et al. |
| 7,335,158 | B2 | 2/2008 | Taylor |
| 7,335,213 | B1 | 2/2008 | Hyde et al. |
| 7,335,218 | B2 | 2/2008 | Wilson et al. |
| 7,335,490 | B2 | 2/2008 | Van Gilst et al. |
| 7,338,484 | B2 | 3/2008 | Schoon et al. |
| 7,338,520 | B2 | 3/2008 | Bailey et al. |
| 7,361,189 | B2 | 4/2008 | Case et al. |
| 7,361,190 | B2 | 4/2008 | Shaoulian et al. |
| 7,364,588 | B2 | 4/2008 | Mathis et al. |
| 7,371,258 | B2 | 5/2008 | Woo et al. |
| 7,374,560 | B2 | 5/2008 | Ressemann et al. |
| 7,374,571 | B2 | 5/2008 | Pease et al. |

(56) References Cited

U.S. PATENT DOCUMENTS 7,377,895 B2 5/2008 Spence et al.
7,377,938 B2 5/2008 Sarac et al.
7,377,940 B2 5/2008 Ryan et al.
7,381,210 B2 6/2008 Zarbatany et al.
7,381,216 B2 6/2008 Buzzard et al.
7,381,218 B2 6/2008 Schreck
7,381,219 B2 6/2008 Salahieh et al.
7,381,220 B2 6/2008 Macoviak et al.
7,384,411 B1 6/2008 Condado
7,387,640 B2 6/2008 Cummings
7,389,874 B2 6/2008 Quest et al.
7,390,325 B2 6/2008 Wang et al.
7,393,358 B2 7/2008 Malewicz
7,393,360 B2 7/2008 Spenser et al.
7,396,364 B2 7/2008 Moaddeb et al.
7,399,315 B2 7/2008 Iobbi
7,402,171 B2 7/2008 Osborne et al.
7,404,792 B2 7/2008 Spence et al.
7,404,793 B2 7/2008 Lau et al.
7,405,259 B2 7/2008 Frye et al.
7,410,499 B2 8/2008 Bicer
7,412,274 B2 8/2008 Mejia
7,412,290 B2 8/2008 Janke et al.
7,415,861 B2 8/2008 Sokel
7,416,530 B2 8/2008 Turner et al.
7,422,603 B2 9/2008 Lane
7,422,606 B2 9/2008 Ung-Chhun et al.
7,423,032 B2 9/2008 Ozaki et al.
7,426,413 B2 9/2008 Balczewski et al.
7,427,279 B2 9/2008 Frazier et al.
7,427,287 B2 9/2008 Turovskiy et al.
7,427,291 B2 9/2008 Liddicoat et al.
7,429,269 B2 9/2008 Schwammenthal et al.
7,430,448 B1 9/2008 Zimmer et al.
7,430,484 B2 9/2008 Ohara
7,431,691 B1 10/2008 Wilk
7,431,733 B2 10/2008 Knight
7,435,059 B2 10/2008 Smith et al.
7,435,257 B2 10/2008 Lashinski et al.
7,442,204 B2 10/2008 Schwammenthal et al.
RE40,570 E 11/2008 Carpentier et al.
7,445,630 B2 11/2008 Lashinski et al.
7,445,631 B2 11/2008 Salahieh et al.
7,445,632 B2 11/2008 McGuckin, Jr. et al.
7,452,371 B2 11/2008 Pavcnik et al.
7,455,689 B2 11/2008 Johnson
7,462,156 B2 12/2008 Mitrev
7,462,184 B2 12/2008 Worley et al.
7,462,191 B2 12/2008 Spenser et al.
7,468,050 B1 12/2008 Kantrowitz
7,470,284 B2 12/2008 Lambrecht et al.
7,470,285 B2 12/2008 Nugent et al.
7,473,271 B2 1/2009 Gunderson
7,473,275 B2 1/2009 Marquez
7,473,417 B2 1/2009 Zeltinger et al.
7,476,196 B2 1/2009 Spence et al.
7,476,199 B2 1/2009 Spence et al.
7,476,200 B2 1/2009 Tal
7,476,244 B2 1/2009 Buzzard et al.
7,481,838 B2 1/2009 Carpentier et al.
7,485,088 B2 2/2009 Murphy et al.
7,485,143 B2 2/2009 Webler et al.
7,488,346 B2 2/2009 Navia
7,491,232 B2 2/2009 Bolduc et al.
7,493,869 B1 2/2009 Foster et al.
7,497,824 B2 3/2009 Taylor
7,500,949 B2 3/2009 Gottlieb et al.
7,500,989 B2 3/2009 Solem et al.
7,503,929 B2 3/2009 Johnson et al.
7,503,930 B2 3/2009 Sharkawy et al.
7,507,199 B2 3/2009 Wang et al.
7,510,572 B2 3/2009 Gabbay
7,510,574 B2 3/2009 Le et al.
7,510,575 B2 3/2009 Spenser et al.
7,510,577 B2 3/2009 Moaddeb et al.
7,513,863 B2 4/2009 Bolling et al.
7,513,909 B2 4/2009 Lane et al.
7,522,950 B2 4/2009 Fuimaono et al.
7,524,330 B2 4/2009 Berreklouw
7,530,253 B2 5/2009 Spenser et al.
7,530,995 B2 5/2009 Quijano et al.
7,534,261 B2 5/2009 Friedman
7,544,206 B2 6/2009 Cohn
7,547,322 B2 6/2009 Sarac et al.
7,553,324 B2 6/2009 Andreas et al.
7,556,386 B2 7/2009 Smith
7,556,646 B2 7/2009 Yang et al.
7,569,071 B2 8/2009 Haverkost et al.
7,578,828 B2 8/2009 Gittings et al.
7,585,321 B2 9/2009 Cribier
7,591,848 B2 9/2009 Allen
7,594,974 B2 9/2009 Cali et al.
7,601,159 B2 10/2009 Ewers et al.
7,601,195 B2 10/2009 Ichikawa
7,608,099 B2 10/2009 Johnson et al.
7,611,534 B2 11/2009 Kapadia et al.
7,618,446 B2 11/2009 Andersen et al.
7,622,276 B2 11/2009 Cunanan et al.
7,625,403 B2 12/2009 Krivoruchko
7,628,802 B2 12/2009 White et al.
7,628,803 B2 12/2009 Pavcnik et al.
7,632,296 B2 12/2009 Malewicz
7,632,298 B2 12/2009 Hijlkema et al.
7,635,386 B1 12/2009 Gammie
7,641,687 B2 1/2010 Chinn et al.
7,651,519 B2 1/2010 Dittman
7,655,034 B2 2/2010 Mitchell et al.
7,674,282 B2 3/2010 Wu et al.
7,682,390 B2 3/2010 Seguin
7,704,222 B2 4/2010 Wilk et al.
7,704,277 B2 4/2010 Zakay et al.
7,708,775 B2 5/2010 Rowe et al.
7,712,606 B2 5/2010 Salahieh et al.
7,715,903 B2 5/2010 Hartley et al.
7,717,955 B2 5/2010 Lane et al.
7,722,638 B2 5/2010 Deyette, Jr. et al.
7,722,662 B2 5/2010 Steinke et al.
7,722,666 B2 5/2010 Lafontaine
7,722,671 B1 5/2010 Carlyle et al.
7,731,742 B2 6/2010 Schlick et al.
7,735,493 B2 6/2010 Van Der Burg et al.
7,736,327 B2 6/2010 Wilk et al.
7,736,388 B2 6/2010 Goldfarb et al.
7,743,481 B2 6/2010 Lafont et al.
7,748,389 B2 7/2010 Salahieh et al.
7,758,625 B2 7/2010 Wu et al.
7,763,065 B2 7/2010 Schmid et al.
7,771,463 B2 8/2010 Ton et al.
7,771,467 B2 8/2010 Svensson
7,776,083 B2 8/2010 Vesely
7,780,725 B2 8/2010 Haug et al.
7,780,726 B2 8/2010 Seguin
7,785,360 B2 8/2010 Freitag
7,794,487 B2 9/2010 Majercak et al.
7,799,046 B2 9/2010 White et al.
7,799,065 B2 9/2010 Pappas
7,803,185 B2 9/2010 Gabbay
7,806,919 B2 10/2010 Bloom et al.
7,823,267 B2 11/2010 Bolduc
7,824,442 B2 11/2010 Salahieh et al.
7,824,443 B2 11/2010 Salahieh et al.
7,833,262 B2 11/2010 McGuckin, Jr. et al.
7,837,727 B2 11/2010 Goetz et al.
7,846,203 B2 12/2010 Cribier
7,846,204 B2 12/2010 Letac et al.
7,854,758 B2 12/2010 Taheri
7,857,845 B2 12/2010 Stacchino et al.
7,862,602 B2 1/2011 Licata et al.
7,867,274 B2 1/2011 Hill et al.
7,887,583 B2 2/2011 Macoviak
7,892,276 B2 2/2011 Stocker et al.
7,892,292 B2 2/2011 Stack et al.
7,896,913 B2 3/2011 Damm et al.
7,896,915 B2 3/2011 Guyenot et al.

(56) References Cited

U.S. PATENT DOCUMENTS 7,914,569 B2 3/2011 Nguyen et al.
7,914,574 B2 3/2011 Schmid et al.
7,914,575 B2 3/2011 Guyenot et al.
7,918,880 B2 4/2011 Austin
7,927,363 B2 4/2011 Perouse
7,938,851 B2 5/2011 Olson et al.
7,947,071 B2 5/2011 Schmid et al.
7,947,075 B2 5/2011 Goetz et al.
7,951,189 B2 5/2011 Haverkost et al.
7,959,666 B2 6/2011 Salahieh et al.
7,959,672 B2 6/2011 Salahieh et al.
7,967,853 B2 6/2011 Eidenschink et al.
7,972,359 B2 7/2011 Kreidler
7,972,376 B1 7/2011 Dove et al.
7,972,378 B2 7/2011 Tabor et al.
7,988,724 B2 8/2011 Salahieh et al.
7,993,386 B2 8/2011 Elliott
8,002,824 B2 8/2011 Jenson et al.
8,002,825 B2 8/2011 Letac et al.
8,012,198 B2 9/2011 Hill et al.
8,021,421 B2 9/2011 Fogarty et al.
RE42,818 E 10/2011 Cali et al.
RE42,857 E 10/2011 Cali et al.
8,038,704 B2 10/2011 Sherburne
8,038,709 B2 10/2011 Palasis et al.
8,043,450 B2 10/2011 Cali et al.
8,048,153 B2 11/2011 Salahieh et al.
8,052,715 B2 11/2011 Quinn et al.
8,052,749 B2 11/2011 Salahieh et al.
8,052,750 B2 11/2011 Tuval et al.
8,057,540 B2 11/2011 Letac et al.
8,062,355 B2 11/2011 Figulla et al.
8,062,536 B2 11/2011 Liu et al.
8,062,537 B2 11/2011 Tuominen et al.
8,062,749 B2 11/2011 Shelestak et al.
8,070,799 B2 12/2011 Righini et al.
8,075,641 B2 12/2011 Aravanis et al.
8,083,788 B2 12/2011 Acosta et al.
8,092,518 B2 1/2012 Schreck
8,092,520 B2 1/2012 Quadri
8,092,521 B2 1/2012 Figulla et al.
8,128,676 B2 3/2012 Cummings
8,128,681 B2 3/2012 Shoemaker et al.
8,133,217 B2 3/2012 Stokes et al.
8,133,270 B2 3/2012 Kheradvar et al.
8,136,659 B2 3/2012 Salahieh et al.
8,137,394 B2 3/2012 Stocker et al.
8,137,398 B2 3/2012 Tuval et al.
8,147,534 B2 4/2012 Berez et al.
8,157,853 B2 4/2012 Laske et al.
8,167,894 B2 5/2012 Miles et al.
8,172,896 B2 5/2012 McNamara et al.
8,182,528 B2 5/2012 Salahieh et al.
8,192,351 B2 6/2012 Fishler et al.
8,206,437 B2 6/2012 Bonhoeffer et al.
8,211,107 B2 7/2012 Parks et al.
8,216,174 B2 7/2012 Wilk et al.
8,216,301 B2 7/2012 Bonhoeffer et al.
8,221,493 B2 7/2012 Boyle et al.
8,226,707 B2 7/2012 White
8,226,710 B2 7/2012 Nguyen et al.
8,230,717 B2 7/2012 Matonick
8,231,670 B2 7/2012 Salahieh et al.
8,236,049 B2 8/2012 Rowe et al.
8,236,241 B2 8/2012 Carpentier et al.
8,246,675 B2 8/2012 Zegdi
8,246,678 B2 8/2012 Salahieh et al.
8,252,051 B2 8/2012 Chau et al.
8,252,052 B2 8/2012 Salahieh et al.
8,277,500 B2 10/2012 Schmid et al.
8,287,584 B2 10/2012 Salahieh et al.
8,303,653 B2 11/2012 Bonhoeffer et al.
8,308,798 B2 11/2012 Pintor et al.
8,317,858 B2 11/2012 Straubinger et al.
8,323,335 B2 12/2012 Rowe et al.
8,328,868 B2 12/2012 Paul et al.
8,343,136 B2 1/2013 Howat et al.
8,343,213 B2 1/2013 Salahieh et al.
8,348,995 B2 1/2013 Tuval et al.
8,348,996 B2 1/2013 Tuval et al.
8,348,999 B2 1/2013 Kheradvar et al.
8,357,387 B2 1/2013 Dove et al.
8,366,767 B2 2/2013 Zhang
8,372,134 B2 2/2013 Schlick et al.
8,376,865 B2 2/2013 Forster et al.
8,377,117 B2 2/2013 Keidar et al.
8,382,822 B2 2/2013 Pavcnik et al.
8,398,704 B2 3/2013 Straubinger et al.
8,398,708 B2 3/2013 Meiri et al.
8,403,983 B2 3/2013 Quadri et al.
8,414,641 B2 4/2013 Stocker et al.
8,414,643 B2 4/2013 Tuval et al.
8,414,644 B2 4/2013 Quadri et al.
8,414,645 B2 4/2013 Dwork et al.
8,439,961 B2 5/2013 Jagger et al.
8,445,278 B2 5/2013 Everaerts et al.
8,460,365 B2 6/2013 Haverkost et al.
8,465,540 B2 6/2013 Straubinger et al.
8,468,667 B2 6/2013 Straubinger et al.
8,470,023 B2 6/2013 Eidenschink et al.
8,491,650 B2 7/2013 Wiemeyer et al.
8,512,394 B2 8/2013 Schmid et al.
8,512,399 B2 8/2013 Lafontaine
8,512,400 B2 8/2013 Tran et al.
8,512,401 B2 8/2013 Murray, III et al.
8,523,936 B2 9/2013 Schmid et al.
8,535,368 B2 9/2013 Headley, Jr. et al.
8,540,762 B2 9/2013 Schmid et al.
8,545,547 B2 10/2013 Schmid et al.
8,545,552 B2 10/2013 Garrison et al.
8,551,160 B2 10/2013 Figulla et al.
8,556,880 B2 10/2013 Freyman et al.
8,556,966 B2 10/2013 Jenson
8,568,475 B2 10/2013 Nguyen et al.
8,579,936 B2 11/2013 Abbott et al.
8,579,962 B2 11/2013 Salahieh et al.
8,579,965 B2 11/2013 Bonhoeffer et al.
8,585,756 B2 11/2013 Bonhoeffer et al.
8,585,759 B2 11/2013 Bumbalough
8,591,570 B2 11/2013 Revuelta et al.
8,597,226 B2 12/2013 Wilk et al.
8,603,159 B2 12/2013 Seguin et al.
8,603,160 B2 12/2013 Salahieh et al.
8,617,235 B2 12/2013 Schmid et al.
8,617,236 B2 12/2013 Paul et al.
8,623,074 B2 1/2014 Ryan
8,623,075 B2 1/2014 Murray, III et al.
8,623,076 B2 1/2014 Salahieh et al.
8,623,078 B2 1/2014 Salahieh et al.
8,628,562 B2 1/2014 Cummings
8,628,571 B1 1/2014 Hacohen et al.
8,647,381 B2 2/2014 Essinger et al.
8,668,733 B2 3/2014 Haug et al.
8,672,997 B2 3/2014 Drasler et al.
8,679,174 B2 3/2014 Ottma et al.
8,685,077 B2 4/2014 Laske et al.
8,696,743 B2 4/2014 Holecek et al.
8,721,713 B2 5/2014 Tower et al.
8,721,717 B2 5/2014 Shoemaker et al.
8,734,508 B2 5/2014 Hastings et al.
8,758,430 B2 6/2014 Ferrari et al.
8,764,818 B2 7/2014 Gregg
8,778,020 B2 7/2014 Gregg et al.
8,790,395 B2 7/2014 Straubinger et al.
8,795,305 B2 8/2014 Martin et al.
8,795,356 B2 8/2014 Quadri et al.
8,808,356 B2 8/2014 Braido et al.
8,808,364 B2 8/2014 Palasis et al.
RE45,130 E 9/2014 Figulla et al.
8,828,078 B2 9/2014 Salahieh et al.
8,828,079 B2 9/2014 Thielen et al.
8,840,662 B2 9/2014 Salahieh et al.
8,840,663 B2 9/2014 Salahieh et al.
8,845,721 B2 9/2014 Braido et al.

(56) References Cited

U.S. PATENT DOCUMENTS 8,851,286 B2 10/2014 Chang et al.
8,852,272 B2 10/2014 Gross et al.
8,858,620 B2 10/2014 Salahieh et al.
8,894,703 B2 11/2014 Salahieh et al.
8,932,349 B2 1/2015 Jenson et al.
8,940,014 B2 1/2015 Gamarra et al.
8,951,243 B2 2/2015 Crisostomo et al.
8,951,299 B2 2/2015 Paul et al.
8,956,383 B2 2/2015 Aklog et al.
8,992,608 B2 3/2015 Haug et al.
8,998,976 B2 4/2015 Gregg et al.
9,005,273 B2 4/2015 Salahieh et al.
9,011,521 B2 4/2015 Haug et al.
9,023,099 B2 5/2015 Duffy et al.
9,028,542 B2 5/2015 Hill et al.
9,039,756 B2 5/2015 White
9,044,318 B2 6/2015 Straubinger et al.
9,131,926 B2 9/2015 Crisostomo et al.
9,138,315 B2 9/2015 Straubinger et al.
9,149,358 B2 10/2015 Tabor et al.
9,168,130 B2 10/2015 Straubinger et al.
9,168,131 B2 10/2015 Yohanan et al.
9,168,136 B2 10/2015 Yang et al.
RE45,790 E 11/2015 Figulla et al.
9,180,005 B1 11/2015 Lashinski et al.
9,186,482 B2 11/2015 Dorn
9,211,266 B2 12/2015 Iwazawa et al.
9,216,082 B2 12/2015 Von Segesser et al.
9,248,037 B2 2/2016 Roeder et al.
9,265,608 B2 2/2016 Miller et al.
9,277,991 B2 3/2016 Salahieh et al.
9,277,993 B2 3/2016 Gamarra et al.
9,295,551 B2 3/2016 Straubinger et al.
9,301,840 B2 4/2016 Nguyen et al.
9,301,843 B2 4/2016 Richardson et al.
9,308,085 B2 4/2016 Salahieh et al.
9,320,599 B2 4/2016 Salahieh et al.
9,326,853 B2 5/2016 Olson et al.
9,358,106 B2 6/2016 Salahieh et al.
9,358,110 B2 6/2016 Paul et al.
9,370,419 B2 6/2016 Hill et al.
9,370,421 B2 6/2016 Crisostomo et al.
9,387,076 B2 7/2016 Paul et al.
9,393,094 B2 7/2016 Salahieh et al.
9,393,113 B2 7/2016 Salahieh et al.
9,393,114 B2 7/2016 Sutton et al.
9,393,115 B2 7/2016 Tabor et al.
9,415,567 B2 8/2016 Sogard et al.
9,421,083 B2 8/2016 Eidenschink et al.
9,439,759 B2 9/2016 Straubinger et al.
9,463,084 B2 10/2016 Stinson
9,474,598 B2 10/2016 Gregg et al.
9,474,609 B2 10/2016 Haverkost et al.
9,492,276 B2 11/2016 Lee et al.
9,510,945 B2 12/2016 Sutton et al.
9,510,947 B2 12/2016 Straubinger et al.
9,526,609 B2 12/2016 Salahieh et al.
9,532,872 B2 1/2017 Salahieh et al.
9,539,091 B2 1/2017 Yang et al.
9,554,924 B2 1/2017 Schlick et al.
9,597,432 B2 3/2017 Nakamura
9,649,212 B2 5/2017 Fargahi
9,675,413 B2 6/2017 Deem et al.
9,717,593 B2 8/2017 Alkhatib et al.
9,744,031 B2 8/2017 Girard et al.
D800,908 S 10/2017 Hariton et al.
9,775,709 B2 10/2017 Miller et al.
9,788,945 B2 10/2017 Ottma et al.
9,861,476 B2 1/2018 Salahieh et al.
9,867,694 B2 1/2018 Girard et al.
9,867,699 B2 1/2018 Straubinger et al.
9,872,768 B2 1/2018 Paul et al.
9,878,127 B2 1/2018 Damm et al.
9,889,002 B2 2/2018 Bonhoeffer et al.
9,901,445 B2 2/2018 Backus et al.
9,918,835 B2 3/2018 Guyenot et al.
9,949,824 B2 4/2018 Bonhoeffer et al.
9,956,075 B2 5/2018 Salahieh et al.
9,968,761 B2 5/2018 Brecker
9,987,133 B2 6/2018 Straubinger et al.
10,092,324 B2 10/2018 Gillespie et al.
10,143,552 B2 12/2018 Wallace et al.
10,154,901 B2 12/2018 Straubinger et al.
10,321,987 B2 6/2019 Wang et al.
10,363,134 B2 7/2019 Figulla et al.
10,543,084 B2 1/2020 Guyenot et al.
10,575,947 B2 3/2020 Straubinger et al.
10,638,918 B2 5/2020 Atarot et al.
10,653,427 B2 5/2020 Goldfarb et al.
10,702,382 B2 7/2020 Straubinger et al.
10,709,555 B2 7/2020 Schreck et al.
10,856,978 B2 12/2020 Straubinger et al.
10,856,987 B2 12/2020 Cabiri et al.
11,065,138 B2 7/2021 Schreck et al.
11,147,669 B2 10/2021 Straubinger et al.
11,154,398 B2 10/2021 Straubinger et al.
11,185,405 B2 11/2021 Girard et al.
11,197,754 B2 12/2021 Saffari et al.
11,266,497 B2 3/2022 Cao et al.
11,357,624 B2 6/2022 Guyenot et al.
11,911,264 B2 2/2024 Chau et al.
11,951,005 B2 4/2024 Gross et al.
12,121,461 B2 10/2024 Schreck et al.
12,232,957 B2 2/2025 Straubinger et al.
12,318,281 B2 6/2025 Girard et al.
12,343,255 B2 7/2025 Schreck et al.
12,414,854 B2 9/2025 Straubinger et al.
12,433,745 B2 10/2025 Saffari et al.
12,447,015 B2 10/2025 Girard et al.
12,569,336 B2 3/2026 Ottma et al.
2001/0000041 A1 3/2001 Selmon et al.
2001/0001314 A1 5/2001 Davison et al.
2001/0002445 A1 5/2001 Vesely
2001/0004683 A1 6/2001 Gambale et al.
2001/0004690 A1 6/2001 Gambale et al.
2001/0004699 A1 6/2001 Gittings et al.
2001/0007956 A1 7/2001 Letac et al.
2001/0008969 A1 7/2001 Evans et al.
2001/0010017 A1 7/2001 Letac et al.
2001/0011187 A1 8/2001 Pavcnik et al.
2001/0011189 A1 8/2001 Drasler et al.
2001/0012948 A1 8/2001 Vanney
2001/0014813 A1 8/2001 Saadat et al.
2001/0016700 A1 8/2001 Eno et al.
2001/0018596 A1 8/2001 Selmon et al.
2001/0020172 A1 9/2001 Selmon et al.
2001/0021872 A1 9/2001 Bailey et al.
2001/0025196 A1 9/2001 Chinn et al.
2001/0025643 A1 10/2001 Foley
2001/0027287 A1 10/2001 Shmulewitz et al.
2001/0027338 A1 10/2001 Greenberg
2001/0027339 A1 10/2001 Boatman et al.
2001/0029385 A1 10/2001 Shennib et al.
2001/0032013 A1 10/2001 Marton
2001/0034547 A1 10/2001 Hall et al.
2001/0037117 A1 11/2001 Gambale et al.
2001/0037141 A1 11/2001 Yee et al.
2001/0037149 A1 11/2001 Wilk
2001/0039426 A1 11/2001 Makower et al.
2001/0039445 A1 11/2001 Hall et al.
2001/0039450 A1 11/2001 Pavcnik et al.
2001/0041902 A1 11/2001 Lepulu et al.
2001/0041928 A1 11/2001 Pavcnik et al.
2001/0041930 A1 11/2001 Globerman et al.
2001/0044631 A1 11/2001 Akin et al.
2001/0044634 A1 11/2001 Don Michael et al.
2001/0044647 A1 11/2001 Pinchuk et al.
2001/0044652 A1 11/2001 Moore
2001/0044656 A1 11/2001 Williamson, IV et al.
2001/0047165 A1 11/2001 Makower et al.
2001/0049523 A1 12/2001 DeVore et al.
2001/0051822 A1 12/2001 Stack et al.
2001/0053932 A1 12/2001 Phelps et al.
2002/0002349 A1 1/2002 Flaherty et al.

(56) References Cited

U.S. PATENT DOCUMENTS

2002/0002396 A1 1/2002 Fulkerson
2002/0002401 A1 1/2002 McGuckin, Jr. et al.
2002/0004662 A1 1/2002 Wilk
2002/0004663 A1 1/2002 Gittings et al.
2002/0007138 A1 1/2002 Wilk et al.
2002/0010489 A1 1/2002 Grayzel et al.
2002/0010508 A1 1/2002 Chobotov
2002/0026233 A1 2/2002 Shaknovich
2002/0029014 A1 3/2002 Jayaraman
2002/0029079 A1 3/2002 Kim et al.
2002/0029981 A1 3/2002 Nigam
2002/0032476 A1 3/2002 Gambale et al.
2002/0032478 A1 3/2002 Boekstegers et al.
2002/0032480 A1 3/2002 Spence et al.
2002/0032481 A1 3/2002 Gabbay
2002/0035390 A1 3/2002 Schaldach et al.
2002/0035396 A1 3/2002 Heath
2002/0042650 A1 4/2002 Vardi et al.
2002/0042651 A1 4/2002 Liddicoat et al.
2002/0045846 A1 4/2002 Kaplon et al.
2002/0045928 A1 4/2002 Boekstegers
2002/0045929 A1 4/2002 Diaz
2002/0049486 A1 4/2002 Knudson et al.
2002/0052651 A1 5/2002 Myers et al.
2002/0055767 A1 5/2002 Forde et al.
2002/0055769 A1 5/2002 Wang
2002/0055772 A1 5/2002 McGuckin, Jr. et al.
2002/0055774 A1 5/2002 Liddicoat
2002/0055775 A1 5/2002 Carpentier et al.
2002/0058897 A1 5/2002 Renati
2002/0058987 A1 5/2002 Butaric et al.
2002/0058993 A1 5/2002 Landau et al.
2002/0058995 A1 5/2002 Stevens
2002/0062146 A1 5/2002 Makower et al.
2002/0065478 A1 5/2002 Knudson et al.
2002/0065485 A1 5/2002 DuBois et al.
2002/0072699 A1 6/2002 Knudson et al.
2002/0072789 A1 6/2002 Hackett et al.
2002/0077566 A1 6/2002 Laroya et al.
2002/0077654 A1 6/2002 Javier, Jr. et al.
2002/0077696 A1 6/2002 Zadno-Azizi et al.
2002/0082584 A1 6/2002 Rosenman et al.
2002/0082609 A1 6/2002 Green
2002/0092535 A1 7/2002 Wilk
2002/0092536 A1 7/2002 LaFontaine et al.
2002/0095111 A1 7/2002 Tweden et al.
2002/0095173 A1 7/2002 Mazzocchi et al.
2002/0095206 A1 7/2002 Addonizio et al.
2002/0095209 A1 7/2002 Zadno-Azizi et al.
2002/0099405 A1 7/2002 Yurek et al.
2002/0099439 A1 7/2002 Schwartz et al.
2002/0100484 A1 8/2002 Hall et al.
2002/0103533 A1 8/2002 Langberg et al.
2002/0107565 A1 8/2002 Greenhalgh
2002/0111627 A1 8/2002 Vincent-Prestigiacomo
2002/0111665 A1 8/2002 Lauterjung
2002/0111668 A1 8/2002 Smith
2002/0111672 A1 8/2002 Kim et al.
2002/0111674 A1 8/2002 Chouinard et al.
2002/0117789 A1 8/2002 Childers et al.
2002/0120322 A1 8/2002 Thompson et al.
2002/0120323 A1 8/2002 Thompson et al.
2002/0120328 A1 8/2002 Pathak et al.
2002/0123698 A1 9/2002 Garibotto et al.
2002/0123786 A1 9/2002 Gittings et al.
2002/0123790 A1 9/2002 White et al.
2002/0123802 A1 9/2002 Snyders
2002/0128552 A1 9/2002 Nowlin et al.
2002/0133183 A1 9/2002 Lentz et al.
2002/0133226 A1 9/2002 Marquez et al.
2002/0138087 A1 9/2002 Shennib et al.
2002/0138138 A1 9/2002 Yang
2002/0143285 A1 10/2002 Eno et al.
2002/0143289 A1 10/2002 Ellis et al.
2002/0143387 A1 10/2002 Soetikno et al.
2002/0144696 A1 10/2002 Sharkawy et al.
2002/0151913 A1 10/2002 Berg et al.
2002/0151970 A1 10/2002 Garrison et al.
2002/0156522 A1 10/2002 Ivancev et al.
2002/0161377 A1 10/2002 Rabkin
2002/0161383 A1 10/2002 Akin et al.
2002/0161390 A1 10/2002 Mouw
2002/0161392 A1 10/2002 Dubrul
2002/0161394 A1 10/2002 Macoviak et al.
2002/0161424 A1 10/2002 Rapacki et al.
2002/0161426 A1 10/2002 Iancea
2002/0165479 A1 11/2002 Wilk
2002/0165576 A1 11/2002 Boyle et al.
2002/0165606 A1 11/2002 Wolf et al.
2002/0173842 A1 11/2002 Buchanan
2002/0177766 A1 11/2002 Mogul
2002/0177772 A1 11/2002 Altman et al.
2002/0177840 A1 11/2002 Farnholtz
2002/0177894 A1 11/2002 Acosta et al.
2002/0179098 A1 12/2002 Makower et al.
2002/0183716 A1 12/2002 Herweck et al.
2002/0183781 A1 12/2002 Casey et al.
2002/0186558 A1 12/2002 Plank et al.
2002/0188341 A1 12/2002 Elliott
2002/0188344 A1 12/2002 Bolea et al.
2002/0193782 A1 12/2002 Ellis et al.
2002/0193871 A1 12/2002 Beyersdorf et al.
2002/0198594 A1 12/2002 Schreck
2003/0004541 A1 1/2003 Linder et al.
2003/0004560 A1 1/2003 Chobotov et al.
2003/0009189 A1 1/2003 Gilson et al.
2003/0014104 A1 1/2003 Cribier
2003/0018377 A1 1/2003 Berg et al.
2003/0018379 A1 1/2003 Knudson et al.
2003/0023300 A1 1/2003 Bailey et al.
2003/0023303 A1 1/2003 Palmaz et al.
2003/0027332 A1 2/2003 Lafrance et al.
2003/0028213 A1 2/2003 Thill et al.
2003/0028247 A1 2/2003 Cali
2003/0033001 A1 2/2003 Igaki
2003/0036791 A1 2/2003 Philipp et al.
2003/0036795 A1 2/2003 Andersen et al.
2003/0040736 A1 2/2003 Stevens et al.
2003/0040771 A1 2/2003 Hyodoh et al.
2003/0040772 A1 2/2003 Hyodoh et al.
2003/0040791 A1 2/2003 Oktay
2003/0040792 A1 2/2003 Gabbay
2003/0042186 A1 3/2003 Boyle
2003/0044315 A1 3/2003 Boekstegers
2003/0045828 A1 3/2003 Wilk
2003/0050694 A1 3/2003 Yang et al.
2003/0055371 A1 3/2003 Wolf et al.
2003/0055495 A1 3/2003 Pease et al.
2003/0057156 A1 3/2003 Peterson et al.
2003/0060844 A1 3/2003 Borillo et al.
2003/0065386 A1 4/2003 Weadock
2003/0069492 A1 4/2003 Abrams et al.
2003/0069646 A1 4/2003 Stinson
2003/0070944 A1 4/2003 Nigam
2003/0073973 A1 4/2003 Evans et al.
2003/0074058 A1 4/2003 Sherry
2003/0078561 A1 4/2003 Gambale et al.
2003/0078652 A1 4/2003 Sutherland
2003/0083730 A1 5/2003 Stinson
2003/0093145 A1 5/2003 Lawrence-Brown et al.
2003/0100918 A1 5/2003 Duane
2003/0100919 A1 5/2003 Hopkins et al.
2003/0100920 A1 5/2003 Akin et al.
2003/0105514 A1 6/2003 Phelps et al.
2003/0109924 A1 6/2003 Cribier
2003/0109930 A1 6/2003 Bluni et al.
2003/0114912 A1 6/2003 Sequin et al.
2003/0114913 A1 6/2003 Spenser et al.
2003/0120195 A1 6/2003 Milo et al.
2003/0125795 A1 7/2003 Pavcnik et al.
2003/0130726 A1 7/2003 Thorpe et al.
2003/0130727 A1 7/2003 Drasler et al.
2003/0130729 A1 7/2003 Paniagua et al.
2003/0130746 A1 7/2003 Ashworth et al.

(56) References Cited

U.S. PATENT DOCUMENTS

2003/0135257 A1 7/2003 Taheri
2003/0139796 A1 7/2003 Sequin et al.
2003/0139798 A1 7/2003 Brown et al.
2003/0139803 A1 7/2003 Sequin et al.
2003/0139804 A1 7/2003 Hankh et al.
2003/0144657 A1 7/2003 Bowe et al.
2003/0144732 A1 7/2003 Cosgrove et al.
2003/0149474 A1 8/2003 Becker
2003/0149475 A1 8/2003 Hyodoh et al.
2003/0149476 A1 8/2003 Damm et al.
2003/0149477 A1 8/2003 Gabbay
2003/0149478 A1 8/2003 Figulla et al.
2003/0153971 A1 8/2003 Chandrasekaran
2003/0153974 A1 8/2003 Spenser et al.
2003/0158573 A1 8/2003 Gittings et al.
2003/0158595 A1 8/2003 Randall et al.
2003/0163193 A1 8/2003 Widenhouse
2003/0163198 A1 8/2003 Morra et al.
2003/0165352 A1 9/2003 Ibrahim et al.
2003/0171803 A1 9/2003 Shimon
2003/0171805 A1 9/2003 Berg et al.
2003/0176884 A1 9/2003 Berrada et al.
2003/0181850 A1 9/2003 Diamond et al.
2003/0181938 A1 9/2003 Roth et al.
2003/0181942 A1 9/2003 Sutton et al.
2003/0187495 A1 10/2003 Cully et al.
2003/0191449 A1 10/2003 Nash et al.
2003/0191516 A1 10/2003 Weldon et al.
2003/0191519 A1 10/2003 Lombardi et al.
2003/0191526 A1 10/2003 Van Tassel et al.
2003/0195457 A1 10/2003 LaFontaine et al.
2003/0195458 A1 10/2003 Phelps et al.
2003/0195609 A1 10/2003 Berenstein et al.
2003/0195620 A1 10/2003 Huynh et al.
2003/0198722 A1 10/2003 Johnston, Jr. et al.
2003/0199759 A1 10/2003 Richard
2003/0199913 A1 10/2003 Dubrul et al.
2003/0199963 A1 10/2003 Tower et al.
2003/0199971 A1 10/2003 Tower et al.
2003/0199972 A1 10/2003 Zadno-Azizi et al.
2003/0204160 A1 10/2003 Kamm et al.
2003/0204249 A1 10/2003 Letort
2003/0208224 A1 11/2003 Broome
2003/0212410 A1 11/2003 Stenzel et al.
2003/0212413 A1 11/2003 Wilk
2003/0212429 A1 11/2003 Keegan et al.
2003/0212452 A1 11/2003 Zadno-Azizi et al.
2003/0212454 A1 11/2003 Scott et al.
2003/0216678 A1 11/2003 March et al.
2003/0216679 A1 11/2003 Wolf et al.
2003/0216774 A1 11/2003 Larson
2003/0220661 A1 11/2003 Mowry et al.
2003/0220667 A1 11/2003 Van Der Burg et al.
2003/0225445 A1 12/2003 Derus et al.
2003/0229366 A1 12/2003 Reggie et al.
2003/0229390 A1 12/2003 Ashton et al.
2003/0233117 A1 12/2003 Adams et al.
2003/0236542 A1 12/2003 Makower
2003/0236567 A1 12/2003 Elliot
2003/0236568 A1 12/2003 Hojeibane et al.
2003/0236570 A1 12/2003 Cook et al.
2004/0004926 A1 1/2004 Maeda
2004/0006298 A1 1/2004 Wilk
2004/0006380 A1 1/2004 Buck et al.
2004/0015225 A1 1/2004 Kim et al.
2004/0015228 A1 1/2004 Lombardi et al.
2004/0018651 A1 1/2004 Nadeau
2004/0019348 A1 1/2004 Stevens et al.
2004/0019374 A1 1/2004 Hojeibane et al.
2004/0026389 A1 2/2004 Kessler et al.
2004/0033364 A1 2/2004 Spiridigliozzi et al.
2004/0034411 A1 2/2004 Quijano et al.
2004/0037946 A1 2/2004 Morra et al.
2004/0039343 A1 2/2004 Eppstein et al.
2004/0039436 A1 2/2004 Spenser et al.
2004/0044350 A1 3/2004 Martin et al.
2004/0044361 A1 3/2004 Frazier et al.
2004/0044392 A1 3/2004 Von Oepen
2004/0044400 A1 3/2004 Cheng et al.
2004/0044402 A1 3/2004 Jung et al.
2004/0049204 A1 3/2004 Harari et al.
2004/0049207 A1 3/2004 Goldfarb et al.
2004/0049224 A1 3/2004 Buehlmann et al.
2004/0049226 A1 3/2004 Keegan et al.
2004/0049262 A1 3/2004 Obermiller et al.
2004/0049266 A1 3/2004 Anduiza et al.
2004/0058097 A1 3/2004 Weder
2004/0059280 A1 3/2004 Makower et al.
2004/0059407 A1 3/2004 Escamilla et al.
2004/0059409 A1 3/2004 Stenzel
2004/0059429 A1 3/2004 Amin et al.
2004/0073157 A1 4/2004 Knudson et al.
2004/0073198 A1 4/2004 Gilson et al.
2004/0073238 A1 4/2004 Makower
2004/0073289 A1 4/2004 Hartley
2004/0077987 A1 4/2004 Rapacki et al.
2004/0077988 A1 4/2004 Tweden et al.
2004/0077990 A1 4/2004 Knudson et al.
2004/0078950 A1 4/2004 Schreck
2004/0082904 A1 4/2004 Houde et al.
2004/0082967 A1 4/2004 Broome et al.
2004/0082989 A1 4/2004 Cook et al.
2004/0087982 A1 5/2004 Eskuri
2004/0088042 A1 5/2004 Kim et al.
2004/0088045 A1 5/2004 Cox
2004/0092858 A1 5/2004 Wilson et al.
2004/0092989 A1 5/2004 Wilson et al.
2004/0093005 A1 5/2004 Durcan
2004/0093016 A1 5/2004 Root et al.
2004/0093060 A1 5/2004 Seguin et al.
2004/0093063 A1 5/2004 Wright et al.
2004/0093070 A1 5/2004 Hojeibane et al.
2004/0093075 A1 5/2004 Kuehne
2004/0097788 A1 5/2004 Mourlas et al.
2004/0098022 A1 5/2004 Barone
2004/0098098 A1 5/2004 McGuckin, Jr. et al.
2004/0098099 A1 5/2004 McCullagh et al.
2004/0098112 A1 5/2004 DiMatteo et al.
2004/0102855 A1 5/2004 Shank
2004/0106931 A1 6/2004 Guiles et al.
2004/0106976 A1 6/2004 Bailey et al.
2004/0106990 A1 6/2004 Spence et al.
2004/0107004 A1 6/2004 Levine et al.
2004/0111096 A1 6/2004 Tu et al.
2004/0113306 A1 6/2004 Rapacki et al.
2004/0116951 A1 6/2004 Rosengart
2004/0116999 A1 6/2004 Ledergerber
2004/0117004 A1 6/2004 Osborne et al.
2004/0117009 A1 6/2004 Cali et al.
2004/0118415 A1 6/2004 Hall et al.
2004/0122318 A1 6/2004 Flaherty et al.
2004/0122347 A1 6/2004 Knudson et al.
2004/0122468 A1 6/2004 Yodfat et al.
2004/0122514 A1 6/2004 Fogarty et al.
2004/0122516 A1 6/2004 Fogarty et al.
2004/0127847 A1 7/2004 DuBois et al.
2004/0127912 A1 7/2004 Rabkin et al.
2004/0127936 A1 7/2004 Salahieh et al.
2004/0127979 A1 7/2004 Wilson et al.
2004/0127982 A1 7/2004 MacHold et al.
2004/0133154 A1 7/2004 Flaherty et al.
2004/0133225 A1 7/2004 Makower
2004/0133274 A1 7/2004 Webler et al.
2004/0138694 A1 7/2004 Tran et al.
2004/0138742 A1 7/2004 Myers et al.
2004/0138743 A1 7/2004 Myers et al.
2004/0138745 A1 7/2004 Macoviak et al.
2004/0147868 A1 7/2004 Bardsley et al.
2004/0147869 A1 7/2004 Wolf et al.
2004/0148018 A1 7/2004 Carpentier et al.
2004/0148021 A1 7/2004 Cartledge et al.
2004/0153094 A1 8/2004 Dunfee et al.
2004/0153145 A1 8/2004 Simionescu et al.
2004/0153146 A1 8/2004 Lashinski et al.

(56) References Cited

U.S. PATENT DOCUMENTS

| | | | |
|---|---|---|---|
| 2004/0158143 | A1 | 8/2004 | Flaherty et al. |
| 2004/0158277 | A1 | 8/2004 | Lowe et al. |
| 2004/0163094 | A1 | 8/2004 | Matsui et al. |
| 2004/0167444 | A1 | 8/2004 | Laroya et al. |
| 2004/0167565 | A1 | 8/2004 | Beulke et al. |
| 2004/0167573 | A1 | 8/2004 | Williamson, IV et al. |
| 2004/0167619 | A1 | 8/2004 | Case et al. |
| 2004/0167620 | A1 | 8/2004 | Ortiz et al. |
| 2004/0168691 | A1 | 9/2004 | Sharkawy et al. |
| 2004/0176791 | A1 | 9/2004 | Lim et al. |
| 2004/0181140 | A1 | 9/2004 | Falwell et al. |
| 2004/0186507 | A1 | 9/2004 | Hall et al. |
| 2004/0186557 | A1 | 9/2004 | Gambale et al. |
| 2004/0186558 | A1 | 9/2004 | Pavcnik et al. |
| 2004/0186563 | A1 | 9/2004 | Lobbi |
| 2004/0186565 | A1 | 9/2004 | Schreck |
| 2004/0186587 | A1 | 9/2004 | Ahern |
| 2004/0193180 | A1 | 9/2004 | Buzzard et al. |
| 2004/0193244 | A1 | 9/2004 | Hartley et al. |
| 2004/0193252 | A1 | 9/2004 | Perez et al. |
| 2004/0193261 | A1 | 9/2004 | Berreklouw |
| 2004/0197695 | A1 | 10/2004 | Aono |
| 2004/0199245 | A1 | 10/2004 | Lauterjung |
| 2004/0204683 | A1 | 10/2004 | McGuckin, Jr. et al. |
| 2004/0204755 | A1 | 10/2004 | Robin |
| 2004/0206363 | A1 | 10/2004 | McCarthy et al. |
| 2004/0210104 | A1 | 10/2004 | Lau et al. |
| 2004/0210190 | A1 | 10/2004 | Kohler et al. |
| 2004/0210240 | A1 | 10/2004 | Saint |
| 2004/0210301 | A1 | 10/2004 | Obermiller |
| 2004/0210304 | A1 | 10/2004 | Seguin et al. |
| 2004/0210306 | A1 | 10/2004 | Quijano et al. |
| 2004/0210307 | A1 | 10/2004 | Khairkhahan |
| 2004/0215317 | A1 | 10/2004 | Cummings |
| 2004/0215331 | A1 | 10/2004 | Chew et al. |
| 2004/0215333 | A1 | 10/2004 | Duran et al. |
| 2004/0215339 | A1 | 10/2004 | Drasler et al. |
| 2004/0219180 | A1 | 11/2004 | Gambale et al. |
| 2004/0220598 | A1 | 11/2004 | Bolduc et al. |
| 2004/0220655 | A1 | 11/2004 | Swanson et al. |
| 2004/0225321 | A1 | 11/2004 | Krolik et al. |
| 2004/0225353 | A1 | 11/2004 | McGuckin, Jr. et al. |
| 2004/0225354 | A1 | 11/2004 | Allen et al. |
| 2004/0225355 | A1 | 11/2004 | Stevens |
| 2004/0236411 | A1 | 11/2004 | Sarac et al. |
| 2004/0236418 | A1 | 11/2004 | Stevens |
| 2004/0243143 | A1 | 12/2004 | Corcoran et al. |
| 2004/0243221 | A1 | 12/2004 | Fawzi et al. |
| 2004/0249343 | A1 | 12/2004 | Cioanta |
| 2004/0254594 | A1 | 12/2004 | Alfaro |
| 2004/0254636 | A1 | 12/2004 | Flagle et al. |
| 2004/0260389 | A1 | 12/2004 | Case et al. |
| 2004/0260390 | A1 | 12/2004 | Sarac et al. |
| 2004/0260393 | A1 | 12/2004 | Rahdert et al. |
| 2004/0260394 | A1 | 12/2004 | Douk et al. |
| 2004/0267357 | A1 | 12/2004 | Allen et al. |
| 2005/0000858 | A1 | 1/2005 | Roovers |
| 2005/0004505 | A1 | 1/2005 | Phelps et al. |
| 2005/0004558 | A1 | 1/2005 | Gambale et al. |
| 2005/0004648 | A1 | 1/2005 | Boekstegers |
| 2005/0008589 | A1 | 1/2005 | Legrand et al. |
| 2005/0009000 | A1 | 1/2005 | Wilhelm et al. |
| 2005/0010246 | A1 | 1/2005 | Streeter et al. |
| 2005/0010285 | A1 | 1/2005 | Lambrecht et al. |
| 2005/0010287 | A1 | 1/2005 | Macoviak et al. |
| 2005/0015112 | A1 | 1/2005 | Cohn et al. |
| 2005/0021136 | A1 | 1/2005 | Xie et al. |
| 2005/0025857 | A1 | 2/2005 | Schoenherr et al. |
| 2005/0027305 | A1 | 2/2005 | Shiu et al. |
| 2005/0027348 | A1 | 2/2005 | Case et al. |
| 2005/0033220 | A1 | 2/2005 | Wilk et al. |
| 2005/0033398 | A1 | 2/2005 | Seguin |
| 2005/0033402 | A1 | 2/2005 | Cully et al. |
| 2005/0038495 | A1 | 2/2005 | Greenan |
| 2005/0038509 | A1 | 2/2005 | Ashe |
| 2005/0043585 | A1 | 2/2005 | Datta et al. |
| 2005/0043711 | A1 | 2/2005 | Corcoran et al. |
| 2005/0043757 | A1 | 2/2005 | Arad et al. |
| 2005/0043759 | A1 | 2/2005 | Chanduszko |
| 2005/0043760 | A1 | 2/2005 | Fogarty et al. |
| 2005/0043781 | A1 | 2/2005 | Foley |
| 2005/0043790 | A1 | 2/2005 | Seguin |
| 2005/0049674 | A1 | 3/2005 | Berra et al. |
| 2005/0049692 | A1 | 3/2005 | Numamoto et al. |
| 2005/0049696 | A1 | 3/2005 | Siess et al. |
| 2005/0055088 | A1 | 3/2005 | Liddicoat et al. |
| 2005/0060016 | A1 | 3/2005 | Wu et al. |
| 2005/0060018 | A1 | 3/2005 | Dittman |
| 2005/0060029 | A1 | 3/2005 | Le et al. |
| 2005/0060030 | A1 | 3/2005 | Lashinski et al. |
| 2005/0065594 | A1 | 3/2005 | DiMatteo et al. |
| 2005/0070794 | A1 | 3/2005 | Deal et al. |
| 2005/0070957 | A1 | 3/2005 | Das |
| 2005/0075584 | A1 | 4/2005 | Cali |
| 2005/0075662 | A1 | 4/2005 | Pedersen et al. |
| 2005/0075712 | A1 | 4/2005 | Biancucci et al. |
| 2005/0075717 | A1 | 4/2005 | Nguyen et al. |
| 2005/0075719 | A1 | 4/2005 | Bergheim |
| 2005/0075720 | A1 | 4/2005 | Nguyen et al. |
| 2005/0075724 | A1 | 4/2005 | Svanidze et al. |
| 2005/0075725 | A1 | 4/2005 | Rowe |
| 2005/0075726 | A1 | 4/2005 | Svanidze et al. |
| 2005/0075727 | A1 | 4/2005 | Wheatley |
| 2005/0075730 | A1 | 4/2005 | Myers et al. |
| 2005/0075731 | A1 | 4/2005 | Artof et al. |
| 2005/0075776 | A1 | 4/2005 | Cho |
| 2005/0084595 | A1 | 4/2005 | Shukla et al. |
| 2005/0085841 | A1 | 4/2005 | Eversull et al. |
| 2005/0085842 | A1 | 4/2005 | Eversull et al. |
| 2005/0085843 | A1 | 4/2005 | Opolski et al. |
| 2005/0085890 | A1 | 4/2005 | Rasmussen et al. |
| 2005/0085900 | A1 | 4/2005 | Case et al. |
| 2005/0090846 | A1 | 4/2005 | Pedersen et al. |
| 2005/0090890 | A1 | 4/2005 | Wu et al. |
| 2005/0096568 | A1 | 5/2005 | Kato |
| 2005/0096692 | A1 | 5/2005 | Linder et al. |
| 2005/0096724 | A1 | 5/2005 | Stenzel et al. |
| 2005/0096726 | A1 | 5/2005 | Sequin et al. |
| 2005/0096734 | A1 | 5/2005 | Majercak et al. |
| 2005/0096735 | A1 | 5/2005 | Hojeibane et al. |
| 2005/0096736 | A1 | 5/2005 | Osse et al. |
| 2005/0096738 | A1 | 5/2005 | Cali et al. |
| 2005/0096768 | A1 | 5/2005 | Huang et al. |
| 2005/0098547 | A1 | 5/2005 | Cali et al. |
| 2005/0100580 | A1 | 5/2005 | Osborne et al. |
| 2005/0101903 | A1 | 5/2005 | Kohler et al. |
| 2005/0101904 | A1 | 5/2005 | Wilk |
| 2005/0101968 | A1 | 5/2005 | Dadourian |
| 2005/0107822 | A1 | 5/2005 | Wasdyke |
| 2005/0107871 | A1 | 5/2005 | Realyvasquez et al. |
| 2005/0113902 | A1 | 5/2005 | Geiser et al. |
| 2005/0113904 | A1 | 5/2005 | Shank et al. |
| 2005/0113910 | A1 | 5/2005 | Paniagua et al. |
| 2005/0119688 | A1 | 6/2005 | Bergheim |
| 2005/0119728 | A1 | 6/2005 | Sarac |
| 2005/0119736 | A1 | 6/2005 | Zilla et al. |
| 2005/0125075 | A1 | 6/2005 | Meade et al. |
| 2005/0131438 | A1 | 6/2005 | Cohn |
| 2005/0137499 | A1 | 6/2005 | Sheets et al. |
| 2005/0137609 | A1 | 6/2005 | Guiraudon |
| 2005/0137681 | A1 | 6/2005 | Shoemaker et al. |
| 2005/0137682 | A1 | 6/2005 | Justino |
| 2005/0137683 | A1 | 6/2005 | Hezi-Yamit et al. |
| 2005/0137686 | A1 | 6/2005 | Salahieh et al. |
| 2005/0137687 | A1 | 6/2005 | Salahieh et al. |
| 2005/0137688 | A1 | 6/2005 | Salahieh et al. |
| 2005/0137689 | A1 | 6/2005 | Salahieh et al. |
| 2005/0137690 | A1 | 6/2005 | Salahieh et al. |
| 2005/0137691 | A1 | 6/2005 | Salahieh et al. |
| 2005/0137692 | A1 | 6/2005 | Haug et al. |
| 2005/0137693 | A1 | 6/2005 | Haug et al. |
| 2005/0137694 | A1 | 6/2005 | Haug et al. |
| 2005/0137695 | A1 | 6/2005 | Salahieh et al. |
| 2005/0137696 | A1 | 6/2005 | Salahieh et al. |

(56) References Cited

U.S. PATENT DOCUMENTS

2005/0137697 A1 6/2005 Salahieh et al.
2005/0137698 A1 6/2005 Salahieh et al.
2005/0137699 A1 6/2005 Salahieh et al.
2005/0137701 A1 6/2005 Salahieh et al.
2005/0137702 A1 6/2005 Haug et al.
2005/0138689 A1 6/2005 Aukerman
2005/0143804 A1 6/2005 Haverkost
2005/0143807 A1 6/2005 Pavcnik et al.
2005/0143809 A1 6/2005 Salahieh et al.
2005/0148997 A1 7/2005 Valley et al.
2005/0149159 A1 7/2005 Andreas et al.
2005/0149166 A1 7/2005 Schaeffer et al.
2005/0149181 A1 7/2005 Eberhardt
2005/0150775 A1 7/2005 Zhang et al.
2005/0159726 A1 7/2005 Evans et al.
2005/0165352 A1 7/2005 Henry et al.
2005/0165477 A1 7/2005 Anduiza et al.
2005/0165479 A1 7/2005 Drews et al.
2005/0171597 A1 8/2005 Boatman et al.
2005/0171598 A1 8/2005 Schaeffer
2005/0177227 A1 8/2005 Heim et al.
2005/0182483 A1 8/2005 Osborne et al.
2005/0182486 A1 8/2005 Gabbay
2005/0186349 A1 8/2005 Loper et al.
2005/0187616 A1 8/2005 Realyvasquez
2005/0192527 A1 9/2005 Gharib et al.
2005/0192665 A1 9/2005 Spenser et al.
2005/0197694 A1 9/2005 Pai et al.
2005/0197695 A1 9/2005 Stacchino et al.
2005/0203549 A1 9/2005 Realyvasquez
2005/0203605 A1 9/2005 Dolan
2005/0203614 A1 9/2005 Forster et al.
2005/0203615 A1 9/2005 Forster et al.
2005/0203616 A1 9/2005 Cribier
2005/0203617 A1 9/2005 Forster et al.
2005/0203618 A1 9/2005 Sharkawy et al.
2005/0203818 A9 9/2005 Rotman et al.
2005/0209580 A1 9/2005 Freyman
2005/0214342 A1 9/2005 Tweden et al.
2005/0222664 A1 10/2005 Parker
2005/0222668 A1 10/2005 Schaeffer et al.
2005/0222674 A1 10/2005 Paine
2005/0228334 A1 10/2005 Knudson et al.
2005/0228472 A1 10/2005 Case et al.
2005/0228495 A1 10/2005 Macoviak
2005/0228496 A1 10/2005 Mensah et al.
2005/0234546 A1 10/2005 Nugent et al.
2005/0240200 A1 10/2005 Bergheim
2005/0240262 A1 10/2005 White
2005/0240263 A1 10/2005 Fogarty et al.
2005/0251243 A1 11/2005 Seppala et al.
2005/0251250 A1 11/2005 Verhoeven et al.
2005/0251251 A1 11/2005 Cribier
2005/0251252 A1 11/2005 Stobie
2005/0256532 A1 11/2005 Nayak et al.
2005/0261759 A1 11/2005 Lambrecht et al.
2005/0267523 A1 12/2005 Devellian et al.
2005/0267560 A1 12/2005 Bates
2005/0267567 A1 12/2005 Shalev
2005/0267573 A9 12/2005 Macoviak et al.
2005/0283231 A1 12/2005 Haug et al.
2005/0283962 A1 12/2005 Boudjemline
2005/0288627 A1 12/2005 Mogul
2005/0288685 A1 12/2005 Gulles et al.
2005/0288706 A1 12/2005 Widomski et al.
2006/0004439 A1 1/2006 Spenser et al.
2006/0004442 A1 1/2006 Spenser et al.
2006/0004469 A1 1/2006 Sokel
2006/0009841 A1 1/2006 McGuckin et al.
2006/0009842 A1 1/2006 Huynh et al.
2006/0015168 A1 1/2006 Gunderson
2006/0025855 A1 2/2006 Lashinski et al.
2006/0025857 A1 2/2006 Bergheim et al.
2006/0028766 A1 2/2006 Khizroev
2006/0041218 A1 2/2006 Phelps et al.
2006/0047338 A1 3/2006 Jenson et al.
2006/0047343 A1 3/2006 Oviatt et al.
2006/0052736 A1 3/2006 Tweden et al.
2006/0052867 A1 3/2006 Revuelta et al.
2006/0058775 A1 3/2006 Stevens et al.
2006/0058864 A1 3/2006 Schaeffer et al.
2006/0058871 A1 3/2006 Zakay et al.
2006/0058872 A1 3/2006 Salahieh et al.
2006/0064151 A1 3/2006 Guterman et al.
2006/0069424 A1 3/2006 Acosta et al.
2006/0074477 A1 4/2006 Berthiaume et al.
2006/0074484 A1 4/2006 Huber
2006/0074485 A1 4/2006 Realyvasquez
2006/0077447 A1 4/2006 Sojian et al.
2006/0085060 A1 4/2006 Campbell
2006/0089711 A1 4/2006 Dolan
2006/0100685 A1 5/2006 Seguin et al.
2006/0111770 A1 5/2006 Pavcnik et al.
2006/0116757 A1 6/2006 Lashinski et al.
2006/0122692 A1 6/2006 Gilad et al.
2006/0135961 A1* 6/2006 Rosenman ......... A61B 17/0057
604/95.04
2006/0135964 A1 6/2006 Vesely
2006/0136034 A1 6/2006 Modesitt et al.
2006/0142846 A1 6/2006 Pavcnik et al.
2006/0142848 A1 6/2006 Gabbay
2006/0149360 A1 7/2006 Schwammenthal et al.
2006/0155312 A1 7/2006 Levine et al.
2006/0155366 A1 7/2006 LaDuca et al.
2006/0161248 A1 7/2006 Case et al.
2006/0161249 A1 7/2006 Realyvasquez et al.
2006/0161265 A1 7/2006 Levine et al.
2006/0167474 A1 7/2006 Bloom et al.
2006/0167543 A1 7/2006 Bailey et al.
2006/0173524 A1 8/2006 Salahieh et al.
2006/0178740 A1 8/2006 Stacchino et al.
2006/0190070 A1 8/2006 Dieck et al.
2006/0193885 A1 8/2006 Leonard Neethling et al.
2006/0195134 A1 8/2006 Crittenden
2006/0195183 A1 8/2006 Navia et al.
2006/0195186 A1 8/2006 Drews et al.
2006/0206192 A1 9/2006 Tower et al.
2006/0206202 A1 9/2006 Bonhoeffer et al.
2006/0210597 A1 9/2006 Hiles
2006/0212110 A1 9/2006 Osborne et al.
2006/0212111 A1 9/2006 Case et al.
2006/0217802 A1 9/2006 Ruiz et al.
2006/0224183 A1 10/2006 Freudenthal
2006/0229561 A1 10/2006 Huszar
2006/0229718 A1 10/2006 Marquez
2006/0229719 A1 10/2006 Marquez et al.
2006/0241745 A1 10/2006 Solem
2006/0246584 A1 11/2006 Covelli
2006/0247570 A1 11/2006 Pokorney
2006/0247763 A1 11/2006 Slater
2006/0253191 A1 11/2006 Salahieh et al.
2006/0259134 A1 11/2006 Schwammenthal et al.
2006/0259135 A1 11/2006 Navia et al.
2006/0259136 A1 11/2006 Nguyen et al.
2006/0259137 A1 11/2006 Artof et al.
2006/0265043 A1 11/2006 Mandrusov et al.
2006/0265056 A1 11/2006 Nguyen et al.
2006/0270958 A1 11/2006 George
2006/0271149 A1 11/2006 Berez et al.
2006/0271161 A1 11/2006 Meyer et al.
2006/0271166 A1 11/2006 Thill et al.
2006/0271175 A1 11/2006 Woolfson et al.
2006/0276872 A1 12/2006 Arbefeuille et al.
2006/0276873 A1 12/2006 Sato
2006/0276874 A1 12/2006 Wilson et al.
2006/0276882 A1 12/2006 Case et al.
2006/0276887 A1 12/2006 Brady et al.
2006/0282161 A1 12/2006 Huynh et al.
2006/0287668 A1 12/2006 Fawzi et al.
2006/0287717 A1 12/2006 Rowe et al.
2006/0287719 A1 12/2006 Rowe et al.
2006/0290027 A1 12/2006 O'Connor et al.
2006/0293745 A1 12/2006 Carpentier et al.
2007/0005129 A1 1/2007 Damm et al.

(56) References Cited

U.S. PATENT DOCUMENTS

| | | | |
|---|---|---|---|
| 2007/0005131 | A1 | 1/2007 | Taylor |
| 2007/0005132 | A1 | 1/2007 | Simionescu et al. |
| 2007/0010876 | A1 | 1/2007 | Salahieh et al. |
| 2007/0010877 | A1 | 1/2007 | Salahieh et al. |
| 2007/0010878 | A1 | 1/2007 | Rafiee et al. |
| 2007/0010887 | A1 | 1/2007 | Williams et al. |
| 2007/0016286 | A1 | 1/2007 | Herrmann et al. |
| 2007/0016288 | A1 | 1/2007 | Gurskis et al. |
| 2007/0020248 | A1 | 1/2007 | Everaerts et al. |
| 2007/0021826 | A1 | 1/2007 | Case et al. |
| 2007/0027518 | A1 | 2/2007 | Case et al. |
| 2007/0027520 | A1 | 2/2007 | Sherburne |
| 2007/0027533 | A1 | 2/2007 | Douk |
| 2007/0027535 | A1 | 2/2007 | Purdy et al. |
| 2007/0032856 | A1 | 2/2007 | Limon |
| 2007/0032879 | A1 | 2/2007 | Levine et al. |
| 2007/0038291 | A1 | 2/2007 | Case et al. |
| 2007/0038295 | A1 | 2/2007 | Case et al. |
| 2007/0043420 | A1 | 2/2007 | Lostetter |
| 2007/0043424 | A1 | 2/2007 | Pryor |
| 2007/0043431 | A1 | 2/2007 | Melsheimer |
| 2007/0043435 | A1 | 2/2007 | Seguin et al. |
| 2007/0050014 | A1 | 3/2007 | Johnson |
| 2007/0051377 | A1 | 3/2007 | Douk et al. |
| 2007/0055340 | A1 | 3/2007 | Pryor |
| 2007/0056346 | A1 | 3/2007 | Spenser et al. |
| 2007/0060998 | A1 | 3/2007 | Butterwick et al. |
| 2007/0061002 | A1 | 3/2007 | Paul et al. |
| 2007/0061008 | A1 | 3/2007 | Salahieh et al. |
| 2007/0073389 | A1 | 3/2007 | Bolduc et al. |
| 2007/0073392 | A1 | 3/2007 | Heyninck-Jantz et al. |
| 2007/0078504 | A1 | 4/2007 | Mialhe |
| 2007/0078509 | A1 | 4/2007 | Lotfy |
| 2007/0078510 | A1 | 4/2007 | Ryan |
| 2007/0088431 | A1 | 4/2007 | Bourang et al. |
| 2007/0093869 | A1 | 4/2007 | Bloom et al. |
| 2007/0093887 | A1 | 4/2007 | Case et al. |
| 2007/0093888 | A1 | 4/2007 | Thistle et al. |
| 2007/0100427 | A1 | 5/2007 | Perouse |
| 2007/0100435 | A1 | 5/2007 | Case et al. |
| 2007/0100439 | A1 | 5/2007 | Cangialosi et al. |
| 2007/0100440 | A1 | 5/2007 | Figulla et al. |
| 2007/0100449 | A1 | 5/2007 | O'Neil et al. |
| 2007/0112355 | A1 | 5/2007 | Salahieh et al. |
| 2007/0112358 | A1 | 5/2007 | Abbott et al. |
| 2007/0112415 | A1 | 5/2007 | Bartlett |
| 2007/0112422 | A1 | 5/2007 | Dehdashtian |
| 2007/0118214 | A1 | 5/2007 | Salahieh et al. |
| 2007/0123700 | A1 | 5/2007 | Ueda et al. |
| 2007/0123979 | A1 | 5/2007 | Perier et al. |
| 2007/0135889 | A1 | 6/2007 | Moore et al. |
| 2007/0142906 | A1 | 6/2007 | Figulla et al. |
| 2007/0142907 | A1 | 6/2007 | Moaddeb et al. |
| 2007/0155010 | A1 | 7/2007 | Farnsworth et al. |
| 2007/0156233 | A1 | 7/2007 | Kapadia et al. |
| 2007/0162102 | A1 | 7/2007 | Ryan et al. |
| 2007/0162103 | A1 | 7/2007 | Case et al. |
| 2007/0162107 | A1 | 7/2007 | Haug et al. |
| 2007/0162113 | A1 | 7/2007 | Sharkawy et al. |
| 2007/0173918 | A1 | 7/2007 | Dreher et al. |
| 2007/0173932 | A1 | 7/2007 | Cali et al. |
| 2007/0179592 | A1 | 8/2007 | Schaeffer |
| 2007/0179600 | A1 | 8/2007 | Vardi |
| 2007/0185513 | A1 | 8/2007 | Woolfson et al. |
| 2007/0185565 | A1 | 8/2007 | Schwammenthal et al. |
| 2007/0185571 | A1 | 8/2007 | Kapadia et al. |
| 2007/0198078 | A1 | 8/2007 | Berra et al. |
| 2007/0198097 | A1 | 8/2007 | Zegdi |
| 2007/0203391 | A1 | 8/2007 | Bloom et al. |
| 2007/0203503 | A1 | 8/2007 | Salahieh et al. |
| 2007/0203560 | A1 | 8/2007 | Forster et al. |
| 2007/0203576 | A1 | 8/2007 | Lee et al. |
| 2007/0208550 | A1 | 9/2007 | Cao et al. |
| 2007/0213813 | A1 | 9/2007 | Von Segesser et al. |
| 2007/0225681 | A1 | 9/2007 | House |
| 2007/0225802 | A1 | 9/2007 | Forsell |
| 2007/0232898 | A1 | 10/2007 | Huynh et al. |
| 2007/0233222 | A1 | 10/2007 | Roeder et al. |
| 2007/0233228 | A1 | 10/2007 | Eberhardt et al. |
| 2007/0233237 | A1 | 10/2007 | Krivoruchko |
| 2007/0233238 | A1 | 10/2007 | Huynh et al. |
| 2007/0238979 | A1 | 10/2007 | Huynh et al. |
| 2007/0239254 | A1 | 10/2007 | Chia et al. |
| 2007/0239265 | A1 | 10/2007 | Birdsall |
| 2007/0239266 | A1 | 10/2007 | Birdsall |
| 2007/0239269 | A1 | 10/2007 | Dolan et al. |
| 2007/0239271 | A1 | 10/2007 | Nguyen |
| 2007/0239273 | A1 | 10/2007 | Allen |
| 2007/0244543 | A1 | 10/2007 | Mitchell |
| 2007/0244544 | A1 | 10/2007 | Birdsall et al. |
| 2007/0244545 | A1 | 10/2007 | Birdsall et al. |
| 2007/0244546 | A1 | 10/2007 | Francis |
| 2007/0244551 | A1 | 10/2007 | Stobie |
| 2007/0244552 | A1 | 10/2007 | Salahieh et al. |
| 2007/0244553 | A1 | 10/2007 | Rafiee et al. |
| 2007/0244554 | A1 | 10/2007 | Rafiee et al. |
| 2007/0244555 | A1 | 10/2007 | Rafiee et al. |
| 2007/0244556 | A1 | 10/2007 | Rafiee et al. |
| 2007/0244557 | A1 | 10/2007 | Rafiee et al. |
| 2007/0250151 | A1 | 10/2007 | Pereira |
| 2007/0250160 | A1 | 10/2007 | Rafiee |
| 2007/0255386 | A1 | 11/2007 | Tenne |
| 2007/0255390 | A1 | 11/2007 | Ducke et al. |
| 2007/0255394 | A1 | 11/2007 | Ryan |
| 2007/0255396 | A1 | 11/2007 | Douk et al. |
| 2007/0260301 | A1 | 11/2007 | Chuter et al. |
| 2007/0260327 | A1 | 11/2007 | Case et al. |
| 2007/0265701 | A1 | 11/2007 | Gurskis et al. |
| 2007/0270751 | A1 | 11/2007 | Stangenes et al. |
| 2007/0270943 | A1 | 11/2007 | Solem et al. |
| 2007/0273813 | A1 | 11/2007 | Yoshida et al. |
| 2007/0282436 | A1 | 12/2007 | Pinchuk |
| 2007/0287717 | A1 | 12/2007 | Fanning et al. |
| 2007/0288000 | A1 | 12/2007 | Bonan |
| 2007/0288087 | A1 | 12/2007 | Fearnot et al. |
| 2007/0288089 | A1 | 12/2007 | Gurskis et al. |
| 2008/0004688 | A1 | 1/2008 | Spenser et al. |
| 2008/0004696 | A1 | 1/2008 | Vesely |
| 2008/0009934 | A1 | 1/2008 | Schneider et al. |
| 2008/0009940 | A1 | 1/2008 | Cribier |
| 2008/0015671 | A1 | 1/2008 | Bonhoeffer |
| 2008/0021546 | A1 | 1/2008 | Patz et al. |
| 2008/0021552 | A1 | 1/2008 | Gabbay |
| 2008/0022504 | A1 | 1/2008 | Melsheimer |
| 2008/0033534 | A1 | 2/2008 | Cook et al. |
| 2008/0033541 | A1 | 2/2008 | Gelbart et al. |
| 2008/0039925 | A1 | 2/2008 | Ishimaru et al. |
| 2008/0039934 | A1 | 2/2008 | Styrc |
| 2008/0045921 | A1 | 2/2008 | Anderson et al. |
| 2008/0048656 | A1 | 2/2008 | Tan et al. |
| 2008/0065001 | A1 | 3/2008 | Dinucci et al. |
| 2008/0065011 | A1 | 3/2008 | Marchand et al. |
| 2008/0065206 | A1 | 3/2008 | Liddicoat |
| 2008/0071361 | A1 | 3/2008 | Tuval et al. |
| 2008/0071362 | A1 | 3/2008 | Tuval et al. |
| 2008/0071363 | A1 | 3/2008 | Tuval et al. |
| 2008/0071366 | A1 | 3/2008 | Tuval et al. |
| 2008/0071368 | A1 | 3/2008 | Tuval et al. |
| 2008/0071369 | A1 | 3/2008 | Tuval et al. |
| 2008/0077227 | A1 | 3/2008 | Ouellette et al. |
| 2008/0077234 | A1 | 3/2008 | Styrc |
| 2008/0077236 | A1 | 3/2008 | Letac et al. |
| 2008/0082165 | A1 | 4/2008 | Wilson et al. |
| 2008/0082166 | A1 | 4/2008 | Styrc et al. |
| 2008/0086205 | A1 | 4/2008 | Gordy et al. |
| 2008/0097586 | A1 | 4/2008 | Pavcnik et al. |
| 2008/0102439 | A1 | 5/2008 | Tian et al. |
| 2008/0109070 | A1 | 5/2008 | Wagner et al. |
| 2008/0125859 | A1 | 5/2008 | Salahieh et al. |
| 2008/0127707 | A1 | 6/2008 | Kokish et al. |
| 2008/0133002 | A1 | 6/2008 | Gelbart et al. |
| 2008/0133003 | A1 | 6/2008 | Seguin et al. |
| 2008/0140188 | A1 | 6/2008 | Rahdert et al. |
| 2008/0140189 | A1 | 6/2008 | Nguyen et al. |

(56) References Cited

U.S. PATENT DOCUMENTS

2008/0147105 A1 6/2008 Wilson et al.
2008/0147180 A1 6/2008 Ghione et al.
2008/0147181 A1 6/2008 Ghione et al.
2008/0147182 A1 6/2008 Righini et al.
2008/0154355 A1 6/2008 Benichou et al.
2008/0154356 A1 6/2008 Obermiller et al.
2008/0161909 A1 7/2008 Kheradvar et al.
2008/0161910 A1 7/2008 Revuelta et al.
2008/0161911 A1 7/2008 Revuelta et al.
2008/0172119 A1 7/2008 Yamasaki et al.
2008/0177381 A1 7/2008 Navia et al.
2008/0183273 A1 7/2008 Mesana et al.
2008/0188928 A1 8/2008 Salahieh et al.
2008/0195193 A1 8/2008 Purdy et al.
2008/0195199 A1 8/2008 Kheradvar et al.
2008/0200977 A1 8/2008 Paul et al.
2008/0208209 A1 8/2008 Fischer et al.
2008/0208327 A1 8/2008 Rowe
2008/0208328 A1 8/2008 Antocci et al.
2008/0208332 A1 8/2008 Lamphere et al.
2008/0215143 A1 9/2008 Seguin
2008/0215144 A1 9/2008 Ryan et al.
2008/0221672 A1 9/2008 Lamphere et al.
2008/0221703 A1 9/2008 Que et al.
2008/0228254 A1 9/2008 Ryan
2008/0228263 A1 9/2008 Ryan
2008/0234443 A1 9/2008 Kiss et al.
2008/0234797 A1 9/2008 Styrc
2008/0234814 A1 9/2008 Salahieh et al.
2008/0243246 A1 10/2008 Ryan et al.
2008/0255651 A1 10/2008 Dwork
2008/0255660 A1 10/2008 Guyenot et al.
2008/0255661 A1 10/2008 Straubinger et al.
2008/0262590 A1 10/2008 Murray
2008/0262592 A1 10/2008 Jordan et al.
2008/0262593 A1 10/2008 Ryan et al.
2008/0262602 A1 10/2008 Wilk et al.
2008/0264102 A1 10/2008 Berra
2008/0269878 A1 10/2008 Iobbi
2008/0275549 A1 11/2008 Rowe
2008/0275550 A1 11/2008 Kheradvar et al.
2008/0288054 A1 11/2008 Pulnev et al.
2009/0005863 A1 1/2009 Goetz et al.
2009/0012356 A1 1/2009 Dann et al.
2009/0012600 A1 1/2009 Styrc et al.
2009/0030512 A1 1/2009 Thielen et al.
2009/0048656 A1 2/2009 Wen
2009/0054968 A1 2/2009 Bonhoeffer et al.
2009/0054969 A1 2/2009 Salahieh et al.
2009/0054976 A1 2/2009 Tuval et al.
2009/0062908 A1 3/2009 Bonhoeffer et al.
2009/0069886 A1 3/2009 Suri et al.
2009/0069887 A1 3/2009 Righini et al.
2009/0069889 A1 3/2009 Suri
2009/0069890 A1 3/2009 Suri
2009/0076598 A1 3/2009 Salahieh et al.
2009/0082844 A1 3/2009 Zacharias et al.
2009/0082858 A1 3/2009 Nugent et al.
2009/0085900 A1 4/2009 Weiner
2009/0093876 A1 4/2009 Nitzan et al.
2009/0093877 A1 4/2009 Keidar et al.
2009/0099640 A1 4/2009 Weng
2009/0099641 A1 4/2009 Wu et al.
2009/0099643 A1 4/2009 Hyodoh et al.
2009/0099653 A1 4/2009 Suri et al.
2009/0112309 A1 4/2009 Jaramillo et al.
2009/0138079 A1 5/2009 Tuval et al.
2009/0157175 A1 6/2009 Benichou
2009/0163951 A1 6/2009 Simmons et al.
2009/0164004 A1 6/2009 Cohn
2009/0164006 A1 6/2009 Seguin et al.
2009/0171432 A1 7/2009 Von Segesser et al.
2009/0171447 A1 7/2009 Von Segesser et al.
2009/0171456 A1 7/2009 Kveen et al.
2009/0182405 A1 7/2009 Arnault De La Menardiere et al.
2009/0192585 A1 7/2009 Bloom et al.
2009/0192586 A1 7/2009 Tabor et al.
2009/0192591 A1 7/2009 Ryan et al.
2009/0192601 A1 7/2009 Rafiee et al.
2009/0198316 A1 8/2009 Laske et al.
2009/0198323 A1 8/2009 Johnson et al.
2009/0210052 A1 8/2009 Forster et al.
2009/0216310 A1 8/2009 Straubinger et al.
2009/0216312 A1 8/2009 Straubinger et al.
2009/0216313 A1 8/2009 Straubinger et al.
2009/0222076 A1 9/2009 Figulla et al.
2009/0222082 A1 9/2009 Lock et al.
2009/0234407 A1 9/2009 Hastings et al.
2009/0234443 A1 9/2009 Ottma et al.
2009/0240264 A1 9/2009 Tuval et al.
2009/0240320 A1 9/2009 Tuval et al.
2009/0248143 A1 10/2009 Laham
2009/0259306 A1 10/2009 Rowe
2009/0264759 A1 10/2009 Byrd
2009/0264997 A1 10/2009 Salahieh et al.
2009/0276040 A1 11/2009 Rowe et al.
2009/0281619 A1 11/2009 Le et al.
2009/0287290 A1 11/2009 Macaulay et al.
2009/0287296 A1 11/2009 Manasse
2009/0287299 A1 11/2009 Tabor et al.
2009/0299462 A1 12/2009 Fawzi et al.
2009/0319037 A1 12/2009 Rowe et al.
2010/0004739 A1 1/2010 Vesely
2010/0004740 A1 1/2010 Seguin et al.
2010/0011564 A1 1/2010 Millwee et al.
2010/0030328 A1 2/2010 Seguin et al.
2010/0036479 A1 2/2010 Hill et al.
2010/0036485 A1 2/2010 Seguin
2010/0049313 A1 2/2010 Alon et al.
2010/0057051 A1 3/2010 Howat et al.
2010/0057185 A1 3/2010 Melsheimer et al.
2010/0063573 A1 3/2010 Hijlkema et al.
2010/0069852 A1 3/2010 Kelley
2010/0069916 A1 3/2010 Cully et al.
2010/0070027 A1 3/2010 Bonhoeffer et al.
2010/0082089 A1 4/2010 Quadri et al.
2010/0082094 A1 4/2010 Quadri et al.
2010/0087913 A1 4/2010 Rabkin et al.
2010/0094399 A1 4/2010 Dorn et al.
2010/0094411 A1 4/2010 Tuval et al.
2010/0100167 A1 4/2010 Bortlein et al.
2010/0121434 A1 5/2010 Paul et al.
2010/0131054 A1 5/2010 Tuval et al.
2010/0131057 A1 5/2010 Subramanian et al.
2010/0137979 A1 6/2010 Tuval et al.
2010/0145439 A1 6/2010 Seguin et al.
2010/0152840 A1 6/2010 Seguin et al.
2010/0160725 A1 6/2010 Kiser et al.
2010/0161045 A1 6/2010 Righini
2010/0168839 A1 7/2010 Braido et al.
2010/0174362 A1 7/2010 Straubinger et al.
2010/0185275 A1 7/2010 Richter et al.
2010/0185277 A1 7/2010 Braido et al.
2010/0191320 A1 7/2010 Straubinger et al.
2010/0191326 A1 7/2010 Alkhatib
2010/0198346 A1 8/2010 Keogh et al.
2010/0210991 A1 8/2010 Wilk et al.
2010/0219092 A1 9/2010 Salahieh et al.
2010/0234932 A1 9/2010 Arbefeuille et al.
2010/0234940 A1 9/2010 Dolan
2010/0239917 A1 9/2010 Lee et al.
2010/0249908 A1 9/2010 Chau et al.
2010/0249915 A1 9/2010 Zhang
2010/0249916 A1 9/2010 Zhang
2010/0249917 A1 9/2010 Zhang
2010/0249918 A1* 9/2010 Zhang .................. A61F 2/2418
623/2.11
2010/0256723 A1 10/2010 Murray
2010/0262231 A1 10/2010 Tuval et al.
2010/0268332 A1 10/2010 Tuval et al.
2010/0280459 A1 11/2010 Werner
2010/0280495 A1 11/2010 Paul et al.
2010/0286768 A1 11/2010 Alkhatib
2010/0292779 A1 11/2010 Straubinger et al.

(56) References Cited

U.S. PATENT DOCUMENTS

2010/0292780 A1 11/2010 Straubinger et al.
2010/0292785 A1 11/2010 Seguin et al.
2010/0298931 A1 11/2010 Quadri et al.
2011/0004297 A1 1/2011 Sogard et al.
2011/0015616 A1 1/2011 Straubinger et al.
2011/0022157 A1 1/2011 Essinger et al.
2011/0028290 A1 2/2011 Ozawa
2011/0029066 A1 2/2011 Gilad et al.
2011/0034852 A1 2/2011 Hausler et al.
2011/0040366 A1 2/2011 Goetz et al.
2011/0040374 A1 2/2011 Goetz et al.
2011/0071613 A1 3/2011 Wood et al.
2011/0093007 A1 4/2011 Abbott et al.
2011/0098805 A1 4/2011 Dwork et al.
2011/0106244 A1 5/2011 Ferrari et al.
2011/0118545 A1 5/2011 Williams et al.
2011/0137397 A1 6/2011 Chau et al.
2011/0166637 A1 7/2011 Irwin et al.
2011/0190862 A1 8/2011 Bashiri et al.
2011/0190874 A1 8/2011 Celermajer et al.
2011/0208290 A1 8/2011 Straubinger et al.
2011/0208297 A1 8/2011 Tuval et al.
2011/0224780 A1 9/2011 Tabor et al.
2011/0238159 A1 9/2011 Guyenot et al.
2011/0238167 A1 9/2011 Dove et al.
2011/0257729 A1 10/2011 Spenser et al.
2011/0257733 A1 10/2011 Dwork
2011/0257735 A1 10/2011 Salahieh et al.
2011/0264191 A1 10/2011 Rothstein
2011/0264196 A1 10/2011 Savage et al.
2011/0264198 A1 10/2011 Murray, III et al.
2011/0264203 A1 10/2011 Dwork et al.
2011/0276091 A1 11/2011 Melanson et al.
2011/0276121 A1 11/2011 Levine
2011/0276129 A1 11/2011 Salahieh et al.
2011/0288626 A1 11/2011 Straubinger et al.
2011/0288634 A1 11/2011 Tuval et al.
2011/0295363 A1 12/2011 Girard et al.
2011/0319989 A1 12/2011 Lane et al.
2012/0016469 A1 1/2012 Salahieh et al.
2012/0016471 A1 1/2012 Salahieh et al.
2012/0022633 A1 1/2012 Olson et al.
2012/0022642 A1 1/2012 Haug et al.
2012/0029627 A1 2/2012 Salahieh et al.
2012/0035719 A1 2/2012 Forster et al.
2012/0035720 A1 2/2012 Cali et al.
2012/0041547 A1 2/2012 Duffy et al.
2012/0041549 A1 2/2012 Salahieh et al.
2012/0041550 A1 2/2012 Salahieh et al.
2012/0046740 A1 2/2012 Paul et al.
2012/0053683 A1 3/2012 Salahieh et al.
2012/0059447 A1 3/2012 Zilla et al.
2012/0065464 A1 3/2012 Ellis et al.
2012/0078347 A1 3/2012 Braido et al.
2012/0078357 A1 3/2012 Conklin
2012/0078360 A1 3/2012 Rafiee
2012/0089224 A1 4/2012 Haug et al.
2012/0100182 A1 4/2012 Mooney et al.
2012/0101571 A1 4/2012 Thambar et al.
2012/0101572 A1 4/2012 Kovalsky et al.
2012/0116496 A1 5/2012 Chuter et al.
2012/0123515 A1 5/2012 Hosford et al.
2012/0123529 A1 5/2012 Levi et al.
2012/0130468 A1 5/2012 Khosravi et al.
2012/0132547 A1 5/2012 Salahieh et al.
2012/0136430 A1 5/2012 Sochman et al.
2012/0143084 A1 6/2012 Shoham
2012/0165957 A1 6/2012 Everland et al.
2012/0172982 A1 7/2012 Stacchino et al.
2012/0179244 A1 7/2012 Schankereli et al.
2012/0185030 A1 7/2012 Igaki et al.
2012/0197379 A1 8/2012 Laske et al.
2012/0197391 A1 8/2012 Alkhatib et al.
2012/0209374 A1 8/2012 Bonhoeffer et al.
2012/0209376 A1 8/2012 Hauser et al.
2012/0221100 A1 8/2012 Huber
2012/0226341 A1 9/2012 Schreck et al.
2012/0265296 A1 10/2012 McNamara et al.
2012/0283715 A1 11/2012 Mihalik et al.
2012/0283823 A1 11/2012 Bonhoeffer et al.
2012/0303113 A1 11/2012 Benichou et al.
2012/0303116 A1 11/2012 Gorman, III et al.
2012/0305441 A1 12/2012 Murray et al.
2012/0310332 A1 12/2012 Murray et al.
2012/0316637 A1 12/2012 Holm et al.
2012/0330408 A1 12/2012 Hillukka et al.
2012/0330409 A1 12/2012 Haug et al.
2013/0013057 A1 1/2013 Salahieh et al.
2013/0018457 A1 1/2013 Gregg et al.
2013/0023984 A1 1/2013 Conklin
2013/0030519 A1 1/2013 Tran et al.
2013/0030520 A1 1/2013 Lee et al.
2013/0046373 A1 2/2013 Cartledge et al.
2013/0053949 A1 2/2013 Pintor et al.
2013/0066342 A1 3/2013 Dell et al.
2013/0066419 A1 3/2013 Gregg
2013/0071441 A1 3/2013 Iwazawa et al.
2013/0073037 A1 3/2013 Gregg et al.
2013/0079867 A1 3/2013 Hoffman et al.
2013/0079869 A1 3/2013 Straubinger et al.
2013/0089655 A1 4/2013 Gregg
2013/0090728 A1 4/2013 Solem
2013/0090729 A1 4/2013 Gregg et al.
2013/0096664 A1 4/2013 Goetz et al.
2013/0116778 A1 5/2013 Gregg et al.
2013/0118949 A1 5/2013 Chang et al.
2013/0123757 A1 5/2013 Crisostomo et al.
2013/0123795 A1 5/2013 Gamarra et al.
2013/0123796 A1 5/2013 Sutton et al.
2013/0123898 A1 5/2013 Tung et al.
2013/0138207 A1 5/2013 Quadri et al.
2013/0144203 A1 6/2013 Wilk et al.
2013/0144276 A1 6/2013 Crisostomo et al.
2013/0158653 A1 6/2013 Gamarra et al.
2013/0158655 A1 6/2013 Sutton et al.
2013/0158656 A1 6/2013 Sutton et al.
2013/0166017 A1 6/2013 Cartledge et al.
2013/0178930 A1 7/2013 Straubinger et al.
2013/0184813 A1 7/2013 Quadri et al.
2013/0190865 A1 7/2013 Anderson
2013/0204359 A1 8/2013 Thubrikar et al.
2013/0231735 A1* 9/2013 Deem .................... A61F 2/243
623/2.11
2013/0245752 A1 9/2013 Goetz et al.
2013/0253342 A1 9/2013 Griswold et al.
2013/0253635 A1 9/2013 Straubinger et al.
2013/0253640 A1 9/2013 Meiri et al.
2013/0268067 A1 10/2013 Forster et al.
2013/0274865 A1 10/2013 Haverkost et al.
2013/0274870 A1 10/2013 Lombardi et al.
2013/0289698 A1 10/2013 Wang et al.
2013/0296999 A1 11/2013 Burriesci et al.
2013/0304199 A1 11/2013 Sutton et al.
2013/0310917 A1 11/2013 Richter et al.
2013/0310923 A1 11/2013 Kheradvar et al.
2013/0310928 A1 11/2013 Morriss et al.
2013/0325101 A1 12/2013 Goetz et al.
2013/0338755 A1 12/2013 Goetz et al.
2013/0345799 A1 12/2013 Lafontaine
2014/0012368 A1 1/2014 Sugimoto et al.
2014/0012370 A1 1/2014 Bonhoeffer et al.
2014/0018911 A1 1/2014 Zhou et al.
2014/0052239 A1 2/2014 Kong et al.
2014/0058501 A1 2/2014 Bonhoeffer et al.
2014/0083190 A1 3/2014 Kaack et al.
2014/0088680 A1 3/2014 Costello et al.
2014/0094904 A1 4/2014 Salahieh et al.
2014/0114390 A1 4/2014 Tobis et al.
2014/0114405 A1 4/2014 Paul et al.
2014/0114406 A1 4/2014 Salahieh et al.
2014/0114407 A1 4/2014 Rajamannan
2014/0121763 A1 5/2014 Duffy et al.
2014/0121766 A1 5/2014 Salahieh et al.
2014/0128969 A1 5/2014 Hill et al.

(56) References Cited

U.S. PATENT DOCUMENTS

| | | | |
|---|---|---|---|
| 2014/0135909 | A1 | 5/2014 | Carr et al. |
| 2014/0135912 | A1 | 5/2014 | Salahieh et al. |
| 2014/0207229 | A1 | 7/2014 | Shoemaker et al. |
| 2014/0222142 | A1 | 8/2014 | Kovalsky et al. |
| 2014/0236287 | A1 | 8/2014 | Clague et al. |
| 2014/0243962 | A1 | 8/2014 | Wilson et al. |
| 2014/0243963 | A1 | 8/2014 | Sheps et al. |
| 2014/0243967 | A1 | 8/2014 | Salahieh et al. |
| 2014/0249621 | A1 | 9/2014 | Eidenschink |
| 2014/0249622 | A1 | 9/2014 | Carmi et al. |
| 2014/0257473 | A1 | 9/2014 | Rajamannan |
| 2014/0277414 | A1 | 9/2014 | Kheradvar |
| 2014/0296962 | A1 | 10/2014 | Cartledge et al. |
| 2014/0309732 | A1 | 10/2014 | Solem |
| 2014/0316518 | A1 | 10/2014 | Kheradvar et al. |
| 2014/0330371 | A1 | 11/2014 | Gloss et al. |
| 2014/0343669 | A1 | 11/2014 | Lane et al. |
| 2014/0364799 | A1 | 12/2014 | Beauvais et al. |
| 2014/0379068 | A1 | 12/2014 | Thielen et al. |
| 2015/0012085 | A1 | 1/2015 | Salahieh et al. |
| 2015/0032056 | A1 | 1/2015 | Okamura et al. |
| 2015/0032198 | A1 | 1/2015 | Folk |
| 2015/0073540 | A1 | 3/2015 | Salahieh et al. |
| 2015/0073541 | A1 | 3/2015 | Salahieh et al. |
| 2015/0088252 | A1 | 3/2015 | Jenson et al. |
| 2015/0094804 | A1 | 4/2015 | Bonhoeffer et al. |
| 2015/0105857 | A1 | 4/2015 | Bonhoeffer et al. |
| 2015/0127092 | A1 | 5/2015 | Straubinger et al. |
| 2015/0127094 | A1 | 5/2015 | Salahieh et al. |
| 2015/0142102 | A1 | 5/2015 | Lafontaine et al. |
| 2015/0148894 | A1 | 5/2015 | Damm et al. |
| 2015/0209142 | A1 | 7/2015 | Paul et al. |
| 2015/0209146 | A1 | 7/2015 | Hill et al. |
| 2015/0223933 | A1 | 8/2015 | Haug et al. |
| 2015/0238315 | A1 | 8/2015 | Rabito et al. |
| 2015/0245909 | A1 | 9/2015 | Salahieh et al. |
| 2015/0272731 | A1 | 10/2015 | Racchini et al. |
| 2015/0320557 | A1 | 11/2015 | Sutton et al. |
| 2015/0335423 | A1 | 11/2015 | Gregg et al. |
| 2015/0352252 | A1 | 12/2015 | Nakamura et al. |
| 2015/0359997 | A1 | 12/2015 | Crisostomo et al. |
| 2016/0022418 | A1 | 1/2016 | Salahieh et al. |
| 2016/0045306 | A1 | 2/2016 | Agrawal et al. |
| 2016/0045307 | A1 | 2/2016 | Yohanan et al. |
| 2016/0051362 | A1 | 2/2016 | Cooper et al. |
| 2016/0067040 | A1 | 3/2016 | Agrawal et al. |
| 2016/0120645 | A1 | 5/2016 | Alon |
| 2016/0135951 | A1 | 5/2016 | Salahieh et al. |
| 2016/0143731 | A1 | 5/2016 | Backus et al. |
| 2016/0158003 | A1 | 6/2016 | Wallace et al. |
| 2016/0166384 | A1 | 6/2016 | Olson et al. |
| 2016/0199184 | A1 | 7/2016 | Ma et al. |
| 2016/0206423 | A1 | 7/2016 | O'Connor et al. |
| 2016/0213467 | A1 | 7/2016 | Backus et al. |
| 2016/0220359 | A1 | 8/2016 | Backus et al. |
| 2016/0220360 | A1 | 8/2016 | Lin et al. |
| 2016/0220365 | A1 | 8/2016 | Backus et al. |
| 2016/0250024 | A1 | 9/2016 | Hill et al. |
| 2016/0256271 | A1 | 9/2016 | Backus et al. |
| 2016/0262878 | A1 | 9/2016 | Backus et al. |
| 2016/0278923 | A1 | 9/2016 | Krans et al. |
| 2016/0346107 | A1 | 12/2016 | Matthison-Hansen et al. |
| 2016/0354203 | A1 | 12/2016 | Tuval et al. |
| 2016/0374793 | A1 | 12/2016 | Lafontaine et al. |
| 2016/0376063 | A1 | 12/2016 | Salahieh et al. |
| 2017/0000609 | A1 | 1/2017 | Gross et al. |
| 2017/0007400 | A1 | 1/2017 | Sogard et al. |
| 2017/0027654 | A1 | 2/2017 | Frimer et al. |
| 2017/0027693 | A1 | 2/2017 | Paul et al. |
| 2017/0049563 | A1 | 2/2017 | Straubinger et al. |
| 2017/0049568 | A1 | 2/2017 | Straubinger et al. |
| 2017/0056172 | A1 | 3/2017 | Salahieh et al. |
| 2017/0065410 | A1 | 3/2017 | Straubinger et al. |
| 2017/0087343 | A1 | 3/2017 | Assaf et al. |
| 2017/0095595 | A1 | 4/2017 | Nakamura |
| 2017/0143481 | A1 | 5/2017 | Morriss et al. |
| 2017/0189177 | A1 | 7/2017 | Schweich, Jr. et al. |
| 2017/0212723 | A1 | 7/2017 | Atarot et al. |
| 2017/0265849 | A1 | 9/2017 | Assaf et al. |
| 2017/0325954 | A1 | 11/2017 | Perszyk |
| 2017/0333230 | A1 | 11/2017 | Folan et al. |
| 2017/0348013 | A1 | 12/2017 | Mottola et al. |
| 2018/0325604 | A1 | 11/2018 | Atarot et al. |
| 2018/0368976 | A1 | 12/2018 | Bonhoeffer et al. |
| 2019/0328522 | A1 | 10/2019 | Straubinger et al. |
| 2020/0054449 | A1 | 2/2020 | Min et al. |
| 2020/0383717 | A1 | 12/2020 | Lederman et al. |
| 2021/0038313 | A1 | 2/2021 | Sholev et al. |
| 2021/0322153 | A1 | 10/2021 | Tuval et al. |
| 2022/0061987 | A1 | 3/2022 | Duffy |
| 2022/0079747 | A1 | 3/2022 | Girard et al. |
| 2022/0192765 | A1 | 6/2022 | Brasset et al. |
| 2022/0304803 | A1 | 9/2022 | Guyenot et al. |
| 2024/0008978 | A1 | 1/2024 | Nawalakhe et al. |
| 2024/0148503 | A1 | 5/2024 | Chu et al. |
| 2024/0164902 | A1 | 5/2024 | Lee et al. |
| 2024/0164903 | A1 | 5/2024 | Chu et al. |
| 2025/0288410 | A1 | 9/2025 | Girard et al. |
| 2026/0026932 | A1 | 1/2026 | Saffari et al. |

FOREIGN PATENT DOCUMENTS

| | | | |
|---|---|---|---|
| AU | 777443 | B2 | 10/2004 |
| AU | 778831 | B2 | 12/2004 |
| AU | 2001281277 | B2 | 9/2005 |
| AU | 2002329324 | B2 | 7/2007 |
| AU | 2006328896 | B2 | 8/2013 |
| CA | 2436258 | A1 | 1/2005 |
| CA | 2595233 | A1 | 7/2006 |
| CA | 2627409 | A1 | 5/2007 |
| CA | 2627555 | A1 | 5/2007 |
| CN | 1338951 | A | 3/2002 |
| CN | 1342443 | A | 4/2002 |
| CN | 1745727 | A | 3/2006 |
| CN | 2762776 | Y | 3/2006 |
| CN | 1897892 | A | 1/2007 |
| CN | 2933337 | Y | 8/2007 |
| CN | 101011298 | A | 8/2007 |
| CN | 101431963 | A | 5/2009 |
| CN | 101605509 | A | 12/2009 |
| CN | 101623217 | A | 1/2010 |
| CN | 101700199 | A | 5/2010 |
| CN | 101720211 | A | 6/2010 |
| CN | 102271626 | A | 12/2011 |
| CN | 102413793 | A | 4/2012 |
| CN | 103118630 | A | 5/2013 |
| DE | 3640745 | C2 | 3/1992 |
| DE | 4316971 | A1 | 11/1994 |
| DE | 19532846 | A1 | 3/1997 |
| DE | 19546692 | A1 | 6/1997 |
| DE | 19633901 | A1 | 2/1998 |
| DE | 20003874 | U1 | 5/2000 |
| DE | 19857887 | A1 | 7/2000 |
| DE | 10010073 | A1 | 9/2001 |
| DE | 10010074 | A1 | 10/2001 |
| DE | 10034105 | C1 | 4/2002 |
| DE | 10049813 | C1 | 4/2002 |
| DE | 10121210 | A1 | 11/2002 |
| DE | 19546692 | C2 | 11/2002 |
| DE | 10301026 | A1 | 2/2004 |
| DE | 10049812 | B4 | 6/2004 |
| DE | 10302447 | A1 | 7/2004 |
| DE | 10335948 | B3 | 2/2005 |
| DE | 10010074 | B4 | 4/2005 |
| DE | 19857887 | B4 | 5/2005 |
| DE | 10049815 | B4 | 10/2005 |
| DE | 10010073 | B4 | 12/2005 |
| DE | 102005051849 | A1 | 5/2007 |
| DE | 102005052628 | A1 | 5/2007 |
| DE | 202007005491 | U1 | 6/2007 |
| DE | 20221871 | U1 | 9/2008 |
| EP | 0084395 | A1 | 7/1983 |
| EP | 0103546 | B1 | 5/1988 |
| EP | 0144167 | B1 | 11/1989 |

(56) References Cited

FOREIGN PATENT DOCUMENTS

| | | | |
|---|---|---|---|
| EP | 0402036 | A1 | 12/1990 |
| EP | 0402176 | A2 | 12/1990 |
| EP | 0411118 | A1 | 2/1991 |
| EP | 0458877 | A1 | 12/1991 |
| EP | 0515324 | A1 | 11/1992 |
| EP | 0402176 | B1 | 4/1994 |
| EP | 0458877 | B1 | 5/1995 |
| EP | 0657147 | A2 | 6/1995 |
| EP | 0592410 | B1 | 10/1995 |
| EP | 0402036 | B1 | 4/1996 |
| EP | 0409929 | B1 | 4/1997 |
| EP | 0778775 | A1 | 6/1997 |
| EP | 0786970 | A1 | 8/1997 |
| EP | 0826346 | A1 | 3/1998 |
| EP | 0850607 | A1 | 7/1998 |
| EP | 0778775 | B1 | 1/1999 |
| EP | 0896813 | A2 | 2/1999 |
| EP | 0903122 | A2 | 3/1999 |
| EP | 0928615 | A1 | 7/1999 |
| EP | 0657147 | B1 | 8/1999 |
| EP | 0938877 | A2 | 9/1999 |
| EP | 0597967 | B1 | 12/1999 |
| EP | 0696447 | B1 | 1/2000 |
| EP | 0986348 | A1 | 3/2000 |
| EP | 1041942 | A1 | 10/2000 |
| EP | 1051204 | A2 | 11/2000 |
| EP | 1117446 | A1 | 7/2001 |
| EP | 0547135 | B1 | 1/2002 |
| EP | 0729364 | B1 | 1/2002 |
| EP | 1206179 | A1 | 5/2002 |
| EP | 0756498 | B1 | 7/2002 |
| EP | 0986348 | B1 | 9/2002 |
| EP | 1251804 | A1 | 10/2002 |
| EP | 1251805 | A2 | 10/2002 |
| EP | 0959815 | B1 | 12/2002 |
| EP | 0971649 | B1 | 12/2002 |
| EP | 1281357 | A2 | 2/2003 |
| EP | 1281375 | A2 | 2/2003 |
| EP | 0888142 | B1 | 5/2003 |
| EP | 1112097 | B1 | 6/2003 |
| EP | 0937439 | B1 | 9/2003 |
| EP | 1017868 | B1 | 9/2003 |
| EP | 1354569 | A1 | 10/2003 |
| EP | 1041943 | B1 | 3/2004 |
| EP | 1356793 | A3 | 3/2004 |
| EP | 0871414 | B1 | 4/2004 |
| EP | 1042045 | B1 | 5/2004 |
| EP | 0819013 | B1 | 6/2004 |
| EP | 1347785 | B1 | 7/2004 |
| EP | 0954248 | B1 | 9/2004 |
| EP | 1452153 | A1 | 9/2004 |
| EP | 0987998 | B1 | 10/2004 |
| EP | 1206179 | B1 | 10/2004 |
| EP | 1087727 | B1 | 11/2004 |
| EP | 1115452 | B1 | 11/2004 |
| EP | 1117446 | B1 | 11/2004 |
| EP | 1107710 | B1 | 12/2004 |
| EP | 1233731 | B1 | 12/2004 |
| EP | 1499366 | A1 | 1/2005 |
| EP | 1143879 | B1 | 3/2005 |
| EP | 1518518 | A2 | 3/2005 |
| EP | 1229864 | B1 | 4/2005 |
| EP | 1253875 | B1 | 4/2005 |
| EP | 1088529 | B1 | 6/2005 |
| EP | 1093771 | B1 | 6/2005 |
| EP | 1251803 | B1 | 6/2005 |
| EP | 1547533 | A2 | 6/2005 |
| EP | 1059894 | B1 | 7/2005 |
| EP | 1000590 | B1 | 8/2005 |
| EP | 1027013 | B1 | 8/2005 |
| EP | 1078610 | B1 | 8/2005 |
| EP | 0943302 | B1 | 10/2005 |
| EP | 1267753 | B1 | 10/2005 |
| EP | 1011523 | B1 | 11/2005 |
| EP | 1067869 | B1 | 11/2005 |
| EP | 1469797 | B1 | 11/2005 |
| EP | 1156757 | B1 | 12/2005 |
| EP | 1021141 | B1 | 1/2006 |
| EP | 1041942 | B1 | 6/2006 |
| EP | 1690515 | A1 | 8/2006 |
| EP | 1051204 | B1 | 12/2006 |
| EP | 1395208 | B1 | 1/2007 |
| EP | 1251805 | B1 | 3/2007 |
| EP | 1255510 | B1 | 4/2007 |
| EP | 1499366 | B1 | 7/2007 |
| EP | 1600121 | B1 | 7/2007 |
| EP | 1112042 | B1 | 11/2007 |
| EP | 1251797 | B1 | 11/2007 |
| EP | 1616531 | B1 | 12/2007 |
| EP | 1878407 | A1 | 1/2008 |
| EP | 1886649 | A2 | 2/2008 |
| EP | 1406561 | A4 | 3/2008 |
| EP | 1900343 | A2 | 3/2008 |
| EP | 1435878 | B1 | 4/2008 |
| EP | 1251804 | B1 | 7/2008 |
| EP | 1605871 | B1 | 7/2008 |
| EP | 1259195 | B1 | 10/2008 |
| EP | 1980220 | A1 | 10/2008 |
| EP | 1994913 | A2 | 11/2008 |
| EP | 2000115 | A2 | 12/2008 |
| EP | 1408882 | B1 | 2/2009 |
| EP | 1255510 | B3 | 3/2009 |
| EP | 1330213 | B1 | 3/2009 |
| EP | 1401359 | B1 | 8/2009 |
| EP | 1968491 | B1 | 7/2010 |
| EP | 1259193 | B1 | 11/2010 |
| EP | 1893132 | B1 | 3/2011 |
| EP | 2059192 | B1 | 7/2011 |
| EP | 1441672 | B1 | 9/2011 |
| EP | 2387977 | A1 | 11/2011 |
| EP | 1603493 | B1 | 12/2011 |
| EP | 1281375 | B1 | 2/2012 |
| EP | 2047824 | B1 | 5/2012 |
| EP | 2474287 | A1 | 7/2012 |
| EP | 2387977 | B1 | 11/2013 |
| EP | 1551274 | B1 | 12/2014 |
| EP | 2749254 | B1 | 6/2015 |
| EP | 1702247 | B1 | 8/2015 |
| EP | 1519697 | B1 | 11/2015 |
| EP | 1863545 | B1 | 11/2015 |
| EP | 1835948 | B1 | 2/2016 |
| EP | 1734902 | B1 | 6/2016 |
| EP | 1539047 | B1 | 11/2016 |
| EP | 1667614 | B1 | 12/2016 |
| EP | 1667614 | B2 | 4/2020 |
| EP | 4175594 | B1 | 5/2024 |
| FR | 2788217 | A1 | 7/2000 |
| FR | 2815844 | A1 | 5/2002 |
| FR | 2828263 | A1 | 2/2003 |
| GB | 2433700 | A | 7/2007 |
| GB | 2440809 | A | 2/2008 |
| JP | S5286296 | A | 7/1977 |
| JP | S54137896 | A | 9/1979 |
| JP | S62227352 | A | 10/1987 |
| JP | S6449571 | A | 2/1989 |
| JP | H0447576 | B2 | 8/1992 |
| JP | H07504091 | A | 5/1995 |
| JP | 2001526574 | A | 12/2001 |
| JP | 2002525168 | A | 8/2002 |
| JP | 2002525169 | A | 8/2002 |
| JP | 2002536115 | A | 10/2002 |
| JP | 2003515386 | A | 5/2003 |
| JP | 2003523262 | A | 8/2003 |
| JP | 2003524504 | A | 8/2003 |
| JP | 2004504111 | A | 2/2004 |
| JP | 2004283461 | A | 10/2004 |
| JP | 2005118585 | A | 5/2005 |
| JP | 2007521125 | A | 8/2007 |
| JP | 2007296375 | A | 11/2007 |
| JP | 2008506497 | A | 3/2008 |
| JP | 2008539985 | A | 11/2008 |
| JP | 4246433 | B2 | 4/2009 |
| JP | 2009131397 | A | 6/2009 |
| JP | 4295460 | B2 | 7/2009 |

(56) References Cited

FOREIGN PATENT DOCUMENTS

| | | | |
|---|---|---|---|
| JP | 2009534157 | A | 9/2009 |
| JP | 2010526609 | A | 8/2010 |
| JP | 4636794 | B2 | 2/2011 |
| JP | 4739223 | B2 | 8/2011 |
| JP | 4904362 | B2 | 3/2012 |
| JP | 4912395 | B2 | 4/2012 |
| JP | 5341455 | B2 | 11/2013 |
| JP | 2013540495 | A | 11/2013 |
| JP | 6144009 | B2 | 6/2017 |
| JP | 6449571 | B2 | 1/2019 |
| WO | WO-8402266 | A1 | 6/1984 |
| WO | WO-9009102 | A1 | 8/1990 |
| WO | WO-9014804 | A1 | 12/1990 |
| WO | WO-9117720 | A1 | 11/1991 |
| WO | WO-9203990 | A1 | 3/1992 |
| WO | WO-9212690 | A1 | 8/1992 |
| WO | WO-9214419 | A1 | 9/1992 |
| WO | WO-9217118 | A1 | 10/1992 |
| WO | WO-9301768 | A1 | 2/1993 |
| WO | WO-9315693 | A1 | 8/1993 |
| WO | WO-9320757 | A2 | 10/1993 |
| WO | WO-9504556 | A2 | 2/1995 |
| WO | WO-9504556 | A3 | 4/1995 |
| WO | WO-9511055 | A1 | 4/1995 |
| WO | WO-9524873 | A1 | 9/1995 |
| WO | WO-9528183 | A1 | 10/1995 |
| WO | WO-9528899 | A1 | 11/1995 |
| WO | WO-9529640 | A1 | 11/1995 |
| WO | WO-9529713 | A1 | 11/1995 |
| WO | WO-9613227 | A1 | 5/1996 |
| WO | WO-9614032 | A1 | 5/1996 |
| WO | WO-9624306 | A1 | 8/1996 |
| WO | WO-9630072 | A1 | 10/1996 |
| WO | WO-9632972 | A1 | 10/1996 |
| WO | WO-9635469 | A1 | 11/1996 |
| WO | WO-9639962 | A1 | 12/1996 |
| WO | WO-9639964 | A1 | 12/1996 |
| WO | WO-9639965 | A1 | 12/1996 |
| WO | WO-9640012 | A1 | 12/1996 |
| WO | WO-9713463 | A1 | 4/1997 |
| WO | WO-9713471 | A1 | 4/1997 |
| WO | WO-9724082 | A1 | 7/1997 |
| WO | WO-9727893 | A1 | 8/1997 |
| WO | WO-9727897 | A1 | 8/1997 |
| WO | WO-9727898 | A1 | 8/1997 |
| WO | WO-9728839 | A1 | 8/1997 |
| WO | WO-9732551 | A1 | 9/1997 |
| WO | WO-9732615 | A1 | 9/1997 |
| WO | WO-9743961 | A1 | 11/1997 |
| WO | WO-9748350 | A1 | 12/1997 |
| WO | WO-9803118 | A1 | 1/1998 |
| WO | WO-9806356 | A1 | 2/1998 |
| WO | WO-9808456 | A1 | 3/1998 |
| WO | WO-9810714 | A1 | 3/1998 |
| WO | WO-9811846 | A1 | 3/1998 |
| WO | WO-9814137 | A1 | 4/1998 |
| WO | WO-9816161 | A1 | 4/1998 |
| WO | WO-9819633 | A1 | 5/1998 |
| WO | WO-9824373 | A1 | 6/1998 |
| WO | WO-9825533 | A1 | 6/1998 |
| WO | WO-9825549 | A1 | 6/1998 |
| WO | WO-9829057 | A1 | 7/1998 |
| WO | WO-9836790 | A1 | 8/1998 |
| WO | WO-9838916 | A1 | 9/1998 |
| WO | WO-9838925 | A1 | 9/1998 |
| WO | WO-9838939 | A1 | 9/1998 |
| WO | WO-9838941 | A1 | 9/1998 |
| WO | WO-9839038 | A1 | 9/1998 |
| WO | WO-9843556 | A1 | 10/1998 |
| WO | WO-9844869 | A1 | 10/1998 |
| WO | WO-9846115 | A2 | 10/1998 |
| WO | WO-9846119 | A1 | 10/1998 |
| WO | WO-9846165 | A1 | 10/1998 |
| WO | WO-9849964 | A1 | 11/1998 |
| WO | WO-9850103 | A1 | 11/1998 |
| WO | WO-9853759 | A2 | 12/1998 |
| WO | WO-9853761 | A1 | 12/1998 |
| WO | WO-9855027 | A2 | 12/1998 |
| WO | WO-9855047 | A1 | 12/1998 |
| WO | WO-9857590 | A1 | 12/1998 |
| WO | WO-9857591 | A1 | 12/1998 |
| WO | WO-9857592 | A1 | 12/1998 |
| WO | WO-9857599 | A2 | 12/1998 |
| WO | WO-9907296 | A1 | 2/1999 |
| WO | WO-9908624 | A1 | 2/1999 |
| WO | WO-9915112 | A1 | 4/1999 |
| WO | WO-9915220 | A1 | 4/1999 |
| WO | WO-9917671 | A1 | 4/1999 |
| WO | WO-9917683 | A1 | 4/1999 |
| WO | WO-9921490 | A1 | 5/1999 |
| WO | WO-9921510 | A1 | 5/1999 |
| WO | WO-9922655 | A1 | 5/1999 |
| WO | WO-9922656 | A1 | 5/1999 |
| WO | WO-9922658 | A1 | 5/1999 |
| WO | WO-9925273 | A1 | 5/1999 |
| WO | WO-9927985 | A1 | 6/1999 |
| WO | WO-9933414 | A1 | 7/1999 |
| WO | WO-9935977 | A1 | 7/1999 |
| WO | WO-9935979 | A1 | 7/1999 |
| WO | WO-9935980 | A1 | 7/1999 |
| WO | WO-9936000 | A1 | 7/1999 |
| WO | WO-9936001 | A1 | 7/1999 |
| WO | WO-9937337 | A2 | 7/1999 |
| WO | WO-9938459 | A2 | 8/1999 |
| WO | WO-9940853 | A1 | 8/1999 |
| WO | WO-9940868 | A1 | 8/1999 |
| WO | WO-9940963 | A1 | 8/1999 |
| WO | WO-9940964 | A1 | 8/1999 |
| WO | WO-9942058 | A1 | 8/1999 |
| WO | WO-9944524 | A2 | 9/1999 |
| WO | WO-9944540 | A2 | 9/1999 |
| WO | WO-9944542 | A2 | 9/1999 |
| WO | WO-9947071 | A1 | 9/1999 |
| WO | WO-9947075 | A1 | 9/1999 |
| WO | WO-9948545 | A1 | 9/1999 |
| WO | WO-9948549 | A2 | 9/1999 |
| WO | WO-9949793 | A1 | 10/1999 |
| WO | WO-9949910 | A2 | 10/1999 |
| WO | WO-9951162 | A1 | 10/1999 |
| WO | WO-9951165 | A1 | 10/1999 |
| WO | WO-9953863 | A1 | 10/1999 |
| WO | WO-9953987 | A1 | 10/1999 |
| WO | WO-9955406 | A1 | 11/1999 |
| WO | WO-9960941 | A1 | 12/1999 |
| WO | WO-9962430 | A1 | 12/1999 |
| WO | WO-9966863 | A2 | 12/1999 |
| WO | WO-0002503 | A1 | 1/2000 |
| WO | WO-0009059 | A2 | 2/2000 |
| WO | WO-0009195 | A1 | 2/2000 |
| WO | WO-0010623 | A1 | 3/2000 |
| WO | WO-0012029 | A1 | 3/2000 |
| WO | WO-0013722 | A1 | 3/2000 |
| WO | WO-0015146 | A1 | 3/2000 |
| WO | WO-0015147 | A1 | 3/2000 |
| WO | WO-0015148 | A1 | 3/2000 |
| WO | WO-0015149 | A1 | 3/2000 |
| WO | WO-0015275 | A2 | 3/2000 |
| WO | WO-0016848 | A1 | 3/2000 |
| WO | WO-0018302 | A2 | 4/2000 |
| WO | WO-0018323 | A2 | 4/2000 |
| WO | WO-0018325 | A1 | 4/2000 |
| WO | WO-0018326 | A1 | 4/2000 |
| WO | WO-0018330 | A1 | 4/2000 |
| WO | WO-0018331 | A2 | 4/2000 |
| WO | WO-0018333 | A1 | 4/2000 |
| WO | WO-0018445 | A1 | 4/2000 |
| WO | WO-0018462 | A2 | 4/2000 |
| WO | WO-0021436 | A1 | 4/2000 |
| WO | WO-0021461 | A2 | 4/2000 |
| WO | WO-0021463 | A1 | 4/2000 |
| WO | WO-0021464 | A1 | 4/2000 |
| WO | WO-0024449 | A1 | 5/2000 |
| WO | WO-0025702 | A1 | 5/2000 |
| WO | WO-0028922 | A1 | 5/2000 |

(56) References Cited

FOREIGN PATENT DOCUMENTS

| | | | |
|---|---|---|---|
| WO | WO-0028924 | A2 | 5/2000 |
| WO | WO-0033725 | A2 | 6/2000 |
| WO | WO-0035376 | A1 | 6/2000 |
| WO | WO-0036997 | A1 | 6/2000 |
| WO | WO-0041632 | A1 | 7/2000 |
| WO | WO-0041633 | A1 | 7/2000 |
| WO | WO-0041652 | A1 | 7/2000 |
| WO | WO-0043051 | A1 | 7/2000 |
| WO | WO-0044211 | A1 | 7/2000 |
| WO | WO-0044308 | A2 | 8/2000 |
| WO | WO-0044311 | A2 | 8/2000 |
| WO | WO-0044313 | A1 | 8/2000 |
| WO | WO-0044331 | A1 | 8/2000 |
| WO | WO-0045711 | A1 | 8/2000 |
| WO | WO-0045874 | A1 | 8/2000 |
| WO | WO-0045886 | A2 | 8/2000 |
| WO | WO-0047136 | A1 | 8/2000 |
| WO | WO-0047139 | A1 | 8/2000 |
| WO | WO-0048531 | A1 | 8/2000 |
| WO | WO-0049952 | A1 | 8/2000 |
| WO | WO-0049954 | A2 | 8/2000 |
| WO | WO-0049956 | A1 | 8/2000 |
| WO | WO-0049970 | A1 | 8/2000 |
| WO | WO-0053122 | A1 | 9/2000 |
| WO | WO-0053125 | A1 | 9/2000 |
| WO | WO-0054660 | A1 | 9/2000 |
| WO | WO-0054661 | A1 | 9/2000 |
| WO | WO-0056224 | A1 | 9/2000 |
| WO | WO-0056225 | A1 | 9/2000 |
| WO | WO-0056387 | A1 | 9/2000 |
| WO | WO-0060995 | A2 | 10/2000 |
| WO | WO-0062714 | A1 | 10/2000 |
| WO | WO-0066007 | A1 | 11/2000 |
| WO | WO-0066009 | A1 | 11/2000 |
| WO | WO-0066035 | A1 | 11/2000 |
| WO | WO-0067661 | A2 | 11/2000 |
| WO | WO-0069345 | A1 | 11/2000 |
| WO | WO-0069367 | A1 | 11/2000 |
| WO | WO-0069504 | A1 | 11/2000 |
| WO | WO-0071195 | A1 | 11/2000 |
| WO | WO-0078226 | A1 | 12/2000 |
| WO | WO-0105331 | A1 | 1/2001 |
| WO | WO-0106959 | A1 | 2/2001 |
| WO | WO-0108566 | A1 | 2/2001 |
| WO | WO-0108596 | A1 | 2/2001 |
| WO | WO-0108602 | A1 | 2/2001 |
| WO | WO-0110209 | A1 | 2/2001 |
| WO | WO-0110320 | A1 | 2/2001 |
| WO | WO-0110340 | A1 | 2/2001 |
| WO | WO-0110341 | A2 | 2/2001 |
| WO | WO-0110343 | A1 | 2/2001 |
| WO | WO-0110347 | A1 | 2/2001 |
| WO | WO-0110348 | A1 | 2/2001 |
| WO | WO-0110349 | A1 | 2/2001 |
| WO | WO-0110350 | A1 | 2/2001 |
| WO | WO-0117440 | A1 | 3/2001 |
| WO | WO-0117456 | A1 | 3/2001 |
| WO | WO-0135864 | A1 | 5/2001 |
| WO | WO-0135870 | A1 | 5/2001 |
| WO | WO-0136870 | A1 | 5/2001 |
| WO | WO-0139700 | A1 | 6/2001 |
| WO | WO-0141679 | A1 | 6/2001 |
| WO | WO-0149185 | A1 | 7/2001 |
| WO | WO-0149187 | A1 | 7/2001 |
| WO | WO-0149213 | A2 | 7/2001 |
| WO | WO-0151104 | A1 | 7/2001 |
| WO | WO-0154625 | A1 | 8/2001 |
| WO | WO-0158503 | A1 | 8/2001 |
| WO | WO-0162189 | A1 | 8/2001 |
| WO | WO-0047139 | A9 | 9/2001 |
| WO | WO-0164137 | A1 | 9/2001 |
| WO | WO-0176510 | A2 | 10/2001 |
| WO | WO-0182837 | A2 | 11/2001 |
| WO | WO-0197715 | A1 | 12/2001 |
| WO | WO-0211647 | A2 | 2/2002 |
| WO | WO-0219926 | A1 | 3/2002 |
| WO | WO-0222054 | A1 | 3/2002 |
| WO | WO-0224118 | A1 | 3/2002 |
| WO | WO-0236048 | A1 | 5/2002 |
| WO | WO-0241789 | A2 | 5/2002 |
| WO | WO-0243620 | A1 | 6/2002 |
| WO | WO-0247575 | A2 | 6/2002 |
| WO | WO-0249540 | A2 | 6/2002 |
| WO | WO-02051489 | A2 | 7/2002 |
| WO | WO-02056798 | A2 | 7/2002 |
| WO | WO-02056955 | A1 | 7/2002 |
| WO | WO-02058745 | A1 | 8/2002 |
| WO | WO-02060509 | A1 | 8/2002 |
| WO | WO-02067782 | A2 | 9/2002 |
| WO | WO-02069842 | A2 | 9/2002 |
| WO | WO-02076349 | A1 | 10/2002 |
| WO | WO-02100297 | A2 | 12/2002 |
| WO | WO-02100301 | A1 | 12/2002 |
| WO | WO-02102286 | A1 | 12/2002 |
| WO | WO-03003943 | A2 | 1/2003 |
| WO | WO-03003949 | A2 | 1/2003 |
| WO | WO-03007795 | A2 | 1/2003 |
| WO | WO-03009785 | A1 | 2/2003 |
| WO | WO-03011195 | A2 | 2/2003 |
| WO | WO-03013239 | A2 | 2/2003 |
| WO | WO-03015851 | A1 | 2/2003 |
| WO | WO-03028592 | A1 | 4/2003 |
| WO | WO-03030776 | A2 | 4/2003 |
| WO | WO-03032869 | A1 | 4/2003 |
| WO | WO-03032870 | A1 | 4/2003 |
| WO | WO-03037222 | A2 | 5/2003 |
| WO | WO-03037227 | A2 | 5/2003 |
| WO | WO-03047460 | A2 | 6/2003 |
| WO | WO-03047468 | A1 | 6/2003 |
| WO | WO-03047648 | A2 | 6/2003 |
| WO | WO-03051231 | A2 | 6/2003 |
| WO | WO-03063729 | A2 | 8/2003 |
| WO | WO-03079928 | A2 | 10/2003 |
| WO | WO-03079932 | A2 | 10/2003 |
| WO | WO-03079933 | A1 | 10/2003 |
| WO | WO-03088873 | A1 | 10/2003 |
| WO | WO-03015851 | B1 | 11/2003 |
| WO | WO-03063729 | A3 | 11/2003 |
| WO | WO-03092554 | A1 | 11/2003 |
| WO | WO-03094793 | A1 | 11/2003 |
| WO | WO-03094797 | A1 | 11/2003 |
| WO | WO-03096932 | A1 | 11/2003 |
| WO | WO-03096935 | A1 | 11/2003 |
| WO | WO-03101195 | A1 | 12/2003 |
| WO | WO-03103949 | A1 | 12/2003 |
| WO | WO-03003949 | A3 | 1/2004 |
| WO | WO-2004004597 | A2 | 1/2004 |
| WO | WO-2004006803 | A1 | 1/2004 |
| WO | WO-2004006804 | A1 | 1/2004 |
| WO | WO-2004014256 | A1 | 2/2004 |
| WO | WO-2004016200 | A1 | 2/2004 |
| WO | WO-2004016201 | A2 | 2/2004 |
| WO | WO-2004019811 | A2 | 3/2004 |
| WO | WO-2004019817 | A1 | 3/2004 |
| WO | WO-2004019825 | A1 | 3/2004 |
| WO | WO-2004021922 | A2 | 3/2004 |
| WO | WO-2004023980 | A2 | 3/2004 |
| WO | WO-2004019811 | A9 | 4/2004 |
| WO | WO-2004026117 | A2 | 4/2004 |
| WO | WO-2004026173 | A2 | 4/2004 |
| WO | WO-2004028399 | A2 | 4/2004 |
| WO | WO-2004030515 | A2 | 4/2004 |
| WO | WO-2004041126 | A1 | 5/2004 |
| WO | WO-2004043293 | A2 | 5/2004 |
| WO | WO-2004043301 | A1 | 5/2004 |
| WO | WO-2004047681 | A1 | 6/2004 |
| WO | WO-2004058106 | A2 | 7/2004 |
| WO | WO-2004062980 | A1 | 7/2004 |
| WO | WO-2004058106 | A3 | 8/2004 |
| WO | WO-2004064671 | A2 | 8/2004 |
| WO | WO-2004066876 | A1 | 8/2004 |
| WO | WO-2004071352 | A1 | 8/2004 |
| WO | WO-2004082527 | A2 | 9/2004 |
| WO | WO-2004082528 | A2 | 9/2004 |

(56) References Cited

FOREIGN PATENT DOCUMENTS

WO WO-2004082536 A1 9/2004
WO WO-2004089250 A1 10/2004
WO WO-2004089253 A1 10/2004
WO WO-2004093728 A2 11/2004
WO WO-2004096100 A1 11/2004
WO WO-2004105651 A1 12/2004
WO WO-2005002466 A2 1/2005
WO WO-2005004753 A1 1/2005
WO WO-2005007343 A1 1/2005
WO WO-2005009285 A2 2/2005
WO WO-2005011534 A1 2/2005
WO WO-2005011535 A2 2/2005
WO WO-2005021063 A2 3/2005
WO WO-2005023155 A1 3/2005
WO WO-2005027790 A1 3/2005
WO WO-2005027797 A1 3/2005
WO WO-2005032622 A2 4/2005
WO WO-2005034812 A1 4/2005
WO WO-2005010215 A3 5/2005
WO WO-2005046528 A1 5/2005
WO WO-2005046529 A1 5/2005
WO WO-2005048883 A1 6/2005
WO WO-2005062980 A2 7/2005
WO WO-2005063980 A1 7/2005
WO WO-2005065585 A1 7/2005
WO WO-2005065594 A1 7/2005
WO WO-2005070343 A1 8/2005
WO WO-2005072654 A1 8/2005
WO WO-2005076890 A2 8/2005
WO WO-2005084595 A1 9/2005
WO WO-2005087140 A1 9/2005
WO WO-2005096993 A1 10/2005
WO WO-2005102015 A2 11/2005
WO WO-2005110240 A1 11/2005
WO WO-2005112779 A1 12/2005
WO WO-2006005015 A2 1/2006
WO WO-2006009690 A1 1/2006
WO WO-2006026371 A1 3/2006
WO WO-2006027499 A2 3/2006
WO WO-2005062980 A3 5/2006
WO WO-2006058163 A2 6/2006
WO WO-2006065949 A2 6/2006
WO WO-2006066327 A1 6/2006
WO WO-2006068944 A2 6/2006
WO WO-2006070372 A2 7/2006
WO WO-2006076890 A1 7/2006
WO WO-2006083763 A1 8/2006
WO WO-2006086135 A2 8/2006
WO WO-2006086736 A2 8/2006
WO WO-2006089517 A1 8/2006
WO WO-2006093795 A1 9/2006
WO WO-2006102063 A2 9/2006
WO WO-2006108090 A2 10/2006
WO WO-2006118766 A1 11/2006
WO WO-2006124649 A2 11/2006
WO WO-2006127756 A2 11/2006
WO WO-2006127765 A1 11/2006
WO WO-2006129441 A1 12/2006
WO WO-2006132948 A1 12/2006
WO WO-2006133959 A1 12/2006
WO WO-2006138391 A2 12/2006
WO WO-2007009117 A1 1/2007
WO WO-2007009609 A1 1/2007
WO WO-2007013999 A2 2/2007
WO WO-2007033093 A2 3/2007
WO WO-2007035471 A2 3/2007
WO WO-2005102015 A3 4/2007
WO WO-2006138391 A9 4/2007
WO WO-2007044285 A2 4/2007
WO WO-2007047488 A2 4/2007
WO WO-2007047945 A2 4/2007
WO WO-2007048529 A1 5/2007
WO WO-2007051620 A1 5/2007
WO WO-2007053243 A2 5/2007
WO WO-2007058847 A2 5/2007
WO WO-2007059252 A1 5/2007
WO WO-2006086736 A3 6/2007
WO WO-2007071436 A2 6/2007
WO WO-2007092354 A2 8/2007
WO WO-2007097983 A2 8/2007
WO WO-2007098232 A2 8/2007
WO WO-2007053243 A3 9/2007
WO WO-2007120543 A1 10/2007
WO WO-2007071436 A3 11/2007
WO WO-2007123658 A1 11/2007
WO WO-2007123956 A2 11/2007
WO WO-2007127351 A1 11/2007
WO WO-2007127352 A1 11/2007
WO WO-2007033093 A3 1/2008
WO WO-2007071436 B1 1/2008
WO WO-2008028569 A1 3/2008
WO WO-2008031103 A2 3/2008
WO WO-2008035337 A2 3/2008
WO WO-2008040555 A2 4/2008
WO WO-2008045949 A2 4/2008
WO WO-2008047354 A2 4/2008
WO WO-2008051554 A2 5/2008
WO WO-2008070442 A1 6/2008
WO WO-2008070797 A2 6/2008
WO WO-2008079962 A1 7/2008
WO WO-2008098191 A2 8/2008
WO WO-2008100599 A1 8/2008
WO WO-2008101083 A2 8/2008
WO WO-2008125153 A1 10/2008
WO WO-2008137603 A2 11/2008
WO WO-2008138584 A1 11/2008
WO WO-2008150529 A1 12/2008
WO WO-2009002548 A1 12/2008
WO WO-2009024859 A2 2/2009
WO WO-2009029199 A1 3/2009
WO WO-2009042196 A2 4/2009
WO WO-2009045334 A1 4/2009
WO WO-2009045338 A1 4/2009
WO WO-2009053497 A1 4/2009
WO WO-2009054397 A1 4/2009
WO WO-2007044285 A3 5/2009
WO WO-2009061389 A2 5/2009
WO WO-2009085206 A2 7/2009
WO WO-2009091509 A1 7/2009
WO WO-2009094188 A2 7/2009
WO WO-2009094501 A1 7/2009
WO WO-2009100198 A2 8/2009
WO WO-2009106545 A1 9/2009
WO WO-2009108615 A1 9/2009
WO WO-2009111241 A2 9/2009
WO WO-2009149462 A2 12/2009
WO WO-2009155561 A2 12/2009
WO WO-2010022138 A2 2/2010
WO WO-2010042950 A2 4/2010
WO WO-2010043950 A2 4/2010
WO WO-2010044851 A1 4/2010
WO WO-2010045238 A2 4/2010
WO WO-2010045297 A2 4/2010
WO WO-2010049160 A1 5/2010
WO WO-2010083558 A1 7/2010
WO WO-2010086460 A1 8/2010
WO WO-2010098857 A1 9/2010
WO WO-2010104638 A2 9/2010
WO WO-2010045238 A3 10/2010
WO WO-2010141626 A2 12/2010
WO WO-2011008812 A2 1/2011
WO WO-2011008853 A2 1/2011
WO WO-2011035327 A1 3/2011
WO WO-2011051043 A1 5/2011
WO WO-2011057087 A1 5/2011
WO WO-2011060386 A2 5/2011
WO WO-2011102968 A1 8/2011
WO WO-2011104269 A1 9/2011
WO WO-2011120050 A1 9/2011
WO WO-2011133368 A1 10/2011
WO WO-2011144351 A2 11/2011
WO WO-2011147849 A1 12/2011
WO WO-2012002228 A1 1/2012
WO WO-2012023980 A1 2/2012

(56) References Cited

FOREIGN PATENT DOCUMENTS

| | | | |
|---|---|---|---|
| WO | WO-2012036742 | A2 | 3/2012 |
| WO | WO-2012038550 | A1 | 3/2012 |
| WO | WO-2012039748 | A2 | 3/2012 |
| WO | WO-2012082952 | A2 | 6/2012 |
| WO | WO-2012106491 | A1 | 8/2012 |
| WO | WO-2012116368 | A2 | 8/2012 |
| WO | WO-2012142189 | A1 | 10/2012 |
| WO | WO-2012145546 | A1 | 10/2012 |
| WO | WO-2012162228 | A1 | 11/2012 |
| WO | WO-2013009975 | A1 | 1/2013 |
| WO | WO-2013028387 | A2 | 2/2013 |
| WO | WO-2013033791 | A1 | 3/2013 |
| WO | WO-2013074671 | A1 | 5/2013 |
| WO | WO-2013096545 | A1 | 6/2013 |
| WO | WO-2013134214 | A1 | 9/2013 |
| WO | WO-2014056644 | A1 | 4/2014 |
| WO | WO-2014072439 | A1 | 5/2014 |
| WO | WO-2014072439 | A9 | 7/2014 |
| WO | WO-2014143126 | A1 | 9/2014 |
| WO | WO-2014144937 | A2 | 9/2014 |
| WO | WO-2015006139 | A1 | 1/2015 |
| WO | WO-2015028209 | A1 | 3/2015 |
| WO | WO-2015063118 | A1 | 5/2015 |
| WO | WO-2015175524 | A1 | 11/2015 |
| WO | WO-2016093877 | A1 | 6/2016 |
| WO | WO-2016126511 | A2 | 8/2016 |
| WO | WO-2021242607 | A1 | 12/2021 |
| WO | WO-2022144741 | A1 | 7/2022 |
| WO | WO-2023156879 | A1 | 8/2023 |

OTHER PUBLICATIONS

US 8,062,356 B2, 11/2011, Salahieh et al. (withdrawn)
US 8,062,357 B2, 11/2011, Salahieh et al. (withdrawn)
US 8,075,614 B2, 12/2011, Salahieh et al. (withdrawn)
US 8,133,271 B2, 03/2012, Salahieh et al. (withdrawn)
US 8,211,170 B2, 07/2012, Paul et al. (withdrawn)

Akins C.W., et al., "Risk of Reoperative Valve Replacement for Failed Mitral and Aortic Bioprostheses," The Annals of Thoracic Surgery, 65:545-1552 (Jan. 1998). Retrieved from the Internet: URL: http://ats.ctsnetjournals.org/cgi/contenUfull/65/6/1545 (Jan. 1998).

Allen et al., "What are the characteristics of the ideal endovascular graft for abdominal aortic aneurysm exclusion?", J. Endovasc. Surg., vol. 4(2), May 1997, pp. 195-202.

Anabtawi I.N., et al., "Experimental evaluation of myocardial tunnelization as a method of myocardial revascularization," Journal of Thoracic and Cardiovascular Surgery, 58(5):638-646 (Nov. 1969).

Andersen H.R., et al., "Transluminal Implantation of Artificial Heart Valves. Description of a New Expandable Aortic Valve and Initial Results with Implantation by Catheter Technique in Closed Chest Pigs," European Heart Journal, May 1992, vol. 13, pp. 704-708.

"Aortenklappenbioprothese erfolgreich in der Entwicklung," May 16, 2003, 1 page (with English Translation).

Archie J.P., et al., "Intramyocardial Pressure: Effect of Preload on Transmural Distribution of Systolic Coronary Blood Flow," The American Journal of Cardiology, 35(6):904-911 (Jun. 1975).

Baba H., et al., "Hemodynamic effects of venous valves in aorta-coronary bypass grafts," The Journal of Thoracic and Cardiovascular Surgery, 71(5):774-778 (May 1976).

Babaliaros V., et al., "State of the Art Percutaneous Intervention for the Treatment of Valvular Heart Disease: A Review of the Current Technologies and Ongoing Research in the Field of Percutaneous Valve Replacement and Repair," Cardiology, 2007, vol. 107, pp. 87-96.

Bailey S.R., "Percutaneous Expandable Prosthetic Valves," Textbook of Interventional Cardiology, Second Edition, W.B. Saunders Company, 1994, vol. 2, pp. 1268-1276.

Block P.C., et al., "Percutaneous Approaches to Valvular Heart Disease," Current Cardiology Reports, Mar. 2005, vol. 7(2), pp. 108-113.

Blum et al., "Endoluminal Stent—Grafts for Intrarenal Abdominal Aortic Aneurysms." New Engl. J. Med., 336:13-20 (Jan. 1997).

Bonhoeffer et al., "Percutaneous Mitral Valve Dilatation with the Multi-Track System," Catheterization and Cardiovascular Interventions—Official Journal of the Society for Cardiac Angiograhy & Interventions, United States (Oct. 1999), pp. 178-183.

Bonhoeffer P., et al., "Percutaneous Insertion of the Pulmonary Valve," Journal of the American College of Cardiology, May 15, 2002, vol. 39, pp. 1664-1669.

Bonhoeffer P., et al., "Percutaneous Replacement of Pulmonary Valve in a Right-Ventricle to Pulmonary-Artery Prosthetic Conduit with Valve Dysfunction," Lancet, Oct. 2000, vol. 356, pp. 1403-1405.

Bonhoeffer P., et al., "Technique and Results of Percutaneous Mitral Valvuloplasty With the Multi-Track System," Journal of Interventional Cadiology, 13(4):263-268 (Aug. 2000).

Bonhoeffer P., et al., "Transcatheter Implantation of a Bovine Valve in Pulmonary Position: A Lamb Study," Circulation, Aug. 15, 2000, vol. 102, pp. 813-816.

Boudjemline et al., "Percutaneous Implantation of a Biological Valve in Aortic Position: Preliminary Results in a Sheep Study," European Heart Journal, vol. 22, p. 630, Abstract Only (Sep. 2001).

Boudjemline Y., et al., "Images in Cardiovascular Medicine: Percutaneous Aortic Valve Replacement in Animals," Circulation, United States, Mar. 16, 2004, vol. 109, page e161.

Boudjemline Y., et al., "Is Percutaneous Implantation of a Bovine Venous Valve in the Inferior Vena Cava a Reliable Technique to Treat Chronic Venous Insufficiency Syndrome?," Medical Science Monitor, Poland, Mar. 2004, vol. 10(3), pp. BR61-BR66.

Boudjemline Y., et al., "Off-Pump Replacement of the Pulmonary Valve in Large Right Ventricular Outflow Tracts: A Hybrid Approach," Journal of Thoracic and Cardiovascular Surgery, United States, Apr. 2005, vol. 129(4), pp. 831-837.

Boudjemline Y., et al., "Percutaneous Aortic Valve Replacement: Will We Get There?," Heart, British Cardiac Society, England, Dec. 2001, vol. 86, pp. 705-706.

Boudjemline Y., et al., "Percutaneous Implantation of a Biological Valve in the Aorta to Treat Aortic Valve Insufficiency—A Sheep Study," Medical Science Monitor, Apr. 12, 2002, vol. 8(4), pp. BR113-BR116.

Boudjemline Y., et al., "Percutaneous Implantation of a Valve in the Descending Aorta in Lambs," European Heart Journal, Jul. 2002, vol. 23, pp. 1045-1049.

Boudjemline Y., et al., "Percutaneous Pulmonary Valve Replacement in a Large Right Ventricular Outflow Tract: An Experimental Study," Journal of the American College of Cardiology, Mar. 17, 2004, vol. 43(6), pp. 1082-1087.

Boudjemline Y., et al., "Percutaneous Valve Insertion: A New Approach?," Journal of Thoracic and Cardiovascular Surgery, United States, Mar. 2003, vol. 125(3), pp. 741-742.

Boudjemline Y., et al., "Stent Implantation Combined with a Valve Replacement to Treat Degenerated Right Ventricle to Pulmonary Artery Prosthetic Conduits," European Heart Journal, Sep. 2001, vol. 22, p. 355.

Boudjemline Y., et al., "Steps Toward Percutaneous Aortic Valve Replacement," Circulation, Feb. 12, 2002, vol. 105, pp. 775-778.

Boudjemline Y., et al., "The Percutaneous Implantable Heart Valve," Progress in Pediatric Cardiology, Ireland, 2001, vol. 14, pp. 89-93.

Boudjemline Y., et al., "Transcatheter Reconstruction of the Right Heart," Cardiology in the Young, England, 2003, vol. 13, pp. 308-311.

Bruce C.J., et al., "Right-sided Valve Disease Deserves Little More Respect," Circulation, 119(2):2726-2734 (May 2009).

Coats L., et al., "The Potential Impact of Percutaneous Pulmonary Valve Stent Implantation on Right Ventricular Outflow Tract Re-Intervention," European Journal of Cardio-Thoracic Surgery, England, Apr. 2005, vol. 27, pp. 536-543.

Commeau P et al., "Percutaneous Balloon Dilatation of calcific aortic Valve Stenosis: Anatomical and Haemodynamic Evaluation," British Heart Journal, 59:227-238 (Feb. 1988).

Co-pending U.S. Appl. No. 18/504,932, inventor Chu; Kevin, filed Nov. 8, 2023.

(56) References Cited

OTHER PUBLICATIONS

Cribier A., et al., "Percutaneous Transcatheter Implantation of an Aortic Valve Prosthesis for Calcific Aortic Stenosis: First Human Case Description," Circulation, 2002, vol. 106, pp. 3006-3008.
Cribier et al., "Early Experience with Percutaneous Transcatheter Implantation of Heart Valve Prosthesis for the Treatment of End-Stage Inoperable Patients with Calcific Aortic Stenosis", J. of Am. Coll. of Cardio, Feb. 18, 2004, 43(4), pp. 698-703.
Cribier et al., "Percutaneous Transluminal Valvuloplasty of Acquired Aortic Stenosis in Elderly Patients: An Alternative to Valve Replacement?", The Lancet, Jan. 11, 1986, pp. 63-67.
Cunanan et al., "Tissue Characterization and Calcification Potential of Commercial Bioprosthetic Heart Valves." Ann. Thorac. Surg., May 15, 2001, pp. S417-421.
Cunliffe et al., "Glutaraldehyde Inactivation of Exotic Animal Viruses in Swine Heart Tissue," Applied and Environmental Microbiology, Greenport, New York, vol. 37, No. 5, May 1979, pp. 1044-1046.
Dake et al., "Transluminal Placement of Endovascular Stent-Grafts for the Treatment of Descending Thoracic Aortic Aneurysms." New Engl. J. of Med., 331(26): 1729-34 (Dec. 1994).
Dalby et al., "Non-Surgical Aortic Valve Replacement" Br. J. Cardiol., 10(6):450-452 (Nov. 2003).
Davidson M.J., et al., "Percutaneous Therapies for Valvular Heart Disease," Cardiovascular Pathology, Jan. 2006, vol. 15, pp. 123-129.
Dewey et al., "Transapical aortic valve implantation: An Animal Feasibility Study", The annals of thoracic surgery, 82:110-116 (Feb. 2006).
Dhasmana et al., "Factors Associated With Periprosthetic Leakage Following Primary Mitral Valve Replacement: With Special Consideration of Suture Technique." Annals of Thorac. Surg., (Feb. 1983), 35(2), pp. 170-178.
Dotter, "Transluminally-Placed Coilspring Endarterial Tube Grafts," Investigative Radiology, pp. 329-332 (Oct. 1969).
Emery et al., "Replacement of the Aortic Valve in Patients Under 50 Years of Age: Long-Term Follow-Up of the St. Jude Medical Prosthesis." Ann. Thorac. Surg., 75:1815-1819 (Jun. 2003).
European Search Report dated Aug. 10, 2011 for EP Application No. 06824992.9.
European Search Report for EP Patent Appl. Serial No. 12179049.7 (1257), dated Oct. 30, 2012, 4 pages.
European Search Report for EP Patent Appl. Serial No. 12179075.2 (1257), dated Oct. 29, 2012, 3 pages.
European Search Report for EP Patent Appl. Serial No. 12179141.2 (1257), dated Nov. 2, 2012, 3 pages.
European Search Report for EP Patent Appl. Serial No. 12179146.1 (1257), dated Nov. 7, 2012, 8 pages.
European Search Report for EP Patent Appl. Serial No. 12179330.1 (1257), dated Nov. 22, 2012, 3 pages.
European Search Report for EP Patent Appl. Serial No. 12179338.4 (1257), dated Nov. 2, 2012, 3 pages.
European Search Report for EP Patent Appl. Serial No. 12179339.2 (1257), dated Oct. 29, 2012, 4 pages.
European Search Report for EP Patent Appl. Serial No. 12179914.2 (1257), dated Nov. 7, 2012, 6 pages.
European Search Report for EP Patent Appl. Serial No. 13150337.7 (1257), dated Jul. 9, 2013, 3 pages.
European Search Report for EP Patent Appl. Serial No. 13183134.9 (1651), dated Nov. 19, 2013, 3 pages.
European Search Report for EP Patent Appl. Serial No. 14159630.4 (1651), dated May 22, 2014, 3 pages.
European Search Report for EP Patent Appl. Serial No. 14161991.6 (1651), dated Jun. 3, 2014, 3 pages.
European Search Report for EP Patent Appl. Serial No. 15167832.3 (1651), dated Jul. 23, 2015, 3 pages.
European Search Report for EP Patent Appl. Serial No. 15167847.1 (1651), dated Jul. 23, 2015, 3 pages.
European Search Report for EP Patent Appl. Serial No. 17196833.2, dated Mar. 6, 2018, 4 pages.
European Search Report for EP Patent Appl. Serial No. 18164490.7, dated Sep. 17, 2018 5 pages.
European Search Report from EP Patent Office for EP Application No. 15177718.2, dated Jan. 18, 2016, 4 pages.
European Search Report from EP Patent Office for EP Application No. 15177731.5, dated Apr. 14, 2016, 4 pages.
European Search Report from EP Patent Office for EP Application No. 16151726.3, dated Feb. 25, 2016, 4 pages.
Extended European Search Report dated Apr. 11, 2008 in EP Patent Appl. Serial No. 081630410, 5 pages.
Extended EP Search Report dated Sep. 24, 2020 in EP Patent Appl. Serial No. 20165841.6 (JVT-0280).
Extended European Search Report for Application No. 10183946.2.4-2320 dated Feb. 14, 2012, 7 pages.
Extended European Search Report dated Aug. 9, 2018 in EP Patent Appl. Serial No. 18158901.1 (1113).
Extended European Search Report dated Jun. 12, 2018 in EP Patent Appl. Serial No. 17209326.2 (1113).
Extended European Search Report dated May 16, 2012 in EP Patent Appl. Serial No. 11178135.7 (1257).
Extended European Search Report for Application No. 11178076.3-1257 dated Feb. 29, 2012, 5 pages.
Extended European Search Report from EP Patent Office for EP Application No. 17162616.1, dated Jul. 27, 2017, 7 pages.
Extended European Search Report dated Apr. 9, 2014 in EP Patent Appl. Serial No. 14164683.6.
Extended European Search Report dated May 9, 2013 in EP Patent Appl. Serial No. 130178309.4,4 pages.
Extended European Search Report dated Aug. 19, 2011 in EP Patent Appl. Serial No. 07827132.7.
Extended European Search Report dated,Feb. 27, 2017 in EP Patent Appl. Serial No. 16186773,6 pages.
Extended European Search Report dated, Sep. 29, 2014 in EP Patent Appl. Serial No. 14164680, 5 pages.
Extended European Search Report for Application No. 07116242.4-2310 dated Mar. 31, 2008, 10 pages.
Extended European Search Report for Application No. 09154935.2, dated May 29, 2009, 7 pages.
Extended European Search Report for Application No. 10012198.7 dated Mar. 23, 2011, 7 pages.
Extended European Search Report for Application No. 10168525.3-1257 dated Feb. 3, 2011, 13 pages.
Extended European Search Report for Application No. 11153142.2-1257 dated Aug. 3, 2011, 10 pages.
Extended European Search Report for Application No. 11165093.3-1257 dated Aug. 30, 2011, 6 pages.
Extended European Search Report for Application No. 11178073.0-1257 dated Oct. 14, 2011, 5 pages.
Extended European Search Report for Application No. 11178145.6-1257 dated Feb. 29, 2012, 5 pages.
Extended European Search Report for Application No. 13188858.8-1651 dated Jan. 13, 2014, 6 pages.
Extended European Search Report for Application No. 19195062 dated Jan. 2, 2020, 7 pages.
Extended European Search Report for EP Patent Appl. Serial No. 06827630.2 dated Jun. 7, 2010, 5 pages.
Extended European Search Report for EP Patent Appl. Serial No. 07110318.8, dated May 29, 2008, 10 pages.
Extended European Search Report for EP Patent Appl. Serial No. 10163478.0, dated Mar. 22, 2011, 9 pages.
Extended European Search Report for EP Patent Appl. Serial No. 10184842.2, dated Mar. 23, 2011, 7 pages.
Extended European Search Report for EP Patent Appl. Serial No. 11162971.3, dated Jun. 30, 2011, 5 pages.
Extended European Search Report for EP Patent Appl. Serial No. 13163918.9, dated Jul. 24, 2013, 8 pages.
Extended European Search Report for EP Patent Appl. Serial No. 14179639.1, dated Mar. 9, 2015, 7 pages.
Extended European Search Report for EP Patent Appl. Serial No. 16201320.5, dated May 19, 2017, 6 pages.
Extended European Search Report for EP Patent Appl. Serial No. 18200191.7, dated May 6, 2019, 8 pages.

(56) References Cited

OTHER PUBLICATIONS

Ferrari, "Entwicklung eines Verfahrens zum transvaskularen Aortenklappenersatz," Habilitationsschrift, Medizinische Fakultat der Friedrich-Schiller-Universitat Jena, Sep. 2003, pp. 1-159. (With English Translation).
Ferrari, "Entwicklung eines Verfahrens zum transvaskularen Aortenklappenersatz," Habilitationsschrift, Medizinische Fakultät der Friedrich-Schiller-Universität Jena, Sep. 2003, pp. 49-52. (With English Translation).
Ferrari M.W., "Transarterial Aortic Valve Replacement with a Self Expanding Stent in Pigs," Heart, vol. 90, No. 11, doi:10.1136/hrt.2003.028951, ISSN 1355-6037, XP055137208, Nov. 2004, pp. 1326-1331.
Filsoufi F., et al., "Long-term Outcomes of Tricuspid Valve Replacement in the Current Era," Ann. Thorac. Surg., 8(3):845-850 (Sep. 2005).
Fluency Vascular Stent Graft Instructions for Use, May 2014, 20 pages.
Greeenberg, "Abdominal Aortic Endografting: Fixation and Sealing." J. Am. Coll. Surg., 194(1):S79-S87 (Jan. 2002).
Grossi A.E. et al., "Impact of Minimally Invasive Valvular Heart Surgery: A Case-Control Study", Ann. Thorac. Surg., 71:807-810 (Mar. 2001).
Gummert J.F. et al., Cardiac Surgery in Germany During 2006: A Report on Behalf of the German Society for Thoracic and Cardiovascular Surgery, Thorac. Cardiov. Surg., vol. 55, (Sep. 2007), pp. 343-350.
Gummert J.F. et al., "Cardiac Surgery in Germany During 2007: A Report on Behalf of the German Society for Thoracic and Cardiovascular Surgery," Thorac. Cardiov. Surg., vol. 56, (Sep. 2008), pp. 328-336.
Hanzel G.S., et al., "Complications of Percutaneous Aortic Valve Replacement: Experience with the Cribier-Edwards TM Percutaneous Heart Valve," EuroIntervention Supplements, 2006, vol. 1(A), pp. A3-A8.
Heinrich R.S., et al., "Experimental analysis of fluid mechanical energy losses in aortic valve stenosis: importance of pressure recovery", Ann Biomed Eng., Nov.-Dec. 1996, vol. 24(6), pp. 685-694.
Hijazi Z.M., "Transcatheter Valve Replacement: A New Era of Percutaneous Cardiac Intervention Begins", J. of Am. College of Cardio., Nov. 6, 2004, vol. 43, No. 6, pp. 1088-1089.
Hourihan M., et al., "Transcatheter Umbrella Closure of Valvular and Paravalvular Leaks", JACC, Boston, Massachusetts, 20(6):1371-1377 (Nov. 1992).
Huber C.H., et al., "Direct Access Valve Replacement (DAVR)—are we entering a new era in cardiac surgery?" European Journal of Cardio-thoracic Surgery, vol. 29, Jan. 19, 2006, pp. 380-385.
Huber C.H., et al., "Direct-Access Valve Replacement: A Novel Approach for Off-Pump Valve Implantation Using Valved Stents," Journal of the American College of Cardiology, Jul. 19, 2005, vol. 46(2), pp. 366-370.
Huber C.H., et al., "Do Valved Stents Compromise Coronary Flow?," European Journal of Cardio-thoracic Surgery, Jan. 23, 2004, vol. 25, pp. 754-759.
Ing F., "Stents: What's Available to the Pediatric Interventional Cardiologist?" Catheterization and Cardiovascular Interventions, 57:374-386 (Jun. 2002).
International Search Report dated Dec. 29, 2003 in Intl PCT Patent Appl. U.S. Appl. No. PCT/DE2003/002669.
International Search Report and Written Opinion for PCT Application No. PCT/EP2009/052230 dated Jun. 29, 2009, 12 pages.
International Search Report and Written Opinion for PCT Application No. PCT/EP2010/052429 dated Jun. 14, 2010, 12 pages.
International Search Report and Written Opinion for PCT Application No. PCT/EP2011/002524 dated Apr. 23, 2012, 15 pages.
International Search Report and Written Opinion for PCT Application No. PCT/EP2011/052674 dated Jul. 5, 2011, 12 pages.
International Search Report for PCT Application No. PCT/US1999/020736 dated Jan. 28, 2000, 3 pages.
International Search Report and Written Opinion for PCT Application No. PCT/EP2009/050762 dated Jun. 23, 2009, 12 pages.
International Search Report & Written Opinion dated Feb. 20, 2024 in Int'l PCT Patent Appl. Serial No. PCT/IB2023/037029.
International Search Report & Written Opinion mailed Jul. 18, 2016 for PCT Patent Appl No. PCT/EP2016/059839, 10 pages.
International Search Report & Written Report Opinion dated Apr. 17, 2024 in Int'l PCT Patent Appl. Serial No. PCT/US2023/080979.
International Search Report and Written Opinion for Appl. No. PCT/EP2016/055783, mailed on May 30, 2016, 15 pages.
International Search Report and Written Opinion for Application No. PCT/EP2013/057431 dated Jul. 26, 2013, 9 pages.
International Search Report and Written Opinion for Application No. PCT/IB2018/050438 mailed Apr. 12, 2018, 11 pages.
International Search Report and Written Opinion for International Application No. PCT/EP2010/063306, dated Nov. 17, 2010, 9 pages.
International Search Report and Written Opinion for PCT Application No. PCT/EP2006/010519 dated Mar. 1, 2007, 13 pages.
International Search Report and Written Opinion for PCT Application No. PCT/US06/36286 dated Jul. 9, 2007, 4 pages.
International Search Report and Written Opinion for PCT Application No. PCT/US2004/041513 dated Jun. 10, 2005, 4 pages.
International Search Report and Written Opinion for PCT Application No. PCT/US2004/043607 dated Mar. 20, 2006, 4 pages.
International Search Report and Written Opinion for PCT Application No. PCT/US2005/020947 dated Oct. 6, 2005, 5 pages.
International Search Report and Written Opinion for PCT Application No. PCT/US2006/038352 dated May 19, 2008, 4 pages.
International Search Report and Written Opinion for PCT Application No. PCT/US2006/043484 dated Jun. 25, 2008, 4 pages.
International Search Report and Written Opinion for PCT Application No. PCT/US2007/003992 dated Jan. 10, 2008, 5 pages.
International Search Report and Written Opinion for PCT Application No. PCT/US2007/02970 dated Oct. 19, 2007, 7 pages.
International Search Report and Written Opinion for PCT Application No. PCT/US2009/060531 dated May 13, 2010, 6 pages.
International Search Report and Written Opinion for PCT/DE2006/000056 dated Jun. 7, 2006, 11 pages.
International Search Report and Written Opinion for PCT/EP2007/061117 dated May 20, 2008, 16 pages.
International Search Report and Written Opinion for PCT/EP2008/003803 dated Aug. 20, 2008, 10 pages.
International Search Report and Written Opinion for PCT/EP2009/055958 dated Oct. 21, 2009, 8 pages.
International Search Report and Written Opinion for PCT/EP2010/056558 dated Oct. 7, 2010, 14 pages.
International Search Report and Written Opinion for PCT/EP2012/067617 dated Dec. 19, 2012, 10 pages.
International Search Report and Written Opinion for PCT/IL2007/001149 dated May 1, 2008, 4 pages.
International Search Report and Written Opinion for PCT/US2011/027730 dated May 25, 2011, 9 pages.
International Search Report and Written Opinion of the International Search Authority for International Application No. PCT/EP2008/064558, date of completion of report is Mar. 18, 2009, 14 pages.
International Search Report dated Jan. 28, 2008 in Int'l PCT Application Serial No. PCT/EP2007/007413, 4 pages.
International Search Report dated Jul. 7, 2015 in Int'l PCT Application Serial No. PCT/EP2014/065817, 6 pages.
International Search Report dated Nov. 3, 2011 in Int'l PCT Application Serial No. PCT/EP2011/058506, 4 pages.
International Search Report dated Dec. 18, 2012 in Int'l PCT Patent Application Serial No. PCT/EP2012/067714, 3 pages.
International Search Report for Application No. PCT/DE2001/000837, dated Aug. 7, 2001, 4 pages.
International Search Report for Application No. PCT/EP2006/012455, mailed Sep. 27, 2007, 5 pages.
International Search Report for Application No. PCT/EP2010/057798, dated Sep. 12, 2010, 6 pages.
International Search Report for Application No. PCT/EP2011/066677, dated Feb. 17, 2012, 7 pages.

(56) References Cited

OTHER PUBLICATIONS

International Search Report for Application No. PCT/EP2012/067617 mailed Dec. 19, 2012, 3 pages.
International Search Report for Application No. PCT/EP2013/073318, dated Apr. 17, 2014, 5 pages.
International Search Report for Application No. PCT/EP2016/055783, mailed on May 30, 2016, 5 pages.
International Search Report for Application No. PCT/EP2016/058532, dated Jul. 11, 2016, 4 pages.
International Search Report for Application No. PCT/IB2008/002180, dated Apr. 15, 2009, 7 pages.
International Search Report for Application No. PCT/IB2018/050438 mailed Apr. 12, 2018, 3 pages.
International Search Report for PCT/DE2001/000836 dated Jun. 13, 2001, 6 pages.
International Search Report for PCT/EP2006/010023 dated Mar. 30, 2007, 6 pages.
International Search Report for PCT/IB2017/052718, dated Sep. 5, 2017, 4 pages.
Invitation to Pay Additional Fees & Partial Search Report dated Feb. 28, 2024 in Int'l PCT Patent Appl. Serial No. PCT/US2023/0809791
Kato et al., "Traumatic Thoracic Aortic Aneurysm: Treatment with Endovascular Stent-Grafts." Radiol., 205:657-662 (Dec. 1997).
Khambadkone S., et al., "Nonsurgical Pulmonary Valve Replacement: Why, When, and How?," Catheterization and Cardiovascular Interventions, United States, Jul. 2004, vol. 62, pp. 401-408.
Khambadkone S., et al., "Percutaneous Implantation of Pulmonary Valves," Expert Review of Cardiovascular Therapy (England), Nov. 2003, vol. 1(4), pp. 541-548.
Khambadkone S., et al., "Percutaneous Pulmonary Valve Implantation: Early and Medium Term Results," Circulation, Oct. 28, 2003, vol. 108(17), p. IV-375.
Klein A.L., et al., "Age-related Prevalence of Valvular Regurgitation in Normal Subjects: A Comprehensive Color Flow Examination of 118 Volunteers," Journal of the American Society of Echocardiography, vol. 3, No. 1, (Jan. 1990), pp. 54-63.
Knudsen et al., "Catheter-implanted prosthetic heart valves", Intl J. of Art. Organs, 16(5): 253-262, May 1993.
Kort et al., "Minimally Invasive Aortic Valve Replacement: Echocardiographic and Clinical Results." Am. Heart J., Sep. 2001, vol. 142(3), pp. 476-481.
Kuzela L., et al., "Experimental evaluation of direct transventricular revascularization," Journal of Thoracic and Cardiovascular Surgery, 57(6):770-773 (Jun. 1969).
Laborde et al., "Percutaneous Implantation of the Corevalve Aortic Valve Prosthesis for Patients Presenting High Risk for Surgical Valve Replacement," EuroIntervention, 1(4):472-474 (Feb. 2006).
Lawrence et al., "Percutaneous Endovascular Graft: Experimental Evaluation", Radiology, May 1987, vol. 163(2), pp. 357-360.
Levi et al., "Future of Interventional Cardiology in Pediactrics." Current Opinion in Cardiol., 18:79-90 (Mar. 2003).
Levy, "*Mycobacterium chelonei* Infection of Porcine Heart Valves." The New England Journal of Medicine, Washington DC, 297(12), Sep. 22, 1977, pp. 667-668.
Lichtenstein et al., "Transapical Transcatheter Aortic Valve Implantation in Humans: Initial Clinical Experience", circulation, American Heart Association vol. 114, Jul. 31, 2006, pp. 591-596.
Lichtenstein, S.V., "Closed heart surgery: Back to the future" The Journal of Thoracic and Cardiovascular Surgery, vol. 131(5), May 2006, pp. 941-943.
Liu et al., "Effect of Fiber Orientation on the Stress Distribution within a Leaflet of a Polymer Composite Heart Valve in be Closed Position", Journal of Biomechanics, 4:1099-1106 (Jan. 2007).
Lonescu et al., "Prevalence and Clinical Significance of Incidental Paraprosthetic Valvar Regurgitation: A prospective study using transesophageal echocardiography." Heart, 89:1316-21 (Oct. 2003).
Love S.C. et al., The Autogenous Tissue Heart Valve: Current Status, Journal of Cardiac Surgery, , Mar. 1991, vol. 6(4), pp. 499-507.
Lutter G., et al., "Percutaneous Aortic Valve Replacement: An Experimental Study. I. Studies on Implantation," Journal of Thoracic and Cardiovascular Surgery, Apr. 2002, vol. 123(4), pp. 768-776.
Lutter G., et al., "Percutaneous Valve Replacement: Current State and Future Prospects," Annals of Thoracic Surgery, Netherlands, Dec. 2004, vol. 78, pp. 2199-2206.
Ma L., et al., "Double-Crowned Valved Stents for Off-Pump Mitral Valve Replacement," European Journal of Cardio-Thoracic Surgery, Jun. 13, 2005, vol. 28(2), pp. 194-199.
Mack, M.J., "Minimally invasive cardiac surgery", Surg Endosc, 20:S488-S492 (Mar. 2006).
Magovern et al., "Twenty-five-Year Review of the Magovern-Cromie Sutureless Aortic Valve", Ann. Thorac. Surg., 48:S33-S334 (Jan. 1989).
Maraj et al., Evaluation of Hemolysis in Patients with Prosthetic Heart Valves, Clin. Cardiol. 21:387-392 (Jun. 1998).
Marcus RH et al., "Assessment of small-diameter aortic mechanical prostheses: physiological relevance of the Doppler gradient, utility of flow augmentation, and limitations of orifice area estimation," Circulation, 98(9):866-872 (Sep. 1998).
Mckay G. R. et al., "The Mansfield Scientific Aortic Valvuloplasty Registry: Overview of Acute Hemodynamic Results and Procedural Complications." J. Am. Coll. Cardiol., 17(2):485-491 (Feb. 1991).
Mills N.L., et al., "Valvulotomy of valves in the saphenous vein graft before coronary artery bypass," The Journal of Thoracic and Cardiovascular Surgery, 71(6):878-879 (Jun. 1976).
Mirich et al., "Percutaneously Placed Endovascular Grafts for Aortic Aneurysms: Feasibility Study", Radiology, 170:1033-1037 (Mar. 1989).
Moazami N. et al. "Transluminal Aortic Valve Placement: a Fesibility Study with a Newly Designed Collapsible Aortic Valve", ASAIO Journal, vol. 42, No. 2, Mar.-Apr. 1996.
Moulopoulos et al., "Catheter-Mounted Aortic Valves," Annals of Thoracic Surg., vol. 11, No. 5, May 1971, pp. 423-430.
Munro I., et al., "The possibility of myocardial revascularization by creation of a left ventriculocoronary artery fistula," The Journal of Thoracic and Cardiovascular Surgery, 58(1):25-32 (Jul. 1969).
Nath J., et al., Impact of Tricuspid Regurgitation on Long-term Survival, Journal of the American College of Cardiology, 43(3):405-406 (Feb. 2004).
Nietlispach F., et al., "Current Balloon-Expandable Transcatheter Heart Valve and Delivery Systems", Catheterization and Cardiovascular Interventions, 75:295-300 (Sep. 2009).
Palacios I.F., "Percutaneous Valve Replacement and Repair: Fiction or Reality?," Journal of American College of Cardiology, Oct. 2004, vol. 44(8), pp. 1662-1663.
Palmaz J.C., et al., "Expandable Intrahepatic Portacaval Shunt Stents: Early Experience in the Dog," American Journal of Roentgenology, 145 (4):821-825 (Oct. 1985).
Palmaz J.C., et al., "Expandable Intrahepatic Portacaval Shunt Stents in Dogs with Chronic Portal Hypertension," American Journal of Roentgenology, 147(6):1251-1254 (Dec. 1986).
Paniagua et al., "Percutaneous Heart Valve in the Chronic in Vitro Testing Model." Circulation, Sep. 17, 2002, vol. 106: e51-e52.
Parodi J.C., et al., "Transfemoral Intraluminal Graft Implantation for Abdominal Aortic Aneurysms", Ann. Vasc. Surg., 5(6):491-499 (Nov. 1991).
Partial European Search Report dated Feb. 28, 2012 in EP Patent Appl. Serial No. 11178135.7 (1257).
Partial European Search Report for Application No. 10168525.3-1269 dated Sep. 20, 2010, 5 pages.
Partial European Search Report for Application No. 07116242.4-2310 dated Jan. 14, 2008, 5 pages.
Partial European Search Report for Application No. 11153142.2-1257 dated Apr. 4, 2011, 5 pages.
Partial European Search Report for EP Patent Appl. Serial No. 07110318.8, dated Mar. 10, 2008, 6 pages.
Partial European Search Report for EP Patent Appl. Serial No. 10163478.0, dated Nov. 2, 2010, 6 pages.
Partial International Search Report for International Application No. PCT/EP2014/055044, filed Mar. 13, 2014, 7 pages.

(56) References Cited

OTHER PUBLICATIONS

Pavcnik D., et al., "Aortic and Venous Valve for Percutaneous Insertion," Minimally Invasive Therapy & Allied Technologies, Jan. 2000, vol. 9(3/4), pp. 287-292.
Pavcnik D., et al., "Development and Initial Experimental Evaluation of a Prosthetic Aortic Valve for Transcatheter Placement." Radiology, 183:151-154 (Apr. 1992).
Pavcnik et al., "Percutaneous Bioprosthetic Venous Valve: A Long-term Study in Sheep," Jounal of Vascular Surg., vol. 35, No. 3, Mar. 2002, pp. 598-603.
Pawelec-Wojtalk M., "Closure of left ventricle perforation with the use of muscular VSD occluder," European Journal of Cardia-Thoracic Surgery, 27(4):714-716 (Apr. 2005).
Pelton A.R., et al., "Medical Uses of Nitinol," Materials Science Forum, Jan. 2000, vol. 327-328, pp. 63-70.
Phillips et al., "A Temporary Catheter-Tip Aortic Valve: Hemodynamic Effects on Experimental Acute Aortic Insufficiency", Annals of Thoracic Surg., Feb. 1976, 21(2), pp. 134-136.
Phillips S.J., et al., "Improvement in Forward Coronary Blood Flow by Using a Reversed Saphenous Vein with a Competent Valve," The Annals of Thoracic Surgery, vol. 21 (1), Jan. 1976, pp. 12-15.
Preliminary Search Report (Rapport De Recherche Preliminaire) dated Jul. 8, 2002 in French Patent Application No. 0110444 (2 pages).
Raillat et al., "Treatment of Iliac Artery Stenosis with the Wallstent Endoprosthesis." AJR, Mar. 1990, vol. 154(3), pp. 613-616.
Remadi et al., "Preliminary results of 130 aortic valve replacements with a new mechanical bileaflet prosthesis: The Edwards MIRA valve," Interactive Cardiovasc. and Thorac. Surg., 2:80-83 (Mar. 2003).
Rogers J.H., et al., "The Tricuspid Valve: Current Perspective and Evolving Management of Tricuspid Regurgitation," Circulation, 119(20):2718-2725 (May 2009).
Ruiz C.E., "Transcatheter Aortic Valve Implantation and Mitral Valve Repair: State of the Art," Pediatric Cardiology, Jun. 2005, vol. 26(3), pp. 289-294.
Saliba Z., et al., "Treatment of Obstructions of Prosthetic Conduits by Percutaneous Implantation of Stents," Archives Des Maladies Du Coeur Et Des Vaisseaux, May 1999, pp. 591-596.
Schurink et al., "Stent Attachment Site—related Endoleakage after Stent Graft Treatment: An in vitro study of the effects of graft size, stent type, and atherosclerotic wall changes", J. Vasc. Surg., vol. 30(4), Oct. 1999, pp. 658-667.
Search Report dated Oct. 15, 2003 from the European Patent Office for European Patent Application No. EP 02291953.4, 2 pages.
Search Report from the European Patent Office dated Dec. 11, 2002 for European Patent Application No. EP 02291954.4, 4 pages.
Sochman et al., "Percutaneous Transcatheter Aortic Disc Valve Prosthesis Implantation: A Feasibility Study." Cardiovasc. Intervent. Radiol., Sep. 2000, 23: 384-388.
Stanley et al., "Evaluation of Patient Selection Guidelines for Endoluminal AAA Repair With the Zenith Stent Graft: The Australasian Experience." J. Endovasc. Ther., 8:457-464 (Oct. 2001).
Stassano P., et al., "Mid-term Results of the Valve-on-Valve Technique for Bioprosthetic Failure," European Journal of Cardiothoracic Surgery, Oct. 2000, vol. 18, pp. 453-457.
Stein D.P., et al., "Turbulent blood flow in the ascending aorta of humans with normal and diseased aortic valves", Circulation Research by American Heart Association, 39:58-65 (Jul. 1976).
Steinhoff et al., "Tissue Engineering of Pulmonary Heart Valves on Allogenic Acellular Matrix Conduits." Circulation102 [suppl. III], pp. III-50-III-55 (Nov. 2000).
Supplemental Search Report from EP Patent Office for EP Application No. 04813777.2, dated Aug. 19, 2011.
Supplemental Search Report from EP Patent Office for EP Application No. 04815634.3, dated Aug. 19, 2011.
Supplemental Search Report from EP Patent Office for EP Application No. 05758878.2, dated Oct. 24, 2011.
Supplementary European Search Report dated Jan. 2, 2012 in EP Patent Appl. Serial No. 09820051.2.
Thompson et al., "Endoluminal stent grafting of the thoracic aorta: Initial experience with the Gore Excluder," Journal of Vascular Surgery, Jun. 2002, pp. 1163-1170.
Triennial Review of the National Nanotechnology Initiative: "A Matter of Size", The National Academies Press, Washington DC, V-13, Retrieved from the Internet: URL: http://www.nap.edu/catalog/11752/a-matter-of-size-triennial-review-of-the-national-nanotechnology, 200 pages (Mar. 2006) (Parts 1-5).
Vahanian et al., "Percutaneous Approaches to Valvular Disease", Circulation, Apr. 6, 2004, 109: 1572-1579.
Van Herwerden et al., "Percutaneous Valve Implantation: Back to the Future?", Euro. Heart J., Sep. 2002, 23(18): 1415-1416.
Walther et al., "Transapical approach for sutureless stent-fixed aortic valve implantation: experimental results", European Journal of Cardio-thoracic Surgery 29, 703-708 (May 2006).
Webb J.G., et al., "Percutaneous Aortic Valve Implantation Retrograde from the Femoral Artery," Circulation, American Heart Association, Feb. 14, 2006, vol. 113, pp. 842-850.
Weerasinghe A., et al., "First Redo Heart Valve Replacement: A 10-Year Analysis," Circulation, 99(5):655-658 (Feb. 1999).
Weyman AB et al., "Aortic Stenosis: Physics and Physiology—What Do the Numbers Really Mean?", Rev Cardiovasc Med., 6(1):23-32 (Jan. 2005).
White et al., "Endoleak as a Complication of Endoluminal Grafting of Abdominal Aortic Aneurysms: Classification, Incidence, Diagnosis, and Management," J. Endovasc. Surg., 4:152-168 (May 1997).
Written Opinion dated Mar. 30, 2007 in Int'l PCT Application Serial No. PCT/EP2006/010023, 10 Pages.
Written Opinion dated Sep. 27, 2007 in Int'l Application No. PCT/EP2006/012455, 11 pages.
Written Opinion for Application No. PCT/EP2007/007413, mailed Jan. 28, 2008, 5 pages.
Written Opinion for Application No. PCT/EP2011/058506, mailed Nov. 3, 2011, 5 pages.
Written Opinion for Application No. PCT/EP2014/065817, mailed Jan. 7, 2015, 7 pages.
Written Opinion for PCT/EP2012/067714 dated Dec. 18, 2012, 5 Pages.
Yonga G.O., et al., "Percutaneous Transvenous Mitral Commissurotomy in Juvenile Mitral Stenosis", East African Medical Journal, 80(4):172-174 (Apr. 2003).
Yoshioka et al., "Self-Expanding Endovascular Graft: An Experimental Study in Dogs." AJR 151, Oct. 1988, pp. 673-676.
Zhou et al., "Self-expandable Valved Stent of Large Size: Off-Bypass Implantation in Pulmonary Position", Eur. J. Cardiothorac, Aug. 2003, 24: 212-216.
Cheng, et al., "Successful trans-apical aortic valve implantation for a high risk patient with aortic stenosis using a new second-generation TAVI device J-Valve system," J. of Cardiothoracic Surgery, 10(5):1-4 (2015).
Ford, Omar, "JC Medical Becoming Serious Challenger in TAVR Fray" (May 31, 2018), available at: https://www.mddionline.com/cardiovascular/jc-medical-becoming-serious-challenger-in-tavr-fray.
Jenavalve, "JenaValve Announces FDA Approval of the Trilogy™ Transcatheter Heart Valve System—the First and Only Transcatheter Device Approved for Symptomatic, Severe Aortic Regurgitation (ssAR) in the United States" (Mar. 18, 2026), available at: https://jenavalve.com/jenavalve-announces-fda-premarket-approval-of-the-trilogy-transcatheter-heart-valve-system.
Olson et al., "Surgical Pathology of Pure Aortic Insufficiency: A Study of 225 Gases," Mayo Clinic Proceedings, 59:835-841 (Dec. 1984).
O'Riordan, "FDA Approves JenaValve's Trilogy for Aortic Regurgitation" (Mar. 23, 2026), available at: https://www.tctmd.com/news/fda-approves-jenavalves-trilogy-aortic-regurgitation.
Wei, et al., "A New Transcatheter Aortic Valve Replacement System for Predominant Aortic Regurgitation Implantation of the J-Valve and Early Outcome," J Am Coll Cardiol Intv., 8(14):1831-1841 (2015).

(56) References Cited

OTHER PUBLICATIONS

Whooley, "JenaValve begins commercial rollout of Trilogy heart valve in US" (Apr. 1, 2026), available at: https://www.massdevice.com/jenavalve-begins-us-rollout-trilogy-thv.

* cited by examiner

Close up

HEART VALVE PROSTHESIS DELIVERY SYSTEM AND METHOD FOR DELIVERY OF HEART VALVE PROSTHESIS WITH INTRODUCER SHEATH

CROSS-REFERENCE TO RELATED APPLICATIONS

This application is a continuation of U.S. patent application Ser. No. 15/559,498, filed Sep. 19, 2017, now U.S. Pat. No. 12,121,461, which is a national phase under 35 U.S.C. § 371 of International PCT Patent Application Serial No. PCT/EP2016/055783, filed Mar. 17, 2016, which claims the benefit of U.S. Provisional Patent Application Ser. No. 62/136,092, filed Mar. 20, 2015, the entire contents of each of which are incorporated herein by reference.

DESCRIPTION

The present disclosure relates to a delivery system, a catheter system and a method for the minimally invasive application of prostheses to an individual in need thereof and a method for loading a prosthesis onto a catheter system and/or a delivery system.

This application is related case of EP13173217.4 & EP13182346.0, U.S. Pat. No. 8,790,395 and US patent publication 2014/0081388A1 (Mar. 20, 2014) all assigned to the instant assignee, the entire disclosures of which are incorporated herein by reference, each as if expressly set forth.

BACKGROUND

The current disclosure relates to the field of medical devices, in particular to prosthesis which are being transplanted into an individual in need thereof in order to re-establish proper body functions by way of minimally invasive methods and means applicable therefor.

Examples of prostheses that are placed by way of minimally invasive methods are stents and heart valves like aortic and mitral heart valves. Heart valves today are applied e.g. by the transapical, transfemoral, or subclavial route. The transapical route is very direct through a cut between the rips of a patient and through the apex of the heart and thus only a short distance has to be passed until the delivery site. The transfemoral route is a very convenient method and widely used because it needs only a cut in the leg of the patient and access to the vasculature.

Usually the prosthesis is applied by way of a delivery system also denoted catheter. The requirements for the catheter by way of transfemoral delivery is more complex as compared with the transapical route because for the delivery of e.g. an aortic heart valve a relatively long distance and bends have to be manoevered through which imply certain difficulties.

One example of such a delivery system is disclosed in EP2387977B1. This patent describes a transfemoral catheter for the delivery of an aortic heart valve. The patent does not disclose nor suggest the embodiments presently disclosed.

Usually the prosthesis has to be loaded in a releasable manner onto the catheter and crimped to a small seize in order be passed through the vasculature of the patient and to be delivered to the implantation site. The different systems known in the prior art use different seizes like 22, 20, or 18 French. Accordingly the prosthesis has to be squeezed together which implies the risk of damaging the pericard material of the valve.

Moreover, the correct positioning is another issue and possibly the capability of the catheter system of repositioning the prosthesis during the course of delivering and applying the prosthesis at the target site and position in the patient. The termination of the procedure after partial release of the prosthesis and complete retrieval of the prosthesis is another advantage which is not possible with many catheter systems of the prior art.

Another issue is the diameter seize of catheter system. The diameter seize of the crimped prosthesis in the catheter for delivery through the vasculature of the patient is critical. Many known systems do not achieve an adequate crimping seize and often the tissue is negatively affected in known systems during the crimping procedure.

Moreover, the crimping of the prosthesis as such represents a challenge. In particular crimping in a manner without damaging, or stretching and/or squeezing the tissue of the prosthesis is often not sufficiently achieved in known systems. Even though immediate damages due to the crimping may not be obvious, often the tissue is still negatively affected by the crimping with a negative impact on the durability of the tissue, e.g. pericard tissue, representing the valve in a heart valve and even the stent component.

Yet another problem in the delivery is the maneuvering of the prosthesis by way of the catheter through the vasculature and its bends. The fact that the vasculature is narrow, and particularly at the aortic entry into the heart a substantive curve with a narrow angle has to be passed through, represents a substantive challenge for such a delivery procedure and device.

Moreover the following has implications for the present disclosure:

Minimally-invasive surgical procedures have evolved substantially since the advent of endovascular technologies and techniques. Embodiments of the present disclosure relate to systems to deliver an endoprosthesis in an implantation site in the heart of a patient. For example, embodiments of the present disclosure relate to systems to deliver and position transcatheter heart valves used in the treatment of a stenosis (narrowing) of a cardiac valve and/or a cardiac valve insufficiency.

Embodiments of the present disclosure also relate to specialized delivery systems for endoprosthetics, including for example, collapsible and expandable prosthetics incorporating a stent which is delivered to the implant site using a specialized catheter and a preshaped sheath.

The expression "narrowing (stenosis) of a cardiac valve and/or cardiac valve insufficiency" is intended to include a functional defect of one or more cardiac valves, which is either genetic or has developed. A cardiac defect of this type might affect each of the four heart valves, although the valves in the left ventricle (aortic and mitral valves) are affected much more often than the right-sided part of the heart (pulmonary and tricuspid valves). The functional defect can result in narrowing (stenosis), inability to close (insufficiency) or a combination of the two (combined vitium). This disclosure relates to delivery systems leveraging an endoprosthesis that includes an expandable stent capable of being implanted transluminally in a patient's body and enlarged radially after being introduced percutaneously for treating heart valve defect, among other indications.

In the current treatment of severe narrowing of a cardiac valve and/or cardiac valve insufficiency, the narrowed or diseased cardiac valve is replaced with an endoprosthesis. Biological or mechanical valves models, which are typically surgically sewn into the cardiac valve bed through an opening in the chest after removal of the diseased cardiac valve, have generally been used for this purpose. Such procedures or operations necessitate the use of a heart-lung machine to maintain the patient's circulation during the procedure and cardiac arrest is induced during implantation of the prosthesis. This is a risky surgical procedure with associated dangers for the patient, as well as a long post-operative treatment and recovery phase. Such an operation can often not be considered with justifiable risk in the case of polypathic patients.

Minimally-invasive forms of treatment have been developed recently which are characterized by allowing the procedure to be performed under local anesthesia. One approach provides for the use of a catheter system to implant a self-expandable stent to which is connected a collapsible valvular prosthesis. Such a self-expandable endoprosthesis can be guided via a catheter system to the implantation site within the heart through an inguinal artery or vein. After reaching the implantation site, the stent can then be unfolded.

However, there is a risk of inexact or incorrect implantation of an endoprosthesis using the solutions described above. Expressed in another way, there is a need for exact positioning and longitudinal alignment of an implanted endoprosthesis. In particular, it is only possible using great skill on the part of the attending surgeon or cardiologist-if at all-to position a stent sufficiently precisely, in both a lateral and longitudinal direction, to ensure that the associated endoprosthesis is located in the correct area of the patient's diseased heart valve to be treated prior to the advent of the instant systems.

On the basis of the problems referenced and outlined above, certain embodiments of the present disclosure address the issue of delivering and positioning a specialized endoprosthesis for treating a narrowed cardiac valve or a cardiac valve insufficiency which realizes optimum positioning accuracy and anchoring of the emplaced device. In addition, the treatment of the narrowed cardiac valve or cardiac valve insufficiency should be by way of a simple procedure to enable routine treatment of narrowed cardiac valve or cardiac valve insufficiency without major stress to the patient.

Objects of the Disclosure

One object of certain embodiments of the present disclosure was to provide a catheter system for delivery of a prosthesis, e.g. a heart valve, which is easy to handle. In particular wherein the heart valve can securely be loaded and crimped without negative side effects due to the loading and crimping procedure.

Another object of certain embodiments of the present disclosure is to provide for a catheter and delivery system for a prosthesis designed in a manner in order to facilitate the delivery of the prosthesis to the target site. In particular provide for a system design wherein the maneuvering through the vasculature of a patient is possible without the disadvantages known in the prior art.

Another object of certain embodiments of the present disclosure is to provide for a design wherein the prosthesis can be securely positioned and delivered to the target site with the possibility to terminate the delivery procedure and to retract the prosthesis until a certain procedural time point. Moreover, it is an object of certain embodiments of the present disclosure to enable the free movement of the prosthesis in axial direction and rotational direction.

Another object of certain embodiments of the present disclosure is to provide for a step-wise liberation of the prosthesis in order to place the prosthesis correctly at the target site, enable repositioning in this manner and/or fine tuning of the positioning procedure.

SUMMARY

Embodiments of the present disclosure relate in one aspect to a catheter system comprising i. a steering means; and ii. a delivery means for a heart valve, optionally balloon expandable or self-expandable, wherein the steering means and the delivery means are coaxially and rotationally independently movable.

In another aspect, embodiments of the present disclosure relate to a delivery system for a heart valve comprising i. a steering means; ii. a delivery means for a heart valve and iii. an introducer sheath wherein the steering means, the delivery means and the introducer sheath are coaxially and circumferentially independently movable.

In yet another aspect, embodiments of the present disclosure relate to a method for the delivery of a heart valve to the heart of a patient comprising the steps i. in a first step placing an introducer comprising an introducer sheath into a patient's vasculature; ii. in a second step introducing a catheter system having fixed thereto a self-expanding heart valve through the introducer into the patient's vasculature; iii. in a third step positioning the self-expanding heart valve proximal to the target site in the patient's heart, optionally positioning the heart valve substantially central in the target area; iv. in a fourth step positioning the self-expanding heart valve at the target site; v. in a fifth step partially releasing the self-expanding heart valve from the catheter system; vi. in a sixth step fully releasing the self-expanding heart valve from the catheter system.

In yet another aspect, embodiments of the present disclosure relate to a method of loading a self-expanding heart valve onto a delivery means of a catheter system having an inner shaft, an attachable distal tip, and at least one outer sheath, consisting of compressing the self-expanding heart valve radially and placing the compressed self-expanding heart valve into a tubular retainer, the retainer preventing the self-expanding valve from expanding radially, passing the inner shaft of the delivery system through the central opening of the compressed self-expanding heart valve, attaching the distal tip to the shaft of the delivery system, advancing the outer sheath onto the compressed heart valve to prevent radial expansion of at least part of the heart valve, and removing the tubular retainer from the compressed self-expanding heart valve.

In yet another aspect, embodiments of the present disclosure relate to a 2-step deployment procedure of a heart valve.

In yet another aspect, embodiments of the present disclosure relate in particular to the attachment of a heart valve in a catheter or delivery system wherein only the lateral parts of the heart valve are fixed and/or covered by a fixation means of the catheter and wherein essentially the middle part of the heart valve is not being covered.

In yet another aspect, embodiments of the present disclosure relate to a steerable catheter for the delivery of a heart valve.

Briefly stated, transcatheter heart valves are delivered by transapical (TA) and/or transfemoral (TF) delivery systems featuring novel preshaped sheaths and/or steerable catheters to enable emplacement leveraging benefits of proprietary JenaValve® brand of prosthetics.

According to the some embodiment, transcatheter heart valve delivery systems include a Pericardial THV system which comprises a specialized prosthesis; a prosthetic delivery system and separate valve loader.

According to some embodiments, the prosthesis is constructed from porcine pericardial tissue and attached to a self-expanding Nitinol stent scaffold with polyester sutures, having specialized struts and the ability to fit into either transapical or transfemoral catheter delivering devices, as further described, illustrated and claimed below.

According to some embodiments, transapical and/or transfemoral catheter delivery systems are effective to collapsibly house and deliver the scaffold, which has a crown-like design, and works with a pre-shaped sheath and/or steerable catheters, as further described, illustrated and claimed below.

According to some embodiments, the instant systems match with at least three valve sizes, accommodating native valve annulus diameters from at least about 21 to 27 mm.

In accordance with an aspect, the present disclosure provides a catheter system for introducing an expandable heart valve into the body of a patient, the catheter system comprising delivering means for the heart valve.

In some aspects of the present disclosure, the delivering means comprises a catheter tip and a catheter shaft. The catheter tip of the delivery means has a seat portion for accommodating the heart valve to be introduced into the patient's body in its collapsed or crimped state. The catheter tip has further holding means for realisably fixing the heart valve to the catheter tip.

The seat portion of the catheter tip is constituted by a first retaining means and a second retaining means. In some embodiments of the present disclosure, the first retaining means and second retaining means may be constituted by a first sleeve-shaped member and a second sleeve-shaped member.

The first retaining means of the catheter tip serves for reversibly securing a distal end section of the heart valve to the delivery means and, in particular, to the catheter tip of the delivery means. On the other hand, the second retaining means of the catheter tip serves for reversibly securing a proximal end section of the heart valve to the delivery means and, in particular, to the catheter tip of the delivery means.

The first and second retaining means are moveable relative to each other and also relative to the holding means of the catheter tip.

According to some embodiments of the present disclosure, the catheter shaft of the delivery means comprises first force transmitting means and second force transmitting means.

A distal end section of the first force transmitting means is connected or connectable to the first retaining means of the catheter tip and a proximal end section of the first force transmitting means is connected or connectable to a first operating means of a handle of the delivery means. A distal end section of the second force transmitting means is connected or connectable to the second retaining means of the catheter tip and a proximal end section of the second force transmitting means is connected or connectable to a second operating means of the handle of the delivery means.

According to some embodiments of the present disclosure, the handle of the delivery means has at least one first operating means and at least one second operating means with which the catheter tip of the delivery means may be appropriately manipulated so that an expandable heart valve secured to the catheter tip may be released from the catheter tip in steps or in a defined or definable sequence of events.

In accordance with preferred embodiments of the present disclosure, the catheter tip has first and second retaining means—for example in the form of sleeve-shaped members which may be manipulated with the handle of the delivery means. These retaining means are used for releasably and reversibly securing a distal and proximal end section of the heart valve to the catheter tip.

In some embodiments of the present disclosure, the first retaining means serves for releasably and reversibly securing first functional components of the heart valve, for example retaining hoops of a stent or alternatively positioning hoops of a stent, while the second retaining means serves for releasably and reversibly securing second functional components of the heart valve, for example, positioning hoops of a stent or alternatively for accommodating retaining hoops of a stent.

In relation to the handle of the delivery means, it is preferably provided that, on one hand, the first operating means cooperate with the first retaining means of the catheter tip so that, on actuation of the first operating means, a previously definable longitudinal displacement of the first retaining means may be effected relative to the holding means. On the other hand, the second operating means cooperates with the second retaining means of the catheter tip so that a previously definable longitudinal displacement of the second retaining means may be affected relative to the holding means.

In accordance with some embodiments of the present disclosure, the first and second retaining means only serve for securing the distal and proximal end sections of the heart valve to the catheter tip. In case the first and second retaining means are configured as first and second sleeve-shaped members, these sleeve-shaped members have a length such that a gap is between the first and second sleeve-shaped members when securing the distal and proximal end sections of the heart valve to the catheter tip.

In accordance with some embodiments of the present disclosure, the first force transmitting means of the delivery means is constituted by a first catheter tube defining a first lumen, and the second force transmitting means of the delivery means is constituted by a second catheter tube defining a second lumen. The second catheter tube has a cross-section less than the cross-section of the first catheter tube. The first catheter tube is disposed concentrically and coaxially with the second catheter tube and the second catheter tube is received within the first lumen defined by the first catheter tube.

Contrary to the first and second sleeve-shaped members of the catheter tip, however, the holding means of the catheter tip is not moveable relative to the handle of the delivery means. Rather, the holding means is connected to the handle of the delivery means by using a holding tube having a distal end connected to the holding means and a proximal end connected to a body of the handle of the delivery means. The holding tube has a cross-section less than the cross-section of the first catheter tube. In particular, the first catheter tube is disposed concentrically and coaxially with both, the second catheter tube on the one hand and the holding tube on the other hand.

Preferably, the holding tube has a cross-section less than the cross-section of the first catheter tube and greater than the cross-section of the second catheter tube such that the holding tube is received within the first lumen defined by the first catheter tube and the second catheter tube is received within a passageway defined by the holding tube. The passageway defined by the holding tube has a diameter sufficient to accommodate the second catheter tube such that the second catheter tube is moveable relative to the holding tube.

The second lumen defined by the second catheter tube has a diameter sufficient to accommodate a guide wire. The second catheter tube is made from a rigid material including, for example, nitinol, stainless steel or a rigid plastic material. The material of the distal end section of the second catheter tube may have an increased flexibility compared to the material of the proximal end section in order to allow the distal end section of the catheter shaft to pass the aortic arch during insertion of the catheter tip.

In some embodiments of the present disclosure, the distal end section of the second catheter tube terminates in a soft catheter end tip having an atraumatic shape. The soft catheter end tip is provided with a channel aligned with the second lumen defined by the second catheter tube such that a guide wire accommodated within the second lumen of the second catheter tube may pass through the channel of the soft catheter end tip. The second sleeve-shaped member of the catheter tip is connected to the soft catheter end tip such that the opened end of the second sleeve-shaped member faces in the proximal direction opposite to the direction of the soft catheter end tip and to the second catheter tube.

The holding tube is preferably made of a rigid material, for example, a rigid plastic material, stainless steel or Nitinol. The distal end of the holding tube terminates in the holding means which is also made of a rigid material, for example, a rigid plastic material or stainless steel. The passageway defined by the holding tube is aligned with a channel which passes through the holding means. In this way, the second catheter tube is accommodated in the passageway of the holding tube and the channel of the holding means such as to be moveable relative to the holding tube and the holding means.

The holding tube is provided for connecting the holding means to the handle of the delivery means. For this purpose, the holding tube has a distal end connected to the holding means and a proximal end connected to a body of the handle of the delivery means.

The first catheter tube is preferably made of a bendable but inelastic material. For example, the first catheter tube may be at least partly made of a braided or non-braided catheter tube. Hence, the first catheter tube may have a stiff braid reinforced body similar to the catheter body described in U.S. Pat. No. 4,665,604 which is incorporated herein by reference.

The first catheter tube shall be adapted to transfer compression and tension forces from the first operating means of the handle of the delivery means to the first retaining means of the catheter tip without overly changing of its total length. The distal end of the first catheter tube terminates at a flared section as the transition to the section defining the first retaining means of the catheter tip.

The flared section and the first retaining means may be formed integrally and may be connected to the distal end section of the first catheter tube. Alternatively, the first retaining means and the flared section of the first catheter tube may be all of the same material and originating from the same raw tube prior to a widening process so that the flared section and the first retaining means are the same elements.

In accordance with another aspect of the present disclosure, the catheter system further comprises steering means. The steering means serves for guiding the delivery means and, in particular, the catheter tip of the delivery means when advancing the catheter tip through the patient's vasculature.

In some embodiments of the present disclosure, the steering means comprises a steerable catheter tube having a proximal end section and a distal end section. The proximal end section of the steerable catheter tube is connected or connectable with a handle of the steering means.

The handle of the steering means is provided with operating means, for example in the form of a rotatable knob or wheel, by means of which a flexural link region of the steerable catheter tube can be controlled.

In accordance with other embodiments disclosed herein, the steerable catheter tube of the steering means is provided without any flexural link region, which can be manipulated by corresponding operating means. Rather, in these embodiments, the material of the distal end section of the steerable catheter tube may have an increased flexibility compared to the material of the proximal end section. In this way, the distal end section of the steerable catheter tube may easily pass, for example, the aortic arch during insertion of the steerable catheter tube.

In some embodiments disclosed herein, the handle of the steering means is provided with operating means by means of which a flexural link region of the steerable catheter tube can be controlled, wherein the operating means preferably has a detent device to allow a set deflection of the flexural link region of the steerable catheter tube to be fixed. For example, it is possible to provide a suitable catch mechanism on the operating means, which cooperates with a body of the handle of the steering means. In particular, it is possible for the flexural link region of the steerable catheter tube to be connected to the operating means of the steering means by way of a control wire whereby, on an actuation of the operating means via the control wire a tensile forces is exerted on the flexural link region of the steerable catheter tube, which produces a predefined or predefinable deflection of the flexural link region.

However it is also possible, of course, to choose other embodiments as the operating means of the steering means for deflecting the steerable catheter tube or a flexural link region of the steerable catheter tube, in case the steerable catheter tube is provided with such a flexural link region.

In accordance with some embodiments disclosed herein, the proximal end section of the steerable catheter tube of the steering means terminates in a port section of the steering means or is connected with a port section of the steering means. The port section of the steering means serves for introducing the catheter tip and catheter shaft of the delivery means into the steerable catheter tube. For this purpose, the port section of the steering means has a lumen defining a passageway which extends through the port section, the distal end section of the passageway being aligned with the proximal end section of the steerable catheter tube.

The port section of the steering means is preferably integrated in or connected with the handle of the steering means.

The catheter tip and catheter shaft of the delivery means is introducible (via the port section of the steering means) into the steerable catheter tube. The catheter shaft of the delivery means and particularly the first catheter tube of the catheter shaft of the delivery means is moveable relative to the steerable catheter tube. In particular, the steerable catheter tube terminates proximal to the catheter tip wherein the cross-section of proximal end section of the introducer sheath shall be substantially the same as or slightly larger than the cross-section of the flared section provided at the proximal end of the first catheter tube.

The proximal end section of the steering means and, in particular, the proximal end section of the port section of the steering means is releasably connectable to the handle of the delivery means.

According to an aspect of the present disclosure, the catheter system further comprises an introducer having an introducer sheath. The introducer sheath has a cross-section greater than the cross-section of the steerable catheter tube of the steering means.

The introducer sheath serves as guiding means when introducing the delivery means and/or the steering means and, in particular, the steerable catheter tube of the steering means into the patient's vasculature. In more detail, the introducer sheath defines a passageway through which the catheter tip and catheter shaft of the delivery means and/or the steerable catheter tube of the steering means may be guided to the implantation side within the patient's body.

The introducer sheath has a distal end, a proximal end and a passageway extending there between. The introducer sheath has a length such that the distal end of the introducer sheath terminates proximal to the catheter tip of the delivery system, when the catheter shaft and the catheter tip of the delivery system has been fully introduced into the introducer sheath.

When at least a section of the catheter shaft of the delivery means or at least a section of the steerable catheter tube of the steering means has been introduced into the passageway defined by the introducer sheath, the introducer sheath is disposed concentrically and coaxially with the section of the catheter shaft of the delivery means or the steerable catheter tube of the steering means.

In any case, however, the catheter shaft of the delivery means and/or the steerable catheter tube of the steering means is moveable relative to the introducer sheath. In particular, the introducer sheath terminates proximal to the catheter tip wherein the cross-section of proximal end section of the introducer sheath shall be substantially the same as or slightly larger than the cross-section of the steerable catheter tube.

The proximal end section of the introducer sheath is connected to an introducer port. The introducer port serves for providing access to the introducer sheath of the introducer required for delivering the delivery means or the steerable catheter tube of the steering means into the introducer sheath.

The introducer port may comprise a base member which is configured to be manually fixable to the handle of the delivery means, when the catheter shaft of the delivery means is introduced into the passageway defined by the introducer sheath, or to be manually fixable to the handle of the steering means, when the steerable catheter tube of the steering means is introduced into the passageway defined by the introducer sheath.

In accordance with some embodiments disclosed herein, the introducer port is provided with a sealing arrangement for preventing leakage of fluid, in particular blood, from the introducer, when the introducer sheath is introduced into the patient's vasculature.

In some embodiments disclosed herein, the proximal end section of the introducer sheath terminates in a crimping section distal to the sealing arrangement of the introducer port. The crimping section of the introducer serves for crimping at least a middle section of a heart valve fixed to the catheter tip of the delivery means during the introduction of the catheter tip into the introducer sheath. As already mentioned above, according to embodiments disclosed herein, preferably only the distal and proximal end sections of the heart valve are fixed to the catheter tip of the delivery means by means of the first and second retaining means, wherein no dedicated retaining means is allocated to the middle section of the heart valve between the distal and proximal end sections of the heart valve.

For crimping the middle section of the heart valve during the introduction of the catheter tip into the introducer sheath, the catheter tip passes through the crimping section of the introducer thereby further reducing the diameter of the middle section of the heart valve fixed to the catheter tip. In some embodiments disclosed herein, the crimping section may comprise a conical tubular member having an inner diameter which decreases in the distal direction of the tubular member.

The introducer sheath may be of a thin material such as to allow length deformation of the introducer sheath upon transfer of compression and tension forces. The introducer sheath material, however, shall have sufficient stiffness in order to mechanically avoid kinking of the flexible sections of the distal portion of the catheter shaft during insertion of the catheter tip.

In some embodiments of the present disclosure, the introducer sheath has a pre-shaped, preferably curved, configuration.

An inlet may be provided at a proximal end section of the steering means, the introducer and/or the delivery means for injection of fluids, if necessary. Furthermore, a check valve may be provided at the proximal end section of the introducer sheath to prevent fluid from leaking out of the introducer sheath.

The introducer sheath may have a length sufficient to protect the inner wall of the blood vessel through which the catheter tip passes. In addition, a separate introducer system (not belonging to the catheter system) may be provided. The introducer system then may serve as a portal for passing the complete catheter system from the catheter tip to the catheter shaft into the patient's body and up to the heart.

In addition, the introducer sheath reduces the compression force exerted on the first catheter tube that is inserted through the introducer sheath. This increases manoeuvrability of the steerable catheter tube and the catheter shaft of the delivery means throughout the procedure. A consequence thereof is that any frictional force is reduced. Moreover, moving the catheter tip after it has been advanced through the vascular system of a patient, is greatly improved while at the same time lowering the risk of injury of the patient.

The length of the introducer sheath depends on the length of the catheter shaft of the delivery means and will typically be between about 20 cm and 100 cm. Those skilled in the art will appreciate, however, that all dimensions provided herein are intended as examples only, and that the introducer sheaths and catheter tubes of different dimensions may be substituted for a particular use.

As will be appreciated, the introducer sheath will be of a size, i.e. has an outer diameter, which will permit insertion in a patient's blood vessel (artery or vein) which is used for moving the stent transarterially or via a vein to an insufficient heart valve.

The introducer sheath may be capable of traversing tortuous pathways in the body of the patient without kinking. The introducer sheath may include an inner lubricious liner, an outer polymeric jacket, and a coil reinforcement between the inner and the outer layers. This introducer sheath may provide favourable flexibility without kinking or compression. One or more radiopaque bands or markers may be incorporated within the introducer sheaths material to allow precise location of the introducer sheaths distal end for positioning accuracy. Those skilled in the art will appreciate that other known materials may also be suitable for a particular purpose.

The catheter system is particularly adapted to deliver and implant a heart valve as described for example in the European Patent Application No. 07 110 318 or in the European Patent Application No. 08 151 963. In some embodiments of the present disclosure, a heart valve is accordingly used which comprises a stent and a heart valve prosthesis attached to the stent. The stent exhibits the following:

- a first retaining region, to which the heart valve prosthesis can be attached;
- an opposing, second retaining region with at least one retaining element, for example in the form of retaining eyes or in the form of retaining heads, whereby at least one retaining element of the stent can be put in releasable engagement with the holding means of the catheter tip of the delivery means;
- at least one retaining hoop, to which the heart valve prosthesis can be fastened; and
- at least one and preferably three positioning hoops, which are designed to engage in pockets of the native heart valve in the implanted state of the stent, thus to enable automatic positioning of the stent in the aorta of the patient.

In particular, a catheter system is disclosed herein, with which an expandable heart valve stent with a heart valve prosthesis attached to this stent can be advanced to the implantation site in a particularly simple way, for example via the aorta of a patient being treated (transarterially or transfemorally). Preferably, during transarterial or transfemoral access by the catheter system, the whole free cross-section available within the aorta is not completely filled up, since the catheter tip provided at the distal end region of the catheter system, in which the stent can be accommodated with the heart valve prosthesis, can be made sufficiently small with respect to its external diameter.

The expandable heart valve stent with the heart valve prosthesis attached to it can be fixed temporarily during implantation in a crimped state to the catheter tip of the delivery means.

The catheter system designed for transarterial or transfemoral access is therefore suitable for inserting a heart valve stent with a heart valve prosthesis attached to it, transarterially or transfemorally into the body of the patient; for example, the catheter tip of the delivery means of the catheter system is inserted via puncture of the A. femoris communis (inguinal artery).

In particular, with the catheter system designed for transarterial or transfemoral access, the catheter shaft of the delivery means may be designed so that it is both kink-resistant and flexible such that a bending radius of up to 4 cm, and preferably up to 3 cm, can be realised, at least at the distal end region of the catheter shaft.

BRIEF DESCRIPTION OF THE DRAWINGS

Various embodiments will be described with reference to the appended drawings below. Of these.

DETAILED DESCRIPTION

In the following, exemplary embodiments of the present disclosure will be described in more detail.

Figure 5:
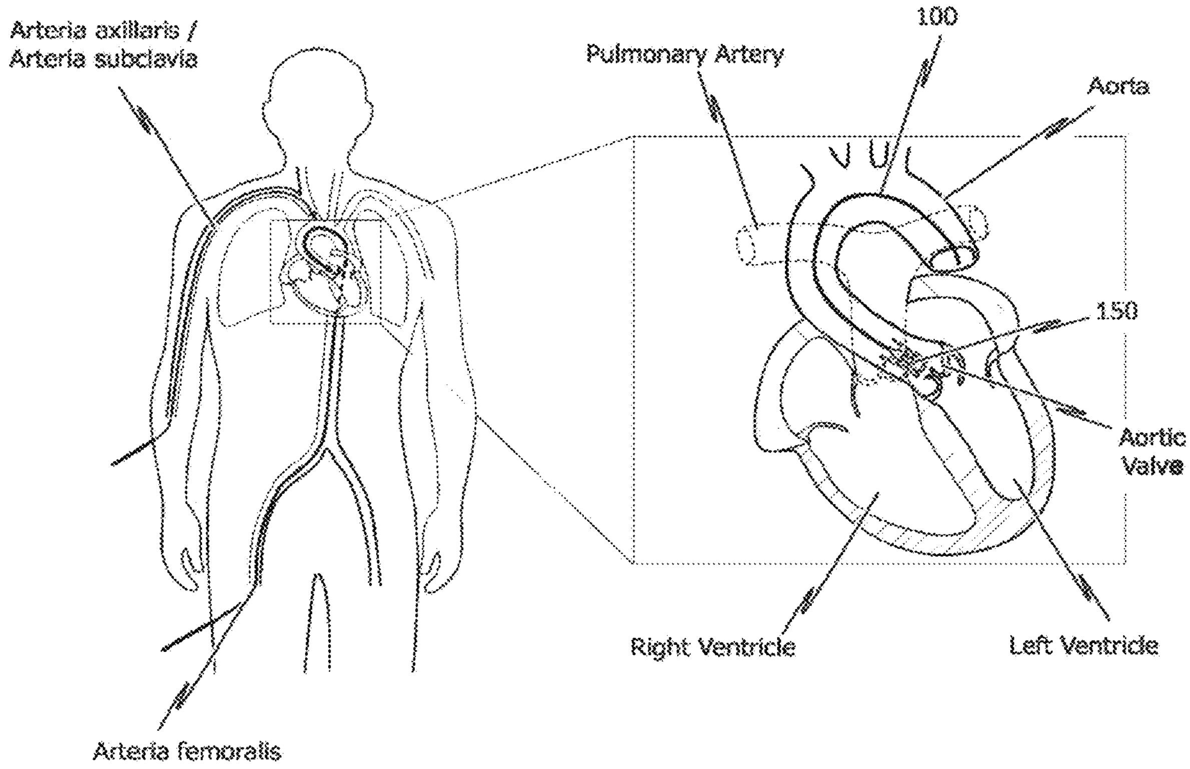
FIG. 5: a schematic view to illustrate a transfemoral/transarterial implantation procedure of a heart valve stent.
Figure 6A:
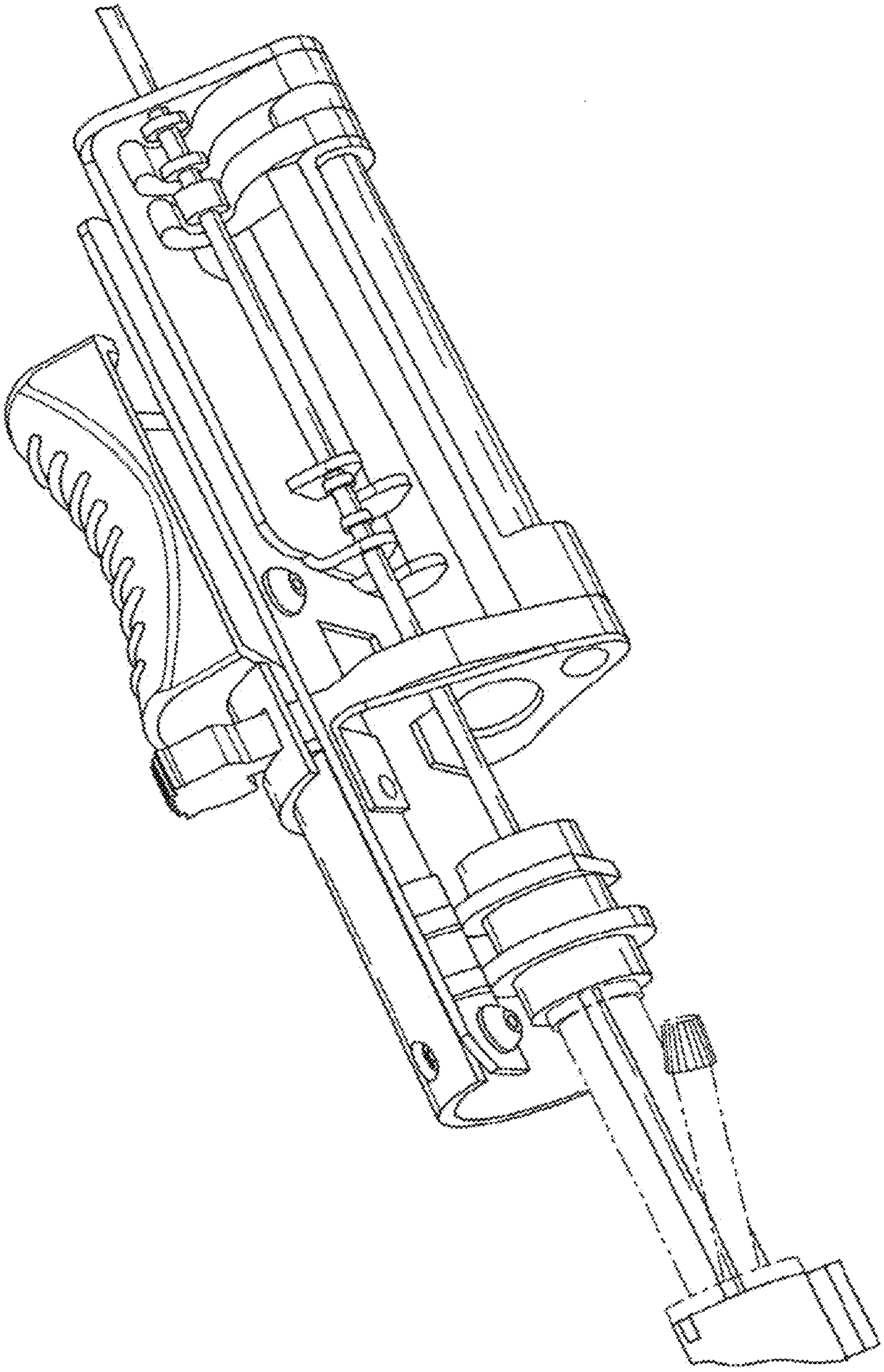
FIGS. 6*a-i*: sectioned side elevations of components of the delivery means of FIG. 2*a;*
Figure 6B:
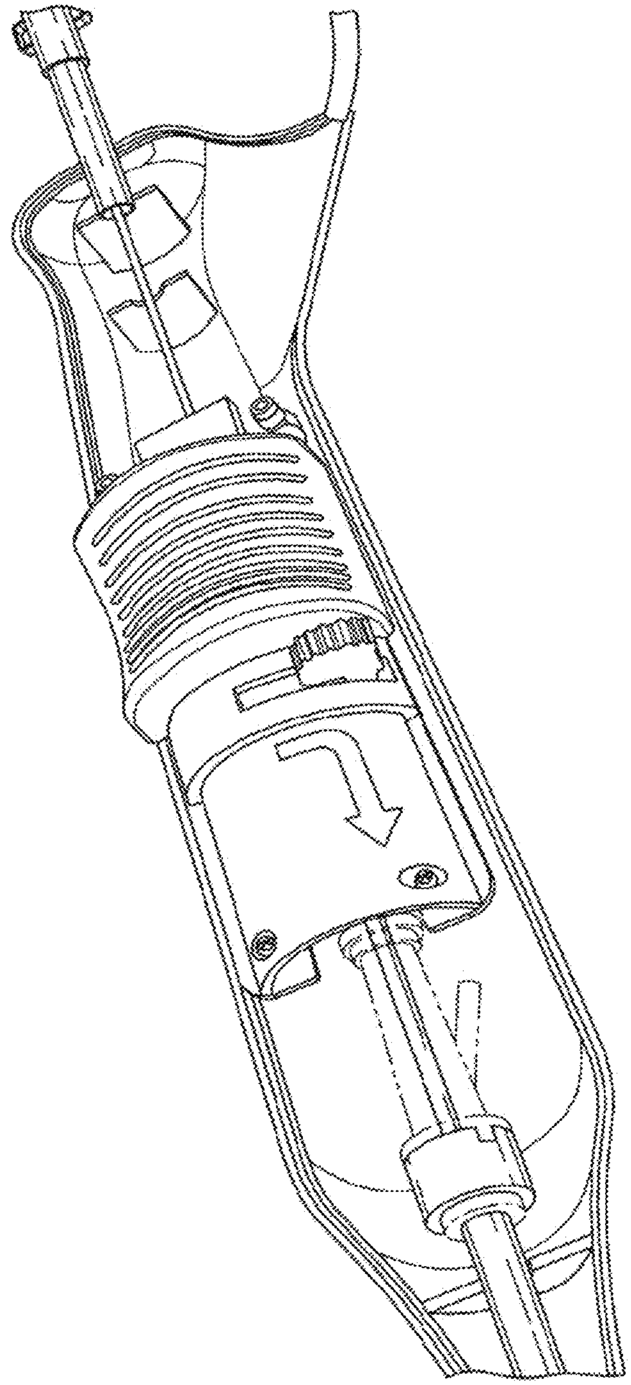
Figure 6C:
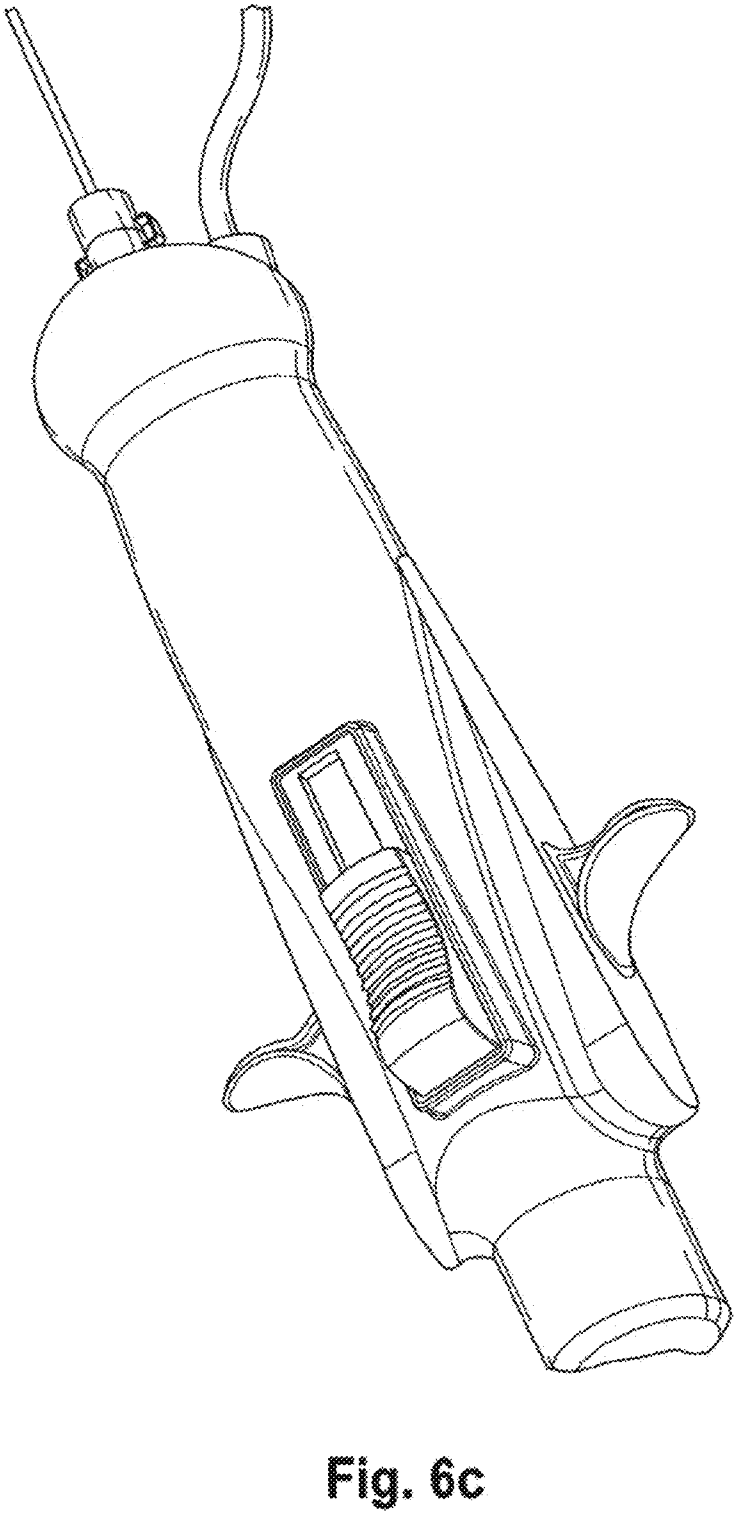
Figure 6D:
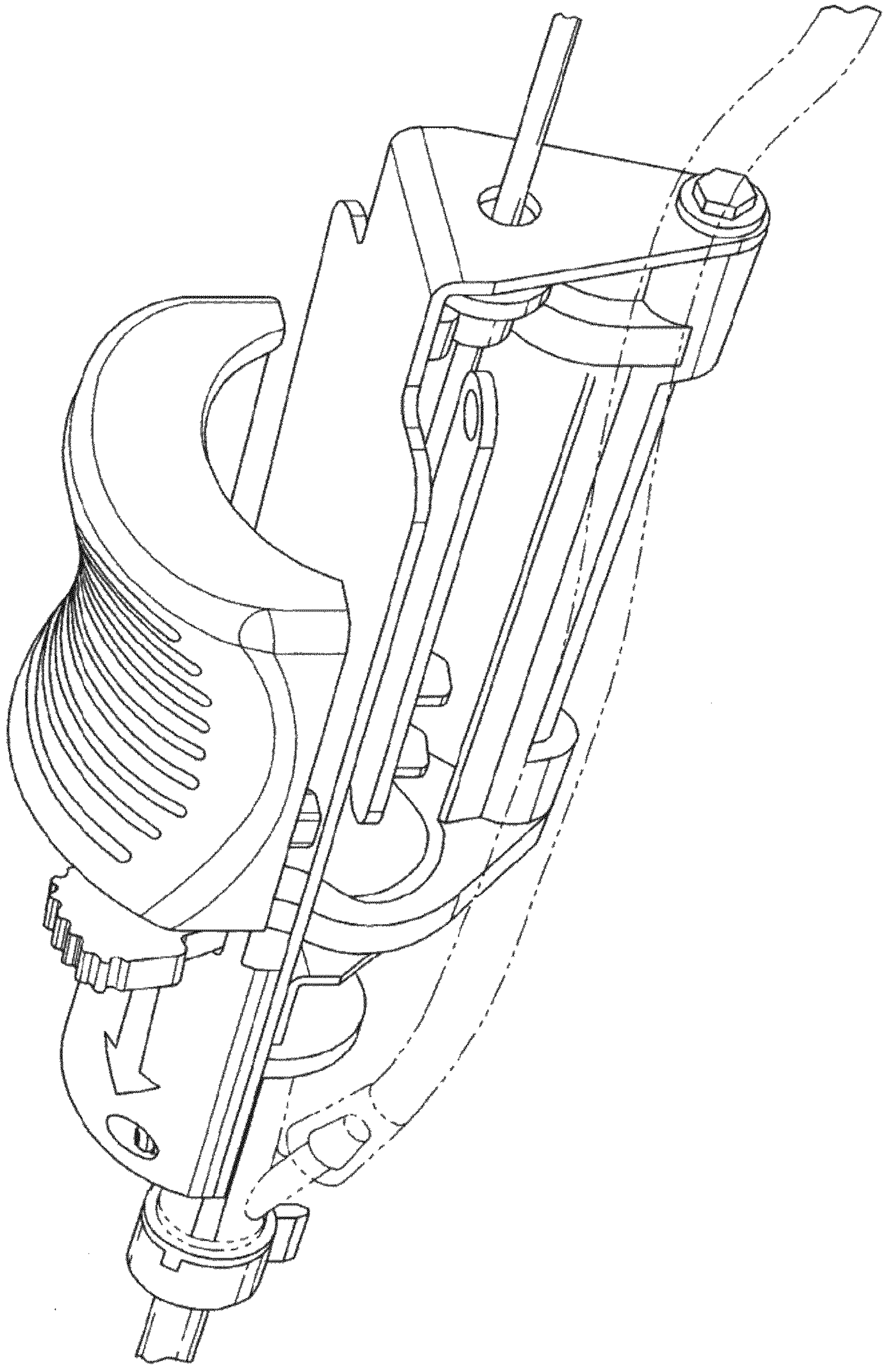
Figure 6E:
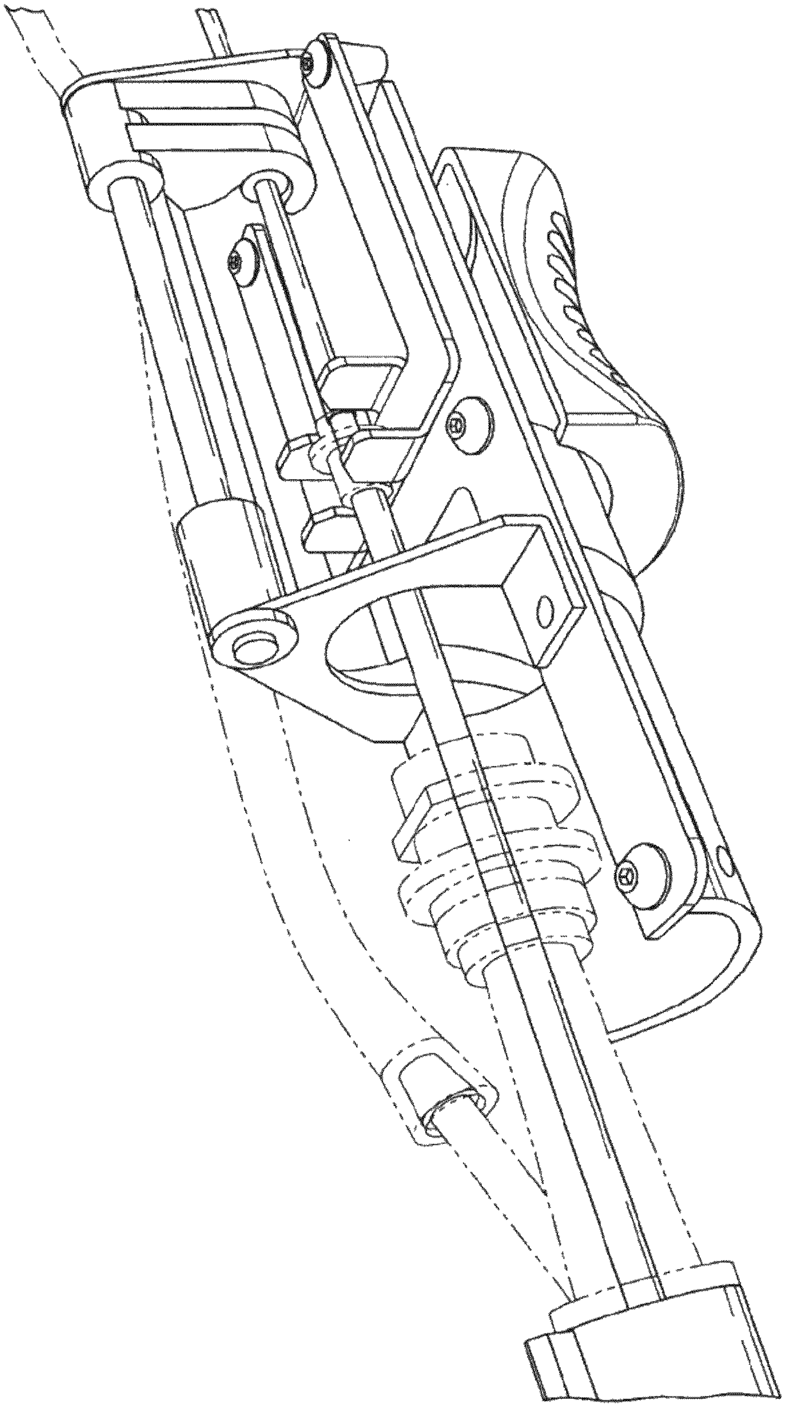
Figure 6F:
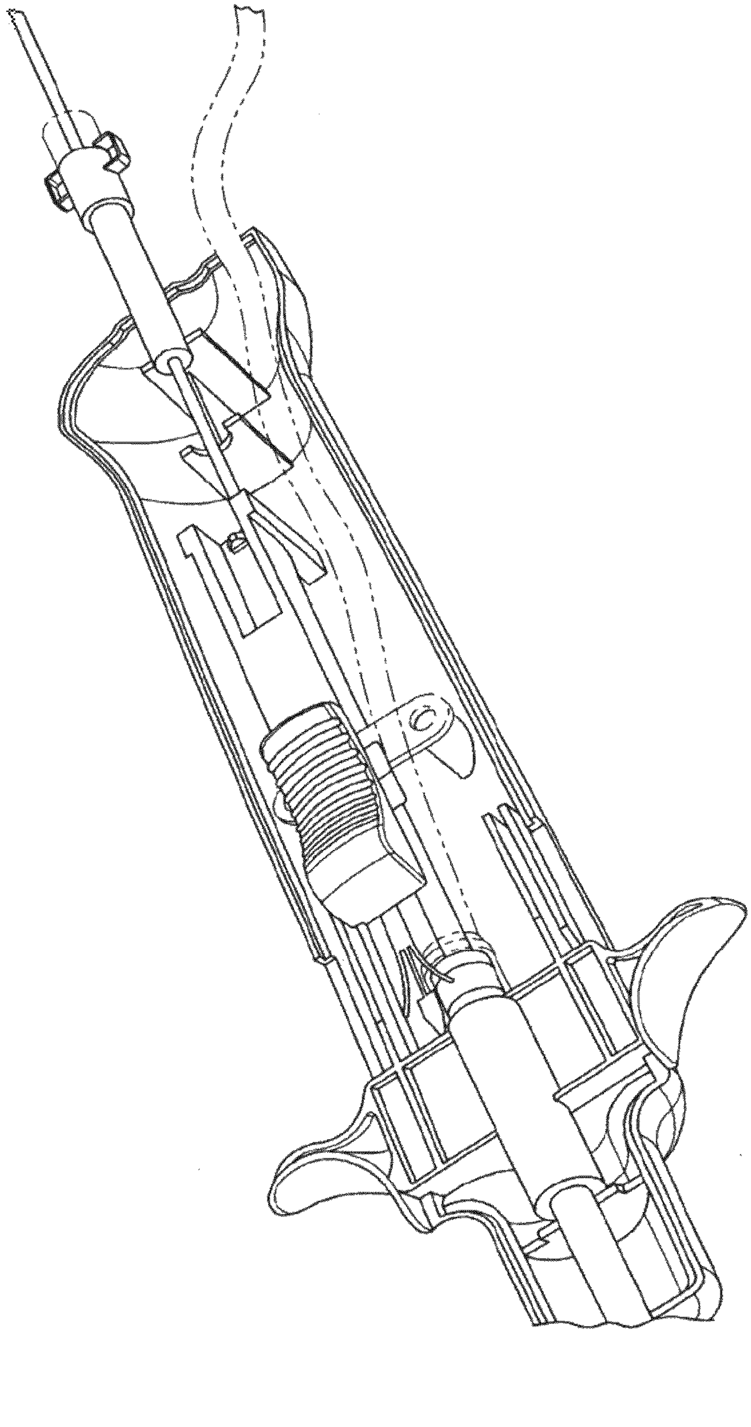
Figure 6G:
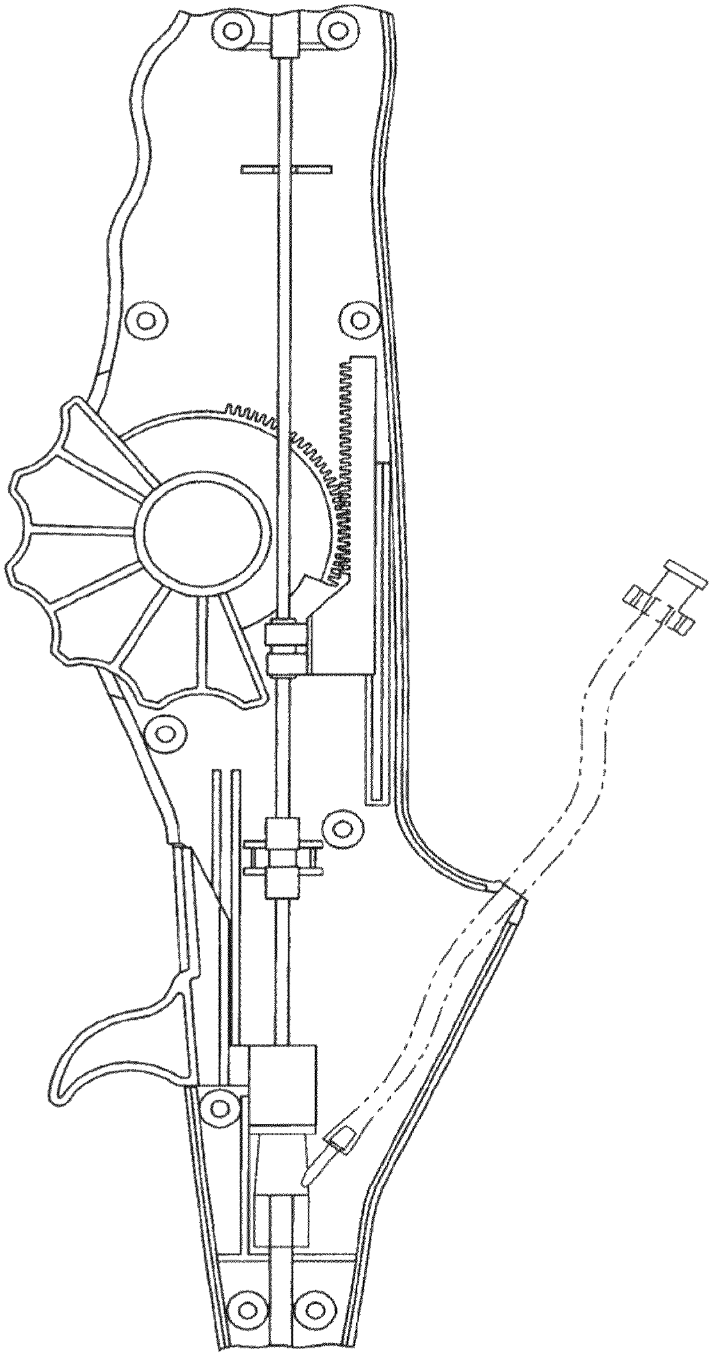
Figure 6H:
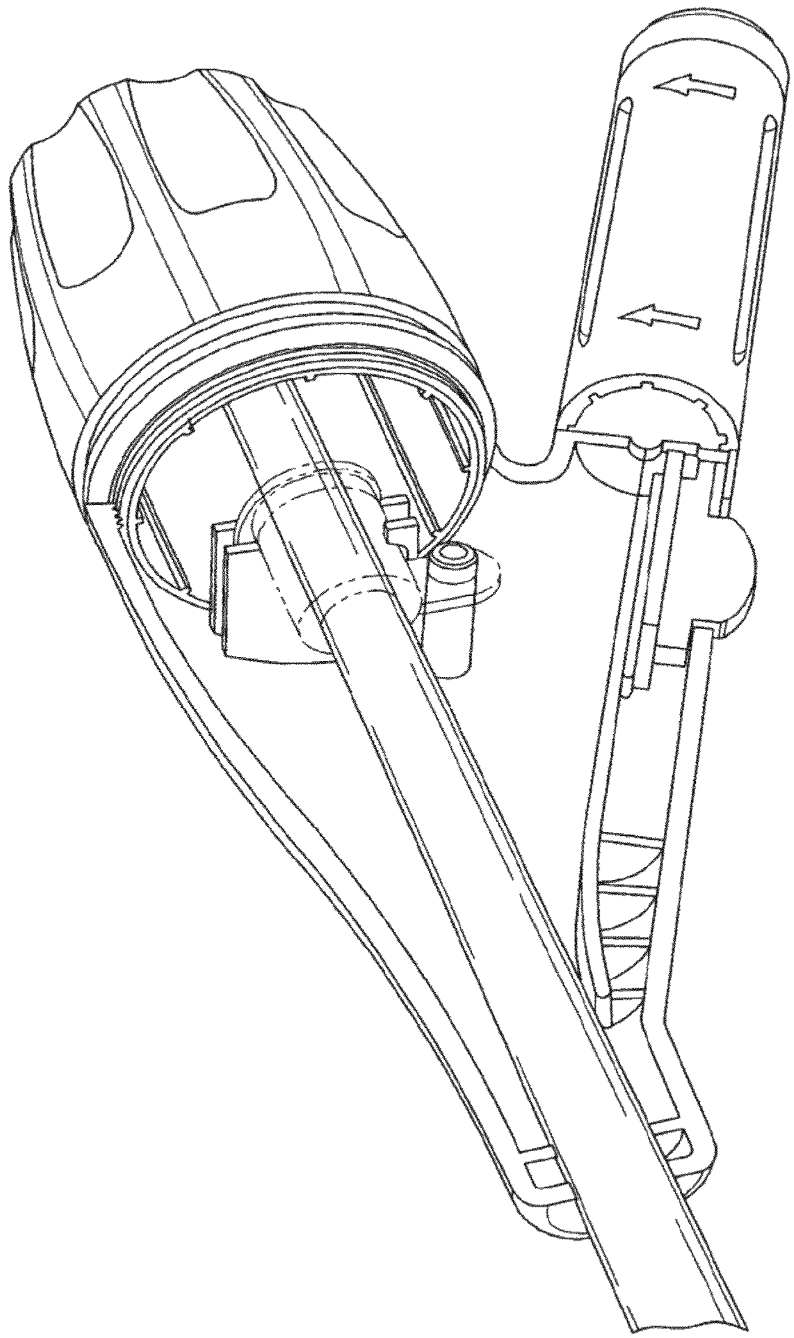
Figure 6I:
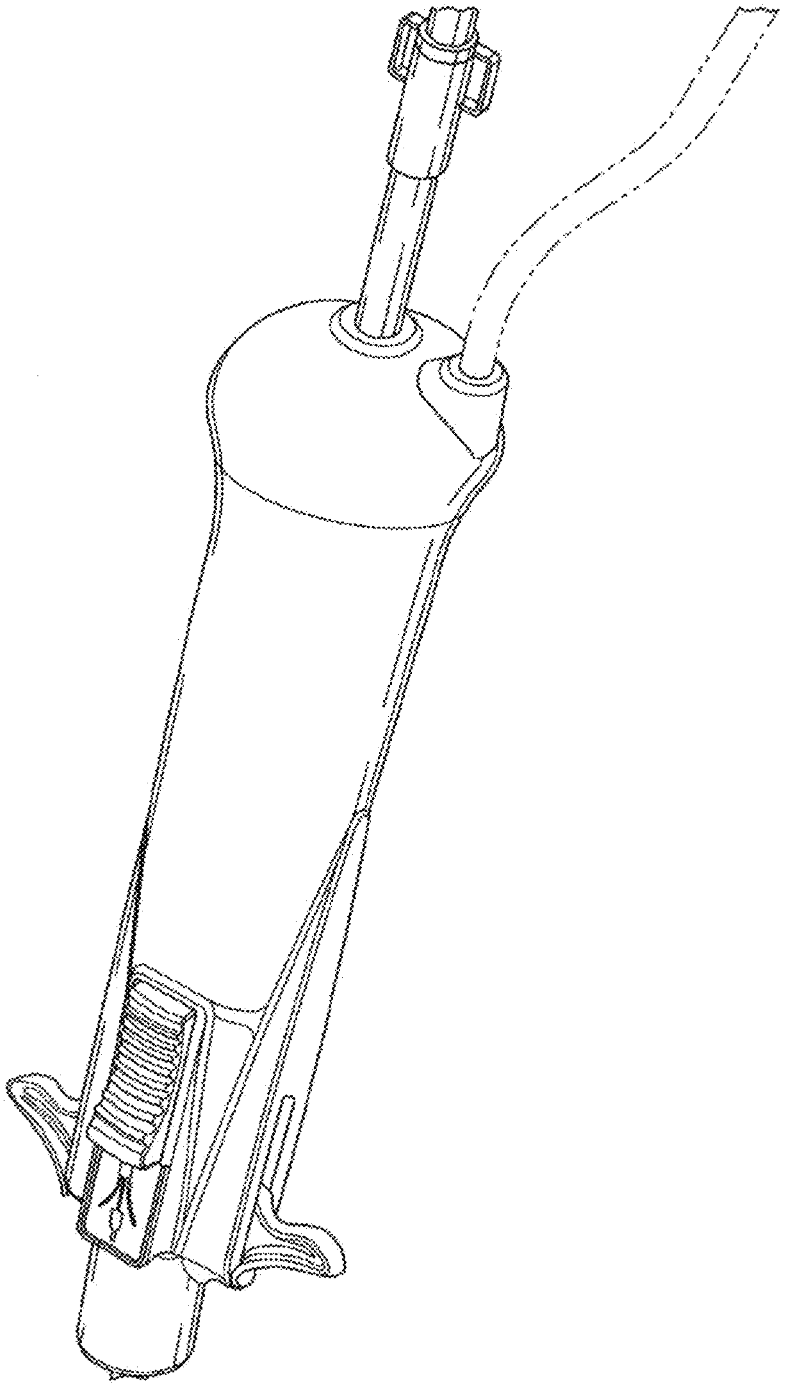

FIG. 5 shows schematically an example of how a transarterial or transfemoral access can be gained to the heart of a patient. In the illustration in accordance with FIG. 5, a heart valve stent 150 is advanced with the aid of a delivery system 100 via the femoral artery to the aortic valve. Embodiments of a delivery system 100, which is suitable for transarterial or transfemoral access, are described in the following.

Figure 1:
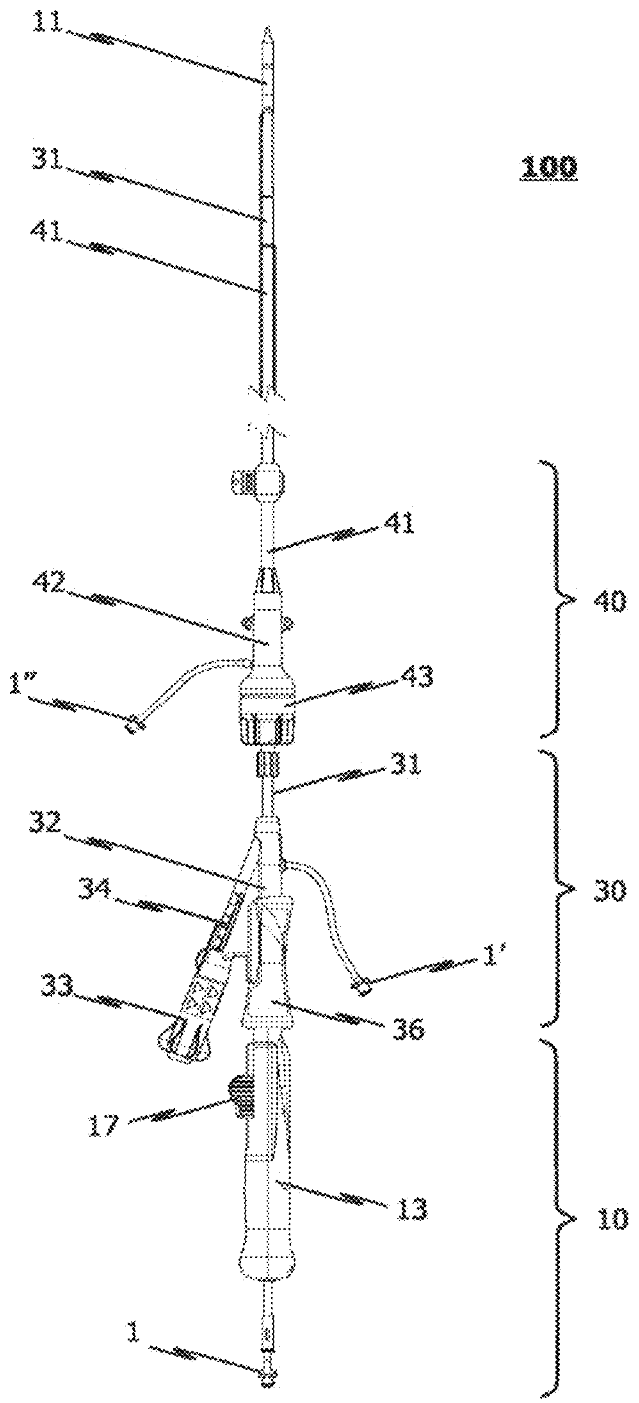
FIG. 1: a side elevation of an embodiment of a delivery system for transfemoral/transarterial insertion of an expandable heart valve.

As depicted, for example, in FIG. 1, the delivery system 100 according to an exemplary embodiment of the present disclosure comprises delivery means 10, steering means 30, and an introducer 40.

The delivery means 10 has a catheter tip 11, a catheter shaft 12, and a handle 13 connected to the proximal end section of the catheter shaft 12. In this regard, reference is also made to FIG. 2*a* and FIG. 2*b*.

Figure 2A:
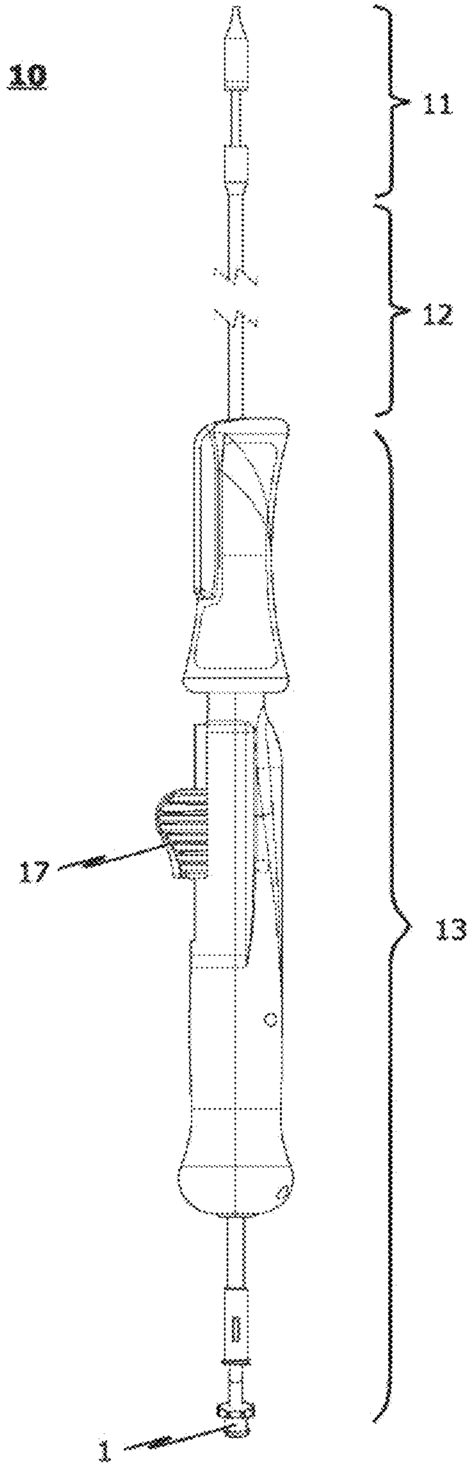
FIG. 2*a*: a side elevation of an embodiment of a delivery means of a delivery system in accordance with FIG. 1.
Figure 2B:
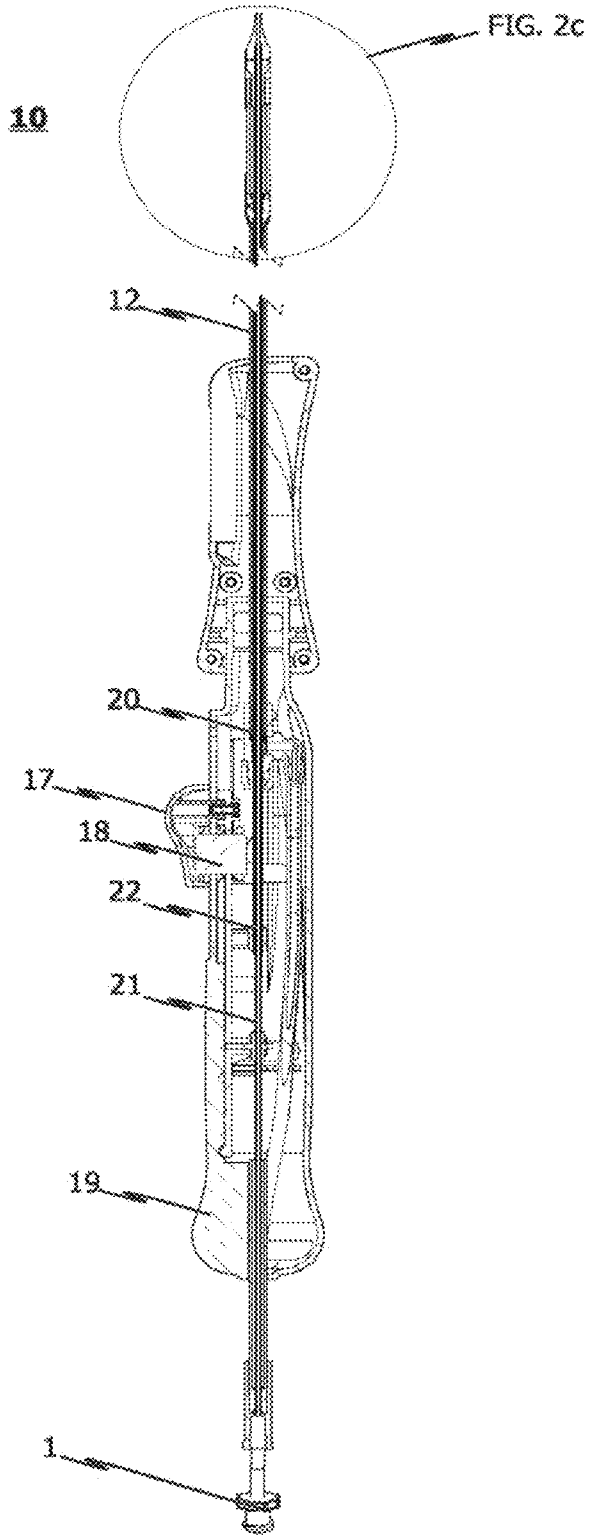
FIG. 2*b*: a sectioned side elevation of the delivery means of FIG. 2*a;*
Figure 2C:
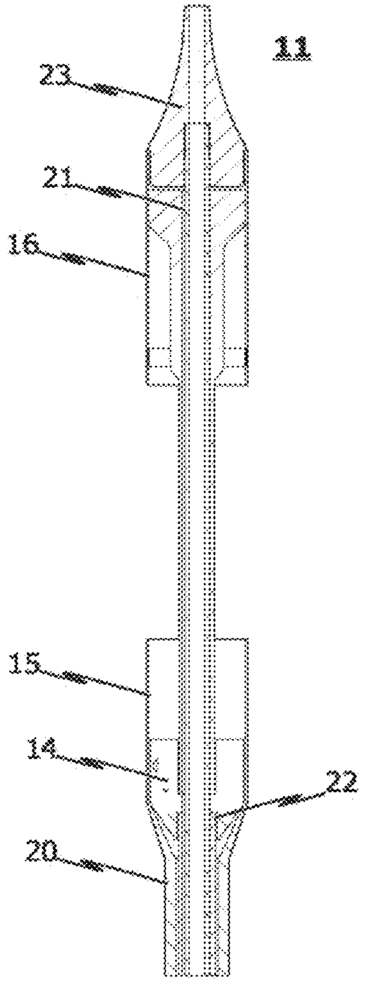
FIG. 2*c*: a sectioned side elevation of the catheter tip of the delivery means of FIG. 2*a;*

As illustrated, for example, in FIG. 2*c*, the catheter tip 11 of the delivery means 10 has a seat portion for accommodating a heart valve to be inserted in its crimped state and holding means 14 for releasably fixing the heart valve to the catheter tip 11.

The delivery means 10 further comprises a catheter shaft 12 for connecting the catheter tip 11 to the handle 13 of the delivery means 10, the distal end section of the catheter shaft 12 being flexible enough such that the catheter tip 11 and the distal end section of the catheter shaft 12 may pass the aortic arch during insertion through the aorta of the patient.

The seat portion of the catheter tip 11 comprises first retaining means 15 and second retaining means 16, the respective cross-sections of the first and second retaining means 15, 16 may be identical to each other. In the exemplary embodiment illustrated in FIG. 2*c*, the first and second retaining means 15, 16 are configured as sleeve-shaped elements, respectively. The lengths of these sleeve-shaped elements are respectively chosen such that the seat portion of the catheter tip is not totally covered by the sleeve-shaped elements. Rather and as illustrated in FIG. 2*c*, a middle section of the seat portion of the catheter tip is always uncovered.

The first and second retaining means 15, 16 are movable relative to each other and relative to the holding means 14. For this purpose, first force transmitting means 20 with a distal end section connected to the first retaining means 15 and a proximal end section connected to first operating means 17 of the handle 13 are provided. In addition, second force transmitting means 21 with a distal end section connected to the second retaining means 16 and a proximal end section connected to second operating means 18 of the handle 13 are provided. When manipulating the first and/or second operating means 17, 18 of the handle 13, the first and/or second retaining means 15, 16 may be moved relative to each other and relative to the holding means 14.

As can be seen from FIG. 2*b* and FIG. 2*c*, the first force transmitting means 20 may be constituted by a first catheter tube defining a first lumen and the second force transmitting means 21 is constituted by a second catheter tube defining a second lumen. The second catheter tube may have a cross-section less than the cross-section of the first catheter tube. The first catheter tube may be disposed concentrically and coaxially with the second catheter tube and the second catheter tube is received within the first lumen defined by the first catheter tube.

Contrary to the first and second retaining means 15, 16 of the catheter tip 11, however, the holding means 14 of the catheter tip 11 are not moveable relative to the handle 13 of the delivery means 10. Rather, the holding means 14 are connected to the body 19 of the handle 13 by using a holding tube 22 having a distal end connected to the holding means 14 and a proximal end connected to a body 19 of the handle 13.

The holding tube 22 may have a cross-section less than the cross-section of the first catheter tube of the first force transmitting means 20. In particular, the first catheter tube of the first force transmitting means 20 may be disposed concentrically and coaxially with both, the second catheter tube of the second force transmitting means 21 on the one hand and the holding tube 22 on the other hand.

In some embodiments, the holding tube 22 has a cross-section less than the cross-section of the first catheter tube and greater than the cross-section of the second catheter tube such that the holding tube 22 is received within the first lumen defined by the first catheter tube and the second catheter tube is received within a passageway defined by the holding tube 22. The passageway defined by the holding tube 22 has a diameter sufficient to accommodate the second catheter tube such that the second catheter tube is moveable relative to the holding tube 22.

The second lumen defined by the second catheter tube has a diameter sufficient to accommodate a guide wire (not shown). The second catheter tube may be made from a rigid material including, for example, Nitinol, stainless steel or a rigid plastic material. The material of the distal end section of the second catheter tube may have an increased flexibility compared to the material of the proximal end section in order to allow the distal end section of the catheter shaft 12 to pass the aortic arch during insertion of the catheter tip 11.

As can been seen, for example, from FIG. 2*c*, the distal end section of the second catheter tube terminates in a soft catheter end tip 23 having an atraumatic shape. The soft catheter end tip 23 is provided with a channel aligned with the second lumen defined by the second catheter tube such that a guide wire accommodated within the second lumen of the second catheter tube may pass through the channel of the soft catheter end tip. The second retaining means 16 of the catheter tip 11 is connected to the soft catheter end tip 23 such that the opened end of the second retaining means 16 faces in the proximal direction opposite to the direction of the soft catheter end tip 23 and to the second catheter tube.

According to the exemplary embodiments of the present disclosure, the holding tube 22 is made of a rigid material, for example, a rigid plastic material, stainless steel or Nitinol. The distal end of the holding tube 22 terminates in the holding means 14 which is also made of a rigid material, for example, a rigid plastic material or stainless steel. The passageway defined by the holding tube 22 is aligned with a channel which passes through the holding means 14. In this way, the second catheter tube is accommodated in the passageway of the holding tube 22 and the channel of the holding means 14 such as to be moveable relative to the holding tube 22 and the holding means 14.

The first catheter tube of the first force transmitting means 20 is made of a bendable but inelastic material. For example, the first catheter tube may be at least partly made of a braided or non-braided catheter tube. The first catheter tube shall be adapted to transfer compression and tension forces from the first operating means 17 of the handle 13 to the first retaining means 15 of the catheter tip 11 without overly changing its total length. The distal end of the first catheter tube terminates at a flared section as a transition to the section defining the first retaining means 15 of the catheter tip 11.

The flared section and the first retaining means 15 may be formed integrally and may be connected to the distal end section of the first catheter tube. In addition, the flared section may constitute the first retaining means 15 of the catheter tip 11. The first retaining means 15 and the flared section of the first catheter tube may be all of the same material and originating from the same raw tube prior to a widening process so that the flared section and the first retaining means 15 are the same elements.

Referring for example to FIG. 1, the delivery system 100 according to an exemplary embodiment of the present disclosure further comprises steering means 30 for guiding the delivery means 10 and, in particular, the catheter tip 11 of the delivery means 10 when advancing the catheter tip 11 through the patient's vasculature.

Figure 3A:
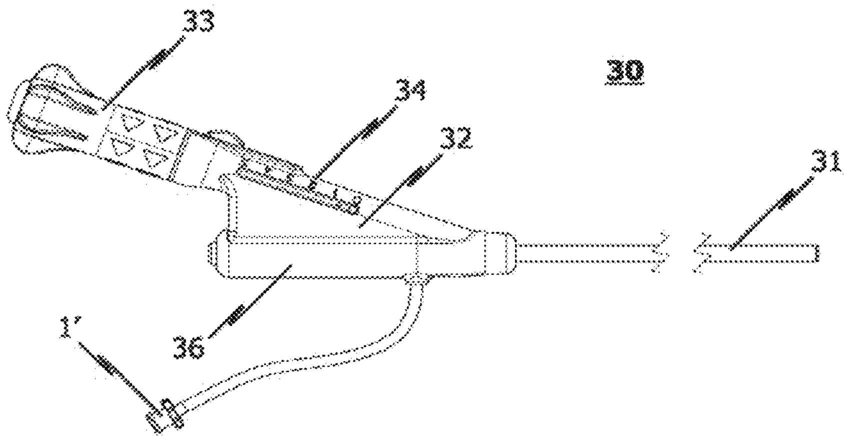
FIG. 3*a*: a side elevation an embodiment of a steering means of a delivery system in accordance with FIG. 1.
Figure 3B:
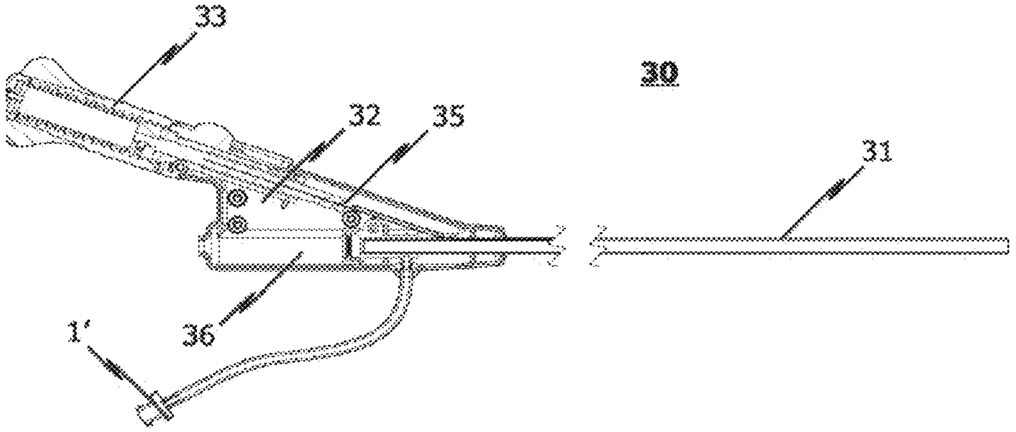
FIG. 3*b*: a sectioned side elevation of the steering means of FIG. 3*a;*

As illustrated in FIGS. 3*a*-*b*, the steering means 30 comprises a steerable catheter tube 31 having a proximal end section and a distal end section. The proximal end section of the steerable catheter tube 31 is connected or connectable with a handle 32 of the steering means 30.

The handle 32 of the steering means 30 is provided with operating means 33, for example in the form of a rotatable knob or wheel, by means of which a flexural link region of the steerable catheter tube 31 can be controlled.

As illustrated in FIG. 3*a*, the handle 32 of the steering means 30 is also provided with indicator means 34 for indicating the degree of deflection applied to the flexural link region of the steerable catheter tube 31 by means of the operating means 33.

Although not explicitly shown in FIG. 3*a*, in some embodiments, the operating means 33 preferably has a detent device to allow a set deflection of the flexural link region of the steerable catheter tube 31 to be fixed. For example, it is possible to provide a suitable catch mechanism on the operating means 33, which cooperates with a body of the handle 32 of the steering means 30.

As can be seen from FIG. 3*b*, a control wire 35 is provided, which connects the operating means 34 with the flexural link region of the steerable catheter tube 31. On an actuation of the operating means 33, a tensile forces is exerted via the control wire 35 on the flexural link region of the steerable catheter tube 31, which produces a predefined or predefinable deflection of the flexural link region.

However it is also possible, of course, to choose other embodiments as the operating means 33 of the steering means 30 for deflecting the steerable catheter tube 31 or a flexural link region of the steerable catheter tube 31.

In the exemplary embodiment of the steering means 30 illustrated in FIG. 3*b*, the proximal end section of the steerable catheter tube 31 of the steering means 30 terminates in a port section 36 of the steering means 30. The port section 36 of the steering means 30 serves for introducing the catheter tip 11 and catheter shaft 12 of the delivery means 10 into the steerable catheter tube 31. For this purpose, the port section 36 of the steering means 30 has a lumen defining a passageway which extends through the port section 36, the distal end section of the passageway being aligned with the proximal end section of the steerable catheter tube 31.

As illustrated in FIG. 1, the catheter tip 11 and catheter shaft 12 of the delivery means 10 is introducible (via the port section 36 of the steering means 30) into the steerable catheter tube 31. The catheter shaft 12 of the delivery means 10 and particularly the first catheter tube of the catheter shaft of the delivery means 10 is moveable relative to the steerable catheter tube 31. In particular, the steerable catheter tube 31 terminates proximal to the catheter tip 11 wherein the cross-section of proximal end section of the introducer sheath shall be substantially the same as or slightly larger than the cross-section of the flared section provided at the proximal end of the first catheter tube.

As illustrated in FIG. 1, the exemplary embodiment of the delivery system 100 is also provided with an introducer 40 having an introducer sheath 41. The introducer sheath 41 has a cross-section greater than the cross-section of the steerable catheter tube 31 of the steering means 30.

The introducer sheath 41 serves as guiding means when introducing the delivery means 10 and/or the steering means 30 and, in particular, the steerable catheter tube 31 of the steering means 30 into the patient's vasculature. In more detail, the introducer sheath 41 defines a passageway through which the catheter tip 11 and catheter shaft 12 of the delivery means 10 and/or the steerable catheter tube 31 of the steering means 30 may be guided to the implantation side within the patient's body.

Figure 4:
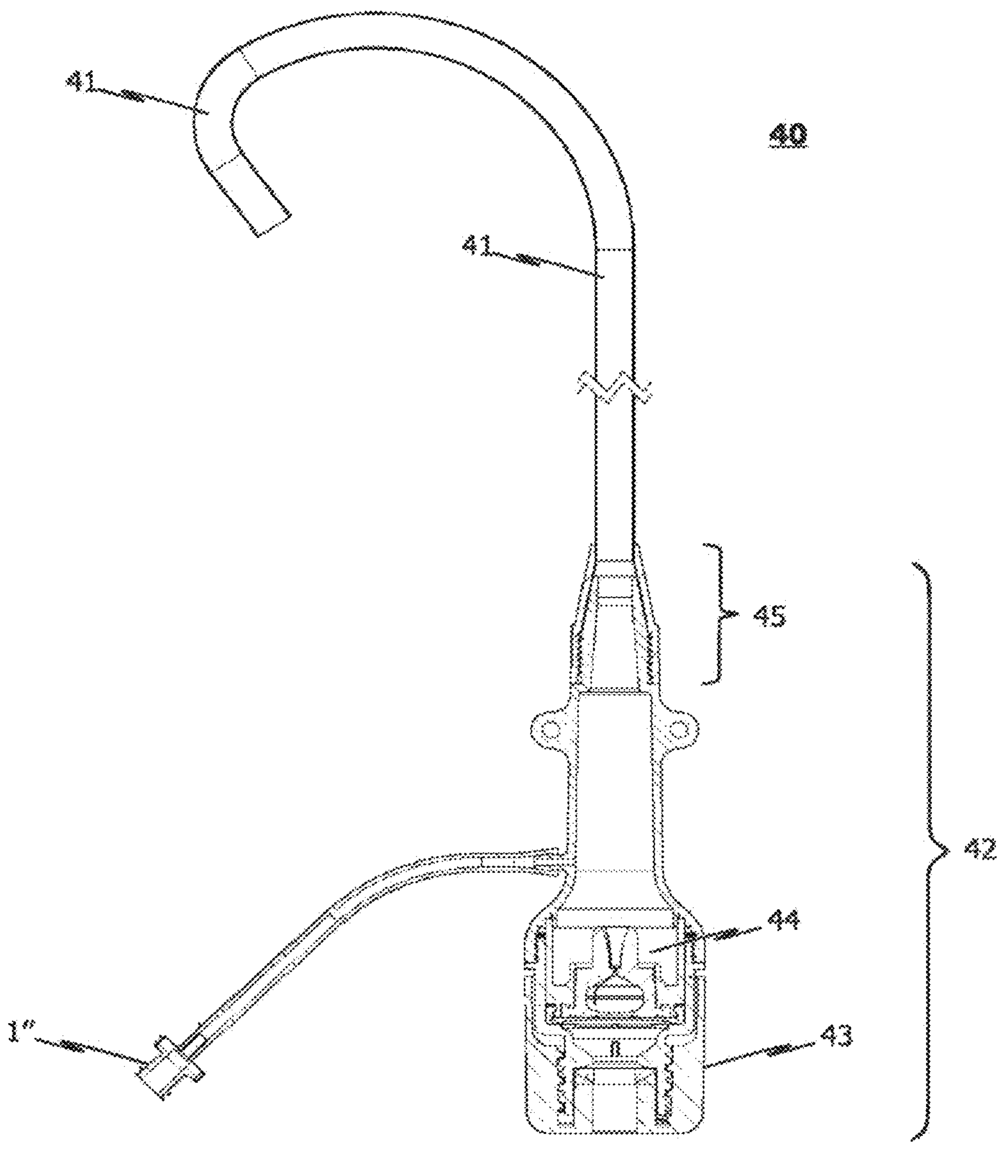
FIG. 4: a sectioned side elevation of an embodiment of an introducer of a delivery system in accordance with FIG. 1.

A sectional-side view of one embodiment of the introducer 40 is illustrated in FIG. 4.

Hence, the introducer sheath 41 has a distal end, a proximal end and a passageway extending there between. The introducer sheath 41 has a length such that the distal end of the introducer sheath 41 terminates proximal to the catheter tip 11 of the delivery system, when the catheter shaft 12 and the catheter tip 11 of the delivery system 100 has been fully introduced into the introducer sheath 41.

When at least a section of the catheter shaft 12 of the delivery means 10 or at least a section of the steerable catheter tube 31 of the steering means 30 has been introduced into the passageway defined by the introducer sheath 41, the introducer sheath 41 is disposed concentrically and coaxially with the section of the catheter shaft 12 of the delivery means 10 or the steerable catheter tube 31 of the steering means 30.

In any case, however, the catheter shaft 12 of the delivery means 10 and/or the steerable catheter tube 31 of the steering means 30 is moveable relative to the introducer sheath 41. In particular, the introducer sheath 41 terminates proximal to the catheter tip 11 wherein the cross-section of proximal end section of the introducer sheath 41 shall be substantially the same as or slightly larger than the cross-section of the steerable catheter tube 31.

The proximal end section of the introducer sheath 41 is connected to an introducer port 42. The introducer port 42 serves for providing access to the introducer sheath 41 of the introducer 40 required for delivering the delivery means 10 or the steerable catheter tube 31 of the steering means 30 into the introducer sheath 41.

The introducer port 42 may comprise a base member 43 which is configured to be manually fixable to the steerable catheter tube 31 is introduced into the passageway defined by the introducer sheath 41, or to be manually fixable to the handle 32 of the steering means 30, when the steerable catheter tube 31 of the steering means 30 is introduced into the passageway defined by the introducer sheath 41.

As can be seen from FIG. 4 the introducer port 42 is provided with a sealing arrangement 44 for preventing leakage of fluid, in particular blood, from the introducer 40, when the introducer sheath 41 is introduced into the patient's vasculature.

Moreover, in the exemplary embodiment of the introducer 40 illustrated in FIG. 4, the proximal end section of the introducer sheath 41 terminates in a crimping section 45 distal to the sealing arrangement 44 of the introducer port 42. The crimping section 45 of the introducer 40 serves for crimping at least a middle section of a heart valve fixed to the catheter tip 11 of the delivery means 10 during the introduction of the catheter tip 11 into the introducer sheath 41. As described with respect to FIG. 2*c* only the distal and proximal end sections of the heart valve are fixed to the catheter tip 11 of the delivery means 10 by means of the first and second retaining means 15, 16, wherein no dedicated retaining means is allocated to the middle section of the heart valve between the distal and proximal end sections of the heart valve.

For crimping the middle section of the heart valve during the introduction of the catheter tip 11 into the introducer sheath 41, the catheter tip 11 passes through the crimping section 45 of the introducer 40 thereby further reducing the diameter of the middle section of the heart valve fixed to the catheter tip 11. As illustrated in FIG. 4, the crimping section 45 may comprise a conical tubular member having an inner diameter which decreases in the distal direction of the tubular member.

The introducer sheath 41 may be of a thin material such as to allow bending of the introducer sheath 41 in order to follow the tortuous pathway from the femoral artery to the implant site. The introducer sheath 41 material, however, shall have sufficient stiffness in order to mechanically avoid kinking of the flexible sections of the distal portion of the catheter shaft 12 during insertion of the catheter tip 11.

An inlet 1, 1', 1" may be provided at a proximal end sections of the steering means 30, the introducer 40 and/or the delivery means 10 for injection of fluids, if necessary. Furthermore, a check valve may be provided at the proximal end section of the introducer sheath 41 to prevent fluid from leaking out of the introducer sheath 41.

The introducer sheath 41 may have a length sufficient to protect the inner wall of the blood vessel through which the catheter tip 11 passes. In addition, a separate introducer system (not belonging to the catheter system) may be provided. The introducer system then may serve as a portal for passing the complete catheter system from the catheter tip 11 to the catheter shaft 12 into the patient's body and up to the heart.

In addition, the introducer sheath 41 reduces the compression force exerted on the first catheter tube that is inserted through the introducer sheath 41. This increases manoeuvrability of the steerable catheter tube 31 and the catheter shaft 12 of the delivery means 10 throughout the procedure. A consequence thereof is that any frictional force is reduced. Moreover, moving the catheter tip 11 after it has been advanced through the vascular system of a patient, is greatly improved while at the same time lowering the risk of injury of the patient.

As will be appreciated, the introducer sheath 41 will be of a size, i.e. has an outer diameter, which will permit insertion in a patient's blood vessel (artery or vein) which is used for moving the stent transarterially or via a vein to an insufficient heart valve.

The FIGS. 6*a* to 6*i* represent sectioned side elevations of components of the delivery means of FIG. 2*a*.

The FIGS. 7 to 12 represent further embodiments of the present disclosure.

In one aspect, embodiments of the present disclosure relate to a catheter system, comprising:

i) a steering means; and ii) a delivery means for a heart valve, optionally balloon expandable or self-expandable, wherein the steering means and the delivery means are coaxially and rotationally independently movable.

In an embodiment, said catheter system is compatible with an introducer for intravascular, optionally transfemora (TF), applications or can be modified to be suitable for transapical (TA) delivery of a replacement heart valve. In such a TA system and means the direction in which the heart prosthesis is releaseably connected with the delivery means in turned by 180° compared to the TF application.

In some embodiments, the catheter system according to the present disclosure is made such that the introducer comprises an introducer sheath which extends or is extendable through the vascular duct and optionally proximal to the target site of the heart and optionally wherein the introducer sheath exhibits a crimping section.

The catheter system according to embodiments of the present disclosure may have a first and a second retaining means at the distal end of the catheter system to reversibly secure the heart valve to the delivery means.

Optionally the catheter system according to embodiments of the present disclosure is characterized in that the first retaining means reversibly secures the distal end of the heart valve to the delivery means and the second retaining means reversibly secures the proximal end of the heart valve to the delivery means.

In an embodiment, the mid-section of the heart valve is not covered by a sleeve means.

It thus rests flexible in terms of diameter and the tissue is not pressured by way of a crimping procedure that results in tension onto the pericard valve material. In this manner the heart valve is only crimped during the deployment procedure and thus the time during which the replacement heart valve is crimped to its smallest diameter is kept relatively short.

Accordingly, in at least one embodiment of a catheter system according to the present disclosure the diameter of the secured heart valve varies over its length, and preferably the heart valve is compressible over its length to the inner diameter of the introducer sheath.

In at least one embodiment thus the catheter system according to the present disclosure the inner diameter if the introducer sheath can be chosen as required by the respective application and may be less than 24 French, for example, less than 20 French, less than 18 French, and even less than 16 French.

In at least one embodiment the introducer sheath has a pre-shaped, preferably a curved, configuration.

The skilled person will appreciate that materials usually applied in catheter and delivery systems can also be used in embodiments according to the present disclosure. For example, in a catheter system according to an embodiment of the present disclosure the introducer sheath is characterized by a flexible polymer, a hydrophilic coating, a PTFE liner, coil reinforcement and/or braid reinforcement.

The replacement heart valve may be attached with useful meant to the delivery means which are compatible with the other parts of the device. In an embodiment the heart valve is attached to the delivery means by way of holding means wherein the heart valve and the delivery means exhibit complementary shapes. For example, the heart valve may have male connector elements at the distal and proximal end to engage with female connector elements on the delivery means.

In at least one embodiment according to the present disclosure in the catheter system the delivery means and steering means are operated by one or two means, optionally one or two handles. The steering means may exhibit means to deflect the shaft of the delivery catheter from a relaxed configuration into a curved configuration.

In at least one embodiment of the catheter system according to the present disclosure the delivery means and steering means are releasably connectable.

In another aspect, embodiments of the present disclosure relate to a delivery system for a heart valve comprising i. a steering means; ii. a delivery means for a heart valve and iii. an introducer sheath wherein the steering means, the delivery means and the introducer sheath are coaxially and circumferentially independently movable.

In an exemplary embodiment the introducer sheath extends or is extendable through the vascular duct and optionally proximal to the heart.

The different parts and sections of the delivery system may be adapted to each other and made in a way that they are compatible in their constructive and functional characteristics. In at least one embodiment, the steering means, the delivery means and the introducer sheath are at least sectionally, partially or substantially completely arranged coaxially to each other. The steering means, the delivery means and the introducer sheath may be coaxially and rotationally independently movable.

In the delivery system according to some embodiments of the present disclosure, the delivery means and steering means can be simultaneously or independently introducible into the introducer sheath.

In the delivery system according to embodiments of the present disclosure the introducer sheath can exhibit a crimping section for reducing the diameter of the heart valve attached to the delivery means. Such a crimping section has the advantage that the replacement heart valve is only crimped over its entire length to its minimal diameter during the delivery and deployment procedure which leads to less stress impact onto the pericard tissue of the replacement heart valve.

In another aspect, embodiments of the present disclosure relate to a method for the delivery of a heart valve to the heart of a patient comprising the steps i. in a first step placing an introducer comprising an introducer sheath into a patient's vasculature; ii. in a second step introducing a catheter system having fixed thereto a self-expanding or balloon expandable heart valve through the introducer into the patient's vasculature; iii. in a third step positioning the heart valve proximal to the target site in the patient's heart, optionally positioning the heart valve substantially central in the target area; iv. in a fourth step positioning the heart valve at the target site; v. in a fifth step partially releasing the heart valve from the catheter system; vi. in a sixth step fully releasing the heart valve from the catheter system.

In some methods according to embodiments of the present disclosure at least one segment of the self-expanding heart valve is compressed from a first diameter to a second diameter that is smaller than the first diameter when the self-expanding heart valve is passed through the introducer sheath, preferably the crimping section.

In another aspect of embodiments of the present disclosure, at least one segment of the self-expanding heart valve expands from a first diameter to a second diameter that is larger than the first diameter when the self-expanding heart valve exits the distal end of the introducer sheath.

In another aspect, embodiments of the present disclosure relate to a method of loading a self-expanding or balloon expandable heart valve onto a delivery means of a catheter system having at least one shaft and at least one outer sheath and/or is characterized as described above and throughout the specification and comprising or consisting of:

- compressing the heart valve radially and placing the compressed heart valve into a tubular retainer, the retainer preventing the self-expanding valve from expanding radially,
- passing the inner shaft of the delivery system through the central opening of the compressed heart valve,
- attaching the distal tip to the shaft of the delivery system,
- advancing the outer sheath onto the compressed heart valve to prevent radial expansion of at least part of the heart valve, and
- removing the tubular retainer from the compressed self-expanding heart valve.

In the following further alternative and/or exemplary embodiments will be described.

In at least one embodiment the present disclosure relates to a delivery system for a prosthesis, e.g. a heart valve, which consists of or comprises in general three components. The three components each consist of a handle wherein each handle is characterized by additional parts as follows.

A port handle comprises a pre-shaped tubular component which can be introduced through the vasculature, e.g. transfemoral, of a patient starting femoral up to proximal to the heart. This introducer sheath has a length of 50 to 150 cm, such as 100 to 120 cm. The tubular element may have a pre-shaped bent or may be designed in a manner so that it easily bents around the main artery proximal the heart. A balloon device can be introduced through this handle/introducer sheath which represents a first step in the prosthesis delivery procedure. This handle exhibits a twist grip and is positioned at the upper leg and is functional to introduce the other components of the delivery system. The tubular component can be pushed through the port handle or is fixed thereto. The tubular component is made from a compatible polymer material reinforced with wire and may include PTFE or Teflon coated at the inside. The port handle may exhibit a valve or other means for closing the hollow entry tube which serves to introduce the introducer sheath and the catheter component of the system. The inner diameter of the introducer sheath is less than 25 French, such as less than 20 French, less than 18 French or has a diameter of 20, 18 or 16 French.

The introducer sheath can be coupled to the second handle (introducer sheath handle) by way of which one can push the introducer sheath combined with the introducer sheath handle. The introducer sheath handle exhibits a wire of similar means in a manner so that the introducer sheath is steerable. In this manner during the deployment of the prosthesis the introducer sheath can be bent or directed in a defined position which will facilitate the deployment procedure. The first and second handles can exhibit a means to releasable connect them to each other.

A third handle represents the catheter component of the delivery system. It comprises a handle, a catheter shaft, a distal capsule for releasable connecting the prosthesis, a tubing for flushing including a closing means. The handle exhibits control means for connecting the prosthesis and releasing it.

Any component or all components can be introduced by way of a guide wire.

The delivery procedure can follow the steps of opening the femoral vasculature as access and introducing a port and/or a guide wire. The port handle and the introducer sheath is positioned at the upper leg and introduced ascending the aorta. In a next step a balloon device is introduced through the port and the introducer sheath for widening by way of balloon expansion the target site. After this task is performed the balloon device is retrieved. In a next step the catheter is introduced through the introducer sheath. The prosthesis is preloaded onto the catheter at the distal capsule. The prosthesis is connected with its ends at defined mounting positions which represent male/female connections which allow the controlled release of the prosthesis at the target site in a step-wise manner. Accordingly, the prosthesis is connected with the catheter so that the connections represent a small diameter and the prosthesis is otherwise not connected and also not covered by way of a sheath or other covering. Thus the diameter of this middle part of the prosthesis is due to the outward tension of the stent material larger than at the connection sites. An advantage of this design is that a small diameter of the loaded prosthesis can be achieved. In the course of introducing the prosthesis loaded onto the catheter capsule into and through the introducer sheath the prosthesis will be crimped to its final diameter pre-defined by the inner diameter of the introducer sheath. The material design of the introducer sheath facilitates the crimping and also the progression through this sheath.

The prosthesis can now be approached in direction to the target site using the introducer sheath and catheter. Another advantage of the delivery system is that the catheter and the introducer sheath are both coaxially and rotationally independently movable. Moreover, by way of the steering means of the second handle the introducer sheath can be bended and thus facilitate to maneuver the prosthesis through the vasculature to its final target site. Another advantage of a system according to embodiments of the present disclosure is that the catheter handle and the second handle of the introducer sheath with the steering means can be moved and operated independently.

The release procedure can be managed by a reversible two-step process. The release process is initiated once the feelers of the prosthesis are placed inside the cusps of the native aortic valve. In a first step the proximal connecting means is pushed in a forward direction/proximal direction. This will release the proximal end of the prosthesis. The catheter of the prosthesis may exhibit visualization means for better visual control. In a second step, the distal connecting means may be retracted or pulled back by way of a control means on the catheter handle to release the distal end of the prosthesis and disconnect the entire prosthesis from the catheter. The control means can be designed as independent means for each connecting means or in a connected manner.

Thus the advantages of embodiments of the present disclosure are that the loading and in particular crimping of the prosthesis is achieved by way of the introducer sheath and thus the crimping procedure is combined with the introduction of the prosthesis into the vasculature which facilitates the process. This implies the advantage that a separate cover means to crimp the prosthesis beforehand is not necessary with the effect and additional advantage that the tissue of the prosthesis is more smoothly and less vigorously crimped. This implies a lower risk of damages to the tissue. Moreover, the crimping procedure is facilitated and the middle part of the prosthesis which is usually the thickest part of a valve prosthesis needs not be crimped by a special device or by hand. Another advantage is the steering mechanism independent from the catheter handle. The extension of the port by way of the introducer sheath for the delivery of heart prosthesis is novel and has the advantages as above described.

A further advantage is that the bending can be managed independently from the delivery capsule. Thus all parts like port, handles, capsule, steerable means and prosthesis are all independently movable and coaxially and rotationally movable which facilitates the deployment of the prosthesis at the target site. Moreover, the prosthesis may be deployed by a two-step procedure and is repositionable. The procedure may also be aborted during the delivery procedure.

The combination of the different components of the delivery system may help to achieve certain advantages and superior delivery and deployment results in a simple and safe manner.

The release of the heart valve prosthesis from the delivery means can occur in a 2-step deployment way.

The skilled person will appreciate that the catheter system, the delivery system, the method for loading and the method for the delivery of the heart valve to the heart may be combined with suitable devices and methods or steps to prepare the target site in the heart for the deployment of the replacement heart valve prosthesis. Accordingly, a balloon device or balloon system can be applied before the delivery of the replacement heart valve to expand the target site within the heart. This system may be introduced by way of the port and/or introducer sheath according to embodiments of the present disclosure which exhibits the advantage that the port and introducer sheath can be positioned in the patient's vasculator entrance femorally and only one access is necessary to perform the dilatation of the target site by way of balloon expansion. After the balloon device is retrieved the replacement prosthesis can be applied as described above.

Parts and devices that are introduced can be guided by a guide wire known in the art and made from materials as usually applied in the field.

It can be advantageous if the tip of the catheter device is made of a soft or semi firm material and/or which is bendable in order to easily pass through the vasculator of the patient. Known materials can be used for such a flexible tip.

It is emphasized that the combination of the introducer sheath with the delivery catheter part according to embodiments of the present disclosure does not only simplify the loading and delivery procedure but an advantage is also that less layers of heart valve prosthesis coverage is needed and thus the diameter and crimping diameter can be reduced or/and the forces applied to the prosthesis is influenced in an advantageous manner. Thus less impact as compared in conventional devices and loading procedures can be expected which implies the advantage of les damage and a longer lifespan of the replacement heart valve.

In view of the particular construction characteristics of various catheters and delivery devices according to embodiments of the present disclosure one can denote two steps to the delivery procedure. The first step being the placement and the port, introducer sheath and loading of the replacement heart valve and the second step the deployment of the heart valve to the target site. The deployment as such is in turn a two-step sequence of steps with a first release step of part of the replacement heart valve and in a second step the final and complete release and final positioning of the replacement heart valve at the target site. In between these steps a retrieval of the replacement heart valve is still possible and offers the option of repositioning and complete retrieval and stop of the deployment procedure.

In accordance with an aspect, the present disclosure provides a catheter system for introducing an expandable heart valve into the body of a patient, the catheter system comprising delivering means for the heart valve.

In some aspects of the present disclosure, the delivering means comprises a catheter tip and a catheter shaft. The catheter tip of the delivery means has a seat portion for accommodating the heart valve to be introduced into the patient's body in its collapsed or crimped state. The catheter tip has further holding means for realisably fixing the heart valve to the catheter tip.

The seat portion of the catheter tip is constituted by a first retaining means and a second retaining means. In some embodiments of the present disclosure, the first retaining means and second retaining means may be constituted by a first sleeve-shaped member and a second sleeve-shaped member.

The first retaining means of the catheter tip serves for reversibly securing a distal end section of the heart valve to the delivery means and, in particular, to the catheter tip of the delivery means. On the other hand, the second retaining means of the catheter tip serves for reversibly securing a proximal end section of the heart valve to the delivery means and, in particular, to the catheter tip of the delivery means.

The first and second retaining means are moveable relative to each other and also relative to the holding means of the catheter tip.

According to some embodiments of the present disclosure, the catheter shaft of the delivery means comprises first force transmitting means and second force transmitting means.

A distal end section of the first force transmitting means is connected or connectable to the first retaining means of the catheter tip and a proximal end section of the first force transmitting means is connected or connectable to a first operating means of a handle of the delivery means. A distal end section of the second force transmitting means is connected or connectable to the second retaining means of the catheter tip and a proximal end section of the second force transmitting means is connected or connectable to a second operating means of the handle of the delivery means.

According to some embodiments of the present disclosure, the handle of the delivery means has at least one first operating means and at least one second operating means with which the catheter tip of the delivery means may be appropriately manipulated so that an expandable heart valve secured to the catheter tip may be released from the catheter tip in steps or in a defined or definable sequence of events.

In accordance with some embodiments of the present disclosure, the catheter tip has first and second retaining means—for example in the form of sleeve-shaped members which may be manipulated with the handle of the delivery means. These retaining means are used for releasably and reversibly securing a distal and proximal end section of the heart valve to the catheter tip.

In some embodiments of the present disclosure, the first retaining means serves for releasably and reversibly securing first functional components of the heart valve, for example retaining hoops of a stent or alternatively positioning hoops of a stent, while the second retaining means serves for releasably and reversibly securing second functional components of the heart valve, for example, positioning hoops of a stent or alternatively for accommodating retaining hoops of a stent.

In relation to the handle of the delivery means, in some embodiments it is preferably provided that, on one hand, the first operating means cooperate with the first retaining means of the catheter tip so that, on actuation of the first operating means, a previously definable longitudinal displacement of the first retaining means may be effected relative to the holding means. On the other hand, the second operating means cooperates with the second retaining means of the catheter tip so that a previously definable longitudinal displacement of the second retaining means may be affected relative to the holding means.

In accordance with some embodiments of the present disclosure, the first and second retaining means only serve for securing the distal and proximal end sections of the heart valve to the catheter tip. In case the first and second retaining means are configured as first and second sleeve-shaped members, these sleeve-shaped members have a length such that a gap is between the first and second sleeve-shaped members when securing the distal and proximal end sections of the heart valve to the catheter tip.

In accordance with some embodiments of the present disclosure, the first force transmitting means of the delivery means is constituted by a first catheter tube defining a first lumen, and the second force transmitting means of the delivery means is constituted by a second catheter tube defining a second lumen. The second catheter tube has a cross-section less than the cross-section of the first catheter tube. The first catheter tube is disposed concentrically and coaxially with the second catheter tube and the second catheter tube is received within the first lumen defined by the first catheter tube.

Contrary to the first and second sleeve-shaped members of the catheter tip, however, the holding means of the catheter tip is not moveable relative to the handle of the delivery means. Rather, the holding means is connected to the handle of the delivery means by using a holding tube having a distal end connected to the holding means and a proximal end connected to a body of the handle of the delivery means. The holding tube has a cross-section less than the cross-section of the first catheter tube. In particular, the first catheter tube is disposed concentrically and coaxially with both, the second catheter tube on the one hand and the holding tube on the other hand.

In some embodiments, the holding tube has a cross-section less than the cross-section of the first catheter tube and greater than the cross-section of the second catheter tube such that the holding tube is received within the first lumen defined by the first catheter tube and the second catheter tube is received within a passageway defined by the holding tube. The passageway defined by the holding tube has a diameter sufficient to accommodate the second catheter tube such that the second catheter tube is moveable relative to the holding tube.

The second lumen defined by the second catheter tube has a diameter sufficient to accommodate a guide wire. The second catheter tube is made from a rigid material including, for example, nitinol, stainless steel or a rigid plastic material. The material of the distal end section of the second catheter tube may have an increased flexibility compared to the material of the proximal end section in order to allow the distal end section of the catheter shaft to pass the aortic arch during insertion of the catheter tip.

In some embodiments of the present disclosure, the distal end section of the second catheter tube terminates in a soft catheter end tip having an atraumatic shape. The soft catheter end tip is provided with a channel aligned with the second lumen defined by the second catheter tube such that a guide wire accommodated within the second lumen of the second catheter tube may pass through the channel of the soft catheter end tip. The second sleeve-shaped member of the catheter tip is connected to the soft catheter end tip such that the opened end of the second sleeve-shaped member faces in the proximal direction opposite to the direction of the soft catheter end tip and to the second catheter tube.

In some embodiments, the holding tube is made of a rigid material, for example, a rigid plastic material, stainless steel or Nitinol. The distal end of the holding tube terminates in the holding means which is also made of a rigid material, for example, a rigid plastic material or stainless steel. The passageway defined by the holding tube is aligned with a channel which passes through the holding means. In this way, the second catheter tube is accommodated in the passageway of the holding tube and the channel of the holding means such as to be moveable relative to the holding tube and the holding means.

The holding tube is provided for connecting the holding means to the handle of the delivery means. For this purpose, the holding tube has a distal end connected to the holding means and a proximal end connected to a body of the handle of the delivery means.

In some embodiments, the first catheter tube is preferably made of a bendable but axially rigid material. For example, the first catheter tube may be at least partly made of a braided or non-braided catheter tube. Hence, the first catheter tube may have a stiff braid reinforced body similar to the catheter body described in U.S. Pat. No. 4,665,604 which is incorporated herein by reference.

The first catheter tube shall be adapted to transfer compression and tension forces from the first operating means of the handle of the delivery means to the first retaining means of the catheter tip without overly changing of its total length. The distal end of the first catheter tube terminates at a flared section as the transition to the section defining the first retaining means of the catheter tip.

The flared section and the first retaining means may be formed integrally and may be connected to the distal end section of the first catheter tube.

Alternatively, the first retaining means and the flared section of the first catheter tube may be all of the same material and originating from the same raw tube prior to a widening process so that the flared section and the first retaining means are the same elements.

In accordance with another aspect of the present disclosure, the catheter system further comprises steering means. The steering means for guiding the delivery means and, in particular, the catheter tip of the delivery means when advancing the catheter tip through the patient's vasculature.

In some embodiments of the present disclosure, the steering means comprises a steerable catheter tube having a proximal end section and a distal end section. The proximal end section of the steerable catheter tube is connected or connectable with a handle of the steering means.

The handle of the steering means is provided with operating means, for example in the form of a rotatable knob or wheel, by means of which a flexural link region of the steerable catheter tube can be controlled.

In accordance with other embodiments disclosed herein, the material of the distal end section of the steerable catheter tube may have an increased flexibility compared to the material of the proximal end section. In this way, the distal end section of the steerable catheter tube may easily pass, for example, the aortic arch during insertion of the steerable catheter tube.

In some embodiments disclosed herein, the handle of the steering means is provided with operating means by means of which a flexural link region of the steerable catheter tube can be controlled, wherein the operating means preferably has a detent device to allow a set deflection of the flexural link region of the steerable catheter tube to be fixed. For example, it is possible to provide a suitable catch mechanism on the operating means, which cooperates with a body of the handle of the steering means. In particular, it is possible for the flexural link region of the steerable catheter tube to be connected to the operating means of the steering means by way of a control wire whereby, on an actuation of the operating means via the control wire a tensile forces is exerted on the flexural link region of the steerable catheter tube, which produces a predefined or predefinable deflection of the flexural link region.

However it is also possible, of course, to choose other embodiments as the operating means of the steering means for deflecting the steerable catheter tube or a flexural link region of the steerable catheter tube, in case the steerable catheter tube is provided with such a flexural link region.

In accordance with some embodiments disclosed herein, the proximal end section of the steerable catheter tube of the steering means terminates in a port section of the steering means or is connected with a port section of the steering means. The port section of the steering means serves for introducing the catheter tip and catheter shaft of the delivery means into the steerable catheter tube. For this purpose, the port section of the steering means has a lumen defining a passageway which extends through the port section, the distal end section of the passageway being aligned with the proximal end section of the steerable catheter tube.

In some embodiments, the port section of the steering means is preferably integrated in or connected with the handle of the steering means.

The catheter tip and catheter shaft of the delivery means is introducible (via the port section of the steering means) into the steerable catheter tube. The catheter shaft of the delivery means and particularly the first catheter tube of the catheter shaft of the delivery means is moveable relative to the steerable catheter tube. In particular, the steerable catheter tube terminates proximal to the catheter tip wherein the cross-section of proximal end section of the introducer sheath shall be substantially the same as or slightly larger than the cross-section of the flared section provided at the proximal end of the first catheter tube.

The proximal end section of the steering means and, in particular, the proximal end section of the port section of the steering means is releasably connectable to the handle of the delivery means.

According to an aspect of the present disclosure, the catheter system further comprises an introducer having an introducer sheath. The introducer sheath has a cross-section greater than the cross-section of the steerable catheter tube of the steering means.

The introducer sheath serves as guiding means when introducing the delivery means and/or the steering means and, in particular, the steerable catheter tube of the steering means into the patient's vasculature. In more detail, the introducer sheath defines a passageway through which the catheter tip and catheter shaft of the delivery means and/or the steerable catheter tube of the steering means may be guided to the implantation side within the patient's body.

The introducer sheath has a distal end, a proximal end and a passageway extending there between. The introducer sheath has a length such that the distal end of the introducer sheath terminates proximal to the catheter tip of the delivery system, when the catheter shaft and the catheter tip of the delivery system has been fully introduced into the introducer sheath.

When at least a section of the catheter shaft of the delivery means or at least a section of the steerable catheter tube of the steering means has been introduced into the passageway defined by the introducer sheath, the introducer sheath is disposed concentrically and coaxially with the section of the catheter shaft of the delivery means or the steerable catheter tube of the steering means.

In any case, however, the catheter shaft of the delivery means and/or the steerable catheter tube of the steering means is moveable relative to the introducer sheath. In particular, the introducer sheath terminates proximal to the catheter tip wherein the cross-section of proximal end section of the introducer sheath shall be substantially the same as or slightly larger than the cross-section of the steerable catheter tube.

The proximal end section of the introducer sheath is connected to an introducer port. The introducer port serves for providing access to the introducer sheath of the introducer required for delivering the delivery means or the steerable catheter tube of the steering means into the introducer sheath.

The introducer port may comprise a base member which is configured to be manually fixable to the handle of the delivery means, when the catheter shaft of the delivery means is introduced into the passageway defined by the introducer sheath, or to be manually fixable to the handle of the steering means, when the steerable catheter tube of the steering means is introduced into the passageway defined by the introducer sheath.

In accordance with some embodiments disclosed herein, the introducer port is provided with a sealing arrangement for preventing leakage of fluid, in particular blood, from the introducer, when the introducer sheath is introduced into the patient's vasculature.

In some embodiments disclosed herein, the proximal end section of the introducer sheath terminates in a crimping section distal to the sealing arrangement of the introducer port. The crimping section of the introducer serves for crimping at least a middle section of a heart valve fixed to the catheter tip of the delivery means during the introduction of the catheter tip into the introducer sheath. As already mentioned above, according to embodiments disclosed herein, preferably only the distal and proximal end sections of the heart valve are fixed to the catheter tip of the delivery means by means of the first and second retaining means, wherein no dedicated retaining means is allocated to the middle section of the heart valve between the distal and proximal end sections of the heart valve.

For crimping the middle section of the heart valve during the introduction of the catheter tip into the introducer sheath, the catheter tip passes through the crimping section of the introducer thereby further reducing the diameter of the middle section of the heart valve fixed to the catheter tip. In some embodiments disclosed herein, the crimping section may comprise a conical tubular member having an inner diameter which decreases in the distal direction of the tubular member.

The introducer sheath may be of a thin material such as to allow length deformation of the introducer sheath upon transfer of compression and tension forces. The introducer sheath material, however, shall have sufficient stiffness in order to mechanically avoid kinking of the flexible sections of the distal portion of the catheter shaft during insertion of the catheter tip.

In some embodiments of the present disclosure, the introducer sheath has a pre-shaped, preferably curved, configuration.

An inlet may be provided at a proximal end section of the steering means, the introducer and/or the delivery means for injection of fluids, if necessary. Furthermore, a check valve may be provided at the proximal end section of the introducer sheath to prevent fluid from leaking out of the introducer sheath.

The introducer sheath may have a length sufficient to protect the inner wall of the blood vessel through which the catheter tip passes. In addition, a separate introducer system (not belonging to the catheter system) may be provided. The introducer system then may serve as a portal for passing the complete catheter system from the catheter tip to the catheter shaft into the patient's body and up to the heart.

In addition, the introducer sheath reduces the compression force exerted on the first catheter tube that is inserted through the introducer sheath. This increases manoeuvrability of the steerable catheter tube and the catheter shaft of the delivery means throughout the procedure. A consequence thereof is that any frictional force is reduced. Moreover, moving the catheter tip after it has been advanced through the vascular system of a patient, is greatly improved while at the same time lowering the risk of injury of the patient.

The length of the introducer sheath depends on the length of the catheter shaft of the delivery means and will typically be between about 20 cm to 60 cm for transaortic (TA) access and 80 cm to 150 cm for transfemoral (TF) access. Those skilled in the art will appreciate, however, that all dimensions provided herein are intended as examples only, and that the introducer sheaths and catheter tubes of different dimensions may be substituted for a particular use.

As will be appreciated, the introducer sheath will be of a size, i.e. has an outer diameter, which will permit insertion in a patient's blood vessel (artery or vein) which is used for moving the stent transarterially or via a vein to an insufficient heart valve.

The introducer sheath may be capable of traversing tortuous pathways in the body of the patient without kinking. The introducer sheath may include an inner lubricious liner, an outer polymeric jacket, and a coil reinforcement between the inner and the outer layers. This introducer sheath may provide favourable flexibility without kinking or compression. One or more radiopaque bands or markers may be incorporated within the introducer sheaths material to allow precise location of the introducer sheaths distal end for positioning accuracy. Those skilled in the art will appreciate that other known materials may also be suitable for a particular purpose.

The catheter system is particularly adapted to deliver and implant a heart valve as described for example in the European Patent Application No. 07 110 318 or in the European Patent Application No. 08 151 963. In some embodiments of the present disclosure, a heart valve is accordingly used which comprises a stent and a heart valve prosthesis attached to the stent. The stent exhibits the following:

- a first retaining region, to which the heart valve prosthesis can be attached;
- an opposing, second retaining region with at least one retaining element, for example in the form of retaining eyes or in the form of retaining heads, whereby at least one retaining element of the stent can be put in releasable engagement with the holding means of the catheter tip of the delivery means;
- at least one retaining hoop, to which the heart valve prosthesis can be fastened; and
- at least one and, in some embodiments, preferably three positioning hoops, which are designed to engage in pockets of the native heart valve in the implanted state of the stent, thus to enable automatic positioning of the stent in the aorta of the patient.

In particular, a catheter system is disclosed herein, with which an expandable heart valve stent with a heart valve prosthesis attached to this stent can be advanced to the implantation site in a particularly simple way, for example via the aorta of a patient being treated (transarterially or transfemorally). In some embodiments, during transarterial or transfemoral access by the catheter system, the whole free cross-section available within the aorta is not completely filled up, since the catheter tip provided at the distal end region of the catheter system, in which the stent can be accommodated with the heart valve prosthesis, can be made sufficiently small with respect to its external diameter.

The expandable heart valve stent with the heart valve prosthesis attached to it can be fixed temporarily during implantation in a crimped state to the catheter tip of the delivery means.

The catheter system designed for transarterial or transfemoral access is therefore suitable for inserting a heart valve stent with a heart valve prosthesis attached to it, transarterially or transfemorally into the body of the patient; for example, the catheter tip of the delivery means of the catheter system is inserted via puncture of the A. femoris communis (inguinal artery).

In particular, with the catheter system designed for transarterial or transfemoral access, the catheter shaft of the delivery means may be designed so that it is both kink-resistant and flexible such that a bending radius of up to 4 cm, e.g., up to 3 cm, can be realised, at least at the distal end region of the catheter shaft.

Exemplary embodiments will be described with reference to the appended drawings below.

In the following section, additional alternative and/or exemplary aspects of the present disclosure will be illustrated:

1. An improved system for delivering a self-expanding implant to an implant site within a blood vessel of a patient consisting of an introducer sheath and a delivery catheter, the introducer sheath extending from outside of the body of the patient to the vicinity of the implant site, the delivery catheter having a first and a second retaining means at the distal end of the delivery catheter to reversibly secure the implant to the delivery catheter, the first retaining means reversibly secures the distal end of the self-expanding implant to the delivery catheter and the second retaining means reversibly secures the proximal end of the self-expanding implant to the delivery catheter, wherein the delivery catheter is passed through the introducer sheath to deliver the self-expanding implant to the implant site, and the central segment of the self-expanding implant is compressed from a first diameter to a second diameter that is smaller than the first diameter when the self-expanding implant is passed through the introducer sheath.
2. The system of aspect 1, wherein the implant is at least one of a stent, a stent graft, and a heart valve prosthesis.
3. The system of aspect 1, wherein the implant has male connector elements at the distal and proximal end to engage with female connector elements on the delivery catheter.
4. The system of aspect 3, where the male connector elements are eyelets and the female elements are recesses in the delivery catheter.
5. The system of aspect 1, wherein the introducer sheath has a hemostasis valve at the proximal end.
6. The system of aspect 1, wherein the retaining means consists of axially moveable sheaths that at least partially restrict radial expansion of the implant.
7. A process for delivering a self-expanding implant to an implant site within a blood vessel, comprising in combination: inserting an introducer sheath from outside the body through an opening in the body into a blood vessel; placing the distal end of the introducer sheath in the vicinity of the implant site; reversibly securing the distal end and the proximal end of the self-expanding implant to the distal end of a delivery catheter; inserting the delivery catheter with the self-expanding implant secured to the delivery catheter into the introducer sheath wherein the central segment of the self-expanding implant is compressed from a first diameter to a second diameter when inserted into the introducer sheath; advancing the delivery catheter through the introducer sheath until the self-expanding implant exits the distal end of the introducer sheath; and releasing the distal end and the proximal end of the self-expanding implant from the delivery catheter at the implant site.
8. A system for delivering an implant to an implant site within a blood vessel of a patient consisting of an introducer sheath, a delivery catheter, and a biasing member, wherein the introducer sheath extends from outside of the body of the patient to the vicinity of the implant site; the delivery catheter has retaining means to reversibly retain an implant at the distal end of the delivery catheter; the biasing member has means to deflect the shaft of the delivery catheter from a relaxed configuration into a curved configuration; wherein the delivery catheter is passed through the introducer sheath to deliver the implant to the implant site; and, the biasing member is axially and rotationally moveable inside the introducer sheath with respect to the introducer sheath and the delivery catheter.
9. The system of aspect 8, wherein the implant is a self-expanding or balloon expandable heart valve prosthesis.
10. The system of aspect 9, wherein the implant site is the native aortic or mitral valve.
11. The system of any one of the aspects herein, wherein the introducer sheath has a pre-shaped curved configuration.
12. A system for maneuvering an implant to an implant site within a blood vessel of a patient consisting of an introducer sheath, a delivery catheter, and a biasing member, which comprises, in combination: the delivery catheter having retaining means to reversibly retain an implant at the distal end of the delivery catheter; the biasing member having means to deflect the shaft of the delivery catheter from a relaxed configuration into a curved configuration; the delivery catheter is inserted into the introducer sheath and is axially and rotationally moveable within the introducer sheath; and the biasing member is inserted into the introducer sheath and is axially and rotationally moveable within the introducer sheath and is axially and rotationally moveable with respect to the delivery catheter.
13. A method of positioning an implant toward a target site within a blood vessel, comprising, the steps of: inserting an introducer sheath from outside the body through an opening in the body into a blood vessel; placing the distal end of the introducer sheath in the vicinity of the implant site; reversibly securing the implant to the distal end of a delivery catheter; placing a biasing member having means to actively deflect the shaft of the delivery system from a relaxed configuration into a curved configuration onto the shaft of the delivery system; inserting the delivery catheter with the implant and biasing member into the introducer sheath; advancing the delivery catheter through the introducer sheath until the implant exits the distal end of the introducer sheath; adjusting the axially and rotationally position of the biasing member within the introducer sheath; activating the biasing member to deflect the shaft of the delivery system into a desired bend configuration; adjusting the axially position of the delivery system to place the implant at the target site; and releasing the implant from the delivery system.
14. A method of loading a self-expanding heart valve onto a delivery catheter having an inner shaft, an attachable distal tip, and at least one outer sheath, comprising: compressing the self-expanding heart valve radially and placing the compressed self-expanding heart valve into a tubular retainer, the retainer preventing the self-expanding valve from expanding radially; passing the inner shaft of the delivery system through the central opening of the compressed self-expanding heart valve; attaching the distal tip to the inner shaft of the delivery system; advancing the outer sheath onto the compressed heart valve to prevent radial expansion of at least part of the heart valve; and removing the tubular retainer from the compressed self-expanding heart valve.

15. A catheter system comprising in combination: i. a steering means; and ii. a delivery means for a heart valve, optionally balloon expandable or self-expandable, wherein the steering means and the delivery means are coaxially and rotationally independently movable.

16. Catheter system according to aspect 15, wherein said system is compatible with an introducer for intravascular, optionally transfemoral, applications.

17. Catheter system according to aspect 16, wherein the introducer comprises an introducer sheath which extends or is extendable through the vascular duct and optionally proximal to the target site of the heart.

18. Catheter system according to aspect 15 or 16 having a first and a second retaining mean at the distal end of the catheter system to reversibly secure the heart valve to the delivery means.

19. Catheter system according to aspect 18 wherein the first retaining mean reversibly secures the distal end of the heart valve to the delivery means and the second retaining mean reversibly secures the proximal end of the heart valve to the delivery means.

20. Catheter system according to any of the preceding aspects wherein the heart valve is compressible to the inner diameter of the introducer sheath.

21. Catheter system according to aspect 20, wherein the inner diameter if the introducer sheeth is less than 24 french, preferably less than 20 french, more preferably less than 18 french and even more preferably less than 16 french.

22. Catheter system according to any of the preceding aspects wherein the introducer sheath has a pre-shaped curved configuration.

23. Catheter system wherein the heart valve has male connector elements at the distal and proximal end to engage with female connector elements on the delivery means.

24. Catheter system wherein the delivery means and steering means are operated by one or two means, optionally one or two handles in operative relationship to the pre-shaped introducer sheath.

25. Catheter system according to aspect 15, wherein the steering means have means to deflect the shaft of the delivery catheter from a relaxed configuration into a curved configuration.

26. A delivery system for a heart valve comprising i. a steering means; ii. a delivery means for a heart valve and iii. a introducer sheath wherein the steering means, the delivery means and the introducer sheath are coaxially and circumferentially independently movable.

27. Delivery system according to aspect 28, wherein the introducer sheath extends or is extendable through the vascular duct and optionally proximal to the heart.

28. A method for the delivery of a heart valve to the heart of a patient comprising the steps of: i. in a first step placing an introducer comprising an introducer sheeth into a patient's vasculature; ii. in a second step introducing a catheter system having fixed thereto a self-expanding heart valve through the introducer into the patient's vasculature; iii. in a third step positioning the self-expanding heart valve proximal to the target site in the patient's heart, optionally positioning the heart valve substantially central in the target area; iv. in a fourth step positioning the self-expanding heart valve at the target site; v. in a fifth step partially releasing the self-expanding heart valve from the catheter system; vi. in a sixth step fully releasing the self-expanding heart valve from the catheter system.

29. The method according to aspect 31, wherein the self-expanding heart valve is compressed from a first diameter to a second diameter that is smaller than the first diameter when the self-expanding heart valve is passed through the introducer sheath.

30. A method of loading a self-expanding heart valve onto a delivery means of a catheter system having an inner shaft, an attachable distal tip, and at least one outer sheath, consisting of: compressing the self-expanding heart valve radially and placing the compressed self-expanding heart valve into a tubular retainer, the retainer preventing the self-expanding valve from expanding radially; passing the inner shaft of the delivery system through the central opening of the compressed self-expanding heart valve; attaching the distal tip to the inner shaft of the delivery system; advancing the outer sheath onto the compressed heart valve to prevent radial expansion of at least part of the heart valve; and removing the tubular retainer from the compressed self-expanding heart valve.

31. A system for delivering a self-expanding implant to an implant site within a blood vessel of a patient consisting of an introducer sheath and a delivery catheter, further comprising: the introducer sheath extending from outside of the body of the patient to the vicinity of the implant site; the delivery catheter having a first and a second retaining mean at the distal end of the delivery catheter to reversibly secure the implant to the delivery catheter; the first retaining mean reversibly secures the distal end of the self-expanding implant to the delivery catheter and the second retaining mean reversibly secures the proximal end of the self-expanding implant to the delivery catheter; wherein the delivery catheter is passed through the introducer sheath to deliver the self-expanding implant to the implant site; and the central segment of the self-expanding implant is compressed from a first diameter to a second diameter that is smaller than the first diameter when self-expanding implant is passed through the introducer sheath.

32. The system of aspect 35, wherein the implant is a stent, a stent graft, or a heart valve prosthesis.

33. The system of aspect 35, wherein the implant has male connector elements at the distal and proximal end to engage with female connector elements on the delivery catheter.

34. The system of aspect 37, where the male connector elements are eyelets and the female elements are recesses in the delivery catheter.

35. The system of aspect 35, wherein the introducer sheath has a hemostasis valve at the proximal end.

36. The system of aspect 35, wherein the retaining means consists of axially moveable sheaths that at least partially restrict radial expansion of the implant.

37. A method of delivering a self-expanding implant to an implant site within a blood vessel consisting of: inserting an introducer sheath from outside the body through an opening in the body into a blood vessel; placing the distal end of the introducer sheath in the vicinity of the implant site; reversibly securing the distal end and the proximal end of the self-expanding implant to the distal end of a delivery catheter; inserting the delivery catheter with the self-expanding secured to the delivery catheter into the introducer sheath wherein the central segment of the self-expanding implant is compressed from a first diameter to a second diameter when inserted into the introducer sheath; advancing the delivery catheter through the introducer sheath until the self-expanding implant exits the distal end of the introducer sheath; and releasing the distal end and the proximal end of the self-expanding implant from the delivery catheter at the implant site.

38. A system for delivering an implant to an implant site within a blood vessel of a patient consisting of an introducer sheath, a delivery catheter, and a biasing member, wherein: the introducer sheath extending from outside of the body of the patient to the vicinity of the implant site; the delivery catheter having retaining means to reversibly retain an implant at the distal end of the delivery catheter; the biasing member having means to deflect the shaft of the delivery catheter from a relaxed configuration into a curved configuration; wherein the delivery catheter is passed through the introducer sheath to deliver the implant to the implant site; and, the biasing member is axially and rotationally moveable inside the introducer sheath with respect to the introducer sheath and the delivery catheter.

39. A system of aspect 38, wherein the implant is a self-expanding or balloon expandable heart valve prosthesis.

40. A system of aspect 38, wherein the implant site is the native aortic or mitral valve.

41. A system of aspect 39, wherein the introducer sheath has a pre-shaped curved configuration.

42. A system for maneuvering an implant to an implant site within a blood vessel of a patient consisting of an introducer sheath, a delivery catheter, and a biasing member, whereby: the delivery catheter having retaining means to reversibly retain an implant at the distal end of the delivery catheter; the biasing member having means to deflect the shaft of the delivery catheter from a relaxed configuration into a curved configuration; the delivery catheter is inserted into the introducer sheath and is axially and rotationally moveable within the introducer sheath; and the biasing member is inserted into the introducer sheath and is axially and rotationally moveable within the introducer sheath and is axially and rotationally moveable with respect to the delivery catheter. A method of positioning an implant toward a target site within a blood vessel consisting of inserting an introducer sheath from outside the body through an opening in the body into a blood vessel, wherein emplacement is achieved by: placing the distal end of the introducer sheath in the vicinity of the implant site; reversibly securing the implant to the distal end of a delivery catheter; placing a biasing member having means to actively deflect the shaft of the delivery system from a relaxed configuration into a curved configuration onto the shaft of the delivery system; inserting the delivery catheter with the implant and biasing member into the introducer sheath; and advancing the delivery catheter through the introducer sheath until the implant exits the distal end of the introducer sheath.

43. A method of loading a self-expanding heart valve onto a delivery catheter having an inner shaft, an attachable distal tip, and at least one outer sheath, consisting of: compressing the self-expanding heart valve radially and placing the compressed self-expanding heart valve into a tubular retainer, the retainer preventing the self-expanding valve from expanding radially; passing the inner shaft of the delivery system through the central opening of the compressed self-expanding heart valve; attaching the distal tip to the inner shaft of the delivery system; advancing the outer sheath onto the compressed heart valve to prevent radial expansion of at least part of the heart valve; removing the tubular retainer from the compressed self-expanding heart valve; adjusting the axially and rotationally position of the biasing member within the introducer sheath; activating the biasing member to deflect the shaft of the delivery system into a desired bend configuration; adjusting the axially position of the delivery system to place the implant at the target site; and releasing the implant from the delivery system.

44. Novel enhanced transcatheter heart valve delivery systems, comprising, in combination: at least a specialized prosthetic; a prosthetic delivery system; and at least a valve loader.

45. The system of aspect 44, or any preceding aspects, further comprising a computer interface having a processor.

46. The system of aspect 45, or any preceding aspects, wherein the processor interfaces with imaging and/or sensing modalities.

47. The system of aspect 46, or any preceding aspects, wherein transapical and/or transfemoral delivery systems emplacement is confirmed by the processor, imaging or sensors and a data stream showing the same is captured, stored and/or transmitted wirelessly.

The embodiments as described in this section above can be combined with the embodiments and with each of the features as depicted in the claims and/or as described above herein.

In particular all aspects 1 to 47 as depicted above and the features contained therein can be combined with the disclosure and in particular with each of the features contained in the attached claims forming part of the disclosure of this application.

The following details will describe and illustrate the above listed alternative and/or exemplary embodiments and wherein the below terms and definitions are to be applied to said aspects 1 to 47: the instant disclosure includes an improved bioproshtetic valve which is indicated for patients with high-grade symptomatic aortic valve stenosis and patients with significant aortic valve regurgitation, who require aortic valve replacement, for whom open heart surgery is associated with increased surgical mortality or patients who are otherwise considered inoperable (e.g. porcelain aorta, chest deformation). Examples of the systems for delivery are described below as proprietary disclosures and ostensively patentable subject matters as offered for consideration.

The system consists of three main components: the Valve Prosthesis, the Delivery System and a separate Valve Loader. Each component comes packaged separately.

The valve prosthesis may be constructed from porcine pericardial tissue that is attached to a self-expanding Nitinol stent scaffold using polyester sutures. The scaffold has a crown design that can collapse to fit inside either a transapical or transfemoral catheter delivery device. The valve prosthesis is available in three valve sizes (23 mm, 25 mm and 27 mm) that accommodate native valve annulus diameters ranging from at least about 21 to 27 mm as indicated in Table 2. The valve comes packaged in a polypropylene jar with glutaraldehyde to maintain sterility. The valve is maintained in the deployed dimensional configuration in the jar with the aid of Polyoxymethylene Ring.

Figure 9:
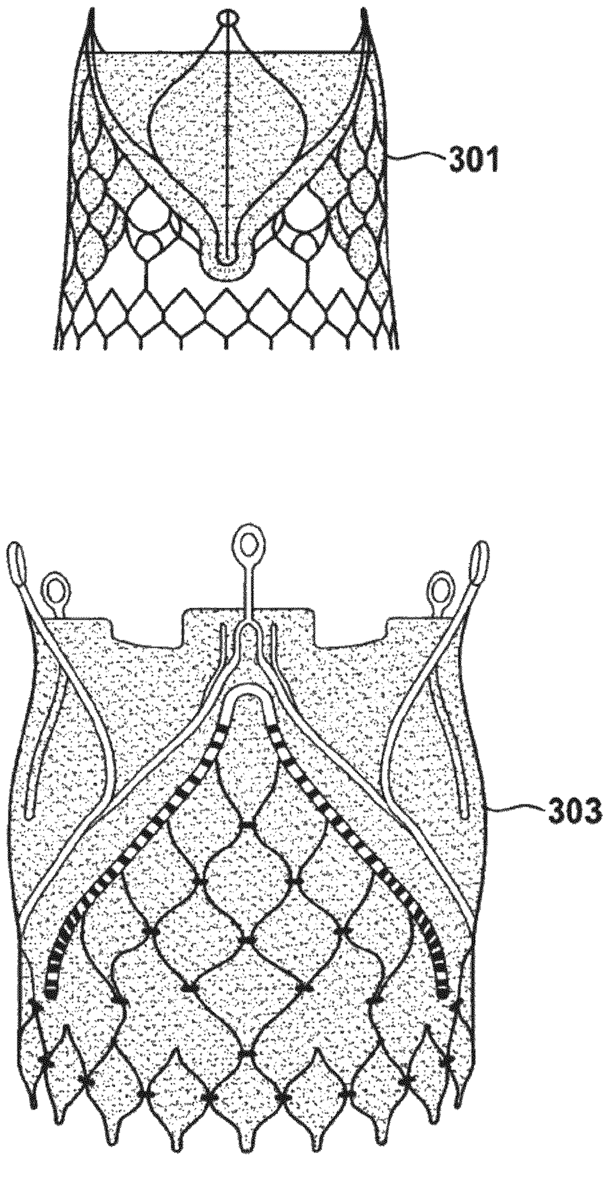
FIG. 9: a schematic of the JenaValve® brand of prosthetic, and an actual view of the same.
Figure 10:
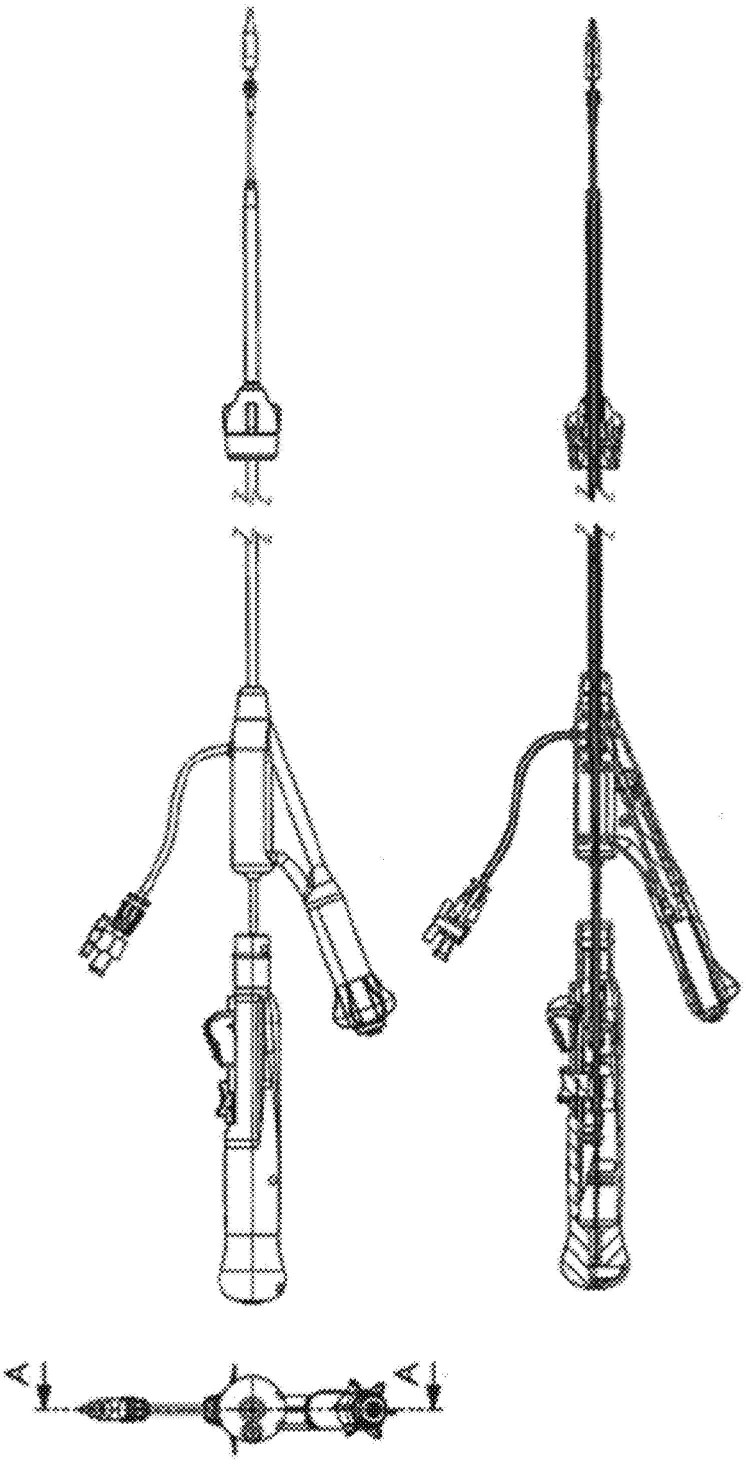
FIG. 10: a depiction of the TF delivery system.
Figure 11:
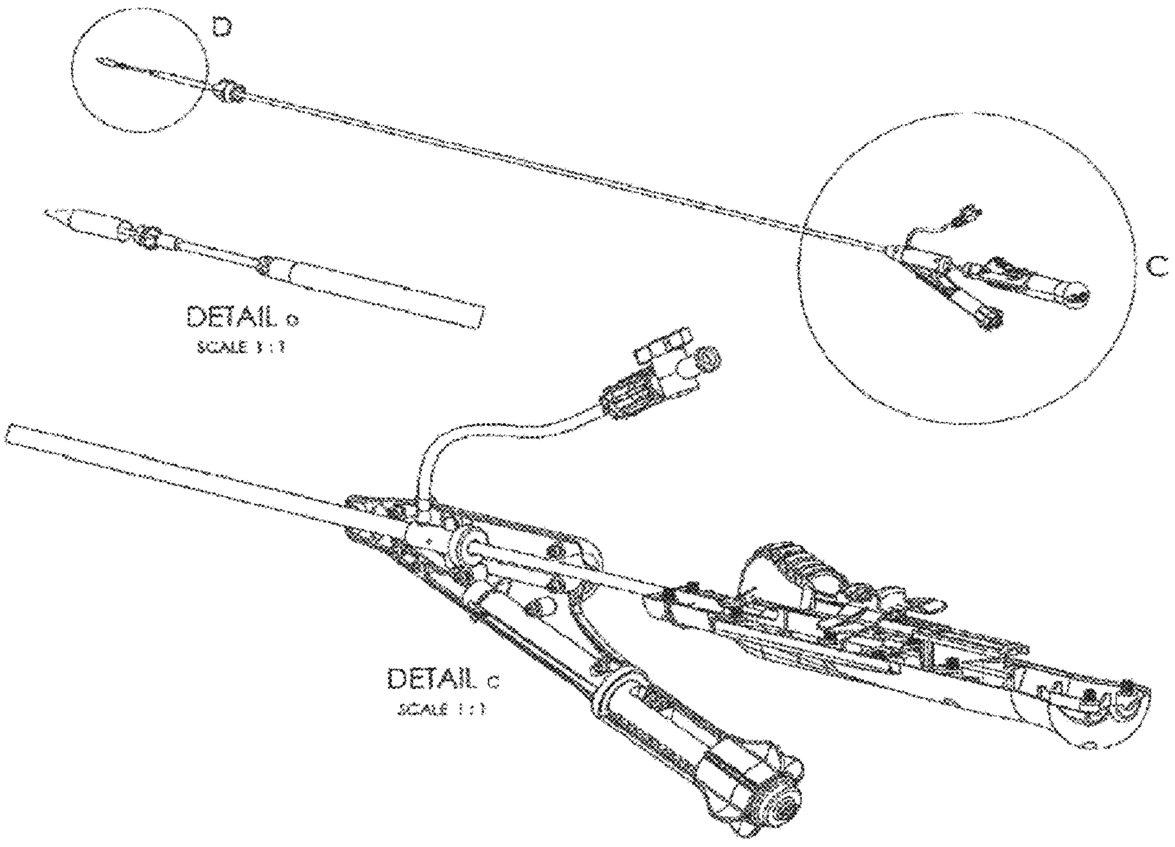
FIG. 11: another view of the TF delivery system.
Figure 12:
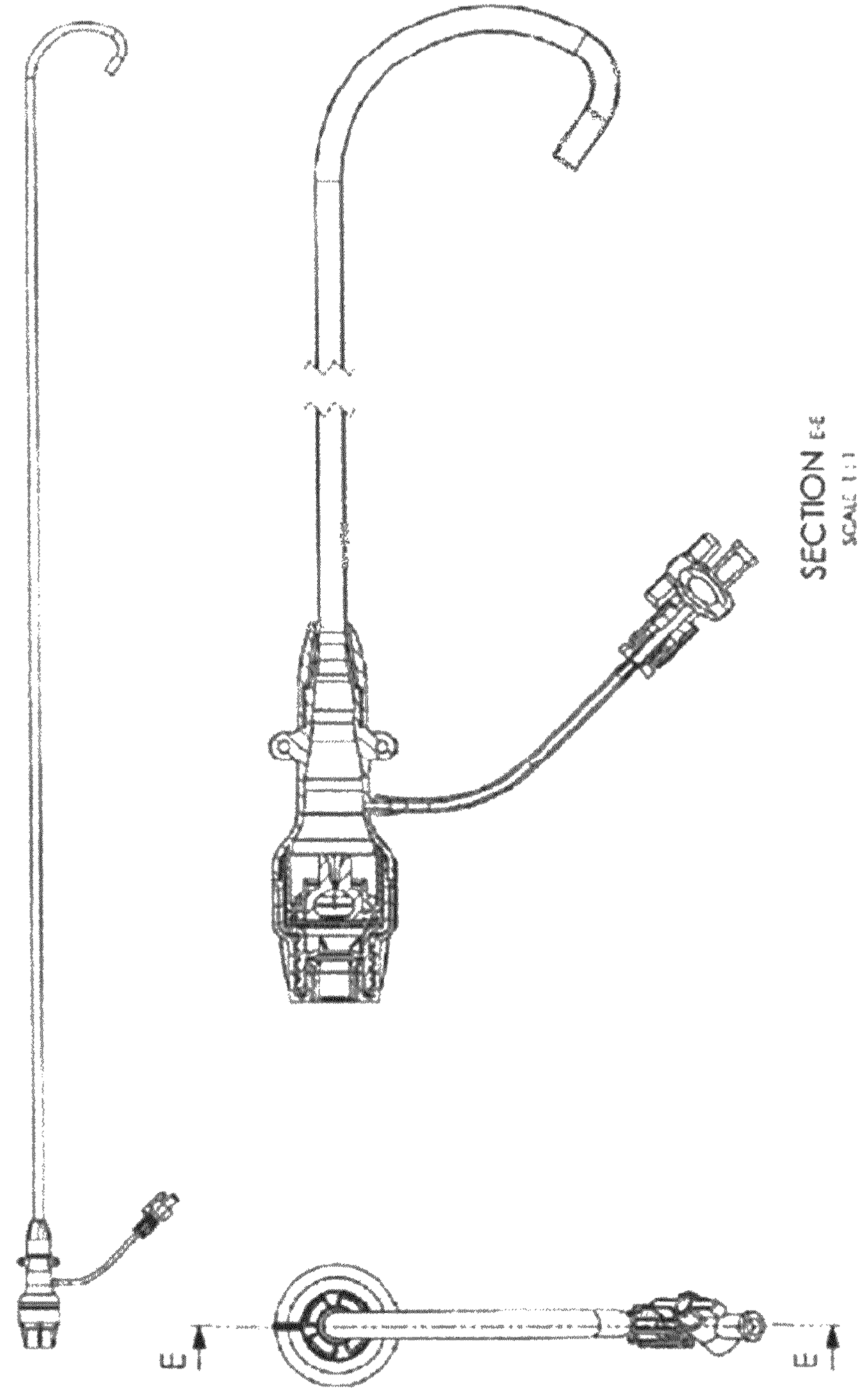
FIG. 12: an additional view illustrating a pre-shaped sheath, according to the instant disclosure.

The valve prosthesis may be constructed from porcine pericardial tissue for the leaflets (or cusps) and the skirt. A glutaraldehyde fixation process is used to cross-link and stabilize the collagen structure of the porcine pericardial tissue. The valve leaflets are formed by joining three tissue panels together and attaching them to the metallic stent scaffold using polyester sutures. The prosthesis is sterilized using a solution based sterilization process and then placed in a glutaraldehyde storage solution until ready for implantation. The following sections provide details on each of the structural elements of the prosthesis and a dimensional summary is provided, to demonstrate how the systems of the instant disclosure improve over, and are technically distinct from any known prior art. FIG. 9 shows this device.

Stent Scaffold: The stent scaffold is produced in three different diameters to accommodate the final intended annular diameter of the valve. The nitinol scaffold has a larger diameter than the final dimension of the valve to ensure a constant outward force on the native valve annulus to avoid any valve movement. In addition, the height of the stent scaffold is also increased with increasing valve size. The outward force of the prosthesis, coupled with the unique fixation feature provided by the clipping mechanism of the feelers, mitigates the known risk of valve movement that has been identified with currently marketed TAVR products.

According to the instant disclosure, in embodiments, the nitinol structure is laser cut from a single tube (OD 7 mm and ID 6 mm). The nitinol is etched in a diamond pattern in the "rhombi" section of the scaffold. The stent scaffold consists of three sets of rails that provide attachment for the leaflet side of the pericardial tissue. It also consists of a nitinol structure below the rail termed as the onion region for pericardial skirt tissue attachment. The stent scaffold additionally consists of nitinol support structures termed as feelers that enable the valve to attach directly to the native valve leaflets for implantation. The stent scaffold may contain eyelets on at least on end of the stent that engage with the delivery system to secure the crimped valve to the delivery system.

Pericardial Tissue: The pericardial tissue is obtained from a vendor that supplies porcine tissue for a variety of medical implants. As described above, the pericardial tissue is used for the prosthetic valve leaflets, for the valve skirt that provides a seal onto the native valve and for the feeler cover to protect the native tissue from potential damage. The tissue is attached to the nitinol stent scaffold with standard surgical polyester suture material. A 6-0 suture is used to sew the pericardial material to the commissure tabs and the rhombi of nitinol. A 5-0 suture is used to sew the pericardial material to the rails and of the nitinol scaffold.

Fabric tabs: The commissure posts and feelers each have a PET fabric tab (pledget) sewn in place using standard surgical polyester 6-0 suture material. The fabric tabs at the commissure are in place to provide structural support during valve assembly and the fabric tabs on feelers covering the pericardial tissue are in place to protect the native tissue from potential damage that may be caused by the nitinol metal.

Valve Implantation Concept

At the outflow section of the valve prosthesis, the self-expanding Nitinol stent scaffold includes three eyelets designed to align with the corresponding recesses at the crown of the delivery system. These mating structures ensure a firm attachment of the prosthesis to the delivery system during the complete course of deployment during implantation. Additional eyelets may be placed on the inflow section of the valve.

According to the instant disclosure, the prosthesis also contains three positional "feelers" that spread apart during delivery of the prosthesis. The feelers are placed in the sinus region behind and at the base of the native leaflets to provide correct positioning with a fixed depth of implant relative to the native leaflet. For enhanced fluoroscopic visualization during the procedure the feelers contain radiopaque markers made of tantalum. The feelers are protected by a small patch of pericardial tissue and fabric sutured to the ends. The Nitinol stent struts at the base of the prosthesis, along with the feelers, provide a securing mechanism of the prosthesis to the native valve leaflets. The inflow of the valve is composed of 24 diamond shaped struts forming a ring that provides the radial strength and seal to securely anchor the valve in position to the native annulus and minimize the paravalvular leakage after implantation.

The rail provides the margin of attachment for the valve leaflets and divides the leaflet and skirt region of the pericardial tissue. The rail is formed in a scalloped shape to mimic the natural shape of a native aortic valve and is designed to allow for commissure deflection which transfers the bulk of the loads from the tissue to the stent to prolong the durability of the prosthesis. The skirt seals the prosthesis to the native annulus.

The instant disclosure contemplates using a transfermoral (TF) delivery system, whereby a prosthetic valve can be inserted via transfemoral delivery using a specially designed catheter system. The approach is to implant the aortic valve prosthesis via transfemoral access using general or local anaesthesia. The TF delivery system is comprised of two catheters: Introducer sheath assembly and a main deployment delivery system.

According to certain embodiments of the instant disclosure, the femoral-iliac vessel will be punctured and the introducer sheath assembly (pre-shaped sheath and introducer) will be inserted into the femoral artery and the tip of the pre-shaped sheath will be positioned in the ascending aorta approximately 2 cm to 4 cm above the native valve. Once in place, the dilator is removed and the pre-shaped sheath is left in position.

The pre-shaped sheath has a generally straight segment to conform to the pathway from the femoral artery to the descending thoracic aorta, and a curved segment to follow the pathway over the arch of the aorta to the aortic valve. The total length of the introducer sheath may be 100 cm to 150 cm. The length of the curved segment may be 15 cm to 30 cm. The radius of curvature of the curved segment may be 3 cm to 15 cm, such as 5 cm to 8 cm. The bend angle from the straight segment to the tip of the sheath maybe 90 degrees to 270 degrees, such as 150 degrees to 210 degrees.

The pre-shaped sheath may be made from flexible polymer material such as PEBAX or Nylon. The wall of the sheath may be reinforced with metal braids or metal coils. The inner wall of the sheath may be lined with PTFE to reduce friction forces. The pre-shaped sheath may have a hydrophilic coating.

A dilator with an atraumatic tip is inserted into the pre-shaped sheath for insertion into the femoral artery and advancement to the aortic valve. The dilator has a guidewire lumen to accommodate a guidewire. The dilator may be pre-shaped. The dilator may be straight. In some embodiments, it may be preferable that the dilator is straight and when inserted into the pre-shaped sheath substantially straightens the curved segment of the pre-shaped sheath for insertion into the femoral artery and passage through the iliac artery and abdominal and descending aorta.

The valve prosthesis is placed into the main delivery system. The inflow segment of the valve prosthesis is restrained by a first sheath. The outflow segment of the valve prosthesis is retrained by a second sheath. The mid-section of the valve prosthesis including the feelers is unconstrained. The first and the second sheath are respectively connected to first and second actuators at the handle of the delivery system. Moving the first actuator distally (toward the tip of the delivery system) moves the first sheath distally and releases the inflow segment of the valve prosthesis. Moving the second actuator proximally (away from the tip of the delivery system) moves the second sheath proximally and releases the outflow segment of the valve prosthesis from the delivery system.

A steerable catheter is mounted on the shaft of the delivery system. The steerable catheter has a handle with a mechanism to deflect the distal segment of the steerable catheter. The mechanism allows for deflection of the steerable catheter by at least 90 degrees from the straight configuration, such as by at least 180 degrees from the straight configuration. Deflecting the steerable catheter will result in a corresponding deflection of the shaft of the delivery system. The steerable catheter is coaxially placed onto the shaft of the delivery system and can move axially and rotationally with respect to the shaft of the delivery system. By rotating the steerable catheter and moving it axially, the location and direction of deflection of the shaft of the delivery system can be selected.

The delivery system with the steerable catheter mounted on the shaft of the delivery system is inserted into the pre-shaped sheath. As the partially crimped valve prosthesis passes into the pre-shaped sheath, the unconstrained mid-section of the valve prosthesis is compressed. The compression of the mid-section of the valve prosthesis may be facilitated by a funnel-shaped inlet into the pre-shaped sheath. Alternatively, a temporary transfer sheath may be placed over the mid-section of the valve prosthesis that compresses the mid-section of the valve prosthesis for insertion into the pre-shaped sheath. The compressed valve prosthesis is advanced through the pre-shaped sheath by pushing the shaft of the delivery system into the pre-shaped sheath.

The distal tip of the pre-shaped sheath is placed in the ascending aorta distal to native aortic valve. When the valve prosthesis exits the distal end of the pre-shaped sheath, the mid-section of the valve prosthesis including the feelers expands. Using the pre-shaped sheath to compress the section of the valve prosthesis for delivery to the native aortic valve, eliminates the need for a separate mechanism to un-sheath the mid-section of the valve prosthesis for release of the feelers.

To place the feelers into the native cusps, it is advantageous to center the valve prosthesis in the aortic root. This can be accomplished by deflecting and rotating the steerable catheter. The point of deflection can be altered by moving the steerable catheter axially along the shaft of the delivery system. Thus, the distal segment of the delivery system can be shaped by the steerable catheter to follow the pathway of the aorta of an individual patient. In some patients the ascending aorta is as short as 3-5 cm. In some patients the ascending aorta is as long as 15-20 cm. In some patients the aortic arch is curved less than 180 degrees. In some patients the aortic arch is curved more than 270 degrees. The degree of deflection of the delivery system can be controlled by the degree of deflection of the steerable catheter. The location of the deflecting region of the delivery system can be controlled by the axial location of the steerable catheter on the delivery system shaft. The direction of deflection of the delivery system can be controlled by the rotational positing of the steerable catheter on the shaft of the delivery system.

An advantage of the pre-shaped sheath is that it deflects the distal end of the delivery system in the general direction of the aortic valve without the use of the steerable catheter. This reduces the bending forces that the steerable catheter has to apply to the shaft of the delivery system to deflect the tip of the delivery system into the final position. Axial movement of the pre-shaped sheath with respect to the delivery system can also be used to adjust the deflection of the shaft of the delivery system. The pre-shaped sheath protects the aortic wall during manipulation of the delivery system and steerable catheter.

Once the distal end of the delivery system is centered in the aortic root with use of the steerable catheter, positioning of the feelers into the native cusps is accomplished by rotationally aligning the feelers with the cusps of the native aortic valve and advancing the valve prosthesis into the aortic annulus. Rotational and axial movement of the valve prosthesis is controlled by axial and rotational movement of the delivery system within the steerable catheter.

Once the feelers are positioned in the native cusps, the valve prosthesis is released by sequentially unsheathing the inflow segment and the outflow segment of the valve prosthesis. Release of the inflow segment of the valve prosthesis anchors the valve prosthesis in the aortic annulus and captures the native leaflets between the feelers and the stent scaffold of the valve prosthesis. Release of the outflow segment of the valve prosthesis disconnects the valve prosthesis from the delivery system.

Alternatively, the outflow segment of the valve prosthesis may be released before the inflow segment of the valve prosthesis. In some cases, it may be preferred to release the inflow segment of the valve prosthesis simultaneously with the outflow segment of the valve prosthesis.

In at least one aspect of the present disclosure, the valve prosthesis may be pre-mounted onto the delivery system by the manufacturer. The mid-section of the valve prosthesis containing the leaflets is unconstrained. The pericardial leaflets located in the mid-section of the valve prosthesis are not compressed avoiding long-term compression damage to the leaflets during shipping and storage. The distal segment including the including the valve prosthesis may be detachable from the shaft of the delivery system. The detached distal segment with the valve prosthesis may be stored separately from the remainder of the delivery system. The distal segment of the delivery system with the mounted partially crimped valve prosthesis may be stored in liquid to avoid de-hydration of the leaflet tissue. Prior to use, the distal segment of the delivery system is connected to the shaft of the delivery system. The connection mechanism used to attach the distal end of the delivery system to the shaft of the delivery system may be in form of male-female thread, magnets, crimping, or bonding.

In another aspect of the present disclosure, the valve prosthesis may have eyelets on at least one end of the stent scaffold to engage the valve prosthesis with the delivery system. The eyelets may sit in recesses in the body of the delivery system. A sheath retains the eyelets in the recesses. By securing the eyelets in the delivery system "melon-seeding" or premature deployment of the self-expanding stent scaffold from the delivery system is prevented. As long as the eyelets are covered by the sheath the valve prosthesis will not deploy. The advantage of this arrangement is that a large segment of the midsection of the valve prosthesis can be un-restrained to allow for full release of the feelers and to minimize compression of the tissue leaflets. Furthermore, the sheaths covering the inflow and outflow segment of the valve prosthesis only require limited travel to release the eyelets in order to disconnect the valve prosthesis from the delivery system.

In another aspect of the present disclosure, the length of the un-restrained midsection of the valve prosthesis is at least 50% of the total length of the valve prosthesis. In another aspect of the present disclosure, the length of the inflow segment of the valve prosthesis restrained by the distal sheath is less than 20% of the length of the valve prosthesis. In another aspect of the present disclosure, the length of the outflow segment of the valve prosthesis restrained by the proximal sheath is less than 20% of the length of the valve prosthesis.

Figure 7:
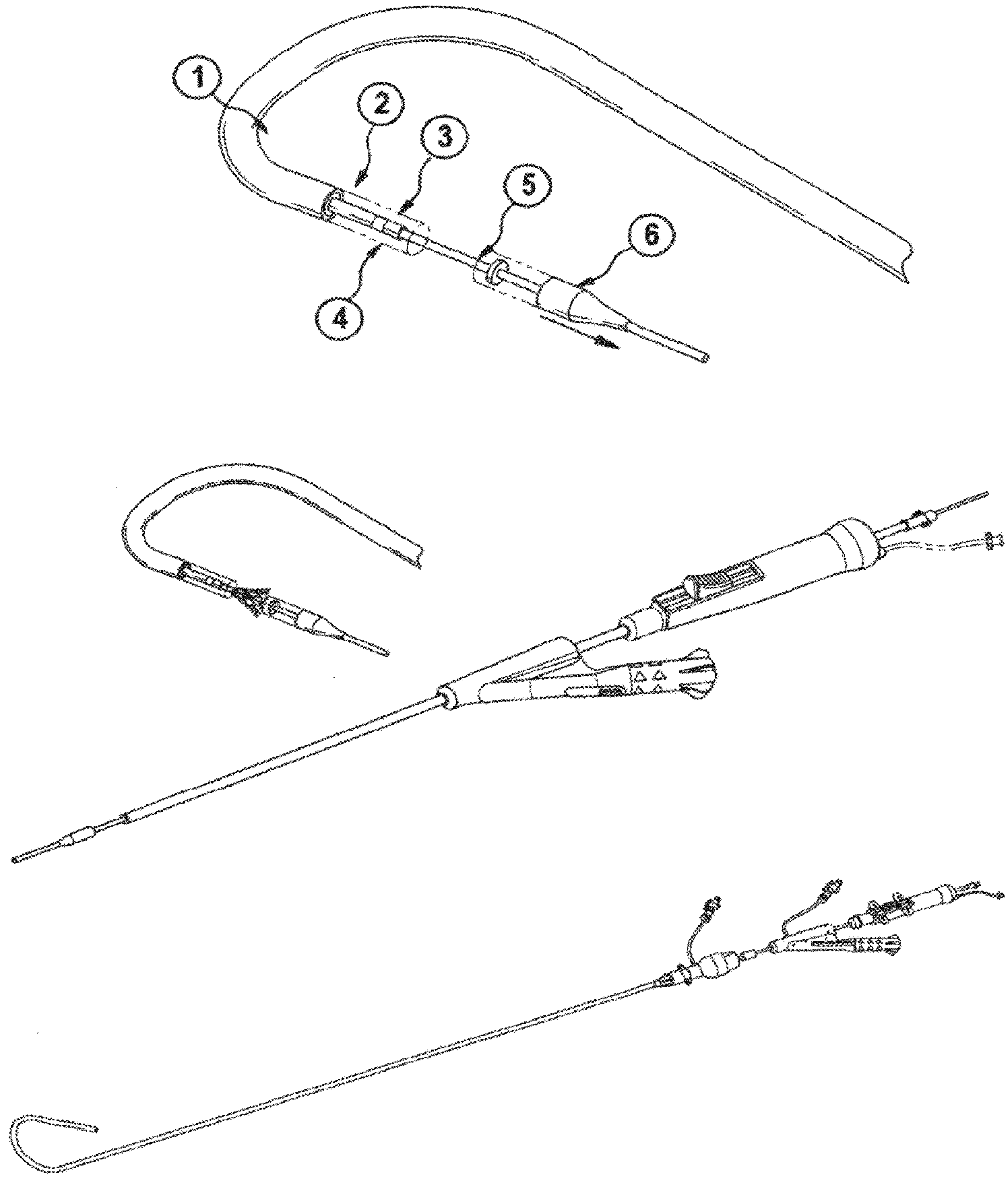
FIG. 7: a plan view of a full system for TF transcatheter heart valve delivery, according to the instant disclosure.

An embodiment of a delivery system according to the present disclosure is represented in FIG. 7. The reference numerals used in FIG. 7 are as follows:

Main Delivery System Distal Assembly:

| ITEM NUMBER | COMPONENT DESCRIPTION | MATERIAL |
|---|---|---|
| 1 | Pre-Shaped Introducer Sheath | Multi Durometer pebax material (55D + 72D)<br>SS 304 V coil reinforced<br>SS 304 V braid reinforced<br>PTFE Liner |
| 2 | Steerable Catheter | Multidurometer pebax 72D + 55D + 25D<br>304SS coil, braid wire and pull wire |
| 3 | Stentholder tubing | Multidurometer pebax 55D + Nylon<br>Ultem or polyimide stentholder<br>PTFE Liner<br>304SS coil, braid wire |
| 4 | Outer Shaft | PTFE Liner<br>Multidurometer pebax 72D + 35D<br>304SS braid wire<br>Plt/Ir marker band |
| 5 | Guidewire tubing/Rhombi Support | Pebax, Polyurethane, Polyimide |
| 6 | Rhombi Sleeve | Nylon<br>304SS braid<br>Plt/Ir marker band |

Figure 8:
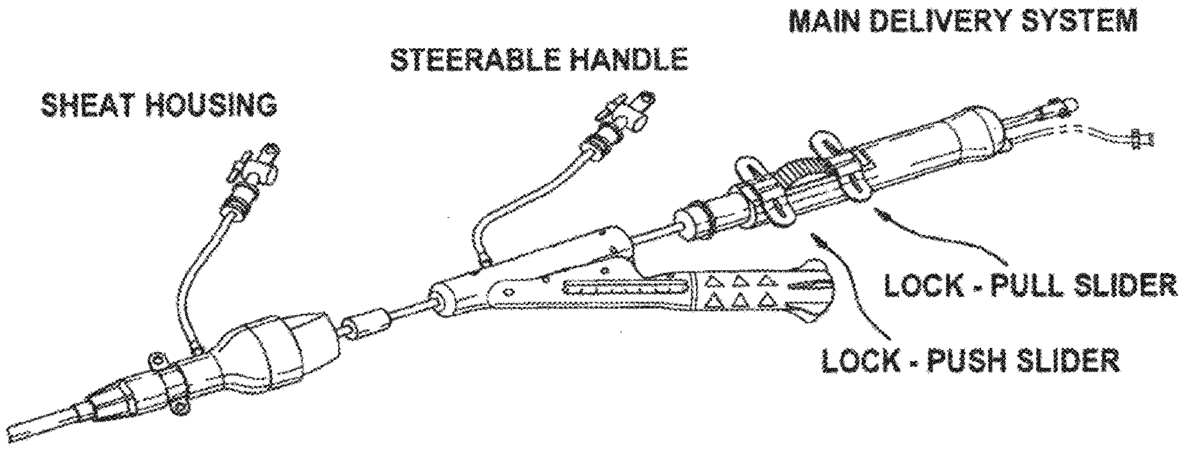
FIG. 8: a close up of the system of FIG. 1, according to the instant disclosure.
Figure 8:
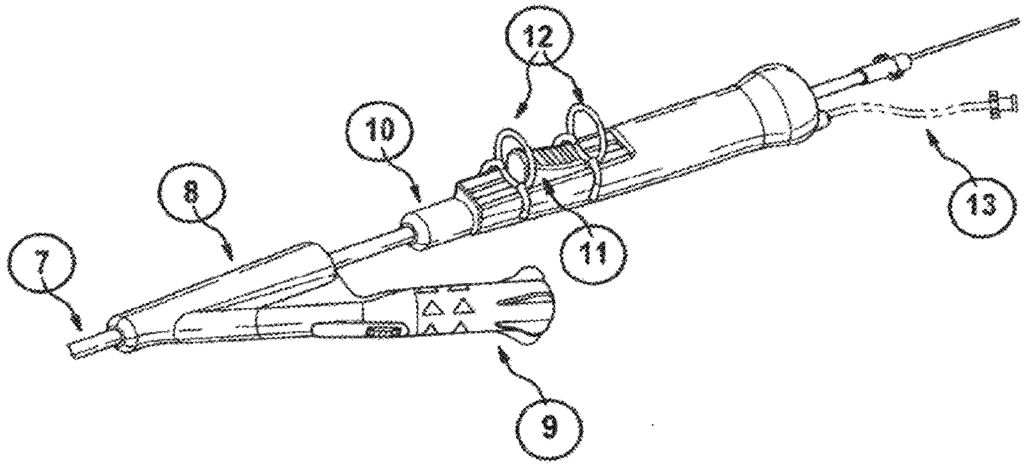

An embodiment of a handle assembly of the delivery system according to the present disclosure is represented in FIG. 8. The reference numerals used in FIG. 8 are as follows:

Main Delivery System Distal Assembly:

| ITEM NUMBER | COMPONENT DESCRIPTION | MATERIAL |
|---|---|---|
| 7 | Shaft of Steerable Sheath | PTFE Liner<br>Multidurometer pebax 72D + 35D<br>304SS braid wire<br>Plt/Ir marker band<br>Stainless steel flat wire |
| 8 | Housing of Steerable Sheath | ABS, Polycarbonate |
| 9 | Steerable Rotational Actuator | ABS, Polycarbonate, stainless steel |
| 10 | Delivery System Handle | ABS, Polycarbonate |
| 11 | Push-pull Actuator | ABS, Polycarbonate |
| 12 | Safety Locks | Nylon ABS, Polycarbonate |
| 13 | Flush Port | Polyurethane tubing |

The final crimping of the prosthesis is assisted by two loading tubes which allows securing the prosthesis with the outer shaft by distal movement. It is EO-sterilized and for single use only. It should be noted that the TF Valve Loader will utilize the same principle of operation as outlined for the TA Valve Loader.

The present disclosure further relates to a device to facilitate the removal of the distal end of a catheter from an introducer sheath or guiding catheter. Delivery catheters for stents or transcatheter heart valves, for example, may have a split capsule which contains the implant. After the implant is released from the catheter, the open end of the split capsule may be difficult to retract back into the opening of an introducer sheath or guiding catheter within a vessel.

This aspect of the present disclosure provides a tapered insertion device to channel the capsule back into the inner diameter of the introducer sheath or guiding catheter for removal from the body. The device may be static or self-expanding. The device may also include a step to support the implant.

Figure 13A:
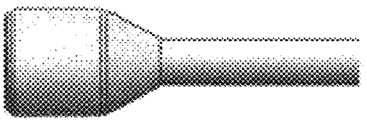
FIGS. 13*a, b*: side views of an embodiment of a device to facilitate the removal of the distal end of a catheter from an introducer sheath or guiding catheter.
Figure 13B:
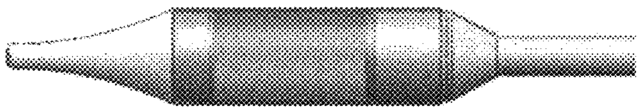

In one embodiment, the device comprises a tapered cylinder that is automatically exposed when capsule is actuated, thereby closing the capsule with a tapered tip. In this regard, reference is made to FIGS. 13*a, b*. In more detail, FIG. 13*a* shows one embodiment of the tapered device, and FIG. 13*b* shows the tapered device with capsule.

Figure 14A:
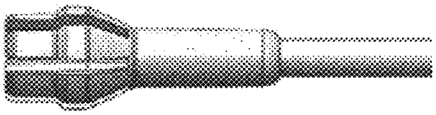
FIGS. 14*a, b*: side views of another embodiment of a device to facilitate the removal of the distal end of a catheter from an introducer sheath or guiding catheter.
Figure 14B:
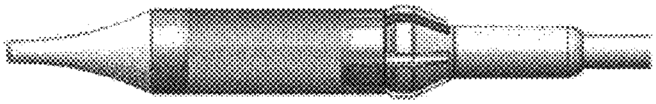

In one embodiment (cf. FIGS. 14*a, b*), the device is self-collapsing, allowing for the device to expand to a larger outer diameter than the capsule when exposed. There is also a straight section on the distal end of the self-collapsing device designed to keep the capsule concentric with the device. The device may be a single piece made from thermoplastic polymer or made from multiple pieces assembled together. In more detail, FIG. 14*a* shows one embodiment of the self-collapsing device, and FIG. 14*b* shows the self-collapsing device with capsule.

Figure 15:
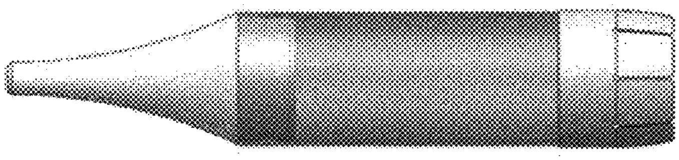
FIG. 15: a side view of another embodiment of a device to facilitate the removal of the distal end of a catheter from an introducer sheath or guiding catheter.

In another embodiment (cf. FIG. 15), the device is incorporated into the capsule and collapses after implant is released from capsule. The device may be made from a single piece of thermoplastic polymer and may contain slits or living hinges. Collapsing of the device may also be mechanically actuated by the user. In more detail, FIG. 15 shows one embodiment of the collapsing capsule.

Figure 16A:
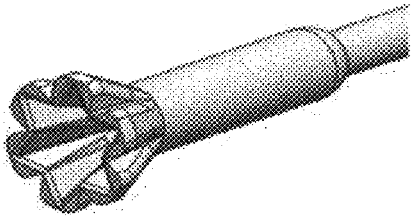
FIGS. 16*a, b*: side views of another embodiment of a device to facilitate the removal of the distal end of a catheter from an introducer sheath or guiding catheter.
Figure 16B:
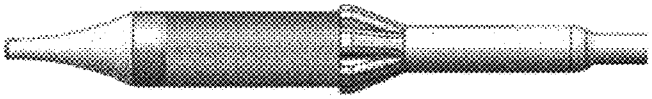

In another embodiment (cf. FIGS. 16*a, b*), the device is self-expanding. The device is made from thermoplastic polymer with living hinges that allow the device to compress to a smaller diameter that will fit inside the capsule when not in use. When the capsule is opened, the device expands back to its original diameter, larger than the capsule diameter. The self-expanding device is tapered to facilitate entry into the introducer sheath or guiding catheter. FIGS. 16*a, b* show the device with a step to support the inner diameter of the implant. In more detail, FIG. 16*a* shows one embodiment of the self-collapsing device, and FIG. 16*b* shows the self-collapsing device with capsule.

Figure 17:
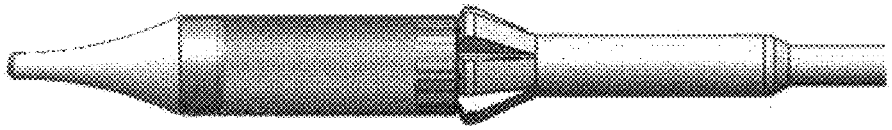
FIG. 17: a side view of another embodiment of a device to facilitate the removal of the distal end of a catheter from an introducer sheath or guiding catheter.

In another embodiment (cf. FIG. 17), the self-expanding device comprises fingers under the capsule to keep the capsule concentric with the device. In more detail, FIG. 17 shows one embodiment of the self-collapsing device with centralizing members.

Figure 18A:
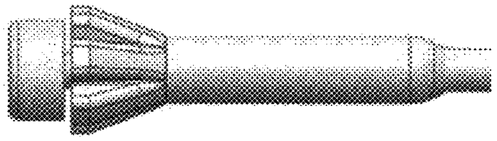
FIGS. 18*a, b*: side views of another embodiment of a device to facilitate the removal of the distal end of a catheter from an introducer sheath or guiding catheter.
Figure 18B:
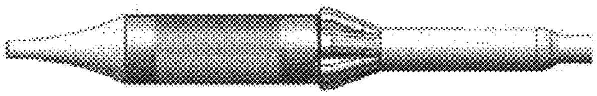

In another embodiment (cf. FIGS. 18*a, b*), the self-expanding device comprises a stabilizer element distal to the self-expanding wedges. The stabilizer maintains the capsule's concentricity with the device. The profile of the stabilizer may vary. In more detail, FIG. 18*a* shows one embodiment of the self-expanding device with stabilizer, and FIG. 18*b* shows the self-expanding device with stabilizer and capsule.

Figure 19A:
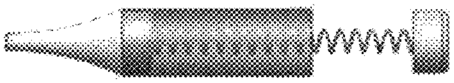
FIGS. 19*a, b*: side views of another embodiment of a device to facilitate the removal of the distal end of a catheter from an introducer sheath or guiding catheter.
Figure 19B:

In another embodiment (cf. FIGS. 19*a, b*), the stabilizer is retractably attached to the inside of the capsule. A spring may be used to actuate the stabilizer. The stabilizer pushes up again the self-expanding device to keep the capsule concentric with the device. The profile of the stabilizer may vary. In more detail, FIG. 19*a* shows one embodiment of the self-expanding device with stabilizer, and FIG. 19*b* shows the self-expanding device with stabilizer and capsule.

Figure 20:
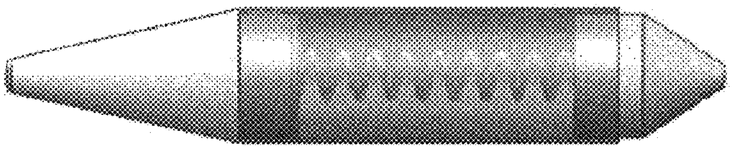
FIG. 20: a side view of another embodiment of a device to facilitate the removal of the distal end of a catheter from an introducer sheath or guiding catheter.

In another embodiment (cf. FIG. 20), the stabilizer and spring may work without the self-expanding device. The stabilizer may have a tapered or conical shape to facilitate entry into the introducer sheath or guiding catheter. In more detail, FIG. 20 shows one embodiment of the self-actuated device in capsule.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by embodiments of the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the present disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing embodiments of the present disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate embodiments of the present disclosure and does not pose a limitation on the scope of the present disclosure otherwise claimed. No language in the specification should be construed as indicating any non-claimed element essential to the practice of embodiments of the present disclosure.

Groupings of alternative elements or embodiments of the present disclosure described herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out embodiments of the present disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present disclosure so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the present disclosure described herein are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

LIST OF REFERENCE NUMBERS

100 delivery means
11 catheter tip
12 catheter shaft
13 handle
14 holding means
15 first retaining means
16 second retaining means
17 first operating means
18 second operating means
19 body of handle
20 first force transmitting means
21 second force transmitting means
22 holding tube
23 catheter end tip
30 steering meens
31 steering catheter tube
32 handle
33 operating means
34 indicator means
35 control wire
36 post section
40 introducer
41 introducer sheath

42 introducer port
43 base member
44 sealing arrangement
45 crimping section

What is claimed:

1. A method for delivering a prosthetic heart valve to a heart of a patient using a catheter system, the method comprising:

inserting an introducer comprising a sheath into the patient;

advancing a delivery catheter and a steering catheter in the introducer, the delivery catheter configured to deliver the prosthetic heart valve and having a proximal end and a distal end, the distal end comprising a tip that includes a first sleeve movable relative to a second sleeve in a proximal-distal direction, a middle section configured to be uncovered when the first sleeve is in a proximal-most position with respect to the second sleeve, and a holder disposed in the second sleeve, the second sleeve positioned proximal to the first sleeve and the first sleeve having an open end facing in a proximal direction;

manipulating an integrated handle to cause the steering catheter to deflect to steer the delivery catheter, the integrated handle comprising a delivery handle portion and a steering handle portion comprising a housing, the housing of the steering handle portion sized and configured to receive the delivery handle portion, the integrated handle configured to control movement of the delivery catheter and the steering catheter, independently; and causing an actuator movably coupled to the delivery handle portion and configured to move with respect to the delivery handle portion to move to manipulate the first sleeve relative to the second sleeve and the holder while the delivery handle portion is received by the housing of the steering handle portion, wherein the steering catheter is fixedly connected to the steering handle portion and the delivery catheter is fixedly connected to the delivery handle portion, and wherein the steering catheter and the delivery catheter are selectively coaxially and rotationally independently movable.

2. The method of claim 1, wherein the steering catheter comprises a control wire configured to deflect the steering catheter to steer the delivery catheter.

3. The method of claim 1, wherein the sheath is extendable through a vascular duct and comprises a crimping section.

4. The method of claim 1, wherein the first sleeve is configured to secure a distal end of the prosthetic heart valve to the delivery catheter and the second sleeve is configured to secure a proximal end of the prosthetic heart valve to the delivery catheter, and wherein at least a portion of the prosthetic heart valve is disposed in the middle section of the tip and not covered by the first sleeve or the second sleeve prior to movement of the first sleeve during deployment of the prosthetic heart valve.

5. The method of claim 4, wherein a diameter of the prosthetic heart valve varies over a length of the prosthetic heart valve when the prosthetic heart valve is secured to the delivery catheter.

6. The method of claim 1, wherein an inner diameter of the sheath is less than 24 French.

7. The method of claim 1, wherein the sheath has a pre-shaped, curved configuration.

8. The method of claim 1, wherein the sheath comprises a flexible polymer, a hydrophilic coating, a PTFE liner, coil reinforcement, braid reinforcement, or a combination thereof.

9. The method of claim 1, wherein the delivery catheter comprises a holding tube, and the prosthetic heart valve is secured to the delivery catheter by the holding tube.

10. The method claim 9, wherein a distal end or a proximal end of the prosthetic heart valve comprises a male connector, and the delivery catheter comprises a female connector complimentary to the male connector of the prosthetic heart valve.

11. The method of claim 1, wherein the delivery handle portion comprises a first handle configured to control movement of the delivery catheter and the steering handle portion comprises a second handle configured to control movement of the steering catheter.

12. The method of claim 11, wherein the second handle of the steering catheter comprises a second actuator to deflect a shaft of the delivery catheter from a relaxed configuration into a curved configuration.

13. The method of claim 1, wherein the steering catheter, the delivery catheter, and the sheath are circumferentially independently movable when the steering catheter and the delivery catheter are simultaneously disposed in the sheath.

14. The method of claim 1, wherein the delivery catheter and the steering catheter are simultaneously introducible into the sheath.

15. A method for delivering a prosthetic heart valve to a heart of a patient using a catheter system, the method comprising:

inserting an introducer comprising a sheath and a crimping section proximal to a sheath into the patient, the crimping section having an inner diameter that decreases in a distal direction;

advancing a delivery catheter and a steering catheter in the introducer, the delivery catheter configured to deliver the prosthetic heart valve and having a proximal end and a distal end, the distal end comprising a tip that includes a first sleeve movable relative to a second sleeve in a proximal-distal direction, and a holder disposed in the second sleeve, the second sleeve positioned proximal to the first sleeve and the first sleeve having an open end facing in a proximal direction, manipulating an integrated handle to cause the steering catheter to deflect to steer the delivery catheter, the integrated handle comprising a delivery handle portion fixedly connected to the delivery catheter and a steering handle portion comprising a housing fixedly connected to the steering catheter, the housing of the steering handle portion sized and configured to receive the delivery handle portion, and the integrated handle configured to control movement of the delivery catheter and the steering catheter, independently; and causing an actuator movably coupled to the delivery handle portion and configured to move with respect to the delivery handle portion to move to manipulate the first sleeve relative to the second sleeve and the holder while the delivery handle portion is received by the housing of the steering handle portion, wherein the delivery catheter and the steering catheter are simultaneously introducible into the crimping section of the introducer; and wherein the steering catheter, the delivery catheter, and the sheath are rotationally independently movable when the steering catheter and the delivery catheter are simultaneously disposed in the sheath.

16. The method of claim 15, wherein a middle section of the tip is uncovered when the first sleeve is in a proximal-most position with respect to the second sleeve.

17. The method of claim 16, wherein the first sleeve secures a distal end of the prosthetic heart valve to the delivery catheter and the second sleeve secures a proximal end of the prosthetic heart valve to the delivery catheter, and wherein at least a portion of the prosthetic heart valve is disposed in the middle section of the tip.

18. The method of claim 17, wherein at least one of the distal end or the proximal end of the prosthetic heart valve comprises a first connector, and the delivery catheter comprises a second connector complimentary to the first connector.

19. The method of claim 18, wherein the first connector comprises eyelets, and the second connector comprises recesses.

20. The method of claim 17, wherein a central segment of the prosthetic heart valve is compressed from a first diameter to a second diameter smaller than the first diameter when the delivery catheter passes through the crimping section.

21. The method of claim 17, wherein a proximal end of the sheath comprises a hemostasis valve.

* * * * *